(12) United States Patent
Roberts et al.

(10) Patent No.: US 10,501,493 B2
(45) Date of Patent: Dec. 10, 2019

(54) BROAD SPECTRUM ANTIBIOTICS

(71) Applicant: RQx Pharmaceuticals, Inc., La Jolla, CA (US)

(72) Inventors: Tucker Curran Roberts, San Diego, CA (US); Peter Andrew Smith, La Jolla, CA (US); David Campbell, San Diego, CA (US); Sergio G. Duron, San Diego, CA (US); Robert I. Higuchi, Solana Beach, CA (US)

(73) Assignee: RQX PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/358,100

(22) Filed: Nov. 21, 2016

(65) Prior Publication Data

US 2017/0073370 A1   Mar. 16, 2017

Related U.S. Application Data

(63) Continuation of application No. 14/123,024, filed as application No. PCT/US2012/039727 on May 25, 2012, now abandoned.

(60) Provisional application No. 61/491,149, filed on May 27, 2011.

(51) Int. Cl.

| | | |
|---|---|---|
| *A61K 38/08* | (2019.01) | |
| *C07K 7/06* | (2006.01) | |
| *A61K 9/00* | (2006.01) | |
| *A61K 9/06* | (2006.01) | |
| *A61K 45/06* | (2006.01) | |
| *A61K 47/02* | (2006.01) | |
| *A61K 47/10* | (2017.01) | |
| *A61K 47/12* | (2006.01) | |
| *A61K 47/14* | (2017.01) | |
| *A61K 9/10* | (2006.01) | |
| *A61K 47/38* | (2006.01) | |
| *A61K 9/20* | (2006.01) | |
| *A61K 9/48* | (2006.01) | |
| *A61K 38/00* | (2006.01) | |

(52) U.S. Cl.
CPC ............ *C07K 7/06* (2013.01); *A61K 9/0014* (2013.01); *A61K 9/0019* (2013.01); *A61K 9/06* (2013.01); *A61K 9/10* (2013.01); *A61K 9/2018* (2013.01); *A61K 9/2054* (2013.01); *A61K 9/2059* (2013.01); *A61K 9/4858* (2013.01); *A61K 38/08* (2013.01); *A61K 45/06* (2013.01); *A61K 47/02* (2013.01); *A61K 47/10* (2013.01); *A61K 47/12* (2013.01); *A61K 47/14* (2013.01); *A61K 47/38* (2013.01); *A61K 38/00* (2013.01)

(58) Field of Classification Search
CPC ........ A61K 38/06; A61K 38/07; A61K 38/08; C07K 5/02; C07K 5/0812; C07K 5/10; C07K 7/02; C07K 7/06
See application file for complete search history.

(56) References Cited

U.S. PATENT DOCUMENTS

| | | |
|---|---|---|
| 3,128,280 A | 4/1964 | Rorig |
| 5,204,328 A | 4/1993 | Nutt et al. |
| 6,025,350 A | 2/2000 | Masamune et al. |
| 9,187,524 B2 | 11/2015 | Romesberg et al. |
| 9,309,285 B2 | 4/2016 | Roberts et al. |
| 2003/0130172 A1 | 7/2003 | Belvo et al. |
| 2004/0024178 A1 | 2/2004 | Ashman et al. |
| 2005/0153876 A1 | 7/2005 | Cameron et al. |
| 2007/0099885 A1 | 5/2007 | Endermann et al. |
| 2008/0275018 A1 | 11/2008 | Endermann et al. |
| 2008/0300231 A1 | 12/2008 | Endermann et al. |
| 2013/0130985 A1 | 5/2013 | Alewood et al. |
| 2013/0244929 A1 | 9/2013 | Gallant et al. |
| 2013/0281360 A1 | 10/2013 | Romesberg et al. |
| 2014/0249073 A1 | 9/2014 | Roberts et al. |
| 2017/0088582 A1 | 3/2017 | Roberts et al. |

FOREIGN PATENT DOCUMENTS

| | | |
|---|---|---|
| CN | 1675236 A | 9/2005 |
| CN | 103788176 A | 5/2014 |
| JP | 2018135357 A | 8/2018 |
| WO | WO-9817679 A1 | 4/1998 |
| WO | WO-0114346 A1 | 3/2001 |
| WO | WO-03106480 A1 | 12/2003 |
| WO | WO-2011109441 A1 | 9/2011 |
| WO | WO-2011112441 A1 | 9/2011 |
| WO | WO-2012036907 A2 | 3/2012 |
| WO | WO-2012166665 A2 | 12/2012 |

(Continued)

OTHER PUBLICATIONS

US 10,351,595 B2, 07/2019, Roberts (withdrawn)*
Braun et al. Imp/OstA is required for cell envelope biogenesis in *Escherichia coli*. Molecular Microbiology 45(5):1289-1302 (2002).
Bruton et al. Lipopeptide substrates for SpsB, the *Staphylococcus aureus* type I signal peptidase: design, conformation and conversion to α-ketoamide inhibitors. European Journal of Medicinal Chemistry 38:351-356. (2003).
Bundgaard et al. Design of Prodrugs pp. 7-9, 21-24 (1985).
Gould et al. Salt Selection for Basic Drugs. Int J. Pharm. 33:201-217. (1986).

(Continued)

*Primary Examiner* — Jeffrey E. Russel
(74) *Attorney, Agent, or Firm* — Wilson Sonsini Goodrich & Rosati

(57) ABSTRACT

Provided herein are analogs of the natural product arylomycin for the treatment of microbial infections. In some embodiments, the compounds described herein have broad spectrum bioactivity. The compounds provided herein can in other embodiments overcome the resistance conferred by single amino acid mutations at defined positions of bacterial Signal Peptidases (SPases) and in other embodiments provide for a broader spectrum of antibiotic bioactivity compared to the natural product. Pharmaceutical compositions and methods for treatment using the compounds described herein are also provided.

19 Claims, 2 Drawing Sheets

Specification includes a Sequence Listing.

(56) References Cited

FOREIGN PATENT DOCUMENTS

| WO | WO-2013138187 A1 | 9/2013 |
| WO | WO-2014081886 A1 | 5/2014 |
| WO | WO-2015179441 A2 | 11/2015 |
| WO | WO-2017064629 A1 | 4/2017 |
| WO | WO-2017084629 A1 | 5/2017 |
| WO | WO-2017084630 A1 | 5/2017 |

OTHER PUBLICATIONS

Hallander et al Synergism Between Aminoglycosides and Cephalosporins with Antipseudomonal Activity: Interaction Index and Killing Curve Method Antimicrob. Agents Chemother. 22:743-752 (1982).
PCT/CN2016/106597 International Search Report and Written Opinion dated Mar. 8, 2017.
PCT/CN2016/106597 Supplementary International Search Report dated Jul. 5, 2017.
PCT/CN2016/106598 International Search Report and Written Opinion dated Mar. 2, 2017.
PCT/CN2016/106598 Supplementary International Search Report dated Jun. 12, 2017.
PCT/US2014/051151 International Preliminary Report on Patentability dated Feb. 25, 2016.
PCT/US2015/031631 International Preliminary Report on Patentability dated Dec. 1, 2016.
PCT/US2015/031631 International Search Report and Written Opinion dated Nov. 3, 2015.
Schimana et al. Arylomycins A and B, new biaryl-bridged lipopeptide antibiotics produced by *Streptomyces* sp. Tü 6075. I. Taxonomy, fermentation, isolation and biological activities. J Antibiot (Tokyo) 55(6):565-570 (2002).
Butler et al. Natural Products—The Future Scaffold for Novel Antibiotics. Biochemical Pharmacology 71:919-929 (2006).
Dufour et al. Total Synthesis of Arlomycin A2, a Signal Peptidase I (SPaseI) Inhibitor. J. P. Synlett 15:2355-2359 (2008).
Holtzel et al. Arylomycins A and B, new biaryl-bridged lipopeptide antibiotics produced by *Streptomyces* sp. Tu 6075. Antibot (Tokyo) 55(6):565-577 (2002).
Liu et al. Efforts toward broadening the spectrum of arylomycin antibiotic activity. Bioorganic & Medicinal Chemistry Letters 23:5654-5659 (2013).
Liu et al. Synthesis and Characterization of the Arylomycin Lipoglycopeptide Antibiotics and the Crystallographic Analysis of Their Complex with Signal Peptidase. J. Am. Chem. Soc. 133:17869-17877 (2011).
Paetzel et al. Crystallographic and biophysical analysis of a bacterial signal peptidase in complex with a lipopeptide-based inhibitor. J Biol Chem 279(29):30781-30790 (2004).
PCT/US2012/39727 International Preliminary Report on Patentability dated Dec. 2, 2013.
PCT/US2012/39727 International Search Report and Written Opinion dated Jan. 3, 2013.
PCT/US2013/071093 International Preliminary Report on Patentability dated Jun. 4, 2015.
PCT/US2013/071093 International Search Report and Written Opinion dated Apr. 1, 2014.
Roberts et al. Initial efforts toward the optimization of arylomycins for antibiotic activity. J. Am. Chem. Soc. 129:15830-15838 (2007).
Roberts et al. Initial efforts toward the optimization of arylomycins for antibiotic activity. J Med Chem. 54(14):4954-4963 (2011).
Roberts et al. Synthesis and Biological Characterization of Arylomycin B Antibiotics. J. Nat. Prod. 74:956-961 (2011).
Smith et al. Broad Spectrum Antibiotic Activity of the Arylomycin Natural Products Is Masked by Natural Target Mutations. Chemisty & Biology 17:1223-1231 (Nov. 24, 2010).
Therien et al. Broadening the Spectrum of β-Lactam Antibiotics through Inhibition of Signal Peptidase Type 1. Antimicrobial Agents and Chemotherapy. 56:4662-4670 (2012).
U.S. Appl. No. 14/086,908 Office Action dated Jan. 5, 2015.
U.S. Appl. No. 14/086,908 Office Action dated May 29, 2015.
U.S. Appl. No. 14/123,024 Office Action dated May 1, 2015.
U.S. Appl. No. 14/123,024 Office Action dated May 19, 2016.
U.S. Appl. No. 14/123,024 Office Action dated Oct. 15, 2015.
PCT/CN2016/106598 International Preliminary Report on Patentability dated May 31, 2018.
PCT/CN2016/106597 International Preliminary Report on Patentability dated May 31, 2018.
PCT/CN2018/076957 International Search Report and Written Opinion dated Jun. 8, 2018.
Roberts et al. Structural and Initial Biological Analysis of Synthetic Arylomycin A2. J Am Chem Soc. 129(51):15830-8 (2007).
Schallenberger et al. Type I Signal Peptidase and Protein Secretion and *Stphylococcus aureus*. J Bacterol 94(10):2677-86 (2012).
U.S. Appl. No. 15/312,614 Office Action dated Jul. 17, 2018.
Buzder-Lantos et al. Substrate based peptide aldehyde inhibits bacterial type I signal peptidase. Bioorg Med Chem Lett 19:2880-2883 (2009).
Banker et al. Modern Pharmaceutices. 3rd ed. ( pp. 451 & 596) (1996).
Silverman. The Organic Chemistry of Drug Design and Drug Action, published 1992 by Academic Press, pp. 19-21.
U.S. Appl. No. 15/777,499 Office Action dated Mar. 20, 2019.
West. Solid State Chemistry and its Applications. Wiley, New York. pp. 358 & 365 (1988).
Wolff. Burger's Medicinal Chemistry and Drug Discovery. 5th Ed. Part 1, pp. 975-977 (1995).
JP2017-513597 Office Action dated May 15, 2019 (w/English translation).

* cited by examiner

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term decanoyl
<220> FEATURE:
<221> NAME/KEY: MOD_RES
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: MOD_RES
<222> LOCATION: (10)..(10)
<223> OTHER INFORMATION: Fluorescence donor 2-aminobenzamide lysine

<400> SEQUENCE: 1

Leu Ser Ser Pro Ala Tyr Ala Ala Asp Lys Pro Asp
1               5                   10

<210> SEQ ID NO 2
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term decanoyl
<220> FEATURE:
<221> NAME/KEY: MOD_RES
<222> LOCATION: (6)..(6)
<223> OTHER INFORMATION: Fluorescence acceptor 3-nitrotyrosine
<220> FEATURE:
<221> NAME/KEY: MISC_FEATURE
<222> LOCATION: (7)..(8)
<223> OTHER INFORMATION: Cleavage site between residues 7 and 8
<220> FEATURE:
<221> NAME/KEY: MOD_RES
<222> LOCATION: (11)..(11)
<223> OTHER INFORMATION: Fluorescence donor 2-aminobenzamide lysine

<400> SEQUENCE: 2

Leu Thr Pro Thr Ala Tyr Ala Ala Ser Lys Lys Asp Asp
1               5                   10
```

BROAD SPECTRUM ANTIBIOTICS

CROSS REFERENCE

This application is a continuation of U.S. patent application Ser. No. 14/123,024, filed Mar. 21, 2014; which is a U.S. National Stage Entry of PCT/US2012/039727, filed May 25, 2012; which claims the benefit of priority from U.S. Provisional Application No. 61/491,149, filed May 27, 2011, all of which are herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 26, 2019, is named 40681-862-301SEQ2.txt and is 1,473 bytes in size.

SEQUENCE IDENTIFIERS NEEDED PER NOTICE

Background of the Invention

The arylomycin class of natural product, which includes the arylomycin A and B series, was initially discovered by the group of Hans-Peter Frielder, and described in a 2002 publication in the Journal of Antibiotics (J. Schimana, et al., J. Antibiotics (2002), 55(6), 565-570 and 571-577). The arylomycins, as characterized in this publication, comprise a unique structural class of natural product composed of a hexapeptide with a unique biaryl bridge between N-methyl-4-hydroxyphenylglycine5 (MeHpg5) and tyrosine7, and N-terminal acyl tails of various lengths.

SUMMARY OF THE INVENTION

Described herein are analogs of the natural product arylomycin for the treatment of microbial infections, such as for the treatment of bacterial infections. In various embodiments, the present disclosure provides classes and subclasses of chemical compounds structurally related to arylomycin for the treatment of bacterial infections. In various embodiments, the bacterial infections are resistant to treatment with the natural product arylomycin, but are susceptible to treatment with an arylomycin analog described herein.

In one aspect described herein are compounds of Formula (I):

wherein:

$E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;

$L^2$ is a bond, or optionally substituted $(C_1-C_6)$alkylene;

X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$ alkyl; and $R^{20b}$ is H or optionally substituted alkyl; or X is a group of formula

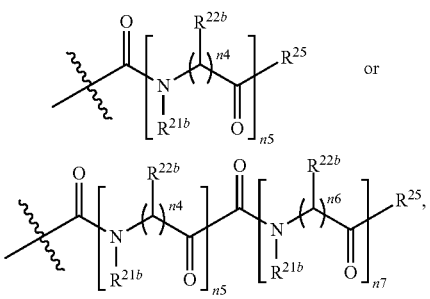

wherein n4, n5, and n6 are each independently 1, 2 or 3; n7 is 0, 1 or 2;

$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$, Formula (I)

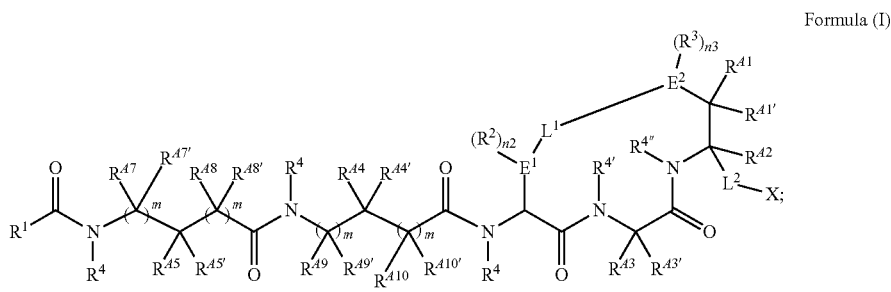

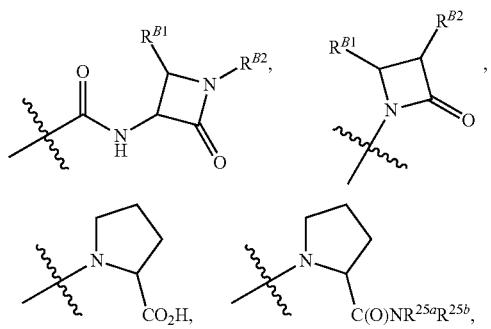

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (I) bearing X; or X is selected from

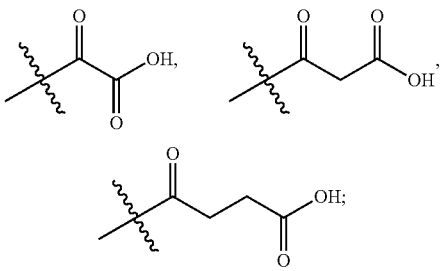

R$^1$ comprises a group of formula (IIA), (IIB), (IIC), (IID), (IIE), or (IIF)

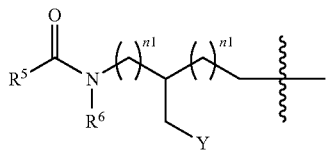 (IIA)

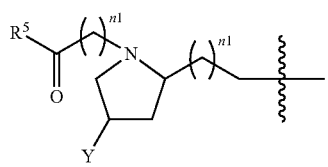 (IIB)

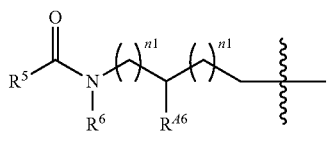 (IIC)

(IID)

(IIE)

(IIF)

wherein n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$) alkyl; R$^{A6}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, (C$_1$-C$_6$)alkoxy, (C$_1$-C$_6$)alkyl, (C$_3$-C$_7$)cycloalkyl, (C$_1$-C$_6$)-mono- or di-alkylamino, (C$_1$-C$_6$)alkoxycarbonyl, (C$_1$-C$_6$)alkylhydroxycarbonyl, (C$_1$-C$_6$)alkylaminocarbonyl, (C$_1$-C$_6$)alkylsulfonylamino, and (C$_6$-C$_{10}$)-arylsulfonylamino; and a wavy line indicates a point of attachment of R$^1$ to an atom of formula (I) bearing R$^1$;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

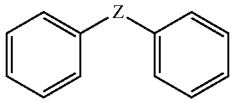

wherein Z is a bond, O, S, NH, CH$_2$ or C≡C;

R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (I) wherein R$^2$ or R$^3$ respectively is hydroxy, wherein any carbon atom is optionally substituted with J; or wherein two R$^2$ groups taken together, and/or two R$^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

R⁴, R⁴', R⁴" and R⁶ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; optionally fused to an aryl or heteroaryl, $(C_3-C_{10})$cycloalkyl or mono- or bicyclic 3-10 membered heterocyclyl; or a pharmaceutically acceptable salt, solvate, or prodrug thereof.

In another aspect described herein are compounds of Formula (II):

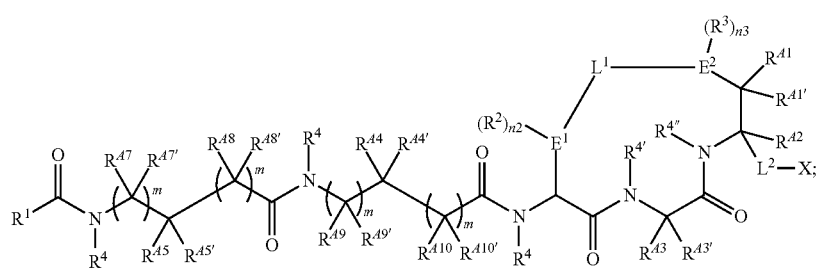

Formula (II)

$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH-C(O)R'$, $(CH_2)_{0-p}N(R')(R'))C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;

wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)alkyl$, $C_1-C_6$alkyl, $C_3-C_5$cycloalkyl, or $C_1-C_6$heteroalkyl; or, when two R' are bound to a nitrogen atom or to two adjacent nitrogen atoms, the two R' groups together with the nitrogen atom or atoms to which they are bound form a 3- to 8-membered monocyclic heterocyclic ring, or an 8- to 20-membered, bicyclic or tricyclic, heterocyclic ring system, wherein any ring or ring system further contains 1-3 additional heteroatoms selected from the group consisting of N, NR', O, S, S(O) and $S(O)_2$, wherein each ring is substituted with 0-3 substituents selected independently from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)alkyl$, $C_1-C_6$alkyl, $C_3-C_5$cycloalkyl, or $C_1-C_6$heteroalkyl; wherein, in any bicyclic or tricyclic ring system, each ring is linearly fused, bridged, or spirocyclic, wherein each ring is either aromatic or nonaromatic, wherein each ring is wherein:

$E^1$ and $E^2$ are each independently $(C_1-C_6)$alkyl, $(C_2-C_7)$ alkenyl, $(C_2-C_7)$alkynyl, $(C_3-C_7)$cycloalkyl, heterocyclyl, heteroaryl, or aryl;

$L^1$ is —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —$C(O)NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;

$L^2$ is a bond, or optionally substituted $(C_1-C_6)$alkylene;

X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$alkyl; and $R^{20b}$ is H or optionally substituted alkyl; or X is a group of formula

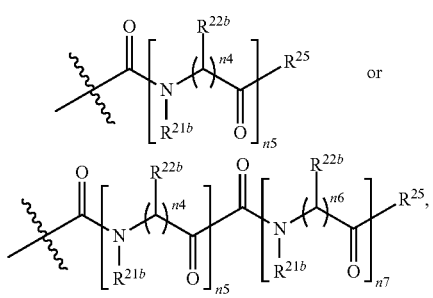

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

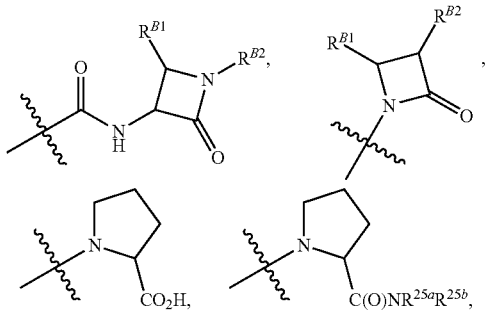

or NR²⁵ᵃR²⁵ᵇ where R²⁵ᵃ and R²⁵ᵇ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (II) bearing X; or
X is CO$_2$H, CH$_2$CO$_2$H, C(=O)NHCH$_2$C(=O)H, CH$_2$C (=O)H, C(=O)NHCH$_2$B(OR$^B$)$_2$ or C(=O)NHCH$_2$P(=O) (OR$^B$)$_2$ wherein R$^B$ is H or (C$_1$-C$_6$)alkyl, or
X is a group of formula

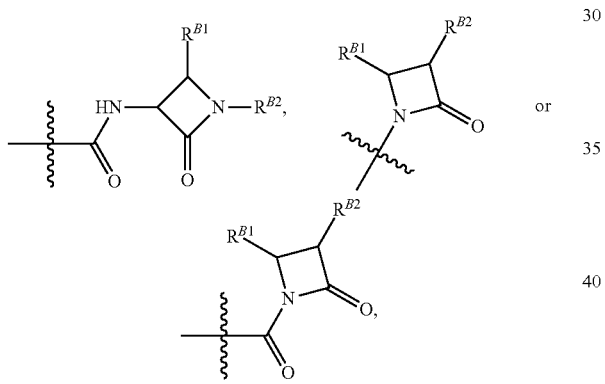

wherein R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O) N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, NR$^C{}_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (II) bearing X; or X is selected from

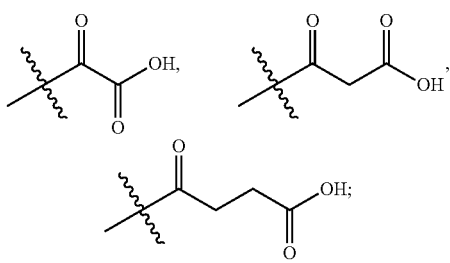

R$^1$ comprises a group of formula (IIA), (IIB), (IIC), (IID), (IIE), or (IIF)

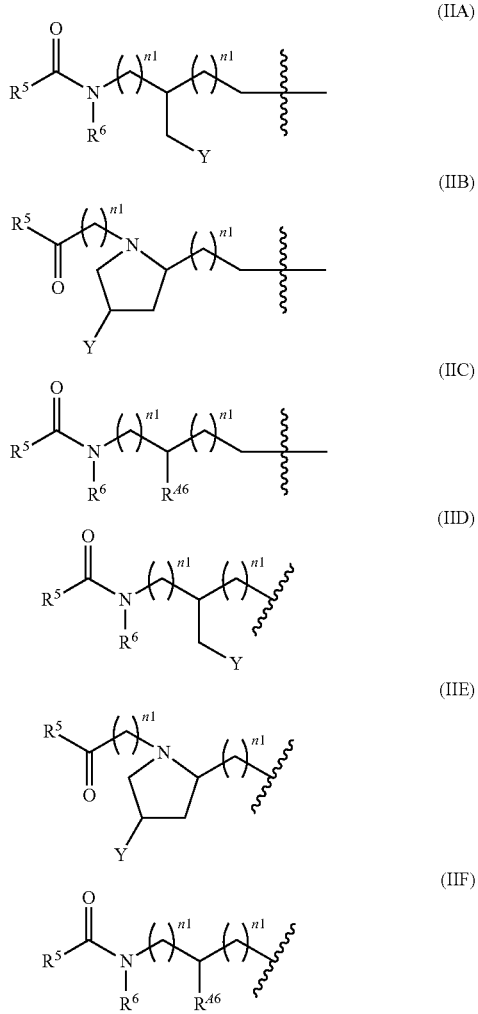

wherein n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$) alkyl; R$^{A6}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, (C$_1$-C$_6$)alkoxy, (C$_1$-C$_6$)alkyl, (C$_3$-C$_7$)cycloalkyl, (C$_1$-C$_6$)-mono- or di-alkylamino, (C$_1$-C$_6$)alkoxycarbonyl, (C$_1$-C$_6$)alkylhydroxycarbonyl, (C$_1$-C$_6$)alkylaminocarbonyl, (C$_1$-C$_6$)alkylsulfonylamino, and (C$_6$-C$_{10}$)-arylsulfonylamino; and a wavy line indicates a point of attachment of R$^1$ to an atom of formula (II) bearing R$^1$;
R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

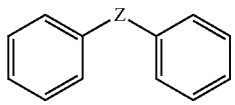

wherein Z is a bond, O, S, NH, CH$_2$ or C≡C;

R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (II) wherein R$^2$ or R$^3$ respectively is hydroxy, wherein any carbon atom is optionally substituted with J; or wherein two R$^2$ groups taken together, and/or two R$^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

R$^4$, R$^{4'}$, R$^{4''}$ and R$^6$ are each independently at every occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

—CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;

or, when two R' are bound to a nitrogen atom or to two adjacent nitrogen atoms, the two R' groups together with the nitrogen atom or atoms to which they are bound optionally form a 3- to 8-membered monocyclic heterocyclic ring, or an 8- to 20-membered, bicyclic or tricyclic, heterocyclic ring system, wherein any ring or ring system optionally further contain 1-3 additional heteroatoms selected from the group consisting of N, NR', O, S, S(O) and S(O)$_2$, wherein each ring is substituted with 0-3 substituents selected independently from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl; wherein, in any bicyclic or tricyclic ring system, each ring is linearly fused, bridged, or spirocyclic, wherein each ring is either aromatic or nonaromatic, wherein each ring is optionally fused to a (C$_6$-C$_{10}$)aryl, mono- or bicyclic 5-10 membered heteroaryl, (C$_3$-C$_{10}$)cycloalkyl or mono- or bicyclic 3-10 membered heterocyclyl; or a pharmaceutically acceptable salt, solvate, or prodrug thereof.

In another aspect described herein are compounds of Formula (III):

Formula (III)

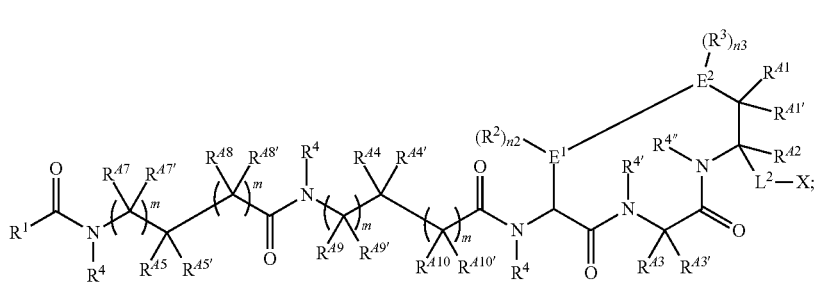

R$^{A1}$, R$^{A1'}$, R$^{A2}$, R$^{A3}$, R$^{A3'}$, R$^{A4}$, R$^{A4'}$, R$^{A5}$, R$^{A5'}$, R$^{A7}$, R$^{A7'}$, R$^{A8}$, R$^{A8'}$, R$^{A9}$, R$^{A9'}$, R$^{A10}$, and R$^{A10'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;

J is halogen, R', OR', CN, CF$_3$, OCF$_3$, C(O), S(O), methylenedioxy, ethylenedioxy, (CH$_2$)$_{0-p}$N(R')$_2$, (CH$_2$)$_{0-p}$SR', (CH$_2$)$_{0-p}$S(O)R', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O)CH$_2$C(O)R', (CH$_2$)$_{0-p}$C(S)R', (CH$_2$)$_{0-p}$ C(O)OR', (CH$_2$)$_{0-p}$OC(O)R', (CH$_2$)$_{0-p}$C(O)N(R')$_2$, (CH$_2$)$_{0-p}$OC(O)N(R')$_2$, (CH$_2$)$_{0-p}$C(S)N(R')$_2$, (CH$_2$)$_{0-p}$NH—C(O)R', (CH$_2$)$_{0-p}$N(R')(R'))$_C$(O)R', (CH$_2$)$_{0-p}$N(R')N(R')C(O)OR', (CH$_2$)$_{0-p}$N(R')N(R')CON(R')$_2$, (CH$_2$)$_{0-p}$N(R')SO$_2$R', (CH$_2$)$_{0-p}$N(R')SO$_2$N(R')$_2$, (CH$_2$)$_{0-p}$N(R')C(O)OR', (CH$_2$)$_{0-p}$N(R')C(O)R', (CH$_2$)$_{0-p}$N(R')C(S)R', (CH$_2$)$_{0-p}$N(R')C(O)N(R')$_2$, (CH$_2$)$_{0-p}$N(R')C(S)N(R')$_2$, (CH$_2$)$_{0-p}$N(COR')COR', (CH$_2$)$_{0-p}$N(OR')R', (CH$_2$)$_{0-p}$C(=NH)N(R')$_2$, (CH$_2$)$_{0-p}$C(O)N(OR')R', or (CH$_2$)$_{0-p}$C(=NOR')R'; wherein p is 4, each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, wherein:

E$^1$ and E$^2$ are each independently (C$_1$-C$_6$)alkyl, (C$_2$-C$_7$) alkenyl, (C$_2$-C$_7$)alkynyl, (C$_3$-C$_7$)cycloalkyl, heterocyclyl, 5-membered heteroaryl, or bicyclic heteroaryl;

L$^2$ is a bond, or optionally substituted (C$_1$-C$_6$)alkylene;

X is C(O)R$^{20}$, S(O)$_2$R$^{20}$, or C(O)NR$^{21a}$C(R$^{22a}$)(R$^{23a}$)B (OR$^{24}$)$_2$ wherein R$^{21a}$, R$^{22a}$, R$^{23a}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, where at least one of R$^{21a}$, R$^{22a}$, R$^{23a}$ is not hydrogen, wherein any alkyl, cycloalkyl, heterocyclyl, aryl or heteroaryl is optionally substituted with 1 to 3 J; R$^{24}$ is H or (C$_1$-C$_6$)alkyl; and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$(C$_1$-C$_6$) alkyl; and R$^{20b}$ is H or optionally substituted alkyl; or X is a group of formula

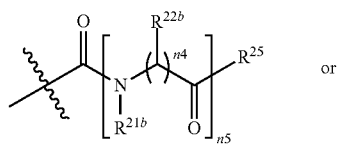

or

-continued

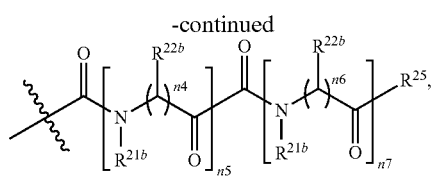

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
$R^{25}$ is H, OH, $OR^C$,

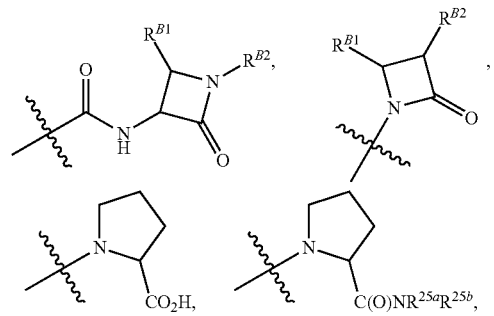

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (III) bearing X; or
X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or
X is a group of formula

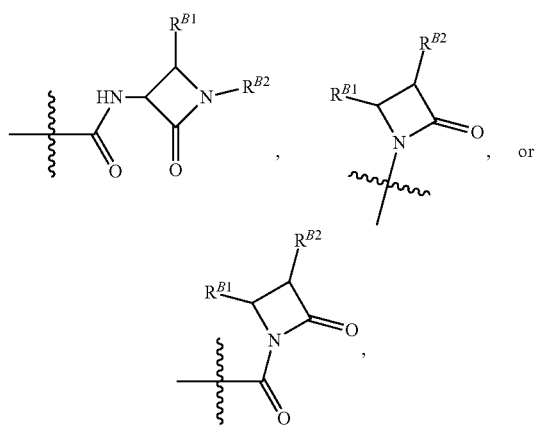

wherein $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)$ $N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (III) bearing X; or X is selected from

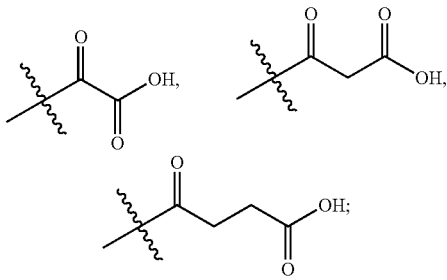

$R^1$ comprises a group of formula (IIA), (IIB), (IIC), (IID), (IIE), or (IIF)

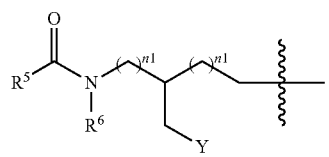
(IIA)

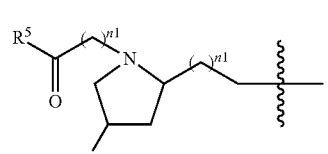
(IIB)

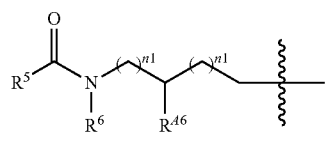
(IIC)

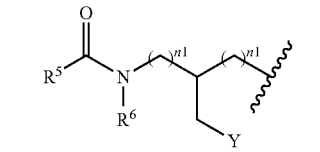
(IID)

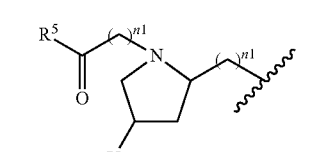
(IIE)

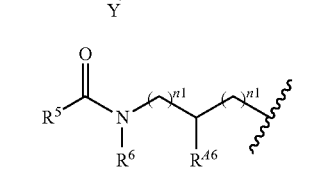
(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (III) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus, any of the following groups: optionally substituted aryl, optionally substituted heteroaryl, or optionally substituted

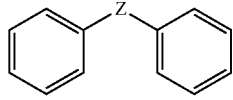

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (III) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH-C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;

wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)$alkyl, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally form a 3- to 8-membered monocyclic heterocyclic ring, or an 8- to 20-membered, bicyclic or tricyclic, heterocyclic ring system, wherein any ring or ring system optionally further contains 1-3 additional heteroatoms selected from the group consisting of N, NR', O, S, S(O) and $S(O)_2$, wherein each ring is substituted with 0-3 substituents selected independently from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)$alkyl, $C_1-C_6$alkyl, $C_3-C_5$cycloalkyl, or $C_1-C_6$heteroalkyl; wherein, in any bicyclic or tricyclic ring system, each ring is linearly fused, bridged, or spirocyclic, wherein each ring is either aromatic or nonaromatic, wherein each ring optionally is fused to a $(C_6-C_{10})$aryl, mono- or bicyclic 5-10 membered heteroaryl, $(C_3-C_{10})$cycloalkyl or mono- or bicyclic 3-10 membered heterocyclyl; or a pharmaceutically acceptable salt, solvate or prodrug thereof.

In another aspect described herein are compounds of Formula (IV):

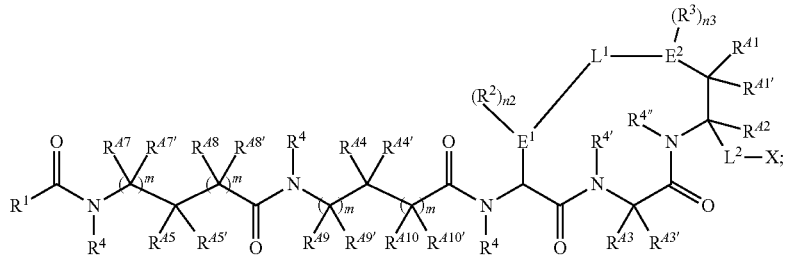

Formula (IV)

$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

wherein:

$E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)

—NR$^4$—, —NR$^4$S(O)$_2$—, —S(O)$_2$NR$^4$—, —NR$^4$C(O) NR$^4$—, —NR$^4$C(O)O—, —OC(O)NR$^4$—, or (C$_1$-C$_4$)alkylene optionally substituted with OH, CN, NO$_2$, halogen, (C$_1$-C$_6$)alkyl;

L$^2$ is a bond, or optionally substituted (C$_1$-C$_6$)alkylene;
X is C(O)R$^{20}$, S(O)$_2$R$^{20}$, or C(O)NR$^{21a}$C(R$^{22a}$)(R$^{23a}$)B(OR$^{24}$)$_2$ wherein R$^{21a}$, R$^{22a}$, R$^{23a}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, where at least one of R$^{21a}$, R$^{22a}$, R$^{23a}$ is not hydrogen, wherein any alkyl, cycloalkyl, heterocyclyl, aryl or heteroaryl is optionally substituted with 1 to 3 J; R$^{24}$ is H or (C$_1$-C$_6$)alkyl; and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$(C$_1$-C$_6$) alkyl; and R$^{20b}$ is H or optionally substituted alkyl; or
X is a group of formula

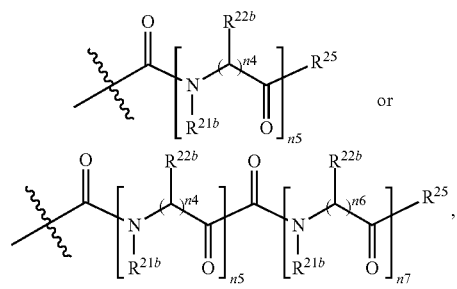

wherein n4, n5, and n6 are each independently 1, 2 or 3; n7 is 0, 1 or 2; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
R$^{25}$ is H, OH, OR$^C$,

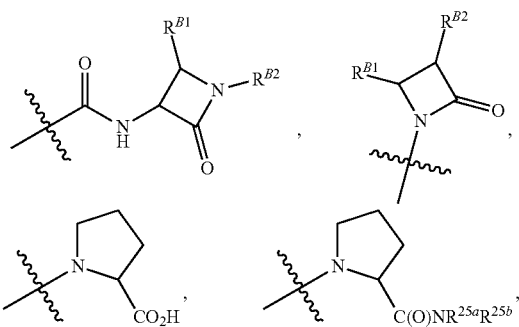

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (IV) bearing X; or
X is CO$_2$H, CH$_2$CO$_2$H, C(=O)NHCH$_2$C(=O)H, CH$_2$C(=O)H, C(=O)NHCH$_2$B(OR$^B$)$_2$ or C(=O)NHCH$_2$P(=O)(OR$^B$)$_2$ wherein R$^B$ is H or (C$_1$-C$_6$)alkyl, or X is a group of formula

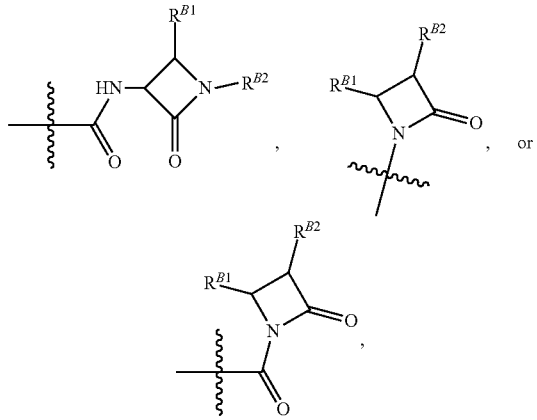

wherein R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, NR$^C_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (IV) bearing X; or X is selected from

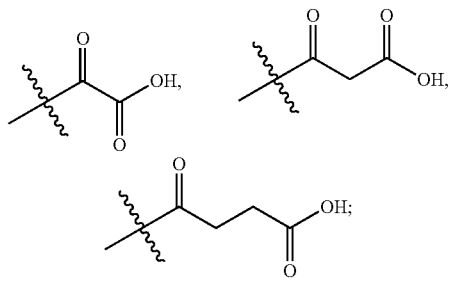

R$^1$ comprises a group of formula (IIA), (IIB), (IIC), (IID), (IIE), or (IIF)

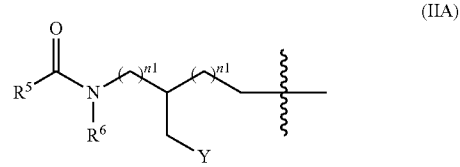
(IIA)

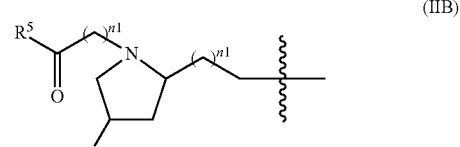
(IIB)

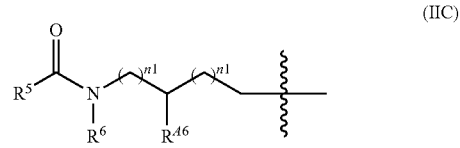
(IIC)

-continued

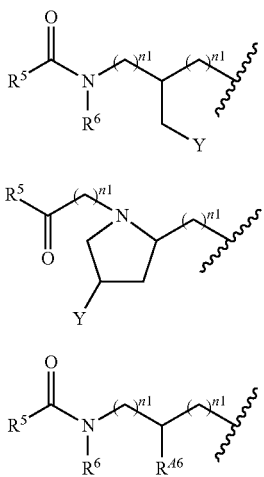

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IV) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

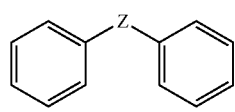

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (IV) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein at least one of $R^{4'}$ and $R^{4''}$ is not hydrogen, wherein any alkyl, cycloalkyl, heterocyclyl, aryl or heteroaryl is optionally substituted with 1 to 3 J;

$R^{41}$, $R^{41'}$, $R^{42}$, $R^{43}$, $R^{43'}$, $R^{44}$, $R^{44'}$, $R^{45}$, $R^{45'}$, $R^{47}$, $R^{47'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with a substituent selected from F, Cl, Br, I, —CN, —NO_2, —OH, —CF_3, —OCF_3, —OCH_3, —NH_2, —N((C_1-C_4)alkyl)_2-, —NH(C_1-C_4)alkyl, $C_1-C_6$alkyl, $C_3-C_5$cycloalkyl, or $C_1-C_6$heteroalkyl; J is halogen, R', OR', CN, CF_3, OCF_3, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;

wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO_2, —OH, —CF_3, —OCF_3, —OCH_3, —NH_2, —N((C_1-C_4)alkyl)_2-, —NH(C_1-C_4)alkyl, $C_1-C_6$alkyl, $C_3-C_8$cycloalkyl, or $C_1-C_6$heteroalkyl;

or, when two R' are bound to a nitrogen atom or to two adjacent nitrogen atoms, the two R' groups together with the nitrogen atom or atoms to which they are bound form a 3- to 8-membered monocyclic heterocyclic ring, or an 8- to 20-membered, bicyclic or tricyclic, heterocyclic ring system, wherein any ring or ring system further contains 1-3 additional heteroatoms selected from the group consisting of N, NR', O, S, S(O) and S(O)_2, wherein each ring is substituted with 0-3 substituents selected independently from F, Cl, Br, I, —CN, —NO_2, —OH, —CF_3, —OCF_3, —OCH_3, —NH_2, —N((C_1-C_4)alkyl)_2-, —NH(C_1-C_4)alkyl, $C_1-C_6$alkyl, $C_3-C_5$cycloalkyl, or $C_1-C_6$heteroalkyl;

wherein, in any bicyclic or tricyclic ring system, each ring is linearly fused, bridged, or spirocyclic, wherein each ring is either aromatic or nonaromatic, wherein each ring is optionally fused to a $(C_6-C_{10})$aryl, mono- or bicyclic 5-10 membered heteroaryl, $(C_3-C_{10})$cycloalkyl or mono- or bicyclic 3-10 membered heterocyclyl; or a pharmaceutically acceptable salt, solvate, or prodrug thereof.

In another aspect described herein are compounds of Formula (V):

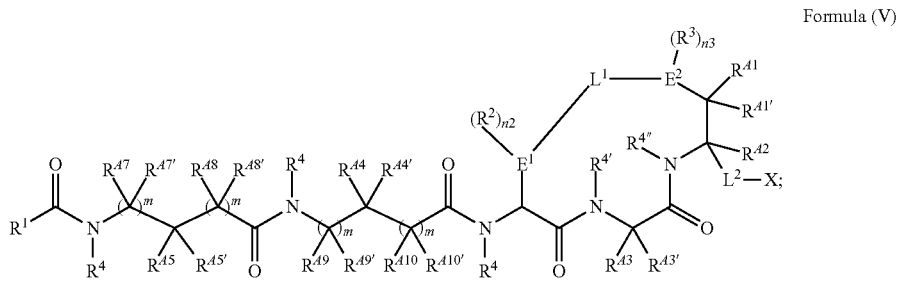

Formula (V)

wherein:

$E^1$ and $E^2$ are each independently aryl;

$L^1$ is a bond;

$L^2$ is a bond;

X is $C(O)R^{20}$, and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1\text{-}C_6)$ alkyl; and $R^{20b}$ is H or optionally substituted alkyl; or X is a group of formula

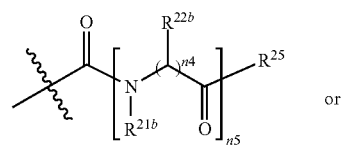

or

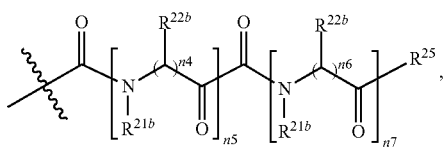

wherein n4, n5, and n6 are each independently 1, 2 or 3; n7 is 0, 1 or 2; $R^{21b}$ and $R^{22b}$ are independently at each occurrence hydrogen, hydroxy, $(C_1\text{-}C_6)$alkyl, wherein any alkyl is optionally substituted with 1 to 3 J; $R^{25}$ is H, OH, $OR^C$,

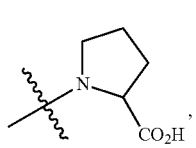 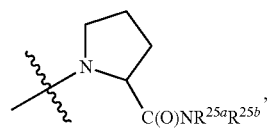

or $NR^{25a}R^{25b}$; where $R^{25a}$ and $R^{25b}$ are each independently H, $SO_2(C_1\text{-}C_6)$alkyl, or optionally substituted alkyl; $R^C$ is independently at each occurrence H or $(C_1\text{-}C_6)$ alkyl, and a wavy line indicates a point of attachment of X to a carbon of formula (V) bearing X; or X is $CO_2H$, $CH_2CO_2H$, $C(=O)NHCH_2C(=O)H$, or $CH_2C(=O)H$, or X is a group of formula

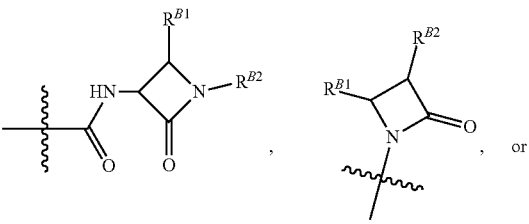

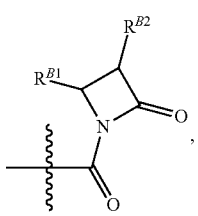

wherein $R^{B1}$ and $R^{B2}$ are each independently H, $(C_1\text{-}C_6)$ alkyl, $(C_3\text{-}C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1\text{-}C_6)$alkoxy, $(C_1\text{-}C_6)$thioalkoxy, $NR^C_2$, 5-7 membered heterocyclyl or 5-7 membered heteroaryl, or $(C_6\text{-}C_{10})$ aryl; $R^C$ is independently at each occurrence H or $(C_1\text{-}C_6)$ alkyl, and a wavy line indicates a point of attachment of X to a carbon of formula (V) bearing X; or X is selected from

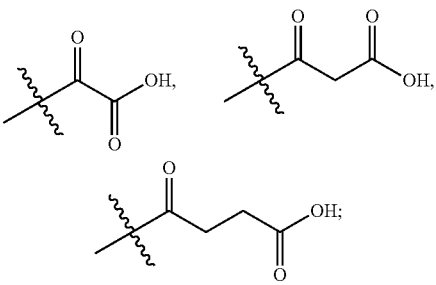

$R^1$ comprises a group of formula (IID), (IIE), or (IIF)

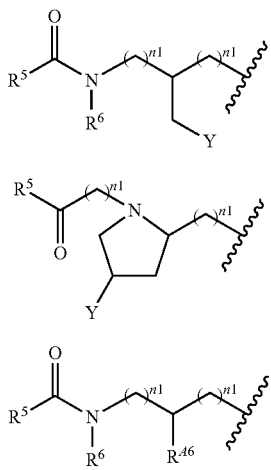

wherein n1 is independently at each occurrence 0, 1, or 2; Y is $(CH_2)_{0-2}H$, or $(CH_2)_{0-2}OH$; $R^{46}$ is hydrogen, or $(C_1-C_6)$ alkyl, wherein alkyl is optionally substituted with 1 to 3 substituents, wherein each substituent is independently selected from the group consisting of halogen, amino, hydroxyl, aminocarbonyl, hydroxycarbonyl, 5- to 7-membered heterocyclyl, $(C_1-C_6)$alkoxy, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (V) bearing $R^1$;

$R^5$ is aryl, heteroaryl, or a linear or branched alkyl chain of about 1-22 carbon atoms, wherein $R^5$ is bonded to the carbonyl carbon to which it is attached directly or by $NR^4$, to provide an amide, or urea linkage, respectively; optionally comprising within the chain or at a chain terminus optionally substituted aryl, optionally substituted heteroaryl, or optionally substituted

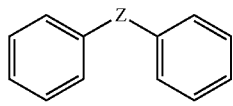

wherein Z is a bond, O, S, NH, $CH_2$ or C≡C; $R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (V) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;
each m is independently 0, 1, or 2;
$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heterocyclyl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH-C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)$alkyl, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring; or a pharmaceutically acceptable salt, solvate, or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

Figure 1A:
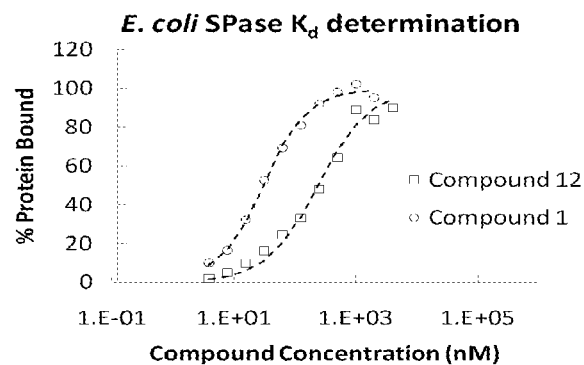
FIG. 1A shows *E. coli* SPase Kd data of compounds disclosed herein.
Figure 1B:
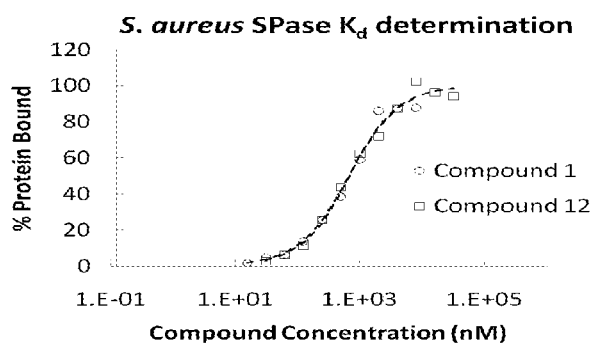
FIG. 1B shows *S. aureus* SPase Kd data of compounds disclosed herein.
Figure 1C:
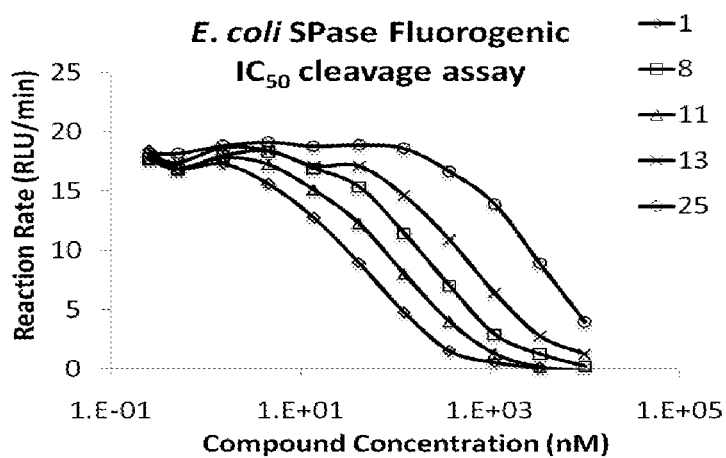
FIG. 1C shows *E. coli* SPase Fluorogenic IC50 cleavage assay of compounds disclosed herein.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats.

Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound described herein that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds described herein are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R'' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. A description herein that a group is alkyl chain "optionally comprising within the chain or at a chain terminus" a moiety, the term signifies that the moiety can be disposed between two subunits of the alkyl chain, or can be disposed at an unsubstituted end of the chain, or can be disposed between the chain and a point of attachment of the chain, for example to a carbonyl, NR, or O group. For example, an alkylbenzoyl group is an alkyl chain with a phenyl group disposed between the alkyl and a carbonyl, fitting the above description; an N-alkylphenyl-carboxamido is an alkyl chain with a phenyl group disposed between the alkyl and the aminocarbonyl group, filling within the above description.

The term "alkylene" means a linear saturated divalent hydrocarbon radical of one to six carbon atoms or a branched saturated divalent hydrocarbon radical of one to six carbon atoms unless otherwise stated, such as methylene, ethylene, propylene, 1-methylpropylene, 2-methylpropylene, butylene, pentylene, and the like.

The term "carbonyl" means C=O.

The terms "carboxy" and "hydroxycarbonyl" mean COOH.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C (CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S (=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "thioalkoxy" refers to an alkyl group previously defined attached to the parent molecular moiety through a sulfur atom.

The term "glycosyloxyoxy" refers to a glycoside attached to the parent molecular moiety through an oxygen atom.

The term "alkoxycarbonyl" represents as ester group; i.e. an alkoxy group, attached to the parent molecular moiety through a carbonyl group such as methoxycarbonyl, ethoxycarbonyl, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1-C_6)$ perfluoroalkyl, more preferred is —$(C_1-C_3)$perfluoroalkyl, most preferred is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkylene, more preferred is —$(C_1-C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_{4+}$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., $-C(O)NR_2$, and $-NRC(O)R$ groups, respectively. Amide groups therefore include but are not limited to primary carboxamide groups ($-C(O)NH_2$) and formamide groups ($-NHC(O)H$). A "carboxamido" or "aminocarbonyl" group is a group of the formula $C(O)NR_2$, wherein R can be H, alkyl, aryl, etc.

The term "azido" refers to an $N_3$ group. An "azide" can be an organic azide or can be a salt of the azide ($N_3-$) anion. The term "nitro" refers to an $NO_2$ group bonded to an organic moiety. The term "nitroso" refers to an NO group bonded to an organic moiety.

The term nitrate refers to an $ONO_2$ group bonded to an organic moiety or to a salt of the nitrate ($NO_3-$) anion.

The term "urethane" ("carbamoyl" or "carbamyl") includes N- and O-urethane groups, i.e., $-NRC(O)OR$ and $-OC(O)NR_2$ groups, respectively.

The term "sulfonamide" (or "sulfonamido") includes S- and N-sulfonamide groups, i.e., $-SO_2NR_2$ and $-NRSO_2R$ groups, respectively. Sulfonamide groups therefore include but are not limited to sulfamoyl groups ($-SO_2NH_2$). An organosulfur structure represented by the formula $-S(O)$ (NR)— is understood to refer to a sulfoximine, wherein both the oxygen and the nitrogen atoms are bonded to the sulfur atom, which is also bonded to two carbon atoms.

The term "amidine" or "amidino" includes groups of the formula $-C(NR)NR_2$. Typically, an amidino group is $-C(NH)NH_2$.

The term "guanidine" or "guanidino" includes groups of the formula $-NRC(NR)NR_2$. Typically, a guanidino group is $-NHC(NH)NH_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_{4+}$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds described herein may take the form of salts. The term "salts" embraces addition salts of free acids or free bases which are compounds described herein. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the present disclosure.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methane sulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the present disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other than water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the present disclosure are described in terms of Markush groups, those skilled in the art will recognize that the presently described compounds is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the present disclosure are described in terms of Markush groups, those skilled in the art will recognize that the present disclosure is also thereby described in terms of any combination of individual members or subgroups of members of Markush groups.

Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present disclosure further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds described herein and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds Described Herein

Tautomerism

Within the present disclosure it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the present disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

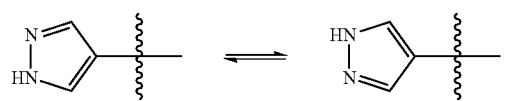 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

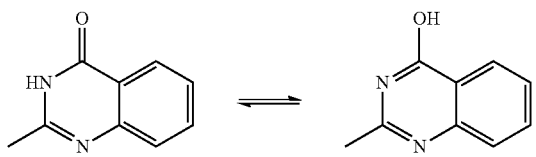

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking.

Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

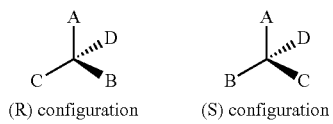

(R) configuration   (S) configuration

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques.

According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of formula (I) which are biologically active in the treatment of cancer or other proliferative disease states.

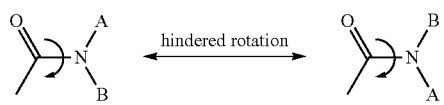

Regioisomerism

In some embodiments, the compounds described herein have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

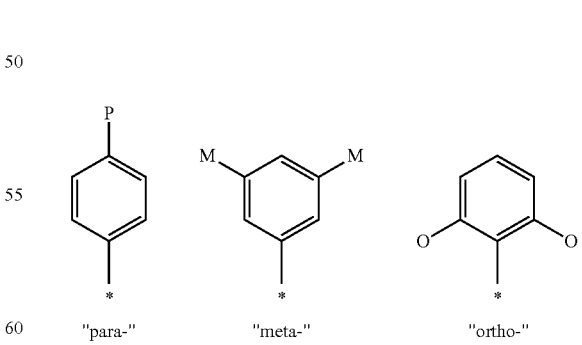

"para-"   "meta-"   "ortho-"

In various embodiments, the compound or set of compounds, such as are among the inventive compounds or are used in the inventive methods, can be any one of any of the combinations and/or sub-combinations of the above-listed embodiments.

EMBODIMENTS

The present disclosure, in various embodiments is directed to analogs of arylomycins A and B. By arylomycins A and B are meant, respectively, the natural products of the following structures:

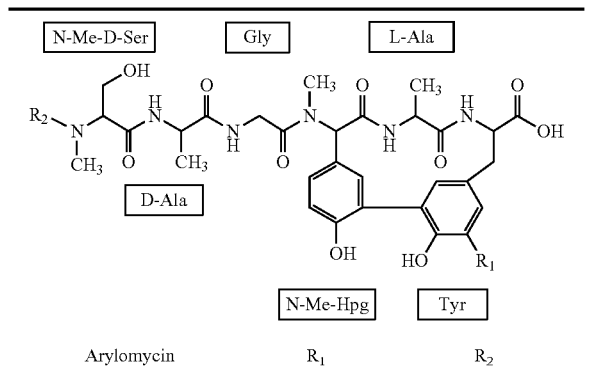

| | | |
|---|---|---|
| A$_1$ | H | iso-C$_{11}$ |
| A$_2$ | H | iso-C$_{12}$ |
| A$_3$ | H | n-C$_{12}$ |
| A$_4$ | H | anteiso-C$_{13}$ |
| A$_5$ | H | iso-C$_{14}$ |
| B$_1$ | NO$_2$ | iso-C$_{11}$ |
| B$_2$ | NO$_2$ | iso-C$_{12}$ |
| B$_3$ | NO$_2$ | n-C$_{12}$ |
| B$_4$ | NO$_2$ | anteiso-C$_{13}$ |
| B$_5$ | NO$_2$ | iso-C$_{13}$ |
| B$_6$ | NO$_2$ | iso-C$_{14}$ |
| B$_7$ | NO$_2$ | anteiso-C$_{15}$ |

The arylomycin A compounds bear a hydrogen atom in the R$_1$ position as defined in the above structure, and the arylomycin B compounds bear a nitro group in that position. The lipid tails, designated as group R$_2$ in the above structure, are n-alkyl, isoalkyl, and anteisoalkyl acyl groups with 11 to 15 total carbon atoms that form an amide bond with the N-Me-D-Ser residue. As used herein, the terms "arylomycins", "arylomycin A", "arylomycin B", "arylomycin A$_x$", "arylomycin natural products" and the like refer to these natural products, unless otherwise specified. The terms "arylomycin analogs", "arylomycin derivatives", and the like, refer to the compounds disclosed herein that do not fit within the herein-defined structural classes of arylomycin A or arylomycin B. Compounds of the present disclosure are distinct from the natural products as specified above.

In various embodiments, the arylomycin analogs described herein, i.e., the novel structures disclosed and claimed herein, exhibit a broader spectrum of antibiotic activity, i.e., against a wider variety of bacterial species, than do the natural products termed arylomycins A and B.

Provided herein are also methods of treating bacterial infections using the compounds described herein, and using arylomycins A and B, such as against bacterial species or strains that would not be expected, based upon ordinary knowledge, to be susceptible to treatment with arylomycins A and B.

In one aspect described herein are compounds of Formula (I):

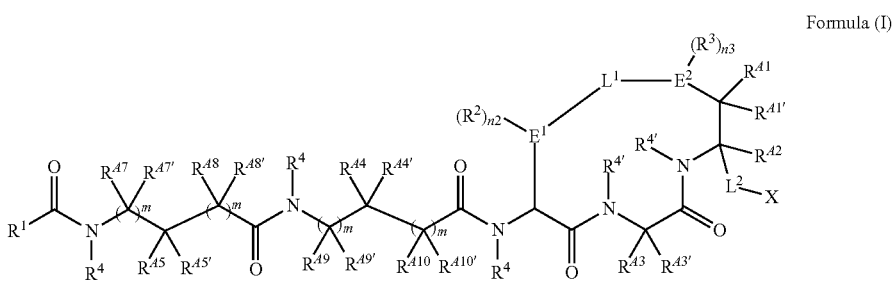

Formula (I)

wherein:

E$^1$ and E$^2$ are each independently (C$_1$-C$_6$)alkyl, (C$_2$-C$_7$)alkenyl, (C$_2$-C$_7$)alkynyl, (C$_3$-C$_7$)cycloalkyl, heterocyclyl, heteroaryl, or aryl;

L$^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or (C$_1$-C$_4$)alkylene optionally substituted with OH, CN, NO$_2$, halogen, (C$_1$-C$_6$)alkyl;

L$^2$ is a bond, or optionally substituted (C$_1$-C$_6$)alkylene;

X is C(O)R$^{20}$, S(O)$_2$R$^{20}$, or C(O)NR$^{21a}$C(R$^{22a}$)(R$^{23a}$)B(OR$^{24}$)$_2$ wherein R$^{21a}$, R$^{22a}$, R$^{23a}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, where at least one of R$^{21a}$, R$^{22a}$, R$^{23a}$ is not hydrogen, wherein any alkyl, cycloalkyl, heterocyclyl, aryl or heteroaryl is optionally substituted with 1 to 3 J; R$^{24}$ is H or (C$_1$-C$_6$)alkyl; and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$(C$_1$-C$_6$)alkyl; and R$^{20b}$ is H or optionally substituted alkyl; or X is a group of formula

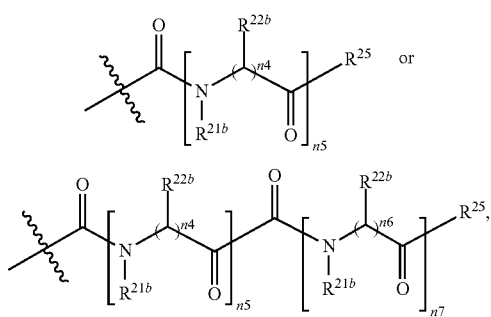

wherein n4, n5, and n6 are each independently 1, 2 or 3; n7 is 0, 1 or 2;

$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

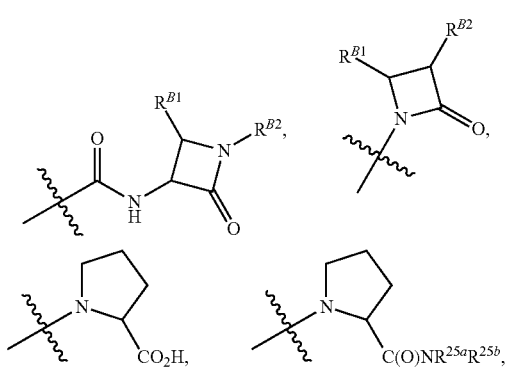

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (I) bearing X; or X is selected from

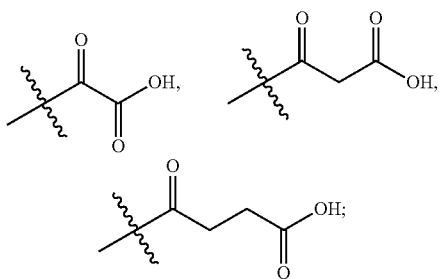

$R^1$ comprises a group of formula (IIA), (IIB), (IIC), (IID), (IIE), or (IIF)

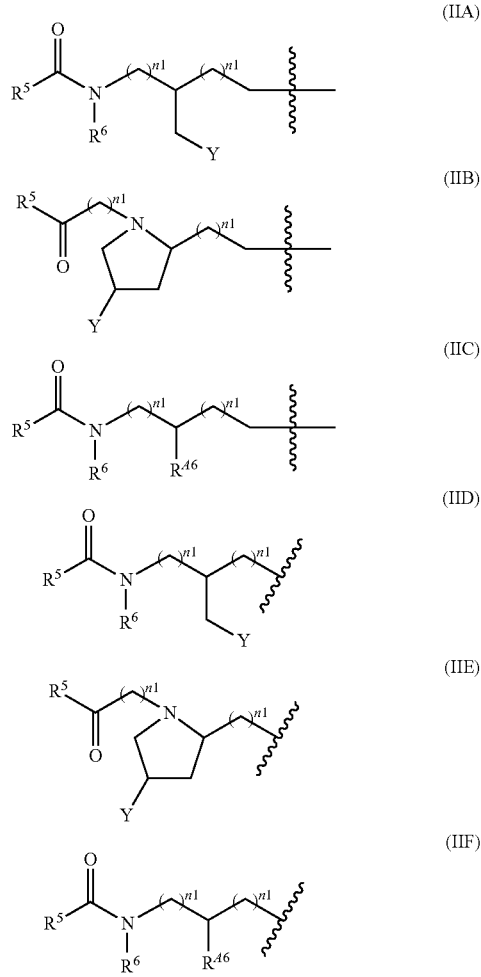

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{A6}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (I) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

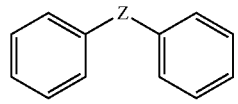

wherein Z is a bond, O, S, NH, CH$_2$ or C≡C;
R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (I) wherein R$^2$ or R$^3$ respectively is hydroxy, wherein any carbon atom is optionally substituted with J; or wherein two R$^2$ groups taken together, and/or two R$^3$ groups taken together, optionally comprise fused cycloalkyl, aryl, heterocyclyl, or heteroaryl ring or rings, any of which is optionally substituted with 1 to 3 J;
n2 and n3 are independently 0, 1, 2, 3 or 4;
each m is independently 0, 1, or 2;
R$^4$, R$^{4'}$, R$^{4''}$ and R$^6$ are each independently at every occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{41}$, R$^{41'}$, R$^{42}$, R$^{43}$, R$^{43'}$, R$^{44}$, R$^{44'}$, R$^{45}$, R A5', R$^{47}$, R$^{47'}$, R$^{48}$, R$^{48'}$, R$^{49}$, R$^{49'}$, R$^{410}$, and R$^{410'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; J is halogen, R', OR', CN, CF$_3$, OCF$_3$, C(O), S(O), methylenedioxy, ethylenedioxy, (CH$_2$)$_{0-p}$N(R')$_2$, (CH$_2$)$_{0-p}$ SR', (CH$_2$)$_{0-p}$S(O)R', (CH$_2$)$_{0-p}$S(O)$_2$R', (CH$_2$)$_{0-p}$S(O)$_2$N(R')$_2$, (CH$_2$)$_{0-p}$SO$_3$R', (CH$_2$)$_{0-p}$C(O)R', (CH$_2$)$_{0-p}$C(O) CH$_2$C(O)R', (CH$_2$)$_{0-p}$C(S)R', (CH$_2$)$_{0-p}$C(O)OR', (CH$_2$)$_{0-p}$ OC(O)R', (CH$_2$)$_{0-p}$C(O)N(R')$_2$, (CH$_2$)$_{0-p}$OC(O)N(R')$_2$, (CH$_2$)$_{0-p}$C(S)N(R')$_2$, (CH$_2$)$_{0-p}$NH—C(O)R', (CH$_2$)$_{0-p}$N(R') N(R')$_c$(O)R', (CH$_2$)$_{0-p}$N(R')N(R')C(O)OR', (CH$_2$)$_{0-p}$N(R')N (R')CON(R')$_2$, (CH$_2$)$_{0-p}$N(R')SO$_2$R', (CH$_2$)$_{0-p}$N(R')SO$_2$N (R')$_2$, (CH$_2$)$_{0-p}$N(R')C(O)OR', (CH$_2$)$_{0-p}$N(R')C(O)R', (CH$_2$)$_{0-p}$N(R')C(S)R', (CH$_2$)$_{0-p}$N(R')C(O)N(R')$_2$, (CH$_2$)$_{0-p}$N (R')C(S)N(R')$_2$, (CH$_2$)$_{0-p}$N(COR')COR', (CH$_2$)$_{0-p}$N(OR')R', (CH$_2$)$_{0-p}$C(=NH)N(R')$_2$, (CH$_2$)$_{0-p}$C(O)N(OR')R', or (CH$_2$)$_{0-p}$C(=NOR')R'; wherein p is 4,
each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;
or, when two R' are bound to a nitrogen atom or to two adjacent nitrogen atoms, the two R' groups together with the nitrogen atom or atoms to which they are bound form a 3- to 8-membered monocyclic heterocyclic ring, or an 8- to 20-membered, bicyclic or tricyclic, heterocyclic ring system, wherein any ring or ring system further contains 1-3 additional heteroatoms selected from the group consisting of N, NR', O, S, S(O) and S(O)$_2$, wherein each ring is substituted with 0-3 substituents selected independently from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;
wherein, in any bicyclic or tricyclic ring system, each ring is linearly fused, bridged, or spirocyclic, wherein each ring is either aromatic or nonaromatic, wherein each ring is optionally fused to an aryl or heteroaryl, (C$_3$-C$_{10}$)cycloalkyl or mono- or bicyclic 3-10 membered heterocyclyl; or a pharmaceutically acceptable salt, solvate, or prodrug thereof.

In one embodiment is a compound of Formula (I) wherein E$^1$ and E$^2$ are each independently (C$_1$-C$_6$)alkyl. In one embodiment, E$^1$ is methylene, ethylene, or propylene. In another embodiment, E$^2$ is methylene, ethylene, or propylene. In a further embodiment is a compound of Formula (I) wherein E$^1$ is (C$_1$-C$_6$)alkyl and L$^1$ is a bond. In another embodiment is a compound of Formula (I) wherein E and E$^2$ are each independently (C$_3$-C$_7$)cycloalkyl. In one embodiment, E$^1$ and E$^2$ are each independently selected from cyclopropyl, cyclobutyl, cyclopentyl, cyclohexyl, and cycloheptyl.

In yet another embodiment is a compound of Formula (I) wherein E and E$^2$ are each independently heteroaryl. In one embodiment, E$^1$ and E$^2$ are each independently selected from thienyl, thianthrenyl, furyl, pyranyl, thiadiazolyl, benzothiadiazolyl, isobenzofuranyl, chromenyl, xanthenyl, phenoxathiinyl, pyrrolyl, imidazolyl, pyrazolyl, isothiazolyl, isoxazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinoxalinyl, quinazolinyl, oxazolyl, cinnolinyl, pteridinyl, 4aH-carbazolyl, carbazolyl, carbolinyl, phenanthridinyl, acridinyl, perimidinyl, phenanthrolinyl, phenazinyl, phenarsazinyl, phenothiazinyl, furazanyl, and phenoxazinyl.

In another embodiment, E$^1$ is pyridyl. In another embodiment, E$^2$ is pyridyl. In a further embodiment, E$^1$ and E$^2$ are optionally substituted with at least one F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl or a combination thereof. In another embodiment, L$^1$ is O. In a further embodiment, L$^1$ is S. In yet another embodiment, L$^1$ is C(O). In yet another embodiment, L$^1$ is a bond.

In another embodiment is a compound of Formula (I) wherein L$^2$ is a bond. In a further embodiment, L$^2$ is methylene, ethylene, n-propylene, iso-propylene, n-butylene, iso-butylene, or tert-butylene.

In one embodiment is a compound of Formula (I) wherein X is selected from

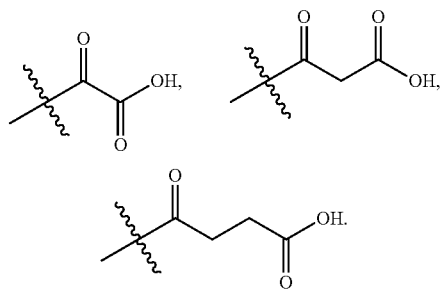

In another embodiment is a compound of Formula (I) wherein X is

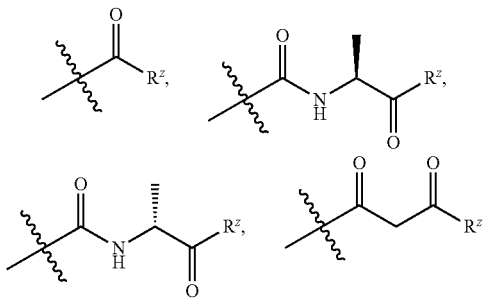

wherein $R^z$ is selected from H, $N(CH_3)_2$, $NHSO_2CH_3$, OH, $NH_2$,

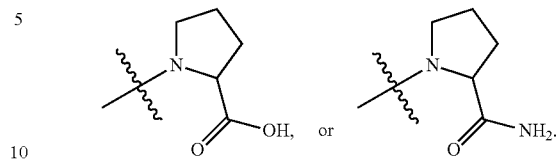

In another embodiment is a compound of Formula (I) wherein $R^4$, $R^{A7}$, $R^{A7'}$, $R^{A5}$, $R^{A5'}$, $R^{A8}$, $R^{A8'}$, $R^{A9}$, $R^{A9'}$, $R^{A4}$, $R^{A4'}$, $R^{A10}$, $R^{A10'}$ are each independently H.

In one embodiment is a compound of Formula (I) having the structure of Formula (IA):

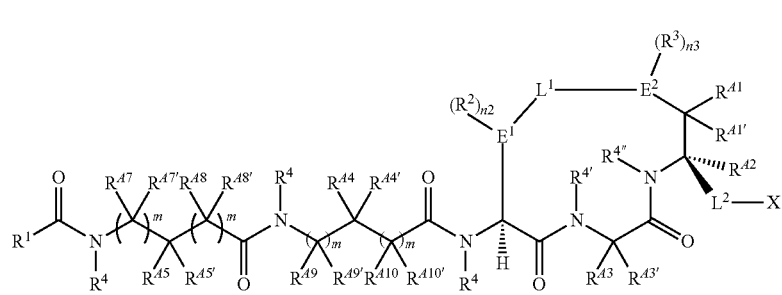

Formula (IA):

wherein $E^1$, $E^2$, $L^1$, $L^2$, X, $R^1$, $R^2$, $R^3$, $R^4$, $R^{4'}$, $R^{4''}$, $R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, $R^{A10'}$, n2, n3, and m are as defined herein, or a pharmaceutically acceptable salt, solvate or prodrug thereof.

In another embodiment is a compound of Formula (IA) having the structure of Formula (IB):

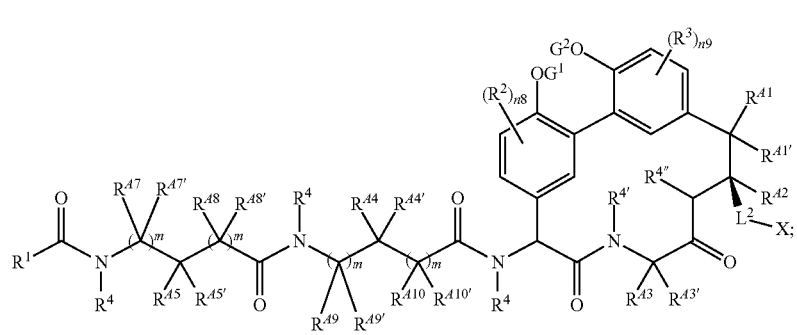

Formula (IB)

wherein n8 and n9 are each independently 0, 1, 2, or 3; $G^1$ and $G^2$ are each independently a hydrogen or a glycosyl residue, or a group cleavable under physiological conditions to provide a compound of Formula (IB) wherein $G^1$ or $G^2$ respectively is hydrogen; or a pharmaceutically acceptable salt, solvate or prodrug thereof.

In another embodiment is a compound having the structure of Formula (IC):

Formula (IC)

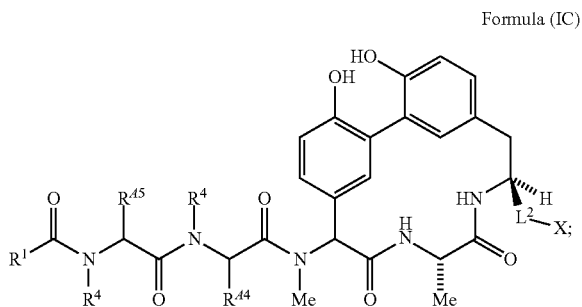

wherein:
L² is a bond;
X is C(O)R²⁰, S(O)₂R²⁰, or C(O)NR²¹ᵃC(R²²ᵃ)(R²³ᵃ)B(OR²⁴)₂ wherein R²¹ᵃ, R²²ᵃ, R²³ᵃ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of R²¹ᵃ, R²²ᵃ, R²³ᵃ is not hydrogen, wherein any alkyl, cycloalkyl, heterocyclyl, aryl or heteroaryl is optionally substituted with 1 to 3 J; R²⁴ is H or $(C_1-C_6)$alkyl; and R²⁰ is optionally substituted alkyl, optionally substituted alkoxy, or NR²⁰ᵃR²⁰ᵇ, where R²⁰ᵃ is H, optionally substituted alkyl, heteroalkyl, or SO₂$(C_1-C_6)$ alkyl; and R²⁰ᵇ is H or optionally substituted alkyl; or X is a group of formula

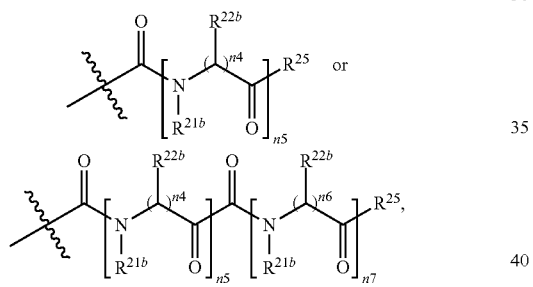

wherein n4, n5, and n6 are each independently 1, 2 or 3; n7 is 0, 1 or 2;
R²¹ᵇ and R²²ᵇ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; R²⁵ is H, OH, OR^C,

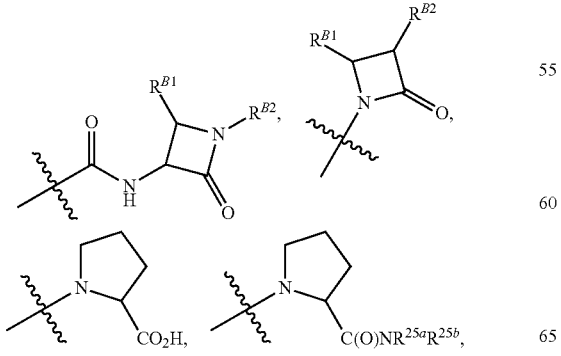

or NR²⁵ᵃR²⁵ᵇ where R²⁵ᵃ and R²⁵ᵇ are each independently H, SO₂$(C_1-C_6)$alkyl, or optionally substituted alkyl; R^{B1} and R^{B2} are each independently H, $(C_1-C_6)$ alkyl, $(C_3-C_6)$ cycloalkyl, OR^C, C(=O)N(R^C)₂, OC(=O)N(R^C)₂, C(=O)OR^C, OC(=O)OR^C, nitro, trifluoromethyl, trifluoromethoxy, $(C_1-C_6)$alkoxy, $(C_1-C_6)$thioalkoxy, N(R^C)₂, 5-7 membered heterocyclyl or 5-7 membered heteroaryl, or $(C_6-C_{10})$ aryl; R^C is independently at each occurrence H or $(C_1-C_6)$ alkyl, and a wavy line indicates a point of attachment of X to a carbon of formula (IC) bearing X; or X is selected from

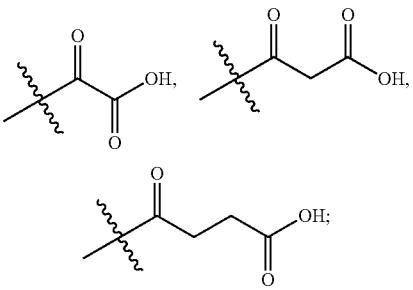

R¹ comprises a group of formula (IIA), (IIB), (IIC), (IID), (IIE), or (IIF)

(IIA)

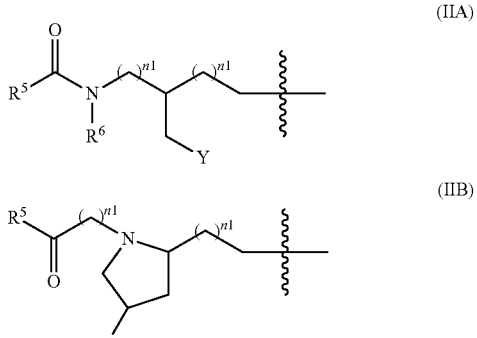

(IIB)

(IIC)

(IID)

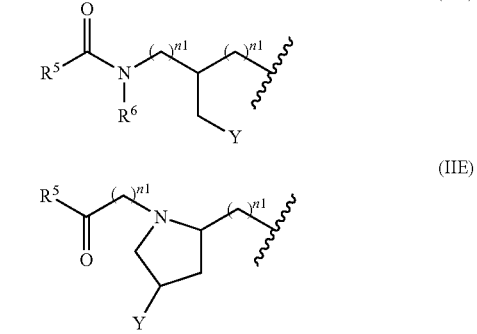

(IIE)

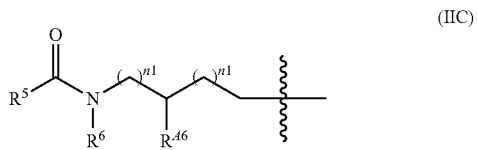

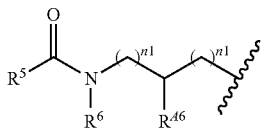

(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IC) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

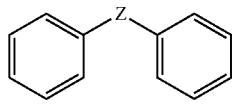

wherein Z is a bond, O, S, NH, $CH_2$ or C≡C;

$R^4$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{44}$ and $R^{45}$ are independently hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH-C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)$alkyl$)_2$-, —NH$(C_1-C_4)$alkyl, $C_1-C_6$alkyl, $C_3-C_8$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In one embodiment is a compound of Formula (IC) wherein X is a group of formula

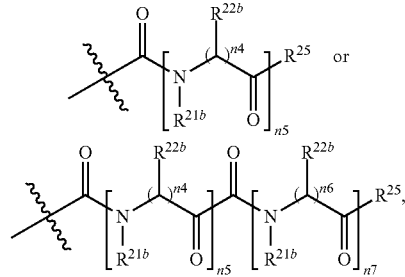

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

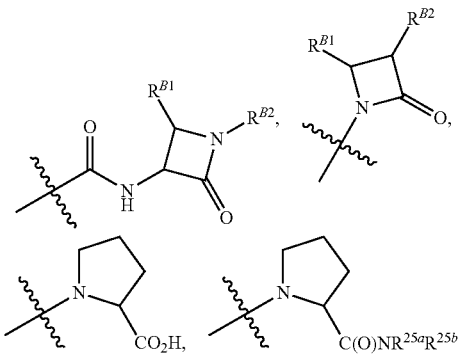

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, C(=O)N$(R^C)_2$, OC(=O)N$(R^C)_2$, C(=O)$OR^C$, OC(=O)$OR^C$, nitro, trifluoromethyl, trifluoromethoxy, $(C_1-C_6)$alkoxy, $(C_1-C_6)$thioalkoxy, N$(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IB) bearing X.

In another embodiment is a compound of Formula (IC) wherein X is a group of formula

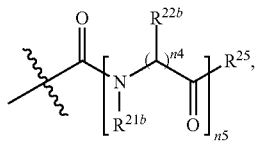

n4 is 1, n5 is 1, $R^{21b}$ is hydrogen, $R^{22b}$ is methyl, and $R^{25}$ is OH.

In another embodiment is a compound of Formula (IC) wherein X is a group of formula

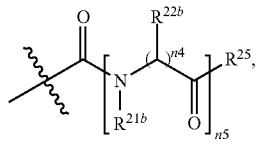

n4 is 1, n5 is 1, $R^{21b}$ is hydrogen, $R^{22b}$ is methyl, and $R^{25}$ is $NH_2$.

In another embodiment is a compound of Formula (IC) wherein X is a group of formula

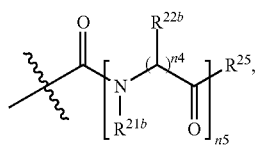

n4 is 1, n5 is 1, $R^{21b}$ is hydrogen, $R^{22b}$ is methyl, and $R^{25}$ is

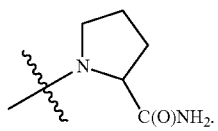

In another embodiment is a compound of Formula (IC) wherein X is a group of formula

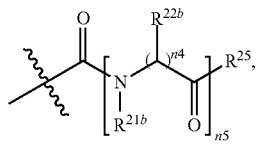

n4 is 1, n5 is 1, $R^{21b}$ is hydrogen, $R^{22b}$ is methyl, and $R^{25}$ is

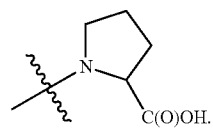

In another embodiment is a compound of Formula (IC) wherein X is a group of formula

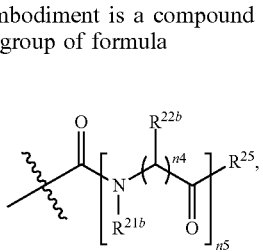

n4 is 1, n5 is 1, $R^{21b}$ is hydrogen, $R^{22b}$ is methyl, and $R^{25}$ is —$NHSO_2Me$.

In another embodiment is a compound of Formula (IC) wherein X is a group of formula

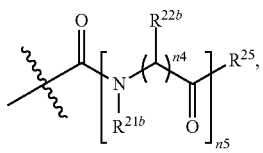

n4 is 1, n5 is 1, $R^{21b}$ is hydrogen, $R^{22b}$ is methyl, and $R^{25}$ is H.

In another embodiment is a compound of Formula (IC) wherein X is a group of formula

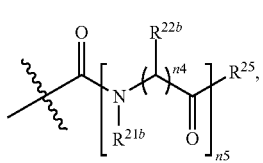

n4 is 1, n5 is 1, $R^{21b}$ is hydrogen, $R^{22b}$ is hydrogen, and $R^{25}$ is OH.

In another embodiment is a compound of Formula (IC) wherein X is a group of formula

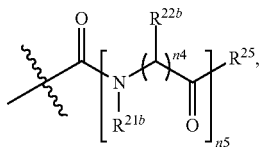

n4 is 1, n5 is 1, $R^{21b}$ is hydrogen, $R^{22b}$ is hydrogen, and $R^{25}$ is $NH_2$.

In another embodiment is a compound of Formula (IC) wherein X is a group of formula

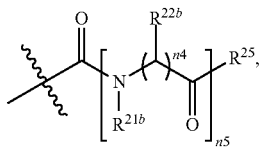

n4 is 1, n5 is 1, $R^{21b}$ is hydrogen, $R^{22b}$ is hydrogen, and $R^{25}$ is

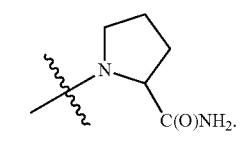

In another embodiment is a compound of Formula (IC) wherein X is a group of formula

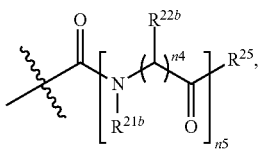

n4 is 1, n5 is 1, $R^{21b}$ is hydrogen, $R^{22b}$ is hydrogen, and $R^{25}$ is

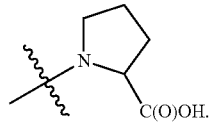

In another embodiment is a compound of Formula (IC) wherein X is a group of formula

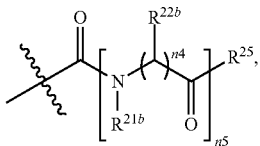

n4 is 1, n5 is 1, $R^{21b}$ is hydrogen, $R^{22b}$ is hydrogen, and $R^{25}$ is —NHSO$_2$Me.

In another embodiment is a compound of Formula (IC) wherein X is a group of formula

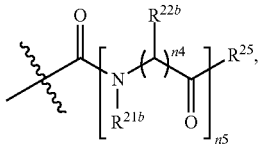

n4 is 1, n5 is 1, $R^{21b}$ is hydrogen, $R^{22b}$ is hydrogen, and $R^{25}$ is H.

In another embodiment is a compound of Formula (IC) wherein X is a group of formula

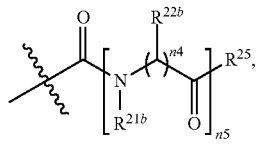

n4 is 2, n5 is 1, $R^{21b}$ is hydrogen, each $R^{22b}$ is independently hydrogen or hydroxy, and $R^{25}$ is NH$_2$.

In another embodiment is a compound of Formula (IC) wherein X is a group of formula

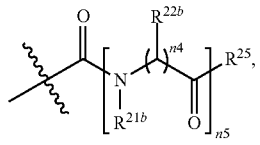

n4 is 2, n5 is 1, $R^{21b}$ is hydrogen, each $R^{22b}$ is independently hydrogen or hydroxy, and $R^{25}$ is NHMe.

In another embodiment is a compound of Formula (IC) wherein X is a group of formula

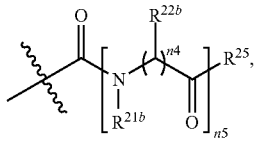

n4 is 2, n5 is 1, $R^{21b}$ is hydrogen, each $R^{22b}$ is independently hydrogen or hydroxy, and $R^{25}$ is OH.

In another embodiment is a compound of Formula (IC) wherein X is a group of formula

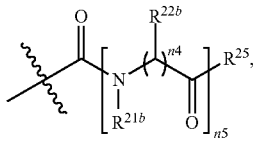

n4 is 2, n5 is 1, $R^{21b}$ is hydrogen, each $R^{22b}$ is independently hydrogen or hydroxy, and $R^{25}$ is OMe.

In another embodiment is a compound of Formula (IC) wherein X is a group of formula

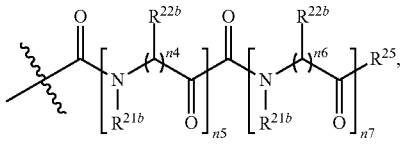

n4 is 1, n5 is 1, n7 is 0, $R^{21b}$ is hydrogen, $R^{22b}$ is methyl, and $R^{25}$ is —NH$_2$.

In another embodiment is a compound of Formula (IC) wherein X is a group of formula

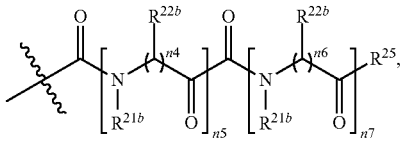

n4 is 1, n5 is 1, n7 is 0, R is hydrogen, R is methyl, and $R^{25}$ is —NHMe.

In another embodiment is a compound of Formula (IC) wherein X is a group of formula

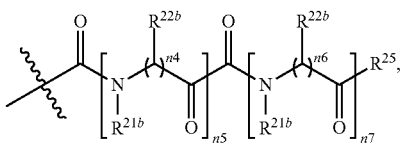

n4 is 1, n5 is 1, n7 is 0, $R^{21b}$ is hydrogen, $R^{22b}$ is methyl, and $R^{25}$ is —NMe$_2$.

In another embodiment is a compound of Formula (IC) wherein X is a group of formula

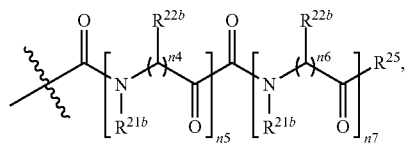

n4 is 1, n5 is 1, n7 is 0, $R^{21b}$ is hydrogen, $R^{22b}$ is hydrogen, and $R^{25}$ is —$NH_2$.

In another embodiment is a compound of Formula (IC) wherein X is a group of formula

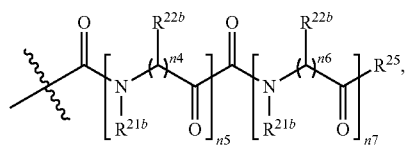

n4 is 1, n5 is 1, n7 is 0, $R^{21b}$ is hydrogen, R is hydrogen, and $R^2$ is OH.

In another embodiment is a compound of Formula (IC) wherein X is $C(O)R^{20}$ and $R^{20}$ is optionally substituted alkyl. In another embodiment is a compound of Formula (IC) wherein X is $C(O)R^{20}$ and $R^{20}$ is optionally substituted alkoxy. In some embodiments is a compound of Formula (IC) wherein $R^{20}$ is alkoxy substituted with $NH_2$.

In another embodiment is a compound of Formula (IC) wherein X is $C(O)R^{20}$ and $R^{20}$ is $NR^{20a}R^{20b}$, $R^{20a}$ is optionally substituted alkyl, and $R^{20b}$ is H. In further embodiments is a compound of Formula (IC) wherein X is $C(O)R^{20}$ and $R^{20}$ is $NR^{20a}R^{20b}$ $R^{20a}$ is alkyl substituted with a hydroxyl group, and $R^{20b}$ is H. In further embodiments is a compound of Formula (IC) wherein X is $C(O)R^{20}$ and $R^{20}$ is $NR^{20a}R^{20b}$, $R^{20a}$ is alkyl substituted with two hydroxyl groups, and $R^{20b}$ is H. In a further embodiment is a compound of Formula (IC) wherein X is $C(O)R^{20}$ and $R^{20}$ is $NR^{20a}R^{20b}$, $R^{20a}$ is alkyl substituted with three hydroxyl groups, and $R^{20b}$ is H. In a further embodiment is a compound of Formula (IC) wherein X is $C(O)R^{20}$ and $R^{20}$ is $NR^{20a}R^{20b}$, $R^{20a}$ is alkyl substituted with a hydroxyl group and a heteroaryl group, and $R^{20b}$ is H. In another embodiment is a compound of Formula (IC) wherein X is $C(O)R^{20}$ and $R^{20}$ is $NR^{20a}R^{20b}R^{20a}$ is alkyl substituted with methoxy, and $R^{20b}$ is H. In another embodiment is a compound of Formula (IC) wherein X is $C(O)R^{20}$ and $R^{20}$ is optionally substituted alkoxy. In some embodiments is a compound of Formula (IC) wherein $R^{20}$ is alkoxy substituted with $NH_2$.

In another embodiment is a compound of Formula (IC) wherein X is selected from

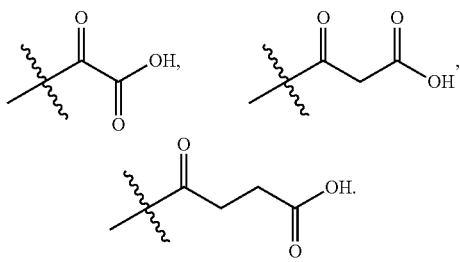

In yet another embodiment is a compound of Formula (IC) wherein X is a group of formula

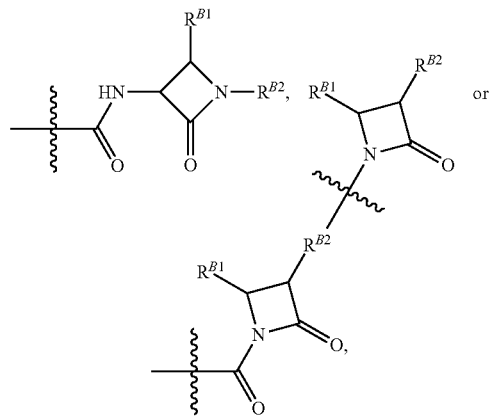

wherein $R^{B1}$ and $R^{B2}$ are each independently H. In another embodiment, $R^{B1}$ and $R^{B2}$ are each independently $(C_1-C_6)$ alkyl.

In one embodiment, $R^{B1}$ and $R^{B2}$ are each independently selected from methyl, ethyl, n-propyl, iso-propyl, n-butyl, iso-butyl, or tert-butyl.

In another embodiment is a compound of Formula (IC) wherein X is

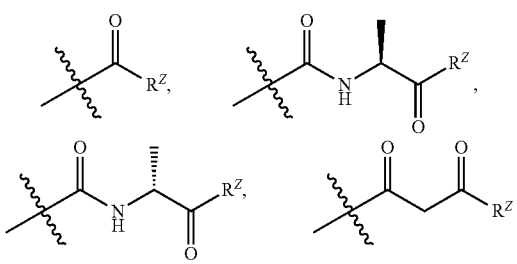

wherein $R^z$ is selected from H, $N(CH_3)_2$, $NHSO_2CH_3$, OH, $NH_2$,

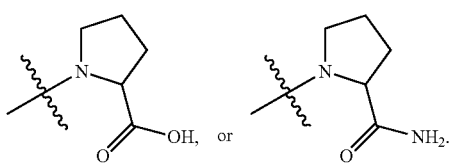 [SMILES: *N1CCCC1C(=O)O ; "or" ; *N1CCCC1C(N)=O]

In a further embodiment, $R^z$ is OH. In another embodiment, $R^z$ is $NH_2$.

In another embodiment is a compound of Formula (IC) wherein $R^1$ comprises a group of formula (IIA), (IIB), (IIC), (IID), (IIE), or (IIF)

(IIA)

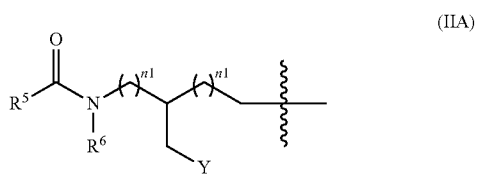

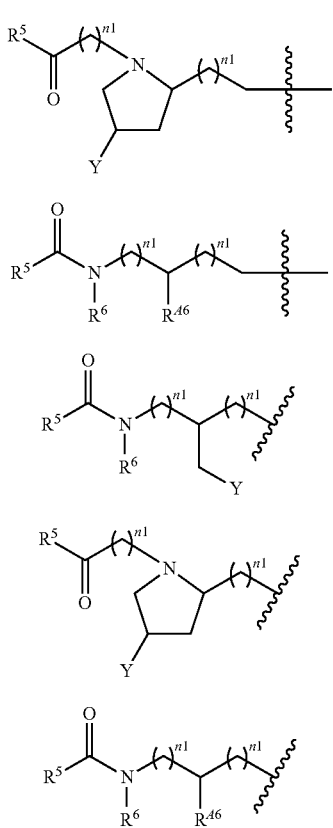

(IIB)

(IIC)

(IID)

(IIE)

(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IC) bearing $R^1$. In one embodiment, Y is H. In another embodiment, Y is OH. In another embodiment, Y is $CH_2OH$. In yet another embodiment, Y is $CH_2OC(=O)CH_3$.

In another embodiment is a compound of Formula (IC) wherein $R^1$ comprises a group of formula (IID), (IIE), or (IIF)

(IID)

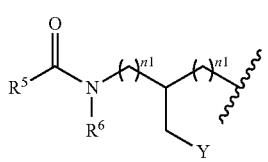

(IIE)

(IIF)

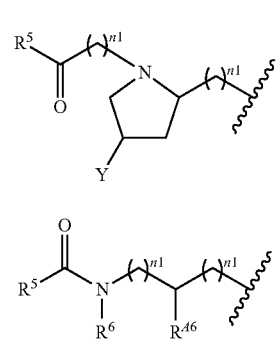

wherein n1 is at each occurrence 0; Y is $(CH_2)_{0-2}H$, or $(CH_2)_{0-2}OH$; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IC) bearing $R^1$. In one embodiment, Y is H. In another embodiment, Y is OH. In another embodiment, Y is $CH_2OH$. In yet another embodiment, Y is $CH_2OC(=O)CH_3$.

In some embodiments is a compound of Formula (IC) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

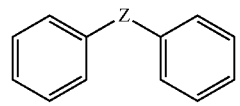

wherein Z is a bond, O, S, NH, $CH_2$ or C≡C. In some embodiments is a compound of Formula (IC) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (IC) is a compound wherein $R^4$ and $R^6$ are each independently at every occurrence hydrogen or $(C_1-C_6)$alkyl. In any of the aforementioned embodiments of Formula (IC) is a compound wherein $R^4$ and $R^6$ are each independently at every occurrence hydrogen or methyl. In any of the aforementioned embodiments of Formula (IC) is a compound wherein $R^{44}$ is hydrogen and $R^{45}$ is methyl. In any of the aforementioned embodiments of Formula (IC) is a compound wherein $R^{44}$ is methyl and $R^{45}$ is methyl.

In another aspect described herein are compounds of Formula (II):

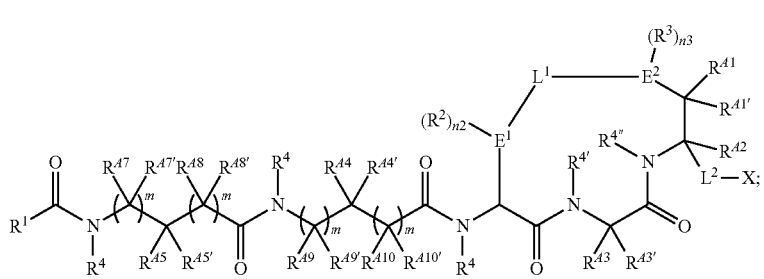

Formula (II)

wherein:

$E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, heteroaryl, or aryl; $L^1$ is —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or $(C_1-C_4)$alkylene optionally substituted with OH, CN, NO$_2$, halogen, $(C_1-C_6)$alkyl;

$L^2$ is a bond, or optionally substituted $(C_1-C_6)$alkylene;

X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$alkyl; and $R^{20b}$ is H or optionally substituted alkyl; or X is a group of formula

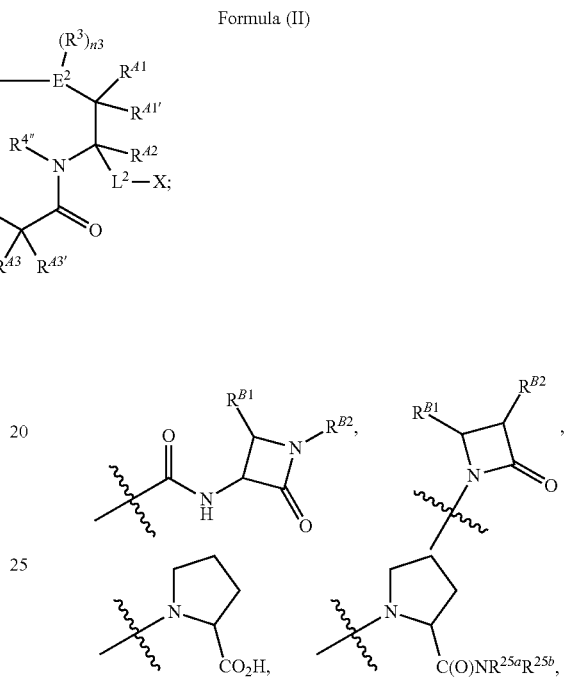

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, $(C_1-C_6)$alkoxy, $(C_1-C_6)$thioalkoxy, N(R$^C$)$_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (II) bearing X; or X is CO$_2$H, CH$_2$CO$_2$H, C(=O)NHCH$_2$C(=O)H, CH$_2$C(=O)H, C(=O)NHCH$_2$B(OR$^B$)$_2$ or C(=O)NHCH$_2$P(=O)(OR$^B$)$_2$ wherein $R^B$ is H or $(C_1-C_6)$alkyl, or X is a group of formula

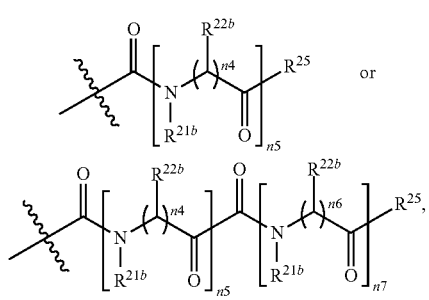

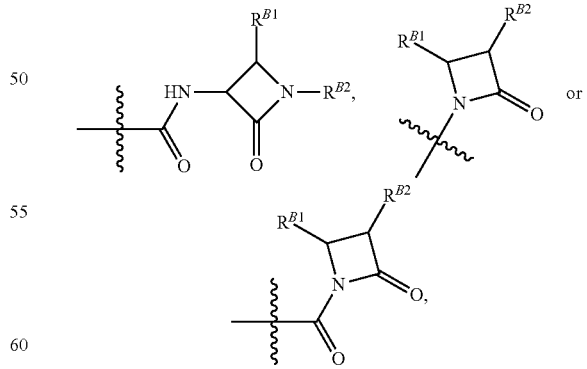

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, OR$^C$, wherein $R^{B1}$ and $R^{B2}$ are each independently H, $(C_1-C_6)$ alkyl, $(C_3-C_6)$ cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, $(C_1-C_6)$alkoxy, $(C_1-C_6)$thioalkoxy, NR$^C_2$, 5-7 membered heterocyclyl or 5-7 membered heteroaryl, or ($C_6$-$C_{10}$) aryl; $R^C$ is independently at each occurrence H or ($C_1$-$C_6$) alkyl, and a wavy line indicates a point of attachment of X to a carbon of formula (II) bearing X; or X is selected from

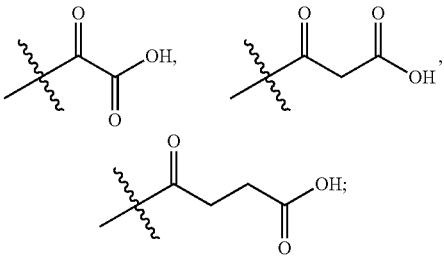

$R^1$ comprises a group of formula (IIA), (IIB), (IIC), (IID), (IIE), or (IIF)

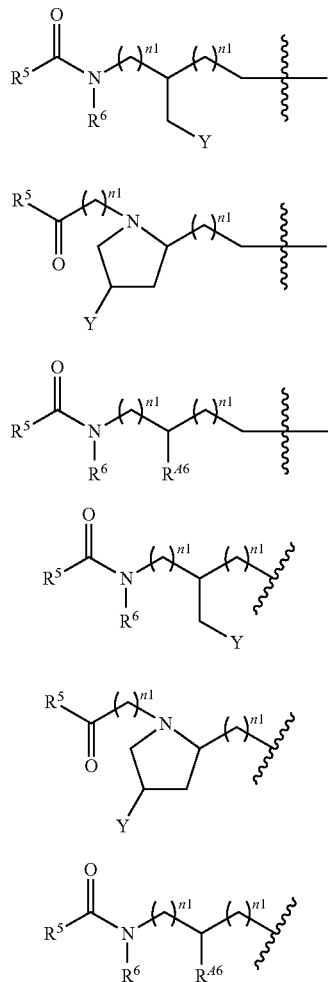

wherein n1 is independently at each occurrence 0, 1, or 2; Y is $(CH_2)_{0-2}H$, $(CH_2)_{0-2}OH$, or $(CH_2)_{0-2}OC(=O)(C_1$-$C_6)$ alkyl; $R^{A6}$ is hydrogen, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1$-$C_6)$alkoxy, $(C_1$-$C_6)$alkyl, $(C_3$-$C_7)$cycloalkyl, $(C_1$-$C_6)$-mono- or di-alkylamino, $(C_1$-$C_6)$alkoxycarbonyl, $(C_1$-$C_6)$alkylhydroxycarbonyl, $(C_1$-$C_6)$alkylaminocarbonyl, $(C_1$-$C_6)$alkylsulfonylamino, and $(C_6$-$C_{10})$-arylsulfonylamino; and a wavy line indicates a point of attachment of $R^1$ to an atom of formula (II) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

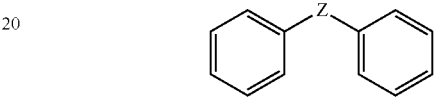

wherein Z is a bond, O, S, NH, $CH_2$ or C≡C;
$R^2$ and $R^3$ are each independently nitro, halo, cyano, hydroxy, glycosyloxy, amino, $(C_1$-$C_4)$alkoxy, $(C_1$-$C_4)$acyloxy, $(C_1$-$C_4)$alkyl, or a group cleavable under physiological conditions to provide a compound of formula (II) wherein $R^2$ or $R^3$ respectively is hydroxy, wherein any carbon atom is optionally substituted with J; or wherein two R groups taken together, and/or two $R^3$ groups taken together, optionally comprise fused cycloalkyl, aryl, heterocyclyl, or heteroaryl ring or rings, any of which is optionally substituted with 1 to 3 J;
n2 and n3 are independently 0, 1, 2, 3 or 4;
each m is independently 0, 1, or 2;
$R^4$, $R^{4'}$, $R^{4''}$ and $R^6$ are each independently at every occurrence hydrogen, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 J;
$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1$-$C_6)$alkyl, $(C_3$-$C_7)$cycloalkyl, 5- to 7-membered heteroaryl, 5- to 7-membered heterocyclyl, or $(C_6$-$C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH$—$C(O)R'$, $(CH_2)_{0-p}N(R')(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$; wherein p is 4,
each R' is independently at each occurrence hydrogen, $(C_1$-$C_6)$-alkyl, $(C_2$-$C_7)$-alkenyl, $(C_2$-$C_7)$-alkynyl, $(C_3$-$C_{10})$-cycloalkyl, $(C_3$-$C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;

or, when two R' are bound to a nitrogen atom or to two adjacent nitrogen atoms, the two R' groups together with the nitrogen atom or atoms to which they are bound optionally form a 3- to 8-membered monocyclic heterocyclic ring, or an 8- to 20-membered, bicyclic or tricyclic, heterocyclic ring system, wherein any ring or ring system optionally further contain 1-3 additional heteroatoms selected from the group consisting of N, NR', O, S, S(O) and S(O)$_2$, wherein each ring is substituted with 0-3 substituents selected independently from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl; wherein, in any bicyclic or tricyclic ring system, each ring is linearly fused, bridged, or spirocyclic, wherein each ring is either aromatic or nonaromatic, wherein each ring is optionally fused to a (C$_6$-C$_{10}$)aryl, mono- or bicyclic 5-10 membered heteroaryl, (C$_3$-C$_{10}$)cycloalkyl or mono- or bicyclic 3-10 membered heterocyclyl; or a pharmaceutically acceptable salt, solvate, or prodrug thereof.

In another embodiment is a compound of Formula (II) having the structure of Formula (IIG):

$L^1$ is —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O)NR$^4$—, —NR$^4$S(O)$_2$—, —S(O)$_2$NR$^4$—, —NR$^4$C(O)NR$^4$—, —NR$^4$C(O)O—, —OC(O)NR$^4$—, or (C$_1$-C$_4$)alkylene optionally substituted with OH, CN, NO$_2$, halogen, (C$_1$-C$_6$)alkyl;

$L^2$ is a bond;

X is CO$_2$H, CH$_2$CO$_2$H, C(=O)NHCH$_2$C(=O)H, CH$_2$C(=O)H, C(=O)NHCH$_2$B(OR$^B$)$_2$ or C(=O)NHCH$_2$P(=O)(OR$^B$)$_2$ wherein R$^B$ is H or (C$_1$-C$_6$)alkyl; or X is C(O)R$^{20}$, S(O)$_2$R$^{20}$, or C(O)NR$^{21a}$C(R$^{22a}$)(R$^{23a}$)B(OR$^{24}$)$_2$ wherein R$^{21a}$, R$^{22a}$, R$^{23a}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, where at least one of R$^{21a}$, R$^{22a}$, R$^{23a}$ is not hydrogen, wherein any alkyl, cycloalkyl, heterocyclyl, aryl or heteroaryl is optionally substituted with 1 to 3 J; R$^{24}$ is H or (C$_1$-C$_6$)alkyl; and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$(C$_1$-C$_6$)alkyl; and R$^{20b}$ is H or optionally substituted alkyl; or X is a group of formula

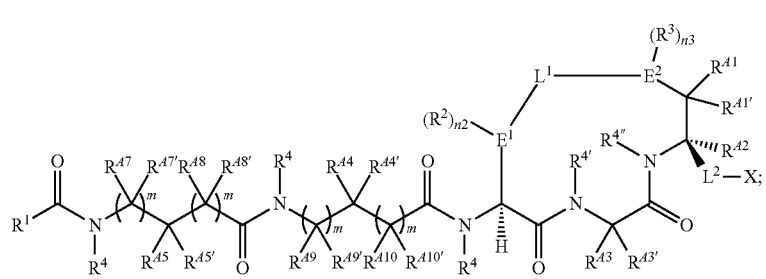

Formula (IIG)

wherein E$^1$, E$^2$, L$^1$, L$^2$, X, R$^1$, R$^2$, R$^3$, R$^4$, R$^{4'}$, R$^{4''}$, R$^{A1}$, R$^{A1'}$, R$^{A2}$, R$^{A3}$, R$^{A3'}$, R$^{A4}$, R$^{A4'}$, R$^{A5}$, R$^{A5'}$, R$^{A7}$, R$^{A7'}$, R$^{A8}$, R$^{A8'}$, R$^{A9}$, R$^{A9'}$, R$^{A10}$, R$^{A10'}$, n2, n3, and m are as defined herein; or a pharmaceutically acceptable salt, solvate, or prodrug thereof.

In another embodiment is a compound having the structure of Formula (IIH):

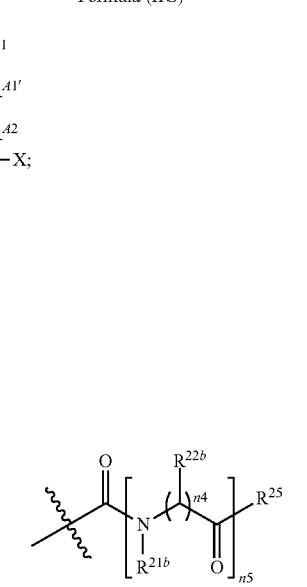

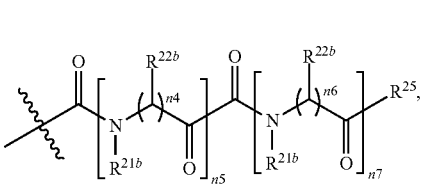

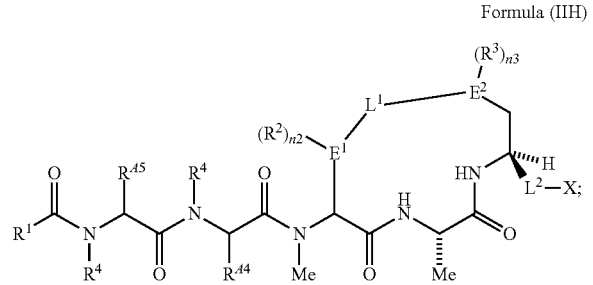

Formula (IIH)

wherein:

E$^1$ and E$^2$ are each independently (C$_1$-C$_6$)alkyl, (C$_2$-C$_7$) alkenyl, (C$_2$-C$_7$)alkynyl, (C$_3$-C$_7$)cycloalkyl, heterocyclyl, heteroaryl, or aryl;

wherein n4, n5, and n6 are each independently 1, 2 or 3; n7 is 0, 1 or 2; R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{25}$ is H, OH, OR$^C$,

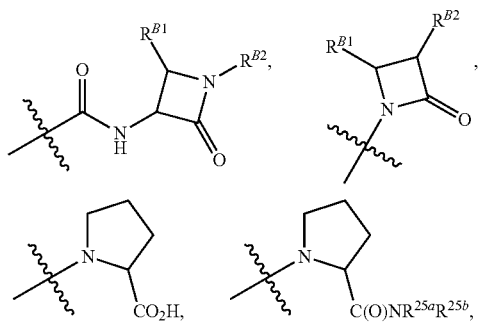

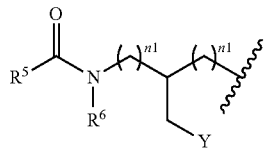

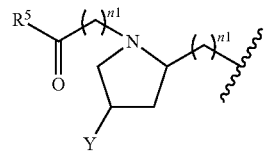

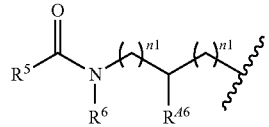

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (IIH) bearing X; or X is selected from

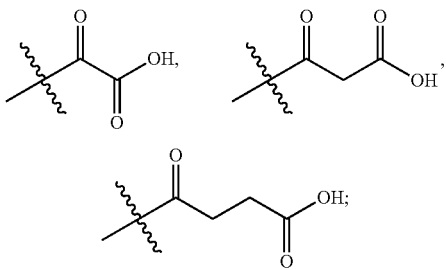

R$^1$ comprises a group of formula (IIA), (IIB), (IIC), (IID), (IIE), or (IIF)

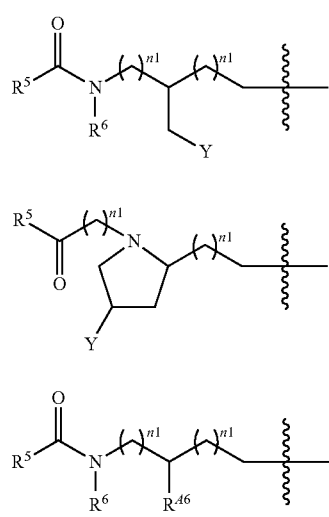

wherein n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$) alkyl; R$^{A6}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, (C$_1$-C$_6$)alkoxy, (C$_1$-C$_6$)alkyl, (C$_3$-C$_7$)cycloalkyl, (C$_1$-C$_6$)-mono- or di-alkylamino, (C$_1$-C$_6$)alkoxycarbonyl, (C$_1$-C$_6$)alkylhydroxycarbonyl, (C$_1$-C$_6$)alkylaminocarbonyl, (C$_1$-C$_6$)alkylsulfonylamino, and (C$_6$-C$_{10}$)-arylsulfonylamino; and a wavy line indicates a point of attachment of R$^1$ to an atom of formula (IIH) bearing R$^1$;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

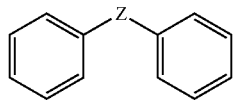

wherein Z is a bond, O, S, NH, CH$_2$ or C≡C;

R$^2$ and R$^3$ are each independently nitro, halo, cyano, hydroxy, glycosyloxy, amino, (C$_1$-C$_4$)alkoxy, (C$_1$-C$_4$)acyloxy, (C$_1$-C$_4$)alkyl, or a group cleavable under physiological conditions to provide a compound of formula (IIH) wherein R$^2$ or R$^3$ respectively is hydroxy, wherein any carbon atom is optionally substituted with J; or wherein two R$^2$ groups taken together, and/or two R$^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

R$^4$ and R$^6$ are each independently at every occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-

$C_{10}$) aryl, wherein any alkyl, cycloalkyl, heterocyclyl, aryl or heteroaryl is optionally substituted with 1 to 3 J;

$R^{44}$ and $R^{45}$ are independently hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH-C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —N(($C_1-C_4$)alkyl)$_2$-, —NH($C_1-C_4$)alkyl, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring; or a pharmaceutically acceptable salt, solvate, or prodrug thereof.

In another embodiment is a compound of Formula (IIH) wherein $E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, heteroaryl, or aryl. In some embodiments is a compound of Formula (IIH) wherein $E^1$ and $E^2$ are each independently $(C_1-C_6)$alkyl, $(C_2-C_7)$alkenyl, or $(C_2-C_7)$alkynyl. In some embodiments is a compound of Formula (IIH) wherein $E^1$ and $E^2$ are each independently $(C_1-C_6)$alkyl. In some embodiments is a compound of Formula (IIH) wherein $E^1$ and $E^2$ are each phenyl.

In another embodiment is a compound of Formula (IIH) wherein $L^1$ is —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, or $(C_1-C_4)$alkylene optionally substituted with OH, CN, $NO_2$, halogen, or $(C_1-C_6)$alkyl. In some embodiments is a compound of Formula (IIH) wherein $L^1$ is —O—. In some embodiments is a compound of Formula (IIH) wherein $L^1$ is —$CH_2O$—. In some embodiments is a compound of Formula (IIH) wherein $L^1$ is —$OCH_2$—. In some embodiments is a compound of Formula (IIH) wherein $L^1$ is —C(O)—. In some embodiments is a compound of Formula (IIH) wherein $L^1$ is $(C_1-C_4)$alkylene optionally substituted with OH or $(C_1-C_6)$alkyl.

In another embodiment is a compound of Formula (IIH) wherein $R^2$ and $R^3$ are each independently halo, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (II) wherein $R^2$ or $R^3$ respectively is hydroxyl. In some embodiments is a compound of Formula (IIH) wherein $R^2$ and $R^3$ are each hydroxyl, n2 is 1 and n3 is 1.

In another embodiment is a compound of Formula (IIH) wherein X is $CO_2H$, $CH_2CO_2H$, C(=O)$NHCH_2$C(=O)H, $CH_2$C(=O)H, C(=O)$NHCH_2$B(OR$^B$)$_2$ or C(=O)$NHCH_2$P(=O)(OR$^B$)$_2$ wherein $R^B$ is H or $(C_1-C_6)$alkyl. In some embodiments is a compound of Formula (IIH) wherein X is $CO_2H$. In some embodiments is a compound of Formula (IIH) wherein X is $CH_2C(=O)H$. In some embodiments is a compound of Formula (IIH) wherein X is C(=O)$NHCH_2$B(OR$^B$)$_2$ and $R^B$ is H or $(C_1-C_6)$alkyl.

In another embodiment is a compound of Formula (IIH) wherein X is a group of formula

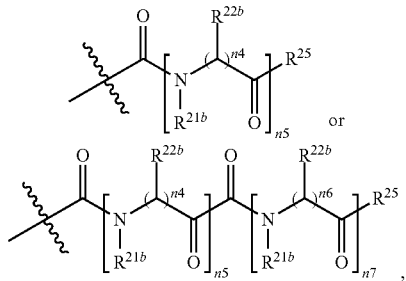

wherein n4, n5, and n6 are each independently 1, 2 or 3; n7 is 0, 1 or 2;

$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, OR$^C$,

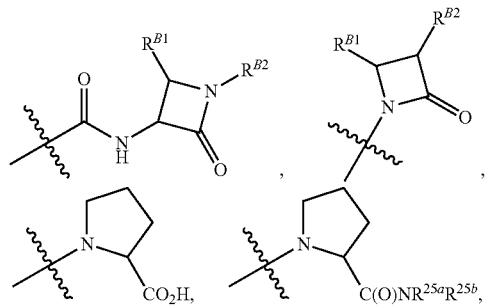

$NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, $(C_1-C_6)$alkoxy, $(C_1-C_6)$thioalkoxy, N(R$^C$)$_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IIH) bearing X.

In another embodiment is a compound of Formula (IIH) wherein X is a group of formula

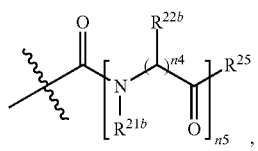

n4 is 1, n5 is 1, $R^{21b}$ is hydrogen, $R^{22b}$ is methyl, and $R^{25}$ is OH.

In another embodiment is a compound of Formula (IIH) wherein X is a group of formula

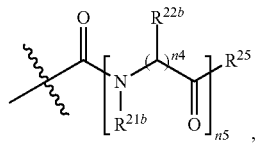

n4 is 1, n5 is 1, $R^{21b}$ is hydrogen, $R^{22b}$ is methyl, and $R^{25}$ is $NH_2$.

In another embodiment is a compound of Formula (IIH) wherein X is a group of formula

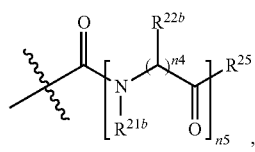

n4 is 1, n5 is 1, $R^{21b}$ is hydrogen, $R^{22b}$ is methyl, and $R^{25}$ is

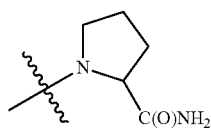

In another embodiment is a compound of Formula (IIH) wherein X is a group of formula

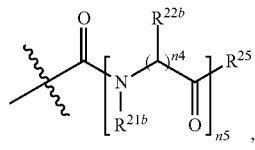

n4 is 1, n5 is 1, $R^{21b}$ is hydrogen, $R^{22b}$ is methyl, and $R^{25}$ is

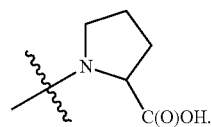

In another embodiment is a compound of Formula (IIH) wherein X is a group of formula

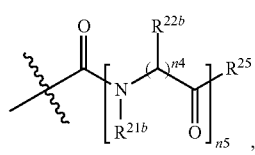

n4 is 1, n5 is 1, $R^{21b}$ is hydrogen, $R^{22b}$ is methyl, and $R^{25}$ is —$NHSO_2Me$.

In another embodiment is a compound of Formula (IIH) wherein X is a group of formula

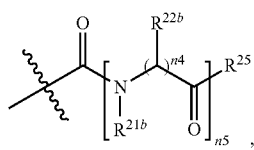

n4 is 1, n5 is 1, $R^{21b}$ is hydrogen, $R^{22b}$ is methyl, and $R^{25}$ is H.

In another embodiment is a compound of Formula (IIH) wherein X is a group of formula

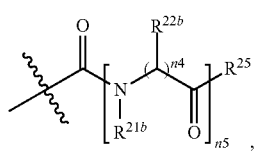

n4 is 1, n5 is 1, $R^{21b}$ is hydrogen, $R^{22b}$ is hydrogen, and $R^{25}$ is OH.

In another embodiment is a compound of Formula (IIH) wherein X is a group of formula

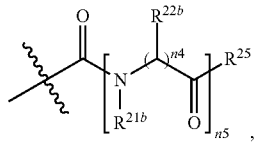

n4 is 1, n5 is 1, $R^{21b}$ is hydrogen, $R^{22b}$ is hydrogen, and $R^{25}$ is $NH_2$.

In another embodiment is a compound of Formula (IIH) wherein X is a group of formula

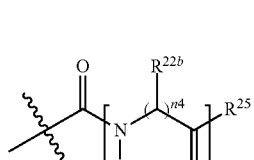

n4 is 1, n5 is 1, $R^{21b}$ is hydrogen, $R^{22b}$ is hydrogen, and $R^{25}$ is

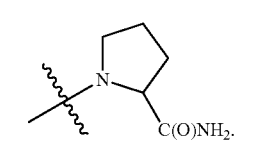

In another embodiment is a compound of Formula (IIH) wherein X is a group of formula

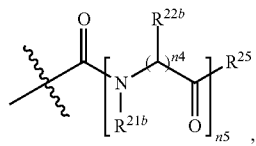

n4 is 1, n5 is 1, $R^{21b}$ is hydrogen, $R^{22b}$ is hydrogen, and $R^{25}$ is

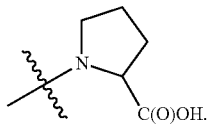

In another embodiment is a compound of Formula (IIH) wherein X is a group of formula

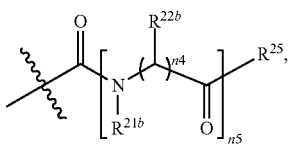

n4 is 1, n5 is 1, $R^{21b}$ is hydrogen, $R^{22b}$ is hydrogen, and $R^{25}$ is —NHSO$_2$Me.

In another embodiment is a compound of Formula (IIH) wherein X is a group of formula

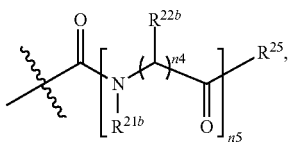

n4 is 1, n5 is 1, $R^{21b}$ is hydrogen, $R^{22b}$ is hydrogen, and $R^{25}$ is H.

In another embodiment is a compound of Formula (IIH) wherein X is a group of formula

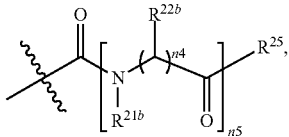

n4 is 2, n5 is 1, $R^{21b}$ is hydrogen, each $R^{22b}$ is independently hydrogen or hydroxy, and $R^{25}$ is NH$_2$.

In another embodiment is a compound of Formula (IIH) wherein X is a group of formula

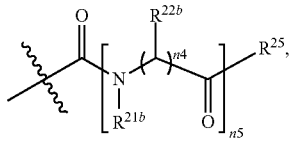

n4 is 2, n5 is 1, $R^{21b}$ is hydrogen, each $R^{22b}$ is independently hydrogen or hydroxy, and $R^{25}$ is NHMe.

In another embodiment is a compound of Formula (IIH) wherein X is a group of formula

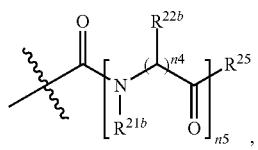

n4 is 2, n5 is 1, $R^{21b}$ is hydrogen, each $R^{22b}$ is independently hydrogen or hydroxy, and $R^{25}$ is OH.

In another embodiment is a compound of Formula (IIH) wherein X is a group of formula

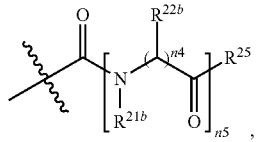

n4 is 2, n5 is 1, $R^{21b}$ is hydrogen, each $R^{22b}$ is independently hydrogen or hydroxy, and $R^{25}$ is OMe.

In another embodiment is a compound of Formula (IIH) wherein X is a group of formula

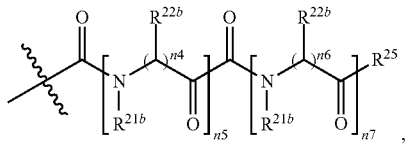

n4 is 1, s 1, n5 is 1, n7 is 0, $R^{21b}$ is hydrogen, $R^{22b}$ is methyl, and $R^{25}$ is —NH$_2$.

In another embodiment is a compound of Formula (IIH) wherein X is a group of formula

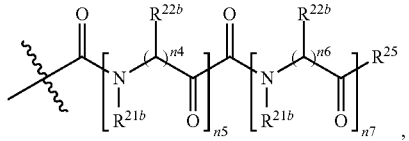

n4 is 1, n5 is 1, n7 is 0, $R^{21b}$ is hydrogen, R is methyl, and $R^{25}$ is —NHMe.

In another embodiment is a compound of Formula (IIH) wherein X is a group of formula

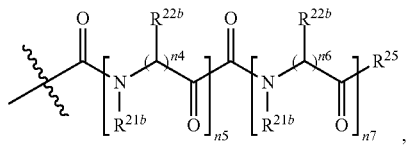

n4 is 1, n5 is 1, n7 is 0, $R^{21b}$ is hydrogen, $R^{22b}$ is methyl, and $R^{25}$ is —NMe$_2$.

In another embodiment is a compound of Formula (IIH) wherein X is a group of formula

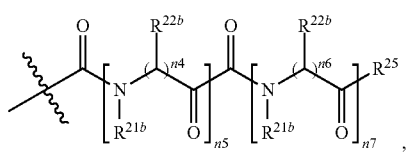

n4 is 1, n5 is 1, n7 is 0, $R^{21b}$ is hydrogen, $R^{22b}$ is hydrogen, and $R^{25}$ is —NH$_2$.

In another embodiment is a compound of Formula (IIH) wherein X is a group of formula

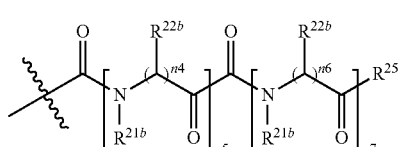

n4 is 1, n5 is 1, n7 is 0, $R^{21b}$ is hydrogen, $R^{22b}$ is hydrogen, and $R^{25}$ is OH.

In another embodiment is a compound of Formula (IIH) wherein X is C(O)R$^{20}$ and R$^{20}$ is optionally substituted alkyl. In another embodiment is a compound of Formula (IIH) wherein X is C(O)R$^{20}$ and R$^{20}$ is optionally substituted alkoxy. In some embodiments is a compound of Formula (IIH) wherein R$^{20}$ is alkoxy substituted with NH$_2$.

In another embodiment is a compound of Formula (IIH) wherein X is C(O)R$^{20}$ and R$^{20}$ is NR$^{20a}$R$^{20b}$, R$^{20a}$ is optionally substituted alkyl, and R$^{20b}$ is H. In further embodiments is a compound of Formula (IIH) wherein X is C(O)R$^{20}$ and R$^{20}$ is NR$^{20a}$R$^{20b}$, R$^{20a}$ is alkyl substituted with a hydroxyl group, and R$^{20b}$ is H. In further embodiments is a compound of Formula (IIH) wherein X is C(O)R$^{20}$ and R$^{20}$ is NR$^{20a}$R$^{20b}$, R$^{20a}$ is alkyl substituted with two hydroxyl groups, and R$^{20b}$ is H. In a further embodiment is a compound of Formula (IIH) wherein X is C(O)R$^{20}$ and R$^{20}$ is NR$^{20a}$R$^{20b}$R$^{20a}$ is alkyl substituted with three hydroxyl groups, and R$^{20b}$ is H. In a further embodiment is a compound of Formula (IIH) wherein X is C(O)R$^{20}$ and R$^{20}$ is NR$^{20a}$R$^{20b}$R$^{20a}$ is alkyl substituted with a hydroxyl group and a heteroaryl group, and R$^{20b}$ is H. In another embodiment is a compound of Formula (IIH) wherein X is C(O)R$^{20}$ and R$^{20}$ is NR$^{20a}$R$^{20b}$, R$^{20a}$ is alkyl substituted with methoxy, and R$^{20b}$ is H. In another embodiment is a compound of Formula (IIH) wherein X is C(O)R$^{20}$ and R$^{20}$ is optionally substituted alkoxy. In some embodiments is a compound of Formula (IIH) wherein R$^{20}$ is alkoxy substituted with NH$_2$.

In another embodiment is a compound of Formula (IIH) wherein X is selected

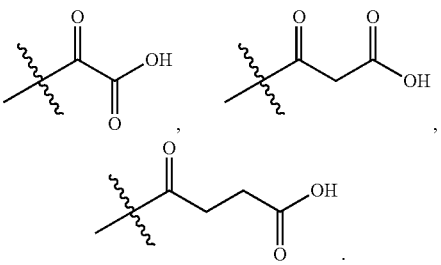

In yet another embodiment is a compound of Formula (IIH) wherein X is a group of formula

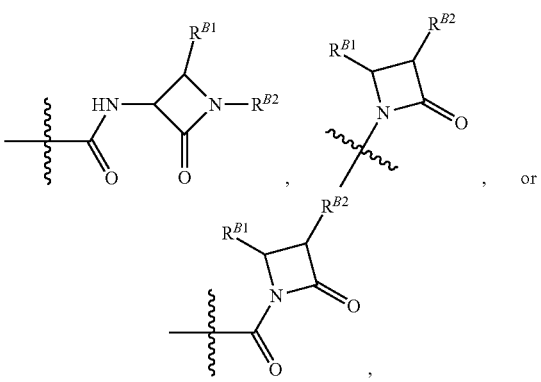

wherein R$^{B1}$ and R$^{B2}$ are each independently H. In another embodiment, R$^{B1}$ and R$^{B2}$ are each independently (C$_1$-C$_6$) alkyl.

In one embodiment, R$^{B1}$ and R$^{B2}$ are each independently selected from methyl, ethyl, n-propyl, iso-propyl, n-butyl, iso-butyl, or tert-butyl.

In another embodiment is a compound of Formula (IIH) wherein X is

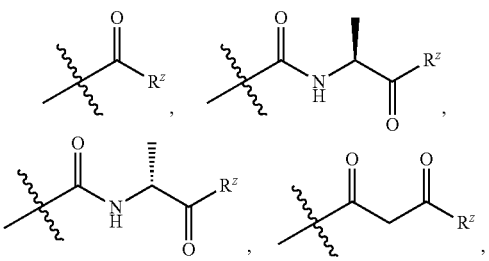

wherein R$^z$ is selected from H, N(CH$_3$)$_2$, NHSO$_2$CH$_3$, OH, NH$_2$,

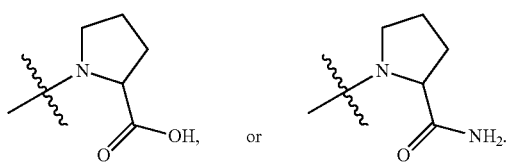 [SMILES: *N1CCCC1C(=O)O ; "or" ; *N1CCCC1C(N)=O]

In a further embodiment, $R^z$ is OH. In another embodiment, $R^z$ is $NH_2$.

In another embodiment is a compound of Formula (IIH) wherein $R^1$ comprises a group of formula (IIA), (IIB), (IIC), (IID), (IIE), or (IIF)

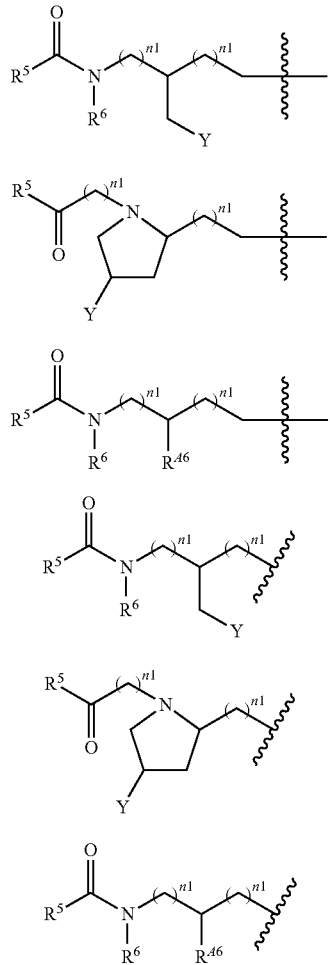

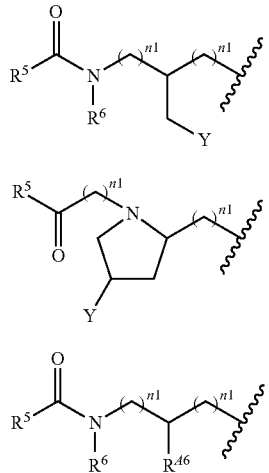

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IIH) bearing $R^1$. In one embodiment, Y is H. In another embodiment, Y is OH. In another embodiment, Y is $CH_2OH$. In yet another embodiment, Y is $CH_2OC(=O)CH_3$.

In another embodiment is a compound of Formula (IIH) wherein $R^1$ comprises a group of formula (IID), (IIE), or (IIF)

wherein n1 is at each occurrence 0; Y is $(CH_2)_{0-2}H$, or $(CH_2)_{0-2}OH$; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IIH) bearing $R^1$. In one embodiment, Y is H. In another embodiment, Y is OH. In another embodiment, Y is $CH_2OH$. In yet another embodiment, Y is $CH_2OC(=O)CH_3$.

In some embodiments is a compound of Formula (IIH) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

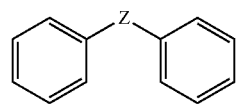

wherein Z is a bond, O, S, NH, $CH_2$ or C≡C. In some embodiments is a compound of Formula (IIH) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (IIH) is a compound wherein $R^4$ and $R^6$ are each independently at every occurrence hydrogen or $(C_1-C_6)$alkyl. In any of the aforementioned embodiments of Formula (IIH) is a compound wherein $R^4$ and $R^6$ are each independently at every occurrence hydrogen or methyl. In any of the aforementioned embodiments of Formula (IIH) is a compound wherein $R^{44}$ is hydrogen and $R^{45}$ is methyl. In any of the aforementioned embodiments of Formula (IIH) is a compound wherein $R^{44}$ is methyl and $R^{45}$ is methyl.

In another aspect described herein are compounds of Formula (III):

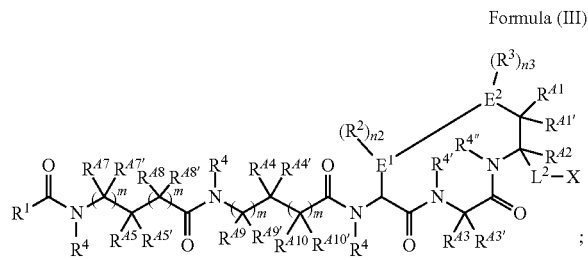

Formula (III)

wherein:
$E^1$ and $E^2$ are each independently $(C_1-C_6)$alkyl, $(C_2-C_7)$ alkenyl, $(C_2-C_7)$alkynyl, $(C_3-C_7)$cycloalkyl, heterocyclyl, 5-membered heteroaryl, or bicyclic heteroaryl;
$L^2$ is a bond, or optionally substituted $(C_1-C_6)$alkylene;
X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$ alkyl; and $R^{20b}$ is H or optionally substituted alkyl; or
X is a group of formula

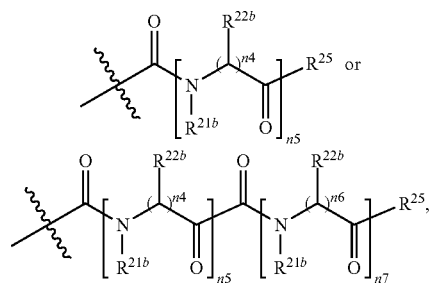

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
$R^{25}$ is H, OH, $OR^C$,

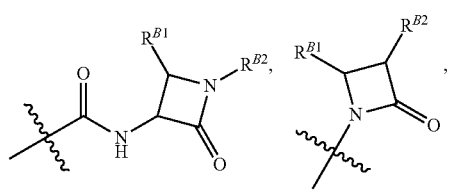

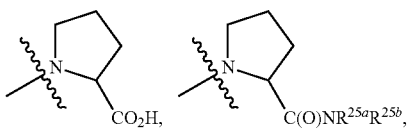

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)$ $OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (III) bearing X; or X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or X is a group of formula

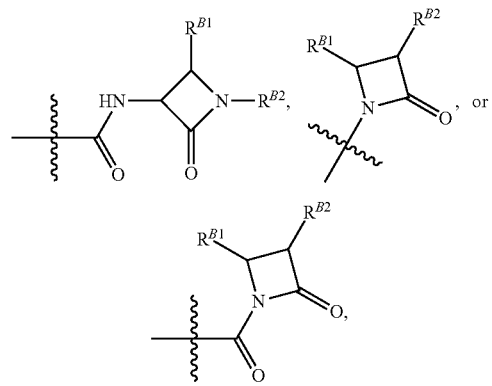

wherein $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (III) bearing X; or X is selected from

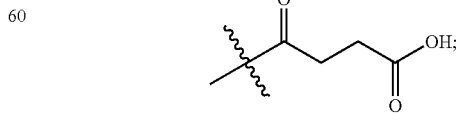

$R^1$ comprises a group of formula (IIA), (IIB), (IIC), (IID), (IIE), or (IIF)

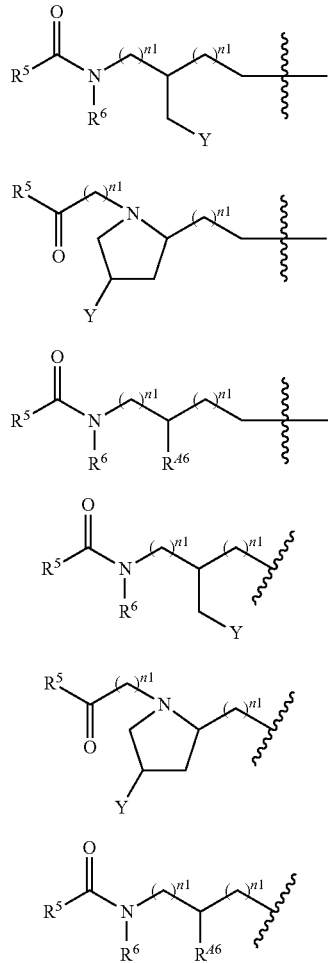

(IIA)
(IIB)
(IIC)
(IID)
(IIE)
(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (III) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus, any of the following groups: optionally substituted aryl, optionally substituted heteroaryl, or optionally substituted

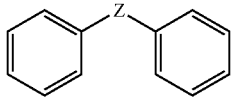

wherein Z is a bond, O, S, NH, $CH_2$ or C≡C;
$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (III) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;
n2 and n3 are independently 0, 1, 2, 3 or 4;
each m is independently 0, 1, or 2;
$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;
$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}—C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}—OC(O)N(R')_2$, $(CH_2)_{0-p}C(S)N(R')_2$, $(CH_2)_{0-p}NH—C(O)R'$, $(CH_2)_{0-p}N(R')N(R')_pC(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;
wherein p is 4,
each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO_2, —OH, —CF_3, —OCF_3, —OCH_3, —NH_2, —N((C_1-C_4)alkyl)_2-, —NH(C_1-C_4)alkyl, $C_1-C_6$alkyl, $C_3-C_5$cycloalkyl, or $C_1-C_6$heteroalkyl;
or, when two R' are bound to a nitrogen atom or to two adjacent nitrogen atoms, the two R' groups together with the nitrogen atom or atoms to which they are bound optionally form a 3- to 8-membered monocyclic heterocyclic ring, or an 8- to 20-membered, bicyclic or tricyclic, heterocyclic ring system, wherein any ring or ring system optionally further contains 1-3 additional heteroatoms selected from the group consisting of N, NR', O, S, S(O) and S(O)_2, wherein each ring is substituted with 0-3 substituents selected independently from F, Cl, Br, I, —CN, —NO_2, —OH, —CF_3, —OCF_3, —OCH_3, —NH_2, —N((C_1-C_4)alkyl)_2-, —NH(C_1-C_4)alkyl, $C_1-C_6$alkyl, $C_3-C_5$cycloalkyl, or $C_1$-$C_6$heteroalkyl; wherein, in any bicyclic or tricyclic ring system, each ring is linearly fused, bridged, or spirocyclic, wherein each ring is either aromatic or nonaromatic, wherein each ring optionally is fused to a ($C_6$-$C_{10}$)aryl, mono- or bicyclic 5-10 membered heteroaryl, ($C_3$-$C_{10}$)cycloalkyl or mono- or bicyclic 3-10 membered heterocyclyl; or a pharmaceutically acceptable salt, solvate or prodrug thereof.

In one embodiment is a compound of Formula (III) having the structure of Formula (IIIA):

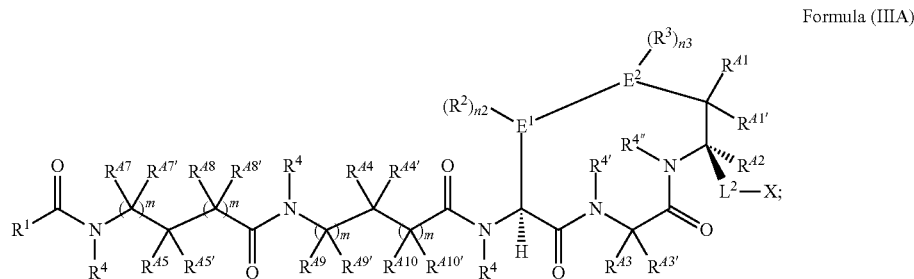

Formula (IIIA)

wherein $E^1$, $E^2$, $L^2$, X, $R^1$, $R^2$, $R^3$, $R^4$, $R^{4'}$, $R^{4''}$, $R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, $R^{A10'}$, n2, n3, and m are as defined herein; or a pharmaceutically acceptable salt, solvate, or prodrug thereof.

In one embodiment is a compound having the structure of Formula (IIIB):

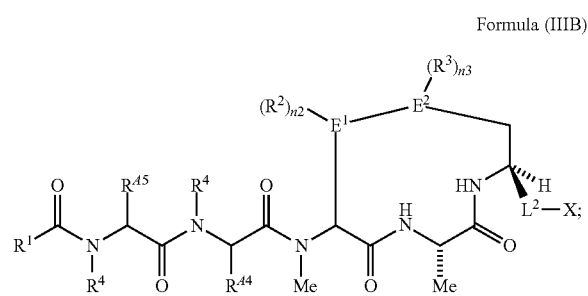

Formula (IIIB)

wherein $E^1$ and $E^2$ are each independently ($C_1$-$C_6$)alkyl, ($C_2$-$C_7$)alkenyl, ($C_2$-$C_7$)alkynyl, ($C_3$-$C_7$)cycloalkyl, heterocyclyl, or 5-membered heteroaryl;

$L^2$ is a bond;

X is $CO_2H$, $CH_2CO_2H$, C(=O)NHCH$_2$C(=O)H, $CH_2$C(=O)H, C(=O)NHCH$_2$B(OR$^B$)$_2$ or C(=O)NHCH$_2$P(=O)(OR$^B$)$_2$ wherein $R^B$ is H or ($C_1$-$C_6$)alkyl; or X is C(O)R$^{20}$, S(O)$_2$R$^{20}$, or C(O)NR$^{21a}$C(R$^{22a}$)(R$^{23a}$)B(OR$^{24}$)$_2$ wherein R$^{21a}$, R$^{22a}$, R$^{23a}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, where at least one of R$^{21a}$, R$^{22a}$, R$^{23a}$ is not hydrogen, wherein any alkyl, cycloalkyl, heterocyclyl, aryl or heteroaryl is optionally substituted with 1 to 3 J; R$^{24}$ is H or ($C_1$-$C_6$)alkyl; and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$($C_1$-$C_6$) alkyl; and R$^{20b}$ is H or optionally substituted alkyl; or X is a group of formula

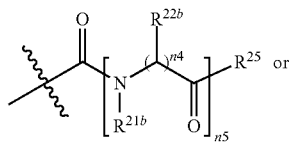

-continued

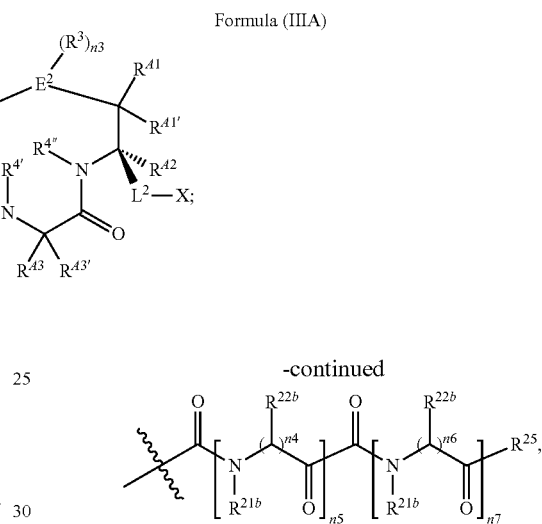

wherein n4, n5, and n6 are each independently 1, 2 or 3; n7 is 0, 1 or 2; R$^{21b}$ and R$^{22b}$ are independently at each occurrence hydrogen, hydroxy, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; R$^{25}$ is H, OH, OR$^C$,

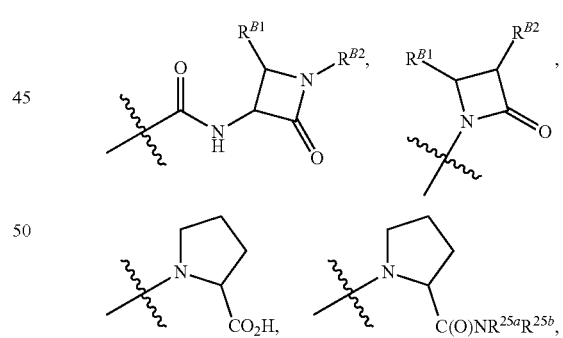

or NR$^{25a}$R$^{25b}$ where R$^{25a}$ and R$^{25b}$ are each independently H, SO$_2$($C_1$-$C_6$)alkyl, or optionally substituted alkyl; R$^{B1}$ and R$^{B2}$ are each independently H, ($C_1$-$C_6$) alkyl, ($C_3$-$C_6$) cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, ($C_1$-$C_6$)alkoxy, ($C_1$-$C_6$)thioalkoxy, N(R$^C$)$_2$, 5-7 membered heterocyclyl or 5-7 membered heteroaryl, or ($C_6$-$C_{10}$) aryl; R$^C$ is independently at each occurrence H or ($C_1$-$C_6$) alkyl, and a wavy line indicates a point of attachment of X to a carbon of formula (IIIB) bearing X; or X is selected from

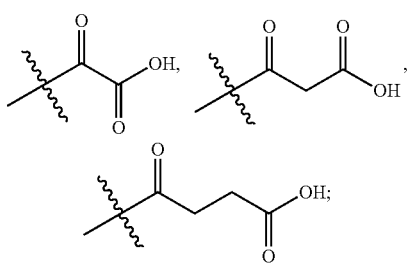

$R^1$ comprises a group of formula (IIA), (IIB), (IIC), (IID), (IIE), or (IIF)

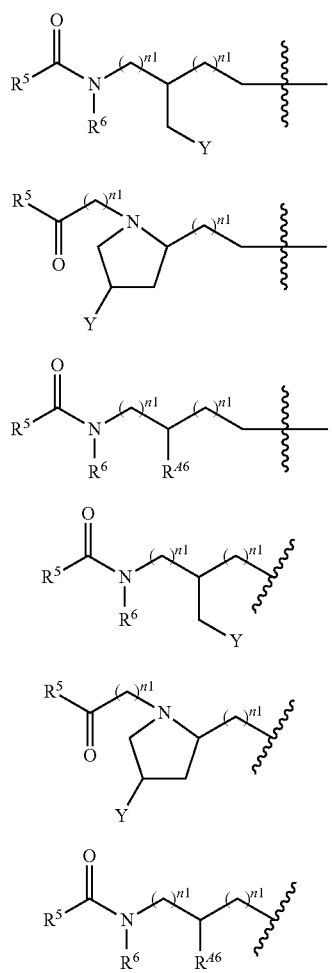

(IIA)

(IIB)

(IIC)

(IID)

(IIE)

(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IIIB) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (IIIB) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

$R^4$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{44}$ and $R^{4}$ are independently hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH—C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)alkyl$, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In another embodiment is a compound of Formula (IIIB) wherein $E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, or 5-membered heteroaryl. In some embodiments is a compound of Formula (IIIB) wherein $E^1$ and $E^2$ are each independently $(C_1-C_6)$alkyl, $(C_2-C_7)$alkenyl, or $(C_2-C_7)$ alkynyl. In some embodiments is a compound of Formula (IIIB) wherein $E^1$ and $E^2$ are each independently $(C_1-C_6)$ alkyl.

In another embodiment is a compound of Formula (IIIB) wherein $R^2$ and $R^3$ are each independently halo, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (II) wherein $R^2$ or $R^3$ respectively is hydroxyl. In some embodiments is a compound of Formula (IIIB) wherein $R^2$ and $R^3$ are each hydroxyl, n2 is 1 and n3 is 1.

In another embodiment is a compound of Formula (IIIB) wherein X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl. In some embodiments is a compound of Formula (IIIB) wherein X is $CO_2H$. In some embodiments is a compound of Formula (IIIB) wherein X is $CH_2C(=O)H$. In some embodiments is a compound of Formula (IIIB) wherein X is $C(=O)NHCH_2B(OR^B)_2$ and $R^B$ is H or $(C_1-C_6)$alkyl.

In another embodiment is a compound of Formula (IIIB) wherein X is a group of formula

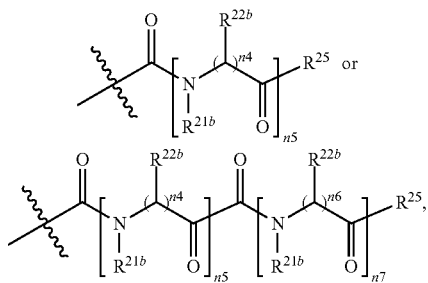

wherein n4, n5, and n6 are each independently 1, 2 or 3; n7 is 0, 1 or 2;
$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

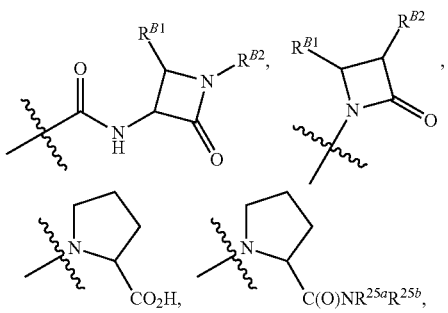

or $NR^{25a}R^{25b}$ where $R^{25}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IB) bearing X.

In another embodiment is a compound of Formula (IIIB) wherein X is a group of formula

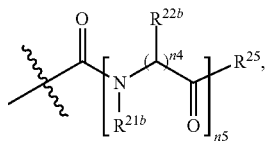

n4 is 1, n5 is 1, $R^{21b}$ is hydrogen, $R^{22b}$ is methyl, and $R^{25}$ is OH.

In another embodiment is a compound of Formula (IIIB) wherein X is a group of formula

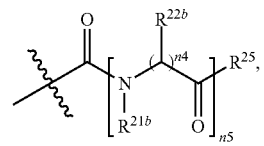

n4 is 1, n5 is 1, $R^{21b}$ is hydrogen, $R^{22b}$ is methyl, and $R^{25}$ is $NH_2$.

In another embodiment is a compound of Formula (IIIB) wherein X is a group of formula

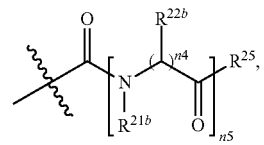

n4 is 1, n5 is 1, $R^{21b}$ is hydrogen, $R^{22b}$ is methyl, and $R^{25}$ is

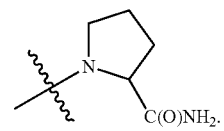

In another embodiment is a compound of Formula (IIIB) wherein X is a group of formula

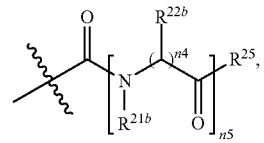

n4 is 1, n5 is 1, $R^{21b}$ is hydrogen, $R^{22b}$ is methyl, and $R^{25}$ is

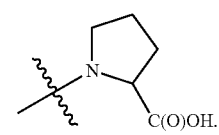

In another embodiment is a compound of Formula (IIIB) wherein X is a group of formula

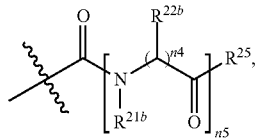

n4 is 1, n5 is 1, $R^{21b}$ is hydrogen, $R^{22b}$ is methyl, and $R^{25}$ is —NHSO$_2$Me.

In another embodiment is a compound of Formula (IIIB) wherein X is a group of formula

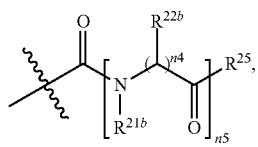

n4 is 1, n5 is 1, $R^{21b}$ is hydrogen, $R^{22b}$ is methyl, and $R^{25}$ is H.

In another embodiment is a compound of Formula (IIIB) wherein X is a group of formula

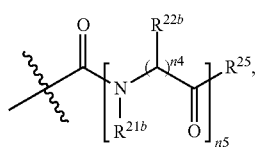

n4 is 1, n5 is 1, $R^{21b}$ is hydrogen, $R^{22b}$ is hydrogen, and $R^{25}$ is OH.

In another embodiment is a compound of Formula (IIIB) wherein X is a group of formula

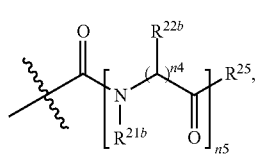

n4 is 1, n5 is 1, $R^{21b}$ is hydrogen, $R^{22b}$ is hydrogen, and $R^{25}$ is NH$_2$.

In another embodiment is a compound of Formula (IIIB) wherein X is a group of formula

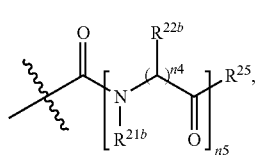

n4 is 1, n5 is 1, $R^{21b}$ is hydrogen, $R^{22b}$ is hydrogen, and $R^{25}$ is

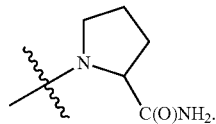

In another embodiment is a compound of Formula (IIIB) wherein X is a group of formula

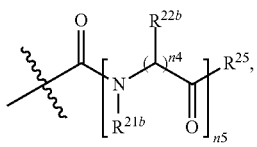

n4 is 1, n5 is 1, $R^{21b}$ is hydrogen, $R^{22b}$ is hydrogen, and $R^{25}$ is

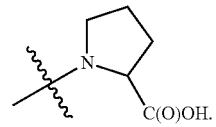

In another embodiment is a compound of Formula (IIIB) wherein X is a group of formula

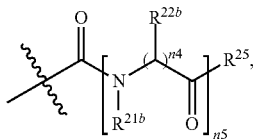

n4 is 1, n5 is 1, $R^{21b}$ is hydrogen, $R^{22b}$ is hydrogen, and $R^{25}$ is —NHSO$_2$Me.

In another embodiment is a compound of Formula (IIIB) wherein X is a group of formula

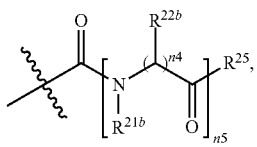

n4 is 1, n5 is 1, $R^{21b}$ is hydrogen, $R^{22b}$ is hydrogen, and $R^{25}$ is H.

In another embodiment is a compound of Formula (IIIB) wherein X is a group of formula

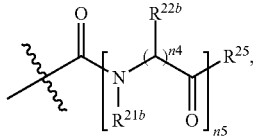

n4 is 2, n5 is 1, $R^{21b}$ is hydrogen, each $R^{22b}$ is independently hydrogen or hydroxy, and $R^{25}$ is NH$_2$.

In another embodiment is a compound of Formula (IIIB) wherein X is a group of formula

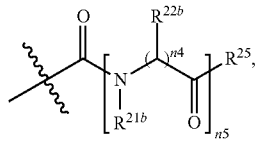

n4 is 2, n5 is 1, $R^{21b}$ is hydrogen, each $R^{22b}$ is independently hydrogen or hydroxy, and $R^{25}$ is NHMe.

In another embodiment is a compound of Formula (IIIB) wherein X is a group of formula

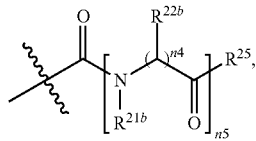

n4 is 2, n5 is 1, $R^{21b}$ is hydrogen, each $R^{22b}$ is independently hydrogen or hydroxy, and $R^{25}$ is OH.

In another embodiment is a compound of Formula (IIIB) wherein X is a group of formula

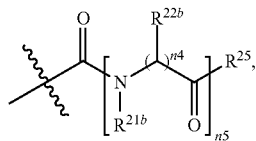

n4 is 2, n5 is 1, $R^{21b}$ is hydrogen, each $R^{22b}$ is independently hydrogen or hydroxy, and $R^{25}$ is OMe.

In another embodiment is a compound of Formula (IIIB) wherein X is a group of formula

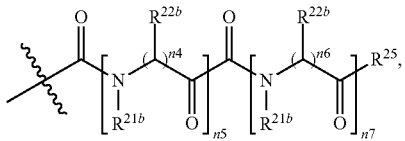

n4 is 1, s 1, n5 is 1, n7 is 0, $R^{21b}$ is hydrogen, $R^{22b}$ is methyl, and $R^{25}$ is —NH$_2$.

In another embodiment is a compound of Formula (IIIB) wherein X is a group of formula

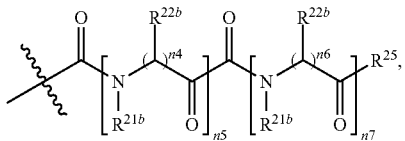

n4 is 1, s 1, n5 is 1, n7 is 0, $R^{21b}$ is hydrogen, $R^{22b}$ is methyl, and $R^{25}$ is —NHMe.

In another embodiment is a compound of Formula (IIIB) wherein X is a group of formula

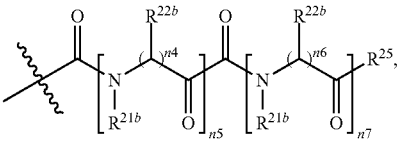

n4 is 1, n5 is 1, n7 is 0, $R^{21b}$ is hydrogen, $R^{22b}$ is methyl, and $R^{25}$ is —NMe$_2$.

In another embodiment is a compound of Formula (IIIB) wherein X is a group of formula

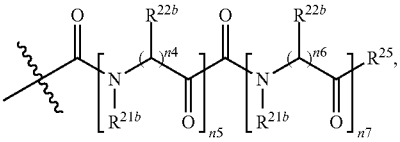

n4 is 1, s 1, n5 is 1, n7 is 0, $R^{21b}$ is hydrogen, R is hydrogen, and $R^{25}$ is —NH$_2$.

In another embodiment is a compound of Formula (IIIB) wherein X is a group of formula

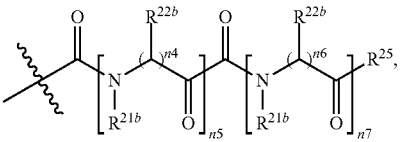

n4 is 1, s 1, n5 is 1, n7 is 0, $R^{21b}$ is hydrogen, R is hydrogen, and $R^{25}$ is OH.

In another embodiment is a compound of Formula (IIIB) wherein X is C(O)$R^{20}$ and $R^{20}$ is optionally substituted alkyl. In another embodiment is a compound of Formula (IIIB) wherein X is C(O)$R^{20}$ and $R^{20}$ is optionally substituted alkoxy. In some embodiments is a compound of Formula (IIIB) wherein $R^{20}$ is alkoxy substituted with NH$_2$.

In another embodiment is a compound of Formula (IIIB) wherein X is C(O)$R^{20}$ and $R^{20}$ is NR$^{20a}$R$^{20b}$, R$^{20a}$ is optionally substituted alkyl, and R$^{20b}$ is H. In further embodiments is a compound of Formula (IIIB) wherein X is C(O)$R^{20}$ and $R^{20}$ is NR$^{20a}$R$^{20b}$, R$^{20a}$ is alkyl substituted with a hydroxyl group, and R$^{20b}$ is H. In further embodiments is a compound of Formula (IIIB) wherein X is C(O)$R^{20}$ and $R^{20}$ is NR$^{20a}$R$^{20b}$, R$^{20a}$ is alkyl substituted with two hydroxyl groups, and R$^{20b}$ is H. In a further embodiment is a compound of Formula (IIIB) wherein X is C(O)$R^{20}$ and $R^{20}$ is NR$^{20a}$R$^{20b}$R$^{20a}$ is alkyl substituted with three hydroxyl groups, and R$^{20b}$ is H. In a further embodiment is a compound of Formula (IIIB) wherein X is C(O)$R^{20}$ and $R^{20}$ is NR$^{20a}$R$^{20b}$R$^{20a}$ is alkyl substituted with a hydroxyl group and a heteroaryl group, and R$^{20b}$ is H. In another embodiment is a compound of Formula (IIIB) wherein X is C(O)$R^{20}$ and $R^{20}$ is NR$^{20a}$R$^{20b}$, R$^{20a}$ is alkyl substituted with methoxy, and R$^{20b}$ is H. In another embodiment is a compound of Formula (IIIB) wherein X is C(O)$R^{20}$ and $R^{20}$ is optionally substituted alkoxy. In some embodiments is a compound of Formula (IIIB) wherein $R^{20}$ is alkoxy substituted with NH$_2$.

In another embodiment is a compound of Formula (IIIB) wherein X is selected from

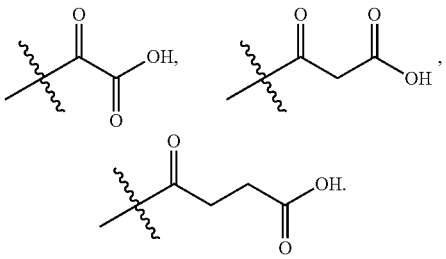

In yet another embodiment is a compound of Formula (IIIB) wherein X is a group of formula

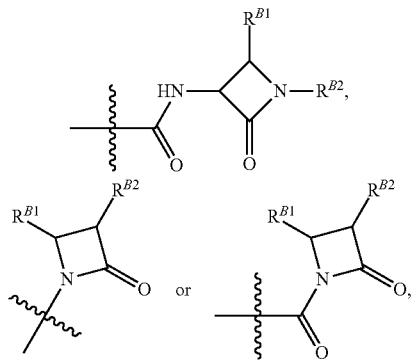

wherein $R^{B1}$ and $R^{B2}$ are each independently H. In another embodiment, $R^{B1}$ and $R^{B2}$ are each independently ($C_1$-$C_6$) alkyl.

In one embodiment, $R^{B1}$ and $R^{B2}$ are each independently selected from methyl, ethyl, n-propyl, iso-propyl, n-butyl, iso-butyl, or tert-butyl.

In another embodiment is a compound of Formula (IIIB) wherein X is

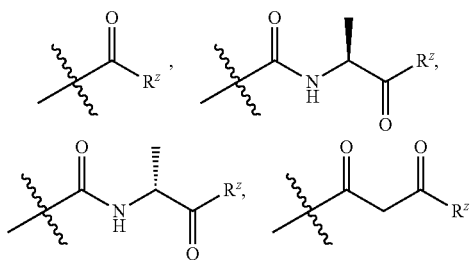

wherein $R^z$ is selected from H, N($CH_3$)$_2$, NHSO$_2$CH$_3$, OH, NH$_2$,

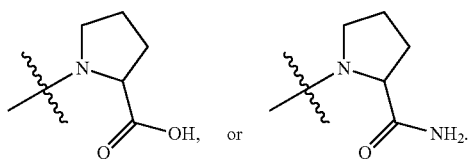 [SMILES: *N1CCCC1C(=O)O ; *N1CCCC1C(N)=O]

In a further embodiment, $R^z$ is OH. In another embodiment, $R^z$ is NH$_2$.

In another embodiment is a compound of Formula (IIIB) wherein $R^1$ comprises a group of formula (IIA), (IIB), (IIC), (IID), (IIE), or (IIF)

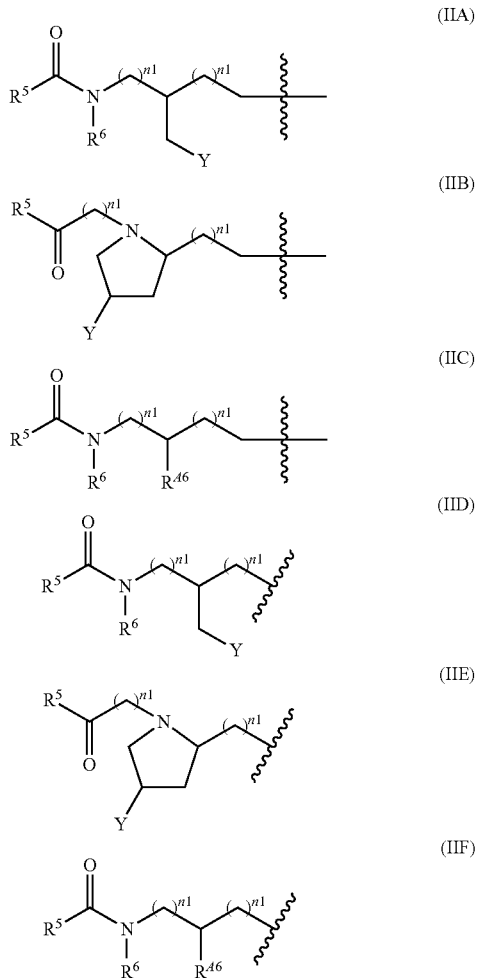

wherein n1 is independently at each occurrence 0, 1, or 2; Y is $(CH_2)_{0-2}$H, $(CH_2)_{0-2}$OH, or $(CH_2)_{0-2}$OC(=O)($C_1$-$C_6$) alkyl; $R^{46}$ is hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, ($C_1$-$C_6$)alkoxy, ($C_1$-$C_6$)alkyl, ($C_3$-$C_7$)cycloalkyl, ($C_1$-$C_6$)-mono- or di-alkylamino, ($C_1$-$C_6$)alkoxycarbonyl, ($C_1$-$C_6$)alkylhydroxycarbonyl, ($C_1$-$C_6$)alkylaminocarbonyl, ($C_1$-$C_6$)alkylsulfonylamino, and ($C_6$-$C_{10}$)-arylsulfonylamino; and a wavy line indicates a point of attachment of $R^1$ to an atom of formula (IIIB) bearing $R^1$. In one embodiment, Y is H. In another embodiment, Y is OH. In another embodiment, Y is CH$_2$OH. In yet another embodiment, Y is CH$_2$OC(=O)CH$_3$.

In another embodiment is a compound of Formula (IIIB) wherein $R^1$ comprises a group of formula (IID), (IIE), or (IIF)

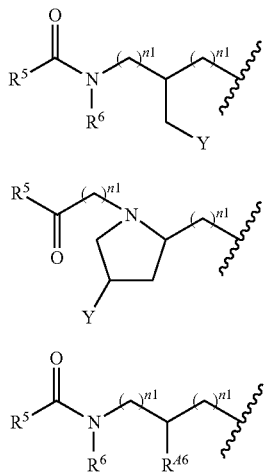

(IID)

(IIE)

(IIF)

wherein n1 is at each occurrence 0; Y is $(CH_2)_{0-2}H$, or $(CH_2)_{0-2}OH$; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IIIB) bearing $R^1$. In one embodiment, Y is H. In another embodiment, Y is OH. In another embodiment, Y is $CH_2OH$. In yet another embodiment, Y is $CH_2OC(=O)CH_3$.

In some embodiments is a compound of Formula (IIIB) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

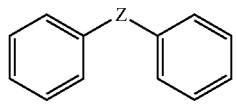

wherein Z is a bond, O, S, NH, $CH_2$ or C≡C. In some embodiments is a compound of Formula (IIIB) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (IIIB) is a compound wherein $R^4$ and $R^6$ are each independently at every occurrence hydrogen or $(C_1-C_6)$alkyl.

In any of the aforementioned embodiments of Formula (IIIB) is a compound wherein $R^4$ and $R^6$ are each independently at every occurrence hydrogen or methyl. In any of the aforementioned embodiments of Formula (IIIB) is a compound wherein $R^{44}$ is hydrogen and $R^{45}$ is methyl. In any of the aforementioned embodiments of Formula (IIIB) is a compound wherein $R^{44}$ is methyl and $R^{45}$ is methyl.

In another aspect described herein are compounds of Formula (IV):

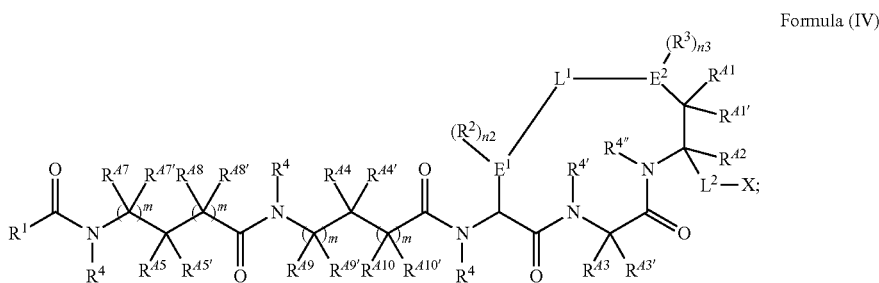

Formula (IV)

wherein:

$E^1$ and $E^2$ are each independently $(C_1-C_6)$alkyl, $(C_2-C_7)$alkenyl, $(C_2-C_7)$alkynyl, $(C_3-C_7)$cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —$C(O)NR^4$—, —$NR^4S(O)_2$—, —$S(O)_2NR^4$—, —$NR^4C(O)NR^4$—, —$NR^4C(O)O$—, —$OC(O)NR^4$—, or $(C_1-C_4)$alkylene optionally substituted with OH, CN, $NO_2$, halogen, $(C_1-C_6)$alkyl;

$L^2$ is a bond, or optionally substituted $(C_1-C_6)$alkylene;

X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$alkyl; and $R^{20b}$ is H or optionally substituted alkyl; or X is a group of formula

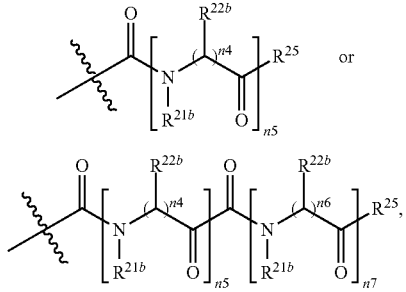

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

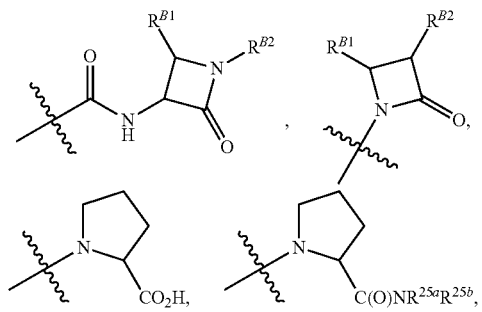

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)$ $OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IV) bearing X; or X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or X is a group of formula

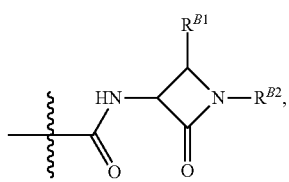

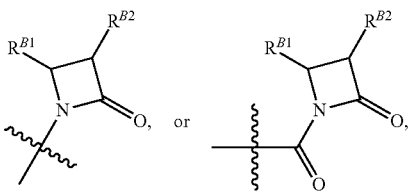

wherein $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)$ $N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IV) bearing X; or X is selected from

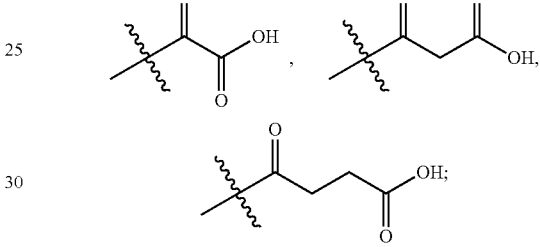

$R^1$ comprises a group of formula (IIA), (IIB), (IIC), (IID), (IIE), or (IIF)

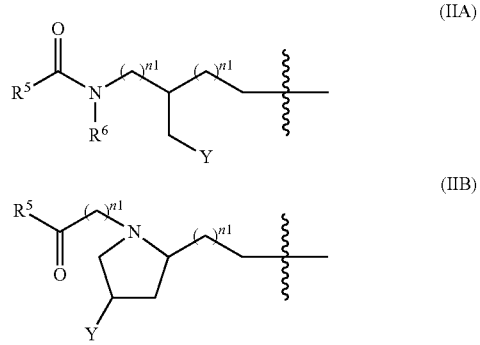

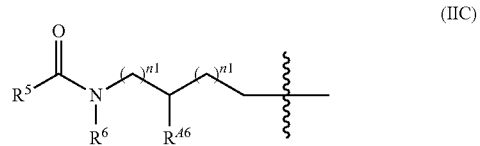

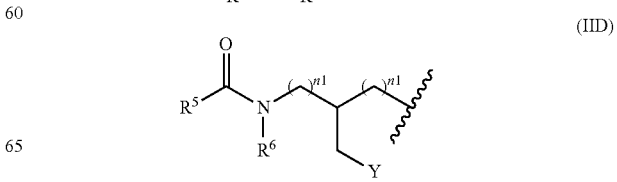

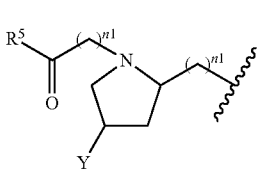

(IIE)

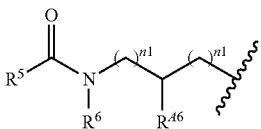

(IIF)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IV) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

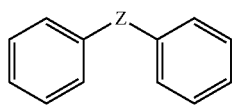

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (IV) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein at least one of $R^{4'}$ and $R^{4''}$ is not hydrogen, wherein any alkyl, cycloalkyl, heterocyclyl, aryl or heteroaryl is optionally substituted with 1 to 3 J; $R^{41}$, $R^{41'}$, $R^{42}$, $R^{43}$, $R^{43'}$, $R^{44}$, $R^{44'}$, $R^{45}$, $R^{45'}$, $R^{47}$, $R^{47'}$, $R^{48}$, $R^{48'}$, $R^{49}$, $R^{49'}$, $R^{410}$, and $R^{410'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with a substituent selected from F, Cl, Br, I, —CN, —NO₂, —OH, —CF₃, —OCF₃, —OCH₃, —NH₂, —N((C₁-C₄)alkyl)₂-, —NH(C₁-C₄)alkyl, C₁-C₆alkyl, C₃-C₈cycloalkyl, or C₁-C₆heteroalkyl;

J is halogen, R', OR', CN, CF₃, OCF₃, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH-C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO₂, —OH, —CF₃, —OCF₃, —OCH₃, —NH₂, —N((C₁-C₄)alkyl)₂-, —NH(C₁-C₄)alkyl, C₁-C₆alkyl, C₃-C₅cycloalkyl, or C₁-C₆heteroalkyl;

or, when two R' are bound to a nitrogen atom or to two adjacent nitrogen atoms, the two R' groups together with the nitrogen atom or atoms to which they are bound form a 3- to 8-membered monocyclic heterocyclic ring, or an 8- to 20-membered, bicyclic or tricyclic, heterocyclic ring system, wherein any ring or ring system further contains 1-3 additional heteroatoms selected from the group consisting of N, NR', O, S, S(O) and S(O)₂, wherein each ring is substituted with 0-3 substituents selected independently from F, Cl, Br, I, —CN, —NO₂, —OH, —CF₃, —OCF₃, —OCH₃, —NH₂, —N((C₁-C₄)alkyl)₂-, —NH(C₁-C₄)alkyl, C₁-C₆alkyl, C₃-C₅cycloalkyl, or C₁-C₆heteroalkyl;

wherein, in any bicyclic or tricyclic ring system, each ring is linearly fused, bridged, or spirocyclic, wherein each ring is either aromatic or nonaromatic, wherein each ring is optionally fused to a $(C_6-C_{10})$aryl, mono- or bicyclic 5-10 membered heteroaryl, $(C_3-C_{10})$cycloalkyl or mono- or bicyclic 3-10 membered heterocyclyl; or a pharmaceutically acceptable salt, solvate, or prodrug thereof.

In one embodiment is a compound of Formula (IV) having the structure of Formula (IVA):

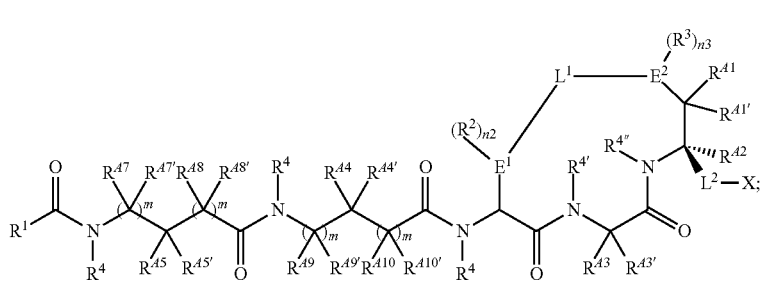

Formula (IVA)

wherein $E^1$, $E^2$, $L^1$, $L^2$, X, $R^1$, $R^2$, $R^3$, $R^4$, $R^{4'}$, $R^{4''}$, $R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, $R^{A10'}$, n2, n3, and m are as defined herein; or a pharmaceutically acceptable salt, solvate, or prodrug thereof.

In another embodiment is a compound of Formula (IVA) having the structure of Formula (IVB):

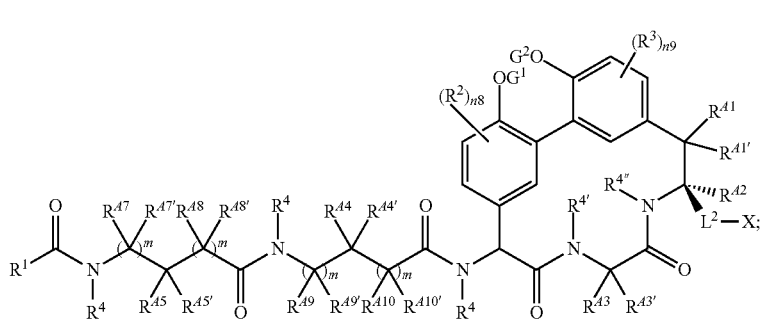

Formula (IVB)

wherein n8 and n9 are each independently 0, 1, 2, or 3; $G^1$ and $G^2$ are each independently a hydrogen or a glycosyl residue, or a group cleavable under physiological conditions to provide a compound of formula (IVB) wherein $G^1$ or $G^2$ respectively is hydrogen; or a pharmaceutically acceptable salt, solvate, or prodrug thereof.

In another embodiment is a compound having the structure of Formula (IVC):

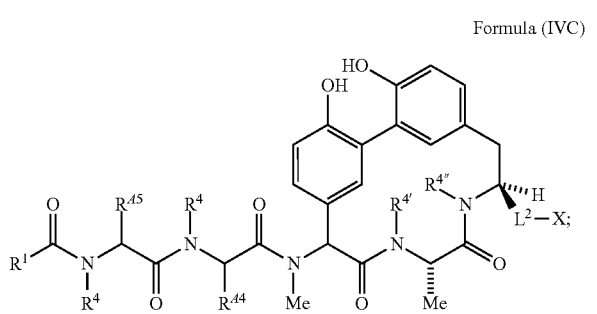

Formula (IVC)

wherein:
$L^2$ is a bond;
X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl; or X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1-C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$ alkyl; and $R^{20b}$ is H or optionally substituted alkyl; or X is a group of formula

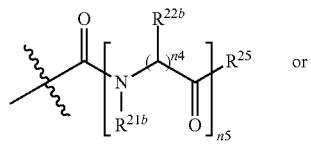

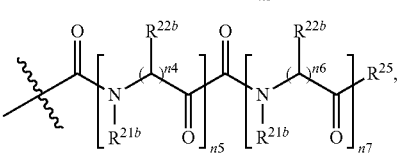

wherein n4, n5, and n6 are each independently 1, 2 or 3; n7 is 0, 1 or 2;

$R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

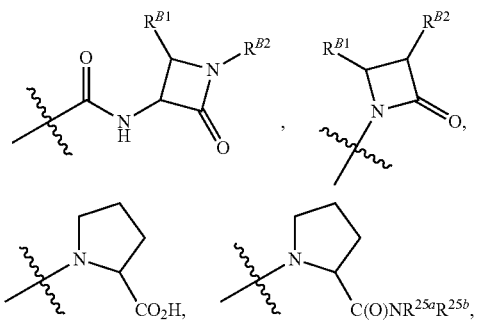

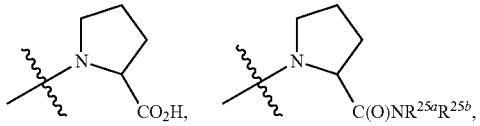

or NR^(25a)R^(25b) where $R^{25'}$ and $R^{25b}$ are each independently H, SO$_2$(C$_1$-C$_6$)alkyl, or optionally substituted alkyl; $R^{B1}$ and $R^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (IVC) bearing X; X is selected from

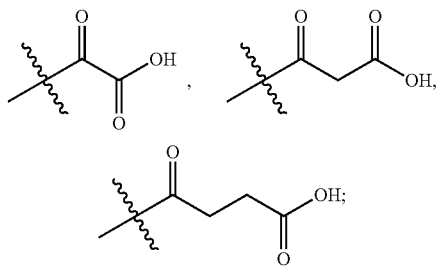

R$^1$ comprises a group of formula (IIA), (IIB), (IIC), (IID), (IIE), or (IIF)

(IIA)

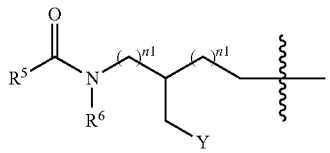

(IIB)

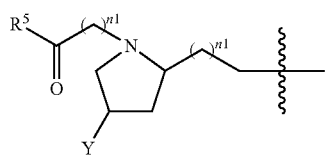

(IIC)

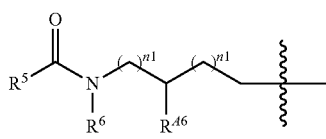

(IID)

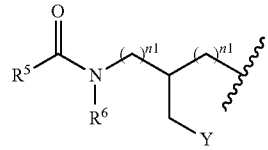

(IIE)

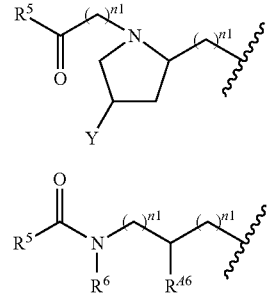

(IIF)

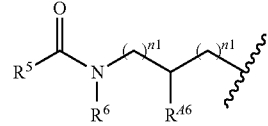

wherein n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$) alkyl; R$^{46}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, (C$_1$-C$_6$)alkoxy, (C$_1$-C$_6$)alkyl, (C$_3$-C$_7$)cycloalkyl, (C$_1$-C$_6$)-mono- or di-alkylamino, (C$_1$-C$_6$)alkoxycarbonyl, (C$_1$-C$_6$)alkylhydroxycarbonyl, (C$_1$-C$_6$)alkylaminocarbonyl, (C$_1$-C$_6$)alkylsulfonylamino, and (C$_6$-C$_{10}$)-arylsulfonylamino; and a wavy line indicates a point of attachment of R$^1$ to an atom of formula (IVC) bearing R$^1$;

R$^5$ is aryl, heteroaryl, or a linear or branched alkyl chain of about 1-22 carbon atoms, wherein R$^5$ is bonded to the carbonyl carbon to which it is attached directly or by an O or NR$^4$, to provide an amide, carbamate, or urea linkage, respectively; optionally comprising within the chain or at a chain terminus optionally substituted aryl, optionally substituted heteroaryl, or optionally substituted

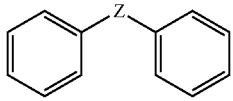

wherein Z is a bond, O, S, NH, CH$_2$ or C≡C;

R$^4$, R$^{4'}$, R$^{4''}$ and R$^6$ are each independently at every occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein at least one of R$^{4'}$ and R$^{4''}$ is not hydrogen, wherein any alkyl, cycloalkyl, heterocyclyl, aryl or heteroaryl is optionally substituted with 1 to 3 J; R$^{44}$ and R$^A$ are independently hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; J is halogen, R', OR', CN, CF$_3$, OCF$_3$, C(O), S(O), methylenedioxy, ethylenedioxy, (CH$_2$)$_{0-p}$N(R')$_2$, (CH$_2$)$_{0-p}$SR', (CH$_2$)$_{0-p}$C(O)R', (CH$_2$)$_{0-p}$C (O)OR', (CH$_2$)$_{0-p}$C(O)N(R')$_2$, (CH$_2$)$_{0-p}$NH—C(O)R', (CH$_2$)$_{0-p}$N(R')SO$_2$R', (CH$_2$)$_{0-p}$N(R')C(O)R', or (CH$_2$)$_{0-p}$C(=NH)N(R')$_2$; wherein p is 4, each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In one embodiment is a compound of Formula (IVC) wherein X is a group of formula

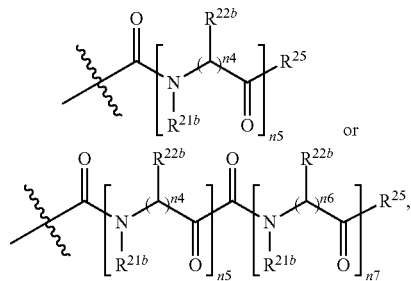

wherein n4, n5, and n6 are each independently 1, 2 or 3; n7 is 0, 1 or 2;

R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{25}$ is H, OH, OR$^C$,

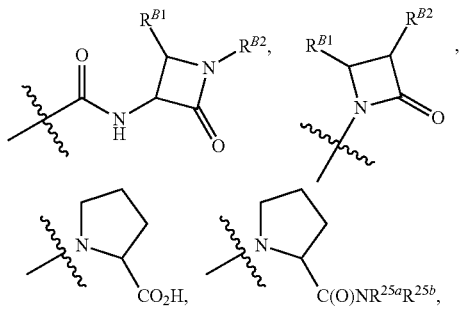

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (IB) bearing X.

In another embodiment is a compound of Formula (IVC) wherein X is a group of formula

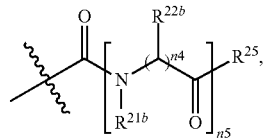

n4 is 1, n5 is 1, R$^{21b}$ is hydrogen, R$^{22b}$ is methyl, and R$^{25}$ is OH.

In another embodiment is a compound of Formula (IVC) wherein X is a group of formula

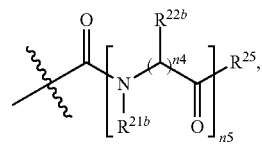

n4 is 1, n5 is 1, R$^{21b}$ is hydrogen, R$^{22b}$ is methyl, and R$^{25}$ is NH$_2$.

In another embodiment is a compound of Formula (IVC) wherein X is a group of formula

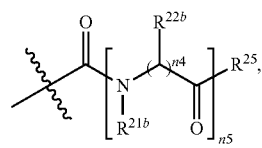

n4 is 1, n5 is 1, R$^{21b}$ is hydrogen, R$^{22b}$ is methyl, and R$^{25}$ is

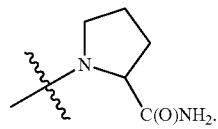

In another embodiment is a compound of Formula (IVC) wherein X is a group of formula

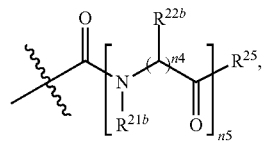

n4 is 1, n5 is 1, R$^{21b}$ is hydrogen, R$^{22b}$ is methyl, and R$^{25}$ is

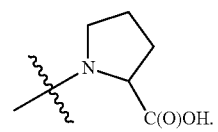

In another embodiment is a compound of Formula (IVC) wherein X is a group of formula

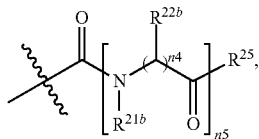

n4 is 1, n5 is 1, $R^{21b}$ is hydrogen, $R^{22b}$ is methyl, and $R^{25}$ is —NHSO$_2$Me.

In another embodiment is a compound of Formula (IVC) wherein X is a group of formula

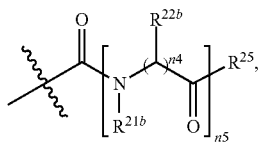

n4 is 1, n5 is 1, $R^{21b}$ is hydrogen, $R^{22b}$ is methyl, and $R^{25}$ is H.

In another embodiment is a compound of Formula (IVC) wherein X is a group of formula

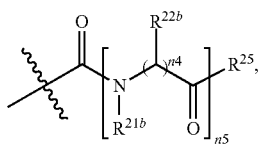

n4 is 1, n5 is 1, $R^{21b}$ is hydrogen, $R^{22b}$ is hydrogen, and $R^{25}$ is OH.

In another embodiment is a compound of Formula (IVC) wherein X is a group of formula

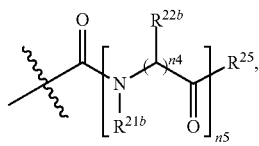

n4 is 1, n5 is 1, $R^{21b}$ is hydrogen, $R^{22b}$ is hydrogen, and $R^{25}$ is NH$_2$.

In another embodiment is a compound of Formula (IVC) wherein X is a group of formula

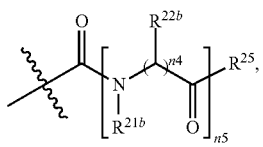

n4 is 1, n5 is 1, $R^{21b}$ is hydrogen, $R^{22b}$ is hydrogen, and $R^{25}$ is

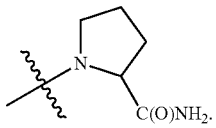

In another embodiment is a compound of Formula (IVC) wherein X is a group of formula

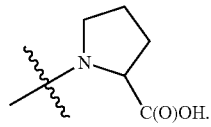

n4 is 1, n5 is 1, $R^{21b}$ is hydrogen, $R^{22b}$ is hydrogen, and $R^{25}$ is

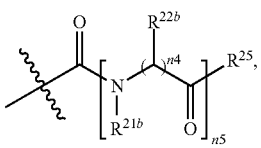

In another embodiment is a compound of Formula (IVC) wherein X is a group of formula

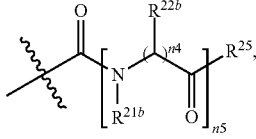

n4 is 1, n5 is 1, $R^{21b}$ is hydrogen, $R^{22b}$ is hydrogen, and $R^{25}$ is —NHSO$_2$Me.

In another embodiment is a compound of Formula (IVC) wherein X is a group of formula

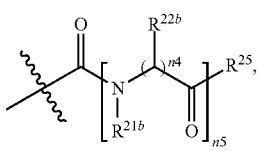

n4 is 1, n5 is 1, $R^{21b}$ is hydrogen, $R^{22b}$ is hydrogen, and $R^{25}$ is H.

In another embodiment is a compound of Formula (IVC) wherein X is a group of formula n4 is 2, n5 is 1, $R^{21b}$ is hydrogen, each $R^{22b}$ is independently hydrogen or hydroxy, and $R^{25}$ is NH$_2$.

In another embodiment is a compound of Formula (IVC) wherein X is a group of formula

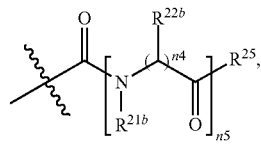

n4 is 2, n5 is 1, $R^{21b}$ is hydrogen, each $R^{22b}$ is independently hydrogen or hydroxy, and $R^{25}$ is NHMe.

In another embodiment is a compound of Formula (IVC) wherein X is a group of formula

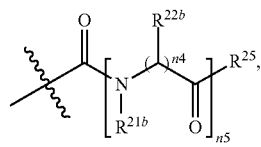

n4 is 2, n5 is 1, $R^{21b}$ is hydrogen, each $R^{22b}$ is independently hydrogen or hydroxy, and $R^{25}$ is OH.

In another embodiment is a compound of Formula (IVC) wherein X is a group of formula

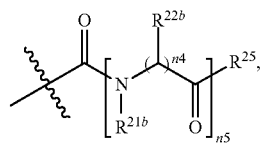

n4 is 2, n5 is 1, $R^{21b}$ is hydrogen, each $R^{22b}$ is independently hydrogen or hydroxy, and $R^{25}$ is OMe.

In another embodiment is a compound of Formula (IVC) wherein X is a group of formula

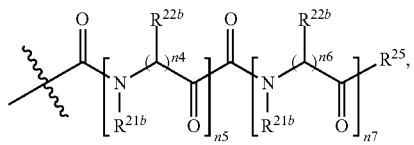

n4 is 1, n5 is 1, n7 is 0, $R^{21b}$ is hydrogen, $R^{22b}$ is methyl, and $R^{25}$ is —NH$_2$.

In another embodiment is a compound of Formula (IVC) wherein X is a group of formula

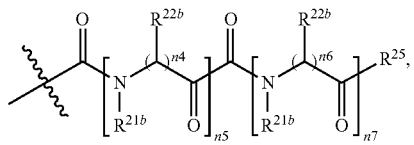

n4 is 1, n5 is 1, n7 is 0, $R^{21b}$ is hydrogen, R is methyl, and $R^{25}$ is —NHMe.

In another embodiment is a compound of Formula (IVC) wherein X is a group of formula

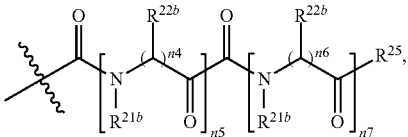

n4 is 1, n5 is 1, n7 is 0, $R^{21b}$ is hydrogen, $R^{22b}$ is methyl, and $R^{25}$ is —NMe$_2$.

In another embodiment is a compound of Formula (IVC) wherein X is a group of formula

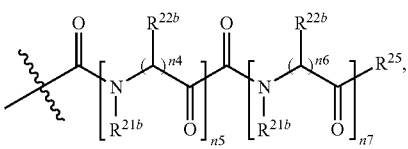

n4 is 1, n5 is 1, n7 is 0, $R^{21b}$ is hydrogen, $R^{22b}$ is hydrogen, and $R^{25}$ is —NH$_2$.

In another embodiment is a compound of Formula (IVC) wherein X is a group of formula

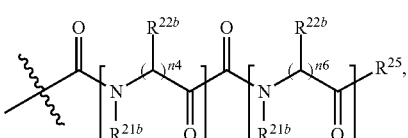

n4 is 1, n5 is 1, n7 is 0, $R^{21b}$ is hydrogen, $R^{22b}$ is hydrogen, and $R^{25}$ is OH.

In another embodiment is a compound of Formula (IVC) wherein X is C(O)$R^{20}$ and $R^{20}$ is optionally substituted alkyl. In another embodiment is a compound of Formula (IVC) wherein X is C(O)$R^{20}$ and $R^{20}$ is optionally substituted alkoxy. In some embodiments is a compound of Formula (IVC) wherein $R^{20}$ is alkoxy substituted with NH$_2$.

In another embodiment is a compound of Formula (IVC) wherein X is C(O)$R^{20}$ and $R^{20}$ is NR$^{20a}$R$^{20b}$, $R^{20a}$ is optionally substituted alkyl, and $R^{20b}$ is H. In further embodiments is a compound of Formula (IVC) wherein X is C(O)$R^{20}$ and $R^{20}$ is NR$^{20a}$R$^{20b}$, $R^{20a}$ is alkyl substituted with a hydroxyl group, and $R^{20b}$ is H. In further embodiments is a compound of Formula (IVC) wherein X is C(O)$R^{20}$ and $R^{20}$ is NR$^{20a}$R$^{20b}$, $R^{20a}$ is alkyl substituted with two hydroxyl groups, and $R^{20b}$ is H. In a further embodiment is a compound of Formula (IVC) wherein X is C(O)$R^{20}$ and $R^{20}$ is NR$^{20a}$R$^{20b}$, $R^{20a}$ is alkyl substituted with three hydroxyl groups, and $R^{20b}$ is H. In a further embodiment is a compound of Formula (IVC) wherein X is C(O)$R^{20}$ and $R^{20}$ is NR$^{20a}$R$^{20b}$, $R^{20a}$ is alkyl substituted with a hydroxyl group and a heteroaryl group, and $R^{20b}$ is H. In another embodiment is a compound of Formula (IVC) wherein X is C(O)$R^{20}$ and $R^{20}$ is NR$^{20a}$R$^{20b}$, $R^{20a}$ is alkyl substituted with methoxy, and $R^{20b}$ is H. In another embodiment is a compound of Formula (IVC) wherein X is C(O)$R^{20}$ and $R^{20}$ is optionally substituted alkoxy. In some embodiments is a compound of Formula (IVC) wherein $R^{20}$ is alkoxy substituted with NH$_2$.

In another embodiment is a compound of Formula (IVC) wherein X is selected from

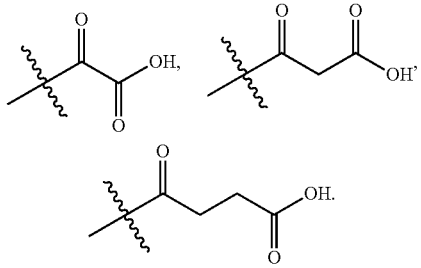

In yet another embodiment is a compound of Formula (IVC) wherein X is a group of formula

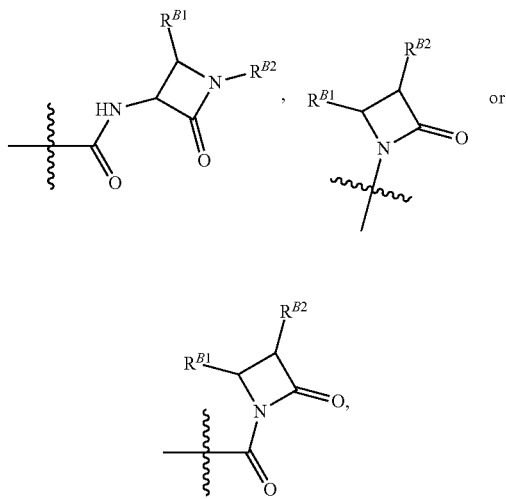

wherein $R^{B1}$ and $R^{B2}$ are each independently H. In another embodiment, $R^{B1}$ and $R^{B2}$ are each independently $(C_1-C_6)$ alkyl.

In one embodiment, $R^{B1}$ and $R^{B2}$ are each independently selected from methyl, ethyl, n-propyl, iso-propyl, n-butyl, iso-butyl, or tert-butyl.

In another embodiment is a compound of Formula (IVC) wherein X is

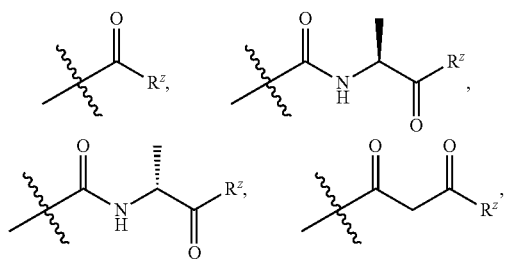

wherein $R^z$ is selected from H, $N(CH_3)_2$, $NHSO_2CH_3$, OH, $NH_2$,

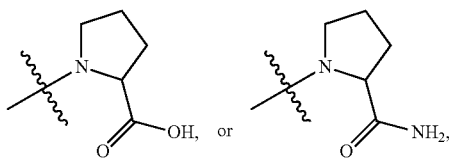 [SMILES: *N1CCCC1C(=O)O ; "or" ; *N1CCCC1C(N)=O]

In a further embodiment, $R^z$ is OH. In another embodiment, $R^z$ is $NH_2$.

In another embodiment is a compound of Formula (IVC) wherein X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl. In some embodiments is a compound of Formula (IVC) wherein X is $CO_2H$. In some embodiments is a compound of Formula (IVC) wherein X is $CH_2C(=O)H$. In some embodiments is a compound of Formula (IVC) wherein X is $C(=O)NHCH_2B(OR^B)_2$ and $R^B$ is H or $(C_1-C_6)$alkyl.

In another embodiment is a compound of Formula (IVC) wherein $R^1$ comprises a group of formula (IIA), (IIB), (IIC), (IID), (IIE), or (IIF)

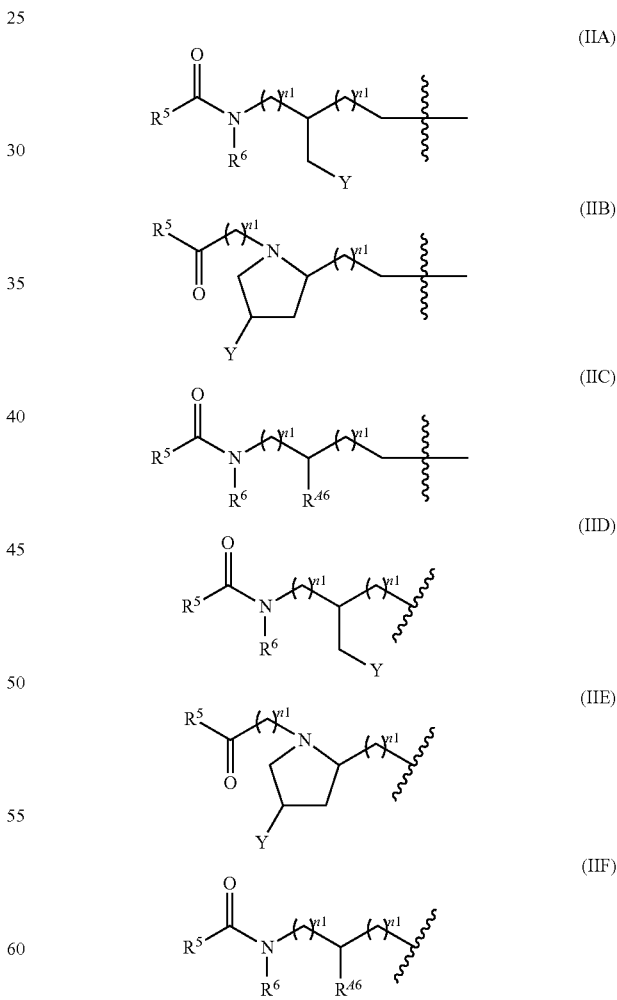

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$ alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IVC) bearing $R^1$. In one embodiment, Y is H. In another embodiment, Y is OH. In another embodiment, Y is $CH_2OH$. In yet another embodiment, Y is $CH_2OC(=O)CH_3$.

In another embodiment is a compound of Formula (IVC) wherein $R^1$ comprises a group of formula (IID), (IIE), or (IIF)

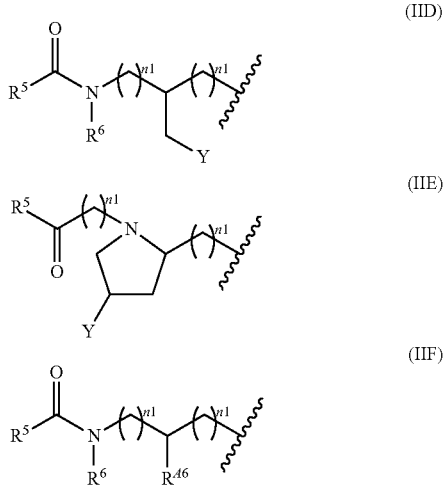

wherein n1 is at each occurrence 0; Y is $(CH_2)_{0-2}H$, or $(CH_2)_{0-2}OH$; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (IVC) bearing $R^1$.

In one embodiment, Y is H. In another embodiment, Y is OH. In another embodiment, Y is $CH_2OH$. In yet another embodiment, Y is $CH_2OC(=O)CH_3$.

In some embodiments is a compound of Formula (IVC) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

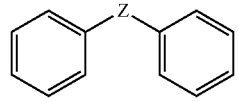

wherein Z is a bond, O, S, NH, $CH_2$ or C≡C. In some embodiments is a compound of Formula (IVC) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (IVC) is a compound wherein $R^4$ and $R^6$ are each independently at every occurrence hydrogen or $(C_1-C_6)$alkyl.

In any of the aforementioned embodiments of Formula (IVC) is a compound wherein $R^4$ and $R^6$ are each independently at every occurrence hydrogen or methyl. In any of the aforementioned embodiments of Formula (IVC) is a compound wherein $R^{A4}$ is hydrogen and $R^{A5}$ is methyl. In any of the aforementioned embodiments of Formula (IVC) is a compound wherein $R^{A4}$ is methyl and $R^{A5}$ is methyl. In any of the aforementioned embodiments of Formula (IVC) is a compound wherein $R^{4'}$ is methyl and $R^{4''}$ is hydrogen. In any of the aforementioned embodiments of Formula (IVC) is a compound wherein $R^{4'}$ is hydrogen and $R^{4''}$ is methyl. In any of the aforementioned embodiments of Formula (IVC) is a compound wherein $R^{4'}$ and $R^{4''}$ are each methyl.

In another aspect described herein are compounds of Formula (V):

Formula (V)

wherein:

$E^1$ and $E^2$ are each independently aryl;

$L^1$ is a bond;

$L^2$ is a bond;

X is $C(O)R^{20}$, and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$ alkyl; and $R^{20b}$ is H or optionally substituted alkyl; or X is a group of formula

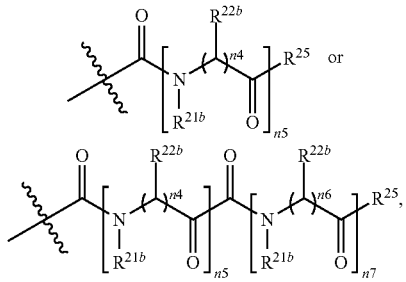

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, wherein any alkyl is optionally substituted with 1 to 3 J; $R^{25}$ is H, OH, $OR^C$,

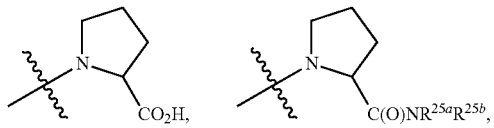

or $NR^{25a}R^{25b}$; where $R^{25a}$ and $R^{25b}$ are each independently H, $SO_2(C_1-C_6)$alkyl, or optionally substituted alkyl; $R^C$ is independently at each occurrence H or $(C_1-C_6)$ alkyl, and a wavy line indicates a point of attachment of X to a carbon of formula (V) bearing X; or X is $CO_2H$, $CH_2CO_2H$, $C(=O)NHCH_2C(=O)H$, or $CH_2C(=O)H$, or X is a group of formula

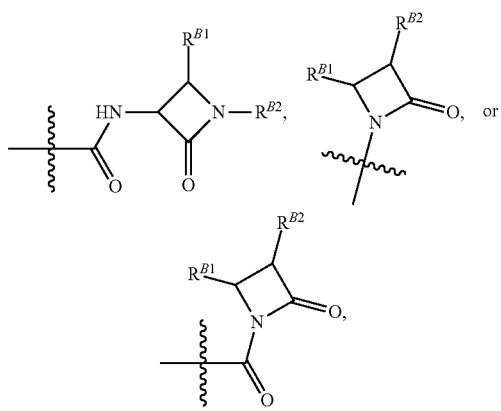

wherein $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (V) bearing X; or X is selected from

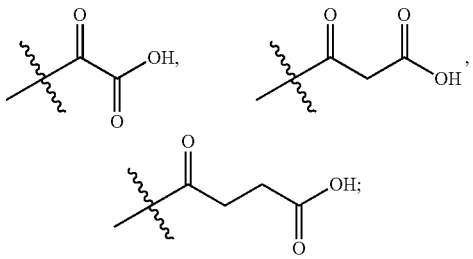

$R^1$ comprises a group of formula (IID), (IIE), or (IIF)

(IID)
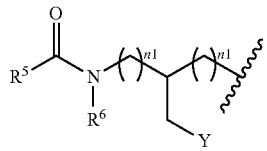

(IIE)
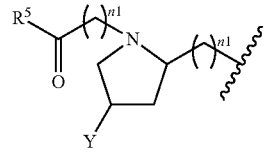

(IIF)
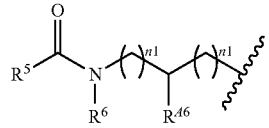

wherein n1 is independently at each occurrence 0, 1, or 2; Y is $(CH_2)_{0-2}H$, or $(CH_2)_{0-2}OH$; $R^{46}$ is hydrogen, or $(C_1-C_6)$ alkyl, wherein alkyl is optionally substituted with 1 to 3 substituents, wherein each substituent is independently selected from the group consisting of halogen, amino, hydroxyl, aminocarbonyl, hydroxycarbonyl, 5- to 7-membered heterocyclyl, $(C_1-C_6)$alkoxy, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (V) bearing $R^1$;

$R^5$ is aryl, heteroaryl, or a linear or branched alkyl chain of about 1-22 carbon atoms, wherein $R^5$ is bonded to the carbonyl carbon to which it is attached directly or by $NR^4$, to provide an amide, or urea linkage, respectively; optionally comprising within the chain or at a chain terminus optionally substituted aryl, optionally substituted heteroaryl, or optionally substituted

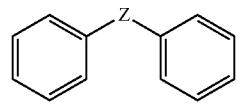

wherein Z is a bond, O, S, NH, $CH_2$ or $C≡C$;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (V) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH-C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)$alkyl, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In one embodiment is a compound of Formula (V) having the structure of Formula (VA):

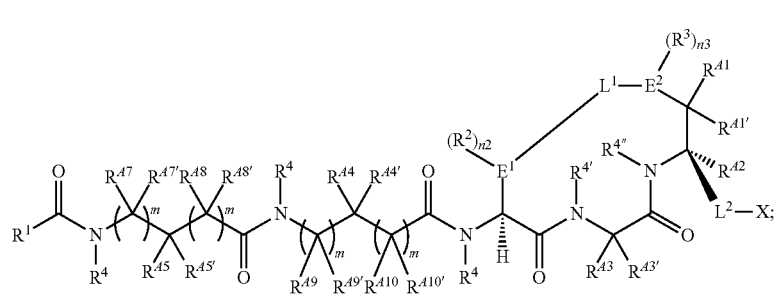

Formula (VA)

wherein $E^1$, $E^2$, $L^1$, $L^2$, X, $R^1$, $R^2$, $R^3$, $R^4$, $R^{4'}$, $R^{4''}$, $R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, $R^{A10'}$, n2, n3, and m are as defined herein; or a pharmaceutically acceptable salt, solvate, or prodrug thereof.

In another embodiment is a compound of Formula (VB):

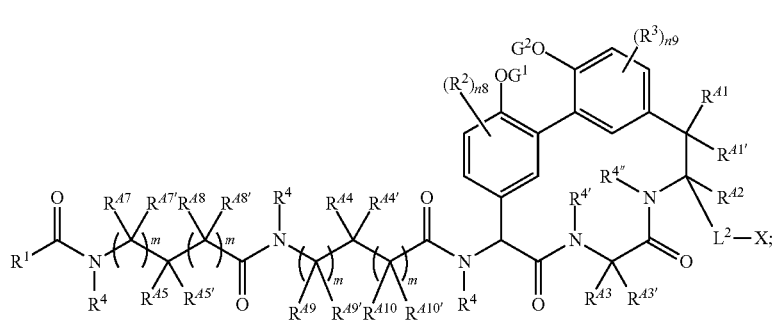

Formula (VB)

wherein:

n8 and n9 are each independently 0, 1, 2, or 3;

$G^1$ and $G^2$ are each independently a hydrogen or a glycosyl residue, or a group cleavable under physiological conditions to provide a compound of formula (VB) wherein $G^1$ or $G^2$ respectively is hydrogen;

$L^2$ is a bond;

X is $C(O)R^{20}$, and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1-C_6)$alkyl; and $R^{20b}$ is H or optionally substituted alkyl; or X is a group of formula

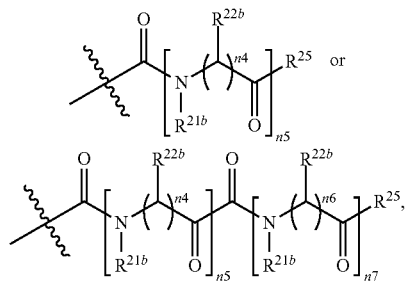

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, wherein any alkyl is optionally substituted with 1 to 3 J; $R^{25}$ is H, OH, $OR^C$,

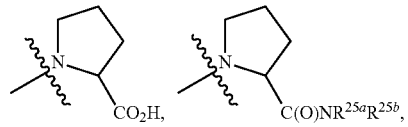

or $NR^{25a}R^{25b}$; where $R^{25a}$ and $R^{25b}$ are each independently H, $SO_2(C_1-C_6)$alkyl, or optionally substituted alkyl; $R^C$ is independently at each occurrence H or $(C_1-C_6)$ alkyl, and a wavy line indicates a point of attachment of X to a carbon of formula (VB) bearing X; or X is $CO_2H$, $CH_2CO_2H$, $C(=O)NHCH_2C(=O)H$, or $CH_2C(=O)H$, or X is a group of formula

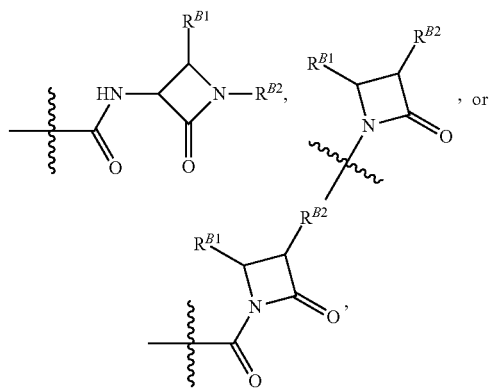

wherein $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)$ $N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (VB) bearing X; or X is selected from

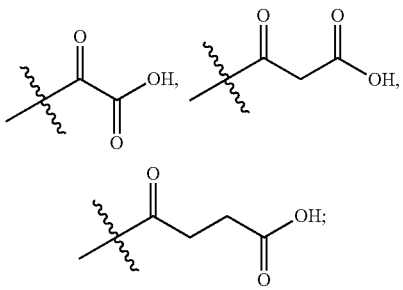

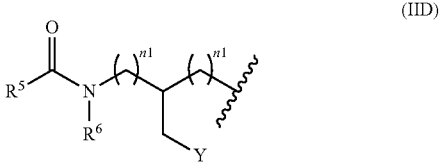

$R^1$ comprises a group of formula (IID), (IIE), or (IIF)

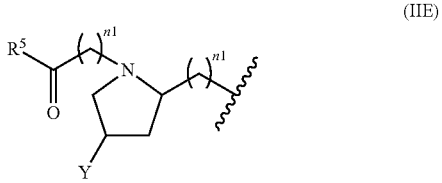
(IID)

(IIE)

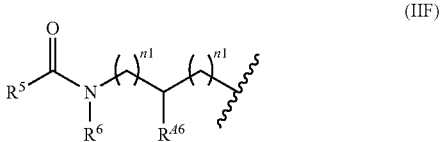
(IIF)

wherein n1 is independently at each occurrence 0, 1, or 2; Y is $(CH_2)_{0-2}H$, or $(CH_2)_{0-2}OH$; $R^{46}$ is hydrogen, or $(C_1-C_6)$ alkyl, wherein alkyl is optionally substituted with 1 to 3 substituents, wherein each substituent is independently selected from the group consisting of halogen, amino, hydroxyl, aminocarbonyl, hydroxycarbonyl, 5- to 7-membered heterocyclyl, $(C_1-C_6)$alkoxy, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (VB) bearing $R^1$;

$R^5$ is aryl, heteroaryl, or a linear or branched alkyl chain of about 1-22 carbon atoms, wherein $R^5$ is bonded to the carbonyl carbon to which it is attached directly or by $NR^4$, to provide an amide, or urea linkage, respectively; optionally comprising within the chain or at a chain terminus optionally substituted aryl, optionally substituted heteroaryl, or optionally substituted

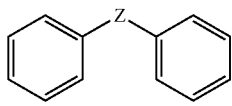

wherein Z is a bond, O, S, NH, CH$_2$ or C≡C;
each m is independently 0, 1, or 2;
R$^4$, R$^{4'}$, R$^{4''}$ and R$^6$ are each independently at every occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J;
R$^{41}$, R$^{41'}$, R$^{42}$, R$^{43}$, R$^{43'}$, R$^{44}$, R$^{44'}$, R$^{45}$, R$^{45'}$, R$^{47}$, R$^{47'}$, R$^{48}$, R$^{48'}$, R$^{49}$, R$^{49'}$, R$^{410}$, and R$^{410'}$ are independently at each occurrence hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; J is halogen, R', OR', CN, CF$_3$, OCF$_3$, C(O), S(O), methylenedioxy, ethylenedioxy, (CH$_2$)$_{0-p}$N(R')$_2$, (CH$_2$)$_{0-p}$SR', (CH$_2$)$_{0-p}$C(O)R', (CH$_2$)$_{0-p}$C(O)OR', (CH$_2$)$_{0-p}$C(O)N(R')$_2$, (CH$_2$)$_{0-p}$NH—C(O)R', (CH$_2$)$_{0-p}$N(R')SO$_2$R', (CH$_2$)$_{0-p}$N(R')C(O)R', or (CH$_2$)$_{0-p}$C(=NH)N(R')$_2$; wherein p is 4,
each R' is independently at each occurrence hydrogen, (C$_1$-C$_6$)-alkyl, (C$_2$-C$_7$)-alkenyl, (C$_2$-C$_7$)-alkynyl, (C$_3$-C$_{10}$)-cycloalkyl, (C$_3$-C$_{10}$)-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;
or, when two R' are bound to a nitrogen atom or to two adjacent nitrogen atoms, the two R' groups together with the nitrogen atom or atoms to which they are bound optionally forms a 3- to 8-membered monocyclic heterocyclic ring;
or a pharmaceutically acceptable salt, solvate, or prodrug thereof.

In another embodiment is a compound of Formula (VC):

Formula (VC)

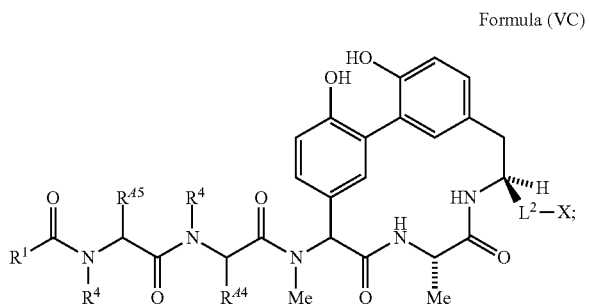

wherein:
L$^2$ is a bond;
X is C(O)R$^{20}$, and R$^{20}$ is optionally substituted alkyl, optionally substituted alkoxy, or NR$^{20a}$R$^{20b}$, where R$^{20a}$ is H, optionally substituted alkyl, heteroalkyl, or SO$_2$(C$_1$-C$_6$) alkyl;
and R$^{20b}$ is H or optionally substituted alkyl; or X is a group of formula

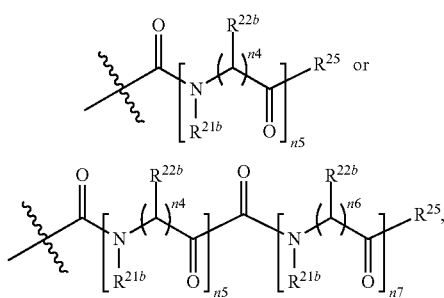

wherein n4, n5, and n6 are each independently 1, 2 or 3; n7 is 0, 1 or 2; R$^{21b}$ and R$^{22b}$ are independently at each occurrence hydrogen, hydroxy, (C$_1$-C$_6$)alkyl, wherein any alkyl is optionally substituted with 1 to 3 J; R$^{25}$ is H, OH, OR$^C$,

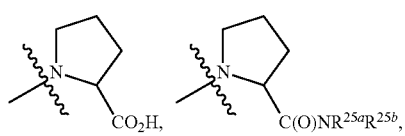

or NR$^{25a}$R$^{25b}$; where R$^{25a}$ and R$^{25b}$ are each independently H, SO$_2$(C$_1$-C$_6$)alkyl, or optionally substituted alkyl; R$^C$ is independently at each occurrence H or (C$_1$-C$_6$) alkyl, and a wavy line indicates a point of attachment of X to a carbon of formula (VC) bearing X; or X is CO$_2$H, CH$_2$CO$_2$H, C(=O)NHCH$_2$C(=O)H, CH$_2$C(=O)H, or C(=O)NHCH$_2$B(OR$^B$)$_2$ wherein R$^B$ is H or (C$_1$-C$_6$)alkyl; or X is a group of formula

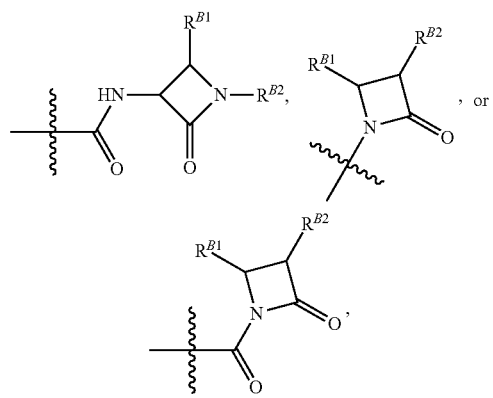

wherein R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O) N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, NR$^C{}_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (VC) bearing X; or X is selected from

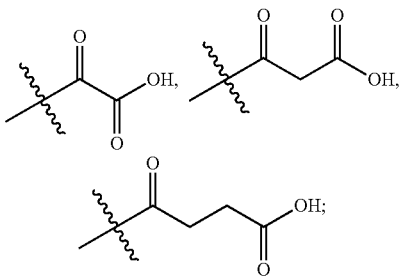

$R^1$ comprises a group of formula (IID), (IIE), or (IIF)

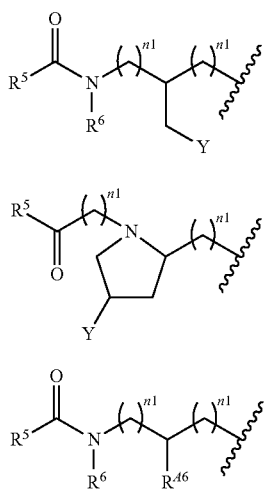

(IID)

(IIE)

(IIF)

wherein n1 is independently at each occurrence 0, 1, or 2; Y is $(CH_2)_{0-2}H$, or $(CH_2)_{0-2}OH$; $R^{46}$ is hydrogen, or $(C_1-C_6)$ alkyl, wherein alkyl is optionally substituted with 1 to 3 substituents, wherein each substituent is independently selected from the group consisting of halogen, amino, hydroxyl, aminocarbonyl, hydroxycarbonyl, 5- to 7-membered heterocyclyl, $(C_1-C_6)$alkoxy, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (VC) bearing $R^1$;

$R^5$ is aryl, heteroaryl, or a linear or branched alkyl chain of about 1-22 carbon atoms, wherein $R^5$ is bonded to the carbonyl carbon to which it is attached directly or by $NR^4$, to provide an amide, or urea linkage, respectively; optionally comprising within the chain or at a chain terminus optionally substituted aryl, optionally substituted heteroaryl, or optionally substituted

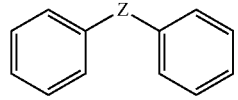

wherein Z is a bond, O, S, NH, $CH_2$ or C≡C;
each m is independently 0, 1, or 2;
$R^4$, and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{44}$ and $R^{45}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH—C(O)R'$, $(CH_2)_{0-p}N(R')SO_2R'$, $(CH_2)_{0-p}—N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —N$((C_1-C_4)$alkyl$)_2$-, —NH$(C_1-C_4)$alkyl, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In one embodiment is a compound of Formula (VC) wherein X is a group of formula

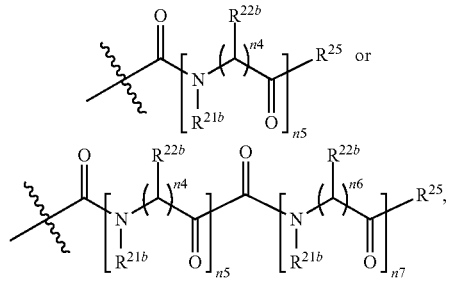

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

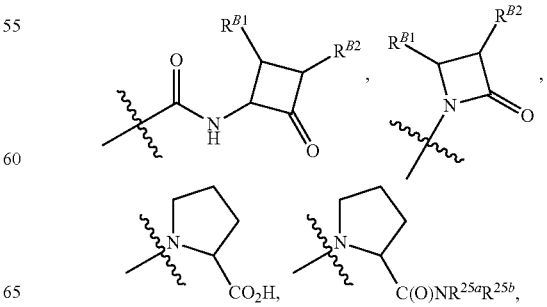

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (IB) bearing X.

In another embodiment is a compound of Formula (VC) wherein X is a group of formula

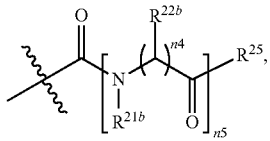

n4 is 1, n5 is 1, $R^{21b}$ is hydrogen, $R^{22b}$ is methyl, and $R^{25}$ is OH.

In another embodiment is a compound of Formula (VC) wherein X is a group of formula

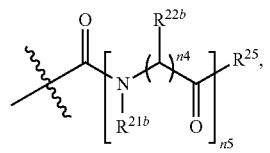

n4 is 1, n5 is 1, $R^{21b}$ is hydrogen, $R^{22b}$ is methyl, and $R^{25}$ is $NH_2$.

In another embodiment is a compound of Formula (VC) wherein X is a group of formula

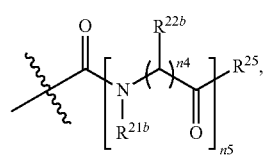

n4 is 1, n5 is 1, $R^{21b}$ is hydrogen, $R^{22b}$ is methyl, and $R^{25}$ is

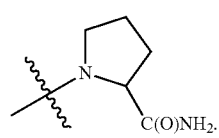

In another embodiment is a compound of Formula (VC) wherein X is a group of formula

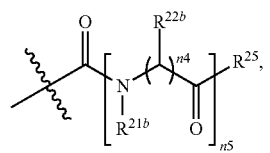

n4 is 1, n5 is 1, $R^{21b}$ is hydrogen, $R^{22b}$ is methyl, and $R^{25}$ is

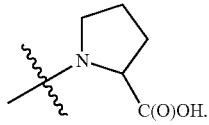

In another embodiment is a compound of Formula (VC) wherein X is a group of formula

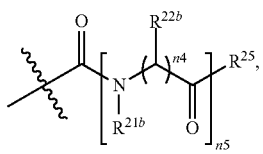

n4 is 1, n5 is 1, $R^{21b}$ is hydrogen, $R^{22b}$ is methyl, and $R^{25}$ is $—NHSO_2Me$.

In another embodiment is a compound of Formula (VC) wherein X is a group of formula

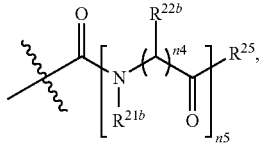

n4 is 1, n5 is 1, $R^{21b}$ is hydrogen, $R^{22b}$ is methyl, and $R^{25}$ is H.

In another embodiment is a compound of Formula (VC) wherein X is a group of formula

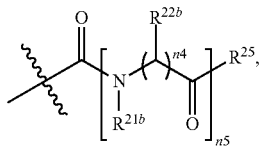

n4 is 1, n5 is 1, $R^{21b}$ is hydrogen, $R^{22b}$ is hydrogen, and $R^{25}$ is OH.

In another embodiment is a compound of Formula (VC) wherein X is a group of formula

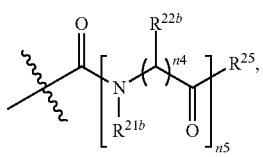

n4 is 1, n5 is 1, $R^{21b}$ is hydrogen, $R^{22b}$ is hydrogen, and $R^{25}$ is $NH_2$.

In another embodiment is a compound of Formula (VC) wherein X is a group of formula

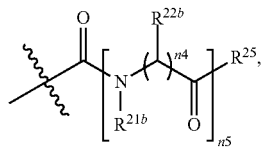

n4 is 1, n5 is 1, $R^{21b}$ is hydrogen, $R^{22b}$ is hydrogen, and $R^{25}$ is

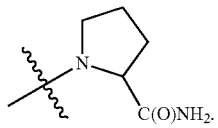

In another embodiment is a compound of Formula (VC) wherein X is a group of formula

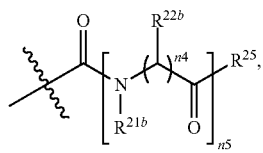

n4 is 1, n5 is 1, $R^{21b}$ is hydrogen, $R^{22b}$ is hydrogen, and $R^{25}$ is

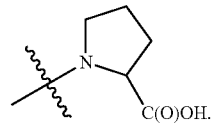

In another embodiment is a compound of Formula (VC) wherein X is a group of formula

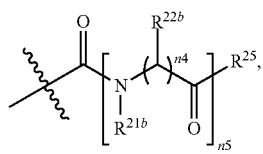

n4 is 1, n5 is 1, $R^{21b}$ is hydrogen, $R^{22b}$ is hydrogen, and $R^{25}$ is —NHSO$_2$Me.

In another embodiment is a compound of Formula (VC) wherein X is a group of formula

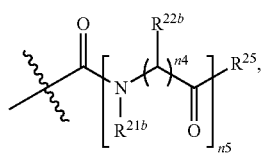

n4 is 1, n5 is 1, $R^{21b}$ is hydrogen, $R^{22b}$ is hydrogen, and $R^{25}$ is H.

In another embodiment is a compound of Formula (VC) wherein X is a group of formula

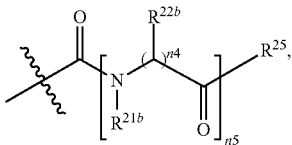

n4 is 2, n5 is 1, $R^{21b}$ is hydrogen, each $R^{22b}$ is independently hydrogen or hydroxy, and $R^{25}$ is NH$_2$.

In another embodiment is a compound of Formula (VC) wherein X is a group of formula

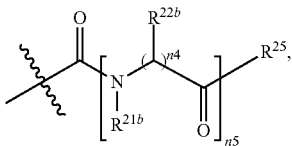

n4 is 2, n5 is 1, $R^{21b}$ is hydrogen, each $R^{22b}$ is independently hydrogen or hydroxy, and $R^{25}$ is NHMe.

In another embodiment is a compound of Formula (VC) wherein X is a group of formula

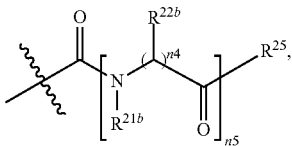

n4 is 2, n5 is 1, $R^{21b}$ is hydrogen, each $R^{22b}$ is independently hydrogen or hydroxy, and $R^{25}$ is OH.

In another embodiment is a compound of Formula (VC) wherein X is a group of formula

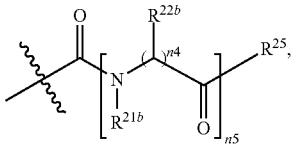

n4 is 2, n5 is 1, $R^{21b}$ is hydrogen, each $R^{22b}$ is independently hydrogen or hydroxy, and $R^{25}$ is OMe.

In another embodiment is a compound of Formula (VC) wherein X is a group of formula

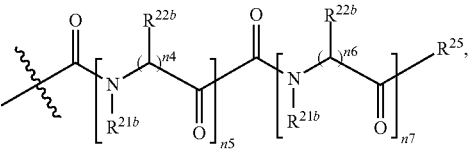

n4 is 1, n5 is 1, n7 is 0, $R^{21b}$ is hydrogen, $R^{22b}$ is methyl, and $R^{25}$ is —NH$_2$.

In another embodiment is a compound of Formula (VC) wherein X is a group of formula

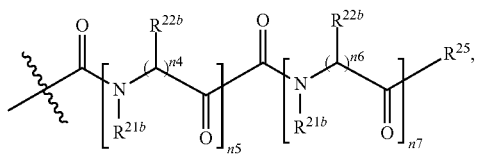

n4 is 1, n5 is 1, n7 is 0, $R^{21b}$ is hydrogen, $R^{22b}$ is methyl, and $R^{25}$ is —NHMe.

In another embodiment is a compound of Formula (VC) wherein X is a group of formula

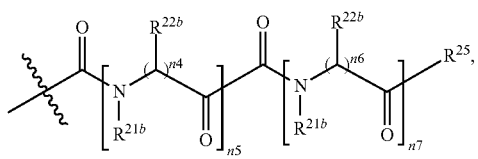

n4 is 1, n5 is 1, n7 is 0, $R^{21b}$ is hydrogen, $R^{22b}$ is methyl, and $R^{25}$ is —NMe$_2$.

In another embodiment is a compound of Formula (VC) wherein X is a group of formula

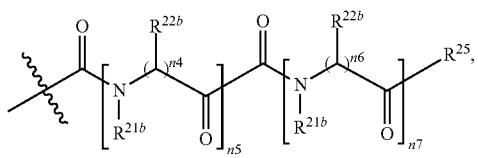

n4 is 1, n5 is 1, n7 is 0, $R^{21b}$ is hydrogen, $R^{22b}$ is hydrogen, and $R^{25}$ is —NH$_2$.

In another embodiment is a compound of Formula (VC) wherein X is a group of formula

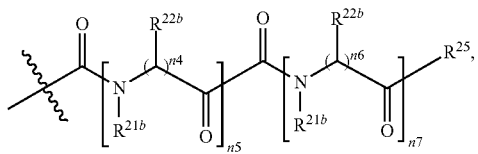

n4 is, s 1, n5 is 1, n7 is 0, $R^{21b}$ is hydrogen, $R^{22b}$ is hydrogen, and $R^{25}$ is OH.

In another embodiment is a compound of Formula (VC) wherein X is C(O)R$^{20}$ and R$^{20}$ is optionally substituted alkyl. In another embodiment is a compound of Formula (VC) wherein X is C(O)R$^{20}$ and R$^{20}$ is optionally substituted alkoxy. In some embodiments is a compound of Formula (VC) wherein R$^{20}$ is alkoxy substituted with NH$_2$.

In another embodiment is a compound of Formula (VC) wherein X is C(O)R$^{20}$ and R$^{20}$ is NR$^{20a}$R$^{20b}$, R$^{20a}$ is optionally substituted alkyl, and R$^{20b}$ is H. In further embodiments is a compound of Formula (VC) wherein X is C(O)R$^{20}$ and R$^{20}$ is NR$^{20a}$R$^{20b}$, R$^{20a}$ is alkyl substituted with a hydroxyl group, and R$^{20b}$ is H. In further embodiments is a compound of Formula (VC) wherein X is C(O)R$^{20}$ and R$^{20}$ is NR$^{20a}$R$^{20b}$, R$^{20a}$ is alkyl substituted with two hydroxyl groups, and R$^{20b}$ is H. In a further embodiment is a compound of Formula (VC) wherein X is C(O)R$^{20}$ and R$^{20}$ is NR$^{20a}$R$^{20b}$, R$^{20a}$ is alkyl substituted with three hydroxyl groups, and R$^{20b}$ is H. In a further embodiment is a compound of Formula (VC) wherein X is C(O)R$^{20}$ and R$^{20}$ is NR$^{20a}$R$^{20b}$, R$^{20a}$ is alkyl substituted with a hydroxyl group and a heteroaryl group, and R$^{20b}$ is H. In another embodiment is a compound of Formula (VC) wherein X is C(O)R$^{20}$ and R$^{20}$ is NR$^{20a}$R$^{20b}$, R$^{20a}$ is alkyl substituted with methoxy, and R$^{20b}$ is H. In another embodiment is a compound of Formula (VC) wherein X is C(O)R$^{20}$ and R$^{20}$ is optionally substituted alkoxy. In some embodiments is a compound of Formula (VC) wherein R$^{20}$ is alkoxy substituted with NH$_2$.

In another embodiment is a compound of Formula (VC) wherein X is selected from

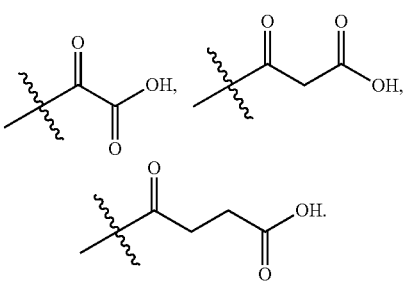

In another embodiment is a compound of Formula (VC) wherein X is CO$_2$H, CH$_2$CO$_2$H, C(=O)NHCH$_2$C(=O)H, CH$_2$C(=O)H, or C(=O)NHCH$_2$B(OR$^B$)$_2$ wherein R$^B$ is H or (C$_1$-C$_6$)alkyl. In some embodiments is a compound of Formula (VC) wherein X is CO$_2$H. In some embodiments is a compound of Formula (VC) wherein X is CH$_2$C(=O)H.

In some embodiments is a compound of Formula (VC) wherein X is C(=O)NHCH$_2$B(OR$^B$)$_2$ and R$^B$ is H or (C$_1$-C$_6$)alkyl.

In another embodiment is a compound of Formula (VC) wherein R$^1$ comprises a group of formula (IID), (IIE), or (IIF)

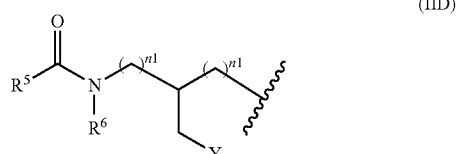
(IID)

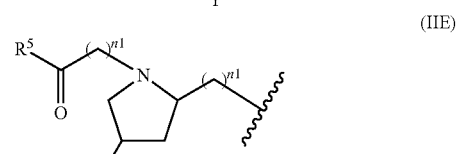
(IIE)

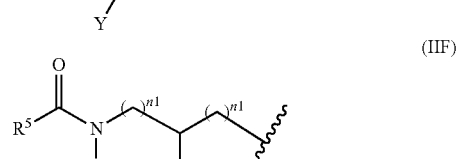
(IIF)

wherein n1 is at each occurrence 0; Y is (CH$_2$)$_{0-2}$H, or (CH$_2$)$_{0-2}$OH; R$^{46}$ is hydrogen, (C$_1$-C$_6$)alkyl, (C$_3$-C$_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, ($C_1$-$C_6$)alkoxy, ($C_1$-$C_6$)alkyl, ($C_3$-$C_7$)cycloalkyl, ($C_1$-$C_6$)-mono- or di-alkylamino, ($C_1$-$C_6$)alkoxycarbonyl, ($C_1$-$C_6$)alkylhydroxycarbonyl, ($C_1$-$C_6$)alkylaminocarbonyl, ($C_1$-$C_6$)alkylsulfonylamino, and ($C_6$-$C_{10}$)-arylsulfonylamino; and a wavy line indicates a point of attachment of $R^1$ to an atom of formula (VC) bearing $R^1$.

In one embodiment, Y is H. In another embodiment, Y is OH. In another embodiment, Y is $CH_2OH$. In yet another embodiment, Y is $CH_2OC(=O)CH_3$.

In some embodiments is a compound of Formula (VC) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

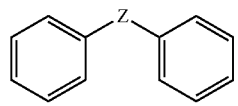

wherein Z is a bond, O, S, NH, $CH_2$ or C≡C. In some embodiments is a compound of Formula (VC) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (VC) is a compound wherein $R^4$ and $R^6$ are each independently at every occurrence hydrogen or ($C_1$-$C_6$)alkyl.

In any of the aforementioned embodiments of Formula (VC) is a compound wherein $R^4$ and $R^6$ are each independently at every occurrence hydrogen or methyl.

In any of the aforementioned embodiments of Formula (VC) is a compound wherein $R^{44}$ is hydrogen and $R^{45}$ is methyl. In any of the aforementioned embodiments of Formula (VC) is a compound wherein $R^{44}$ is methyl and $R^{45}$ is methyl.

In another aspect described herein are compounds of Formula (VI):

wherein:

$E^1$ and $E^2$ are each independently ($C_1$-$C_6$)alkyl, ($C_2$-$C_7$)alkenyl, ($C_2$-$C_7$)alkynyl, ($C_3$-$C_7$)cycloalkyl, heterocyclyl, heteroaryl, or aryl;

$L^1$ is a bond, —O—, —S—, —$NR^4$—, —C(O)—, —$CH_2O$—, —$OCH_2$—, —$CH_2S$—, —$SCH_2$—, —$CH_2NR^4$—, —$NR^4CH_2$—, —$NR^4C(O)$—, —C(O)$NR^4$—, —$NR^4S(O)_2$—, —$S(O)_2NR^4$—, —$NR^4C(O)NR^4$—, —$NR^4C(O)O$—, —$OC(O)NR^4$—, or ($C_1$-$C_4$)alkylene optionally substituted with OH, CN, $NO_2$, halogen, ($C_1$-$C_6$)alkyl;

$L^2$ is a bond, or optionally substituted ($C_1$-$C_6$)alkylene;

X is $C(O)R^{20}$, $S(O)_2R^{20}$, or $C(O)NR^{21a}C(R^{22a})(R^{23a})B(OR^{24})_2$ wherein $R^{21a}$, $R^{22a}$, $R^{23a}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or ($C_1$-$C_6$)alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1$-$C_6)$alkyl; and $R^{20b}$ is H or optionally substituted alkyl; or X is a group of formula

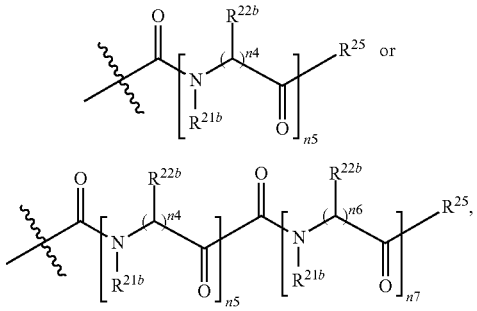

wherein n4, n5, and n6 are each independently 1, 2 or 3; n7 is 0, 1 or 2; $R^{21b}$ and $R^{22b}$ are independently at each occurrence hydrogen, hydroxy, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J; $R^{25}$ is H, OH, $OR^C$, Formula (VI)

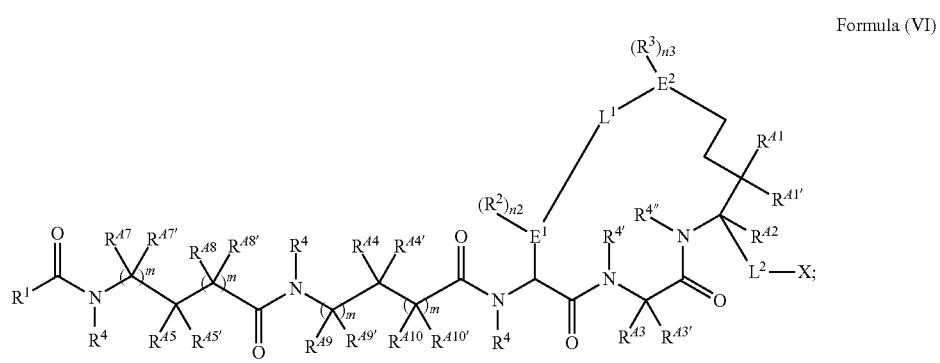

131

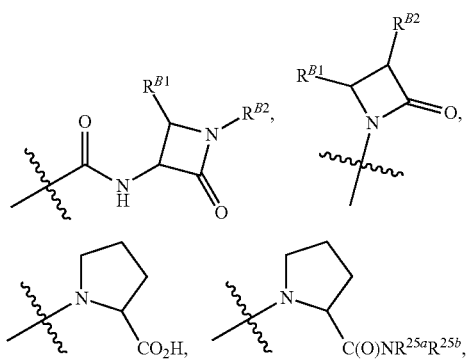

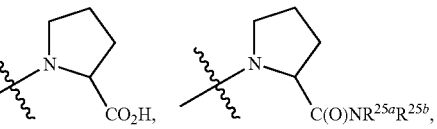

or NR²⁵ᵃR²⁵ᵇ where R²⁵ᵃ and R²⁵ᵇ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (VI) bearing X; or X is CO$_2$H, CH$_2$CO$_2$H, C(=O)NHCH$_2$C(=O)H, CH$_2$C(=O)H, C(=O)NHCH$_2$B(OR$^B$)$_2$ or C(=O)NHCH$_2$P(=O)(OR$^B$)$_2$ wherein R$^B$ is H or (C$_1$-C$_6$)alkyl, or X is a group of formula

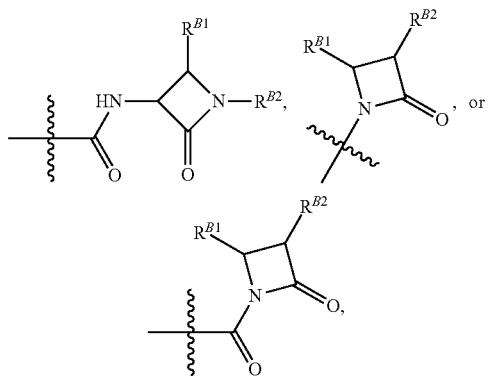

wherein R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O)OR$^C$, OC(=O)OR$^C$, nitro, trifluoromethyl, trifluoromethoxy, (C$_1$-C$_6$)alkoxy, (C$_1$-C$_6$)thioalkoxy, NR$^C_2$, 5-7 membered heterocyclyl or 5-7 membered heteroaryl, or (C$_6$-C$_{10}$) aryl; R$^C$ is independently at each occurrence H or (C$_1$-C$_6$) alkyl, and a wavy line indicates a point of attachment of X to a carbon of formula (VI) bearing X; or X is selected from

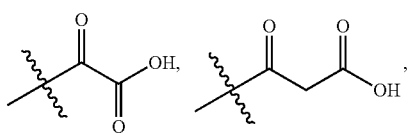

132

-continued

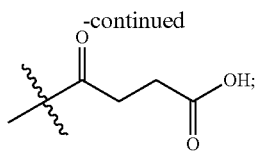

R$^1$ comprises a group of formula (IIA), (IIB), (IIC), (IID), (IIE), or (IIF)

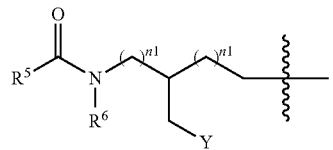
(IIA)

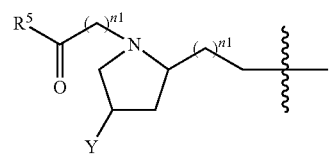
(IIB)

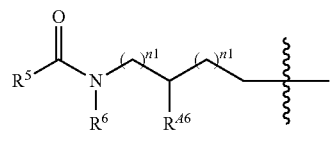
(IIC)

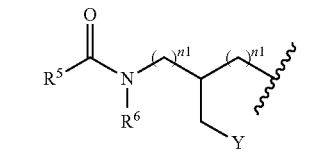
(IID)

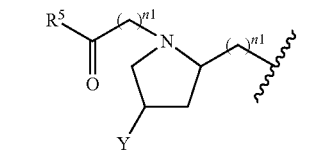
(IIE)

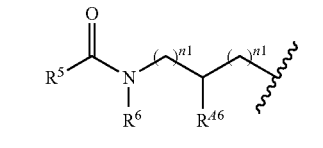
(IIF)

wherein n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$) alkyl; R$^{46}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (VI) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

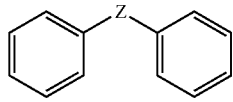

wherein Z is a bond, O, S, NH, $CH_2$ or C≡C;

$R^2$ and $R^3$ are each independently nitro, halo, cyano, hydroxy, glycosyloxy, amino, $(C_1-C_4)$alkoxy, $(C_1-C_4)$acyloxy, $(C_1-C_4)$alkyl, or a group cleavable under physiological conditions to provide a compound of formula (VI) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, and $R^{A10'}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH-C(O)R'$, $(CH_2)_{0-p}N(R')(R'))_cC(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;

wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring, or an 8- to 20-membered, bicyclic or tricyclic, heterocyclic ring system, wherein any ring or ring system optionally further contain 1-3 additional heteroatoms selected from the group consisting of N, NR', O, S, S(O) and S(O)$_2$, wherein each ring is substituted with 0-3 substituents selected independently from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_5$cycloalkyl, or C$_1$-C$_6$heteroalkyl; wherein, in any bicyclic or tricyclic ring system, each ring is linearly fused, bridged, or spirocyclic, wherein each ring is either aromatic or nonaromatic, wherein each ring is optionally fused to a $(C_6-C_{10})$aryl, mono- or bicyclic 5-10 membered heteroaryl, $(C_3-C_{10})$cycloalkyl or mono- or bicyclic 3-10 membered heterocyclyl; or a pharmaceutically acceptable salt, solvate, or prodrug thereof.

In one embodiment is a compound of Formula (VI) having the structure of Formula (VIA):

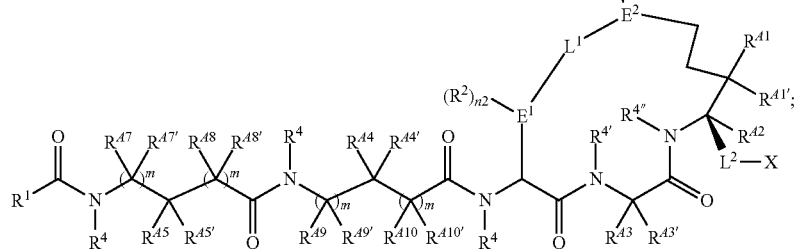

Formula (VIA)

wherein $E^1$, $E^2$, $L^1$, $L^2$, X, $R^1$, $R^2$, $R^3$, $R^4$, $R^{4'}$, $R^{4''}$, $R^{A1}$, $R^{A1'}$, $R^{A2}$, $R^{A3}$, $R^{A3'}$, $R^{A4}$, $R^{A4'}$, $R^{A5}$, $R^{A5'}$, $R^{A7}$, $R^{A7'}$, $R^{A8}$, $R^{A8'}$, $R^{A9}$, $R^{A9'}$, $R^{A10}$, $R^{A10'}$, n2, n3, and m are as defined herein; or a pharmaceutically acceptable salt, solvate, or prodrug thereof.

In another embodiment is a compound having the structure of Formula (VIB):

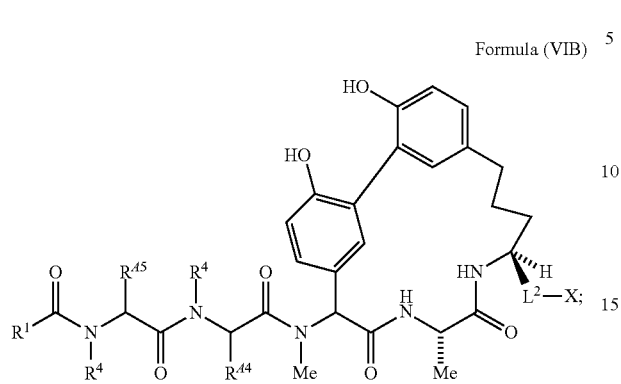

Formula (VIB)

wherein:

$L^2$ is a bond;

X is $C(O)R^{20}$, and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1\text{-}C_6)$ alkyl; and $R^{20b}$ is H or optionally substituted alkyl; or X is a group of formula

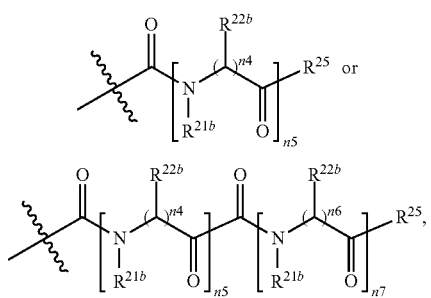

wherein n4, n5, and n6 are each independently 1, 2 or 3; n7 is 0, 1 or 2; $R^{21b}$ and $R^{22b}$ are independently at each occurrence hydrogen, hydroxy, $(C_1\text{-}C_6)$alkyl, wherein any alkyl is optionally substituted with 1 to 3 J; $R^{25}$ is H, OH, $OR^C$,

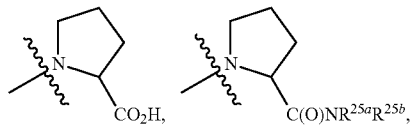

or $NR^{25a}R^{25b}$; where $R^{25a}$ and $R^{25b}$ are each independently H, $SO_2(C_1\text{-}C_6)$alkyl, or optionally substituted alkyl; $R^C$ is independently at each occurrence H or $(C_1\text{-}C_6)$ alkyl, and a wavy line indicates a point of attachment of X to a carbon of formula (VIB) bearing X; or X is $CO_2H$, $CH_2CO_2H$, $C(=O)NHCH_2C(=O)H$, $CH_2C(=O)H$, or $C(=O)NHCH_2B(OR^B)_2$ wherein $R^B$ is H or $(C_1\text{-}C_6)$alkyl; or X is a group of formula

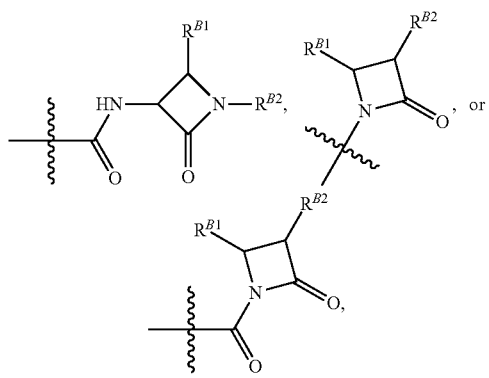

wherein $R^{B1}$ and $R^{B2}$ are each independently H, $(C_1\text{-}C_6)$ alkyl, $(C_3\text{-}C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1\text{-}C_6)$alkoxy, $(C_1\text{-}C_6)$thioalkoxy, $NR^C_2$, 5-7 membered heterocyclyl or 5-7 membered heteroaryl, or $(C_6\text{-}C_{10})$ aryl; $R^C$ is independently at each occurrence H or $(C_1\text{-}C_6)$ alkyl, and a wavy line indicates a point of attachment of X to a carbon of formula (VIB) bearing X; or X is selected from

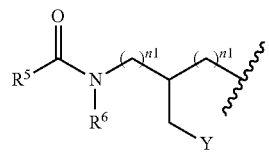

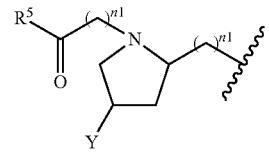

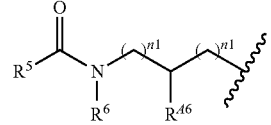

$R^1$ comprises a group of formula (IID), (IIE), or (IIF)

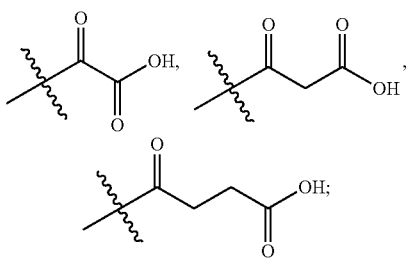

(IID)

(IIE)

(IIF)

wherein n1 is independently at each occurrence 0, 1, or 2; Y is $(CH_2)_{0\text{-}2}H$, or $(CH_2)_{0\text{-}2}OH$; $R^{46}$ is hydrogen, or $(C_1\text{-}C_6)$ alkyl, wherein alkyl is optionally substituted with 1 to 3 substituents, wherein each substituent is independently selected from the group consisting of halogen, amino, hydroxyl, aminocarbonyl, hydroxycarbonyl, 5- to 7-membered heterocyclyl, $(C_1-C_6)$alkoxy, $(C_1-C_6)$-mono- or di-alkylamino, $(C_1-C_6)$alkoxycarbonyl, $(C_1-C_6)$alkylhydroxy-carbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (VIB) bearing $R^1$;

$R^5$ is aryl, heteroaryl, or a linear or branched alkyl chain of about 1-22 carbon atoms, wherein $R^5$ is bonded to the carbonyl carbon to which it is attached directly or by $NR^4$, to provide an amide, or urea linkage, respectively; optionally comprising within the chain or at a chain terminus optionally substituted aryl, optionally substituted heteroaryl, or optionally substituted

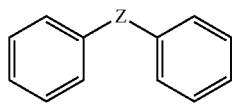

wherein Z is a bond, O, S, NH, $CH_2$ or C≡C; each m is independently 0, 1, or 2;

$R^4$, and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

$R^{A4}$ and $R^{A5}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J;

J is halogen, R', OR', CN, $CF_3$, $OCF_3$, C(O), S(O), methylenedioxy, ethylenedioxy, $(CH_2)_{0-p}N(R')_2$, $(CH_2)_{0-p}SR'$, $(CH_2)_{0-p}C(O)R'$, $(CH_2)_{0-p}C(O)OR'$, $(CH_2)_{0-p}C(O)N(R')_2$, $(CH_2)_{0-p}NH-C(O)R'$, $(CH_2)_{0-p}N(R')SO_2R'$, $(CH_2)_{0-p}N(R')C(O)R'$, or $(CH_2)_{0-p}C(=NH)N(R')_2$; wherein p is 4, each R' is independently at each occurrence hydrogen, $(C_1-C_6)$-alkyl, $(C_2-C_7)$-alkenyl, $(C_2-C_7)$-alkynyl, $(C_3-C_{10})$-cycloalkyl, $(C_3-C_{10})$-cycloalkenyl, aryl, or heteroaryl wherein any alkyl, alkenyl, alkynyl, cycloalkyl, cycloalkenyl, aryl or heteroaryl is optionally substituted with a substituent selected from F, Cl, Br, I, —CN, —$NO_2$, —OH, —$CF_3$, —$OCF_3$, —$OCH_3$, —$NH_2$, —$N((C_1-C_4)alkyl)_2$-, —$NH(C_1-C_4)alkyl$, $C_1-C_6$alkyl, $C_3-C_5$cycloalkyl, or $C_1-C_6$heteroalkyl;

or, when two R' are bound to a nitrogen atom or to two adjacent nitrogen atoms, the two R' groups together with the nitrogen atom or atoms to which they are bound optionally forms a 3- to 8-membered monocyclic heterocyclic ring;

or a pharmaceutically acceptable salt, solvate, or prodrug thereof.

In one embodiment is a compound of Formula (VIB) wherein X is a group of formula

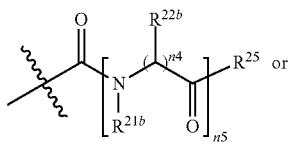

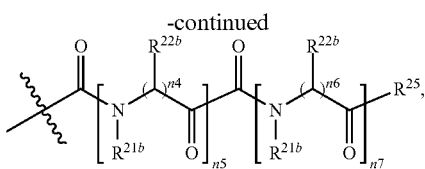

wherein n4, n5, and n6 are each independently 1, 2 or 3; n7 is 0, 1 or 2; $R^{21b}$ and $R^{22b}$ are independently at each occurrence hydrogen, hydroxy, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 J; $R^{25}$ is H, OH, $OR^C$,

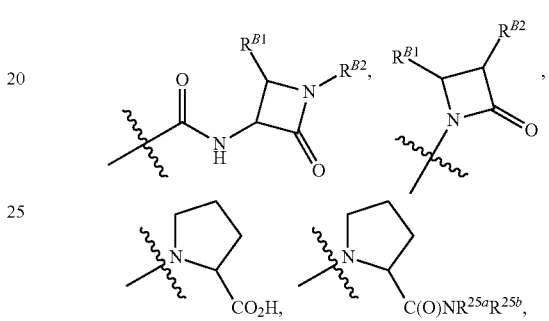

or $NR^{25a}R^{25b}$ where $R^{25a}$ and $R^{25b}$ are each independently H, $SO_2(C_1-C_6)$alkyl, or optionally substituted alkyl; $R^{B1}$ and $R^{B2}$ are each independently H, $(C_1-C_6)$ alkyl, $(C_3-C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1-C_6)$alkoxy, $(C_1-C_6)$thioalkoxy, $N(R^C)_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of X to a carbon of formula (VIB) bearing X.

In another embodiment is a compound of Formula (VIB) wherein X is a group of formula

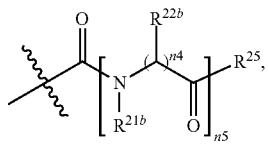

n4 is 1, n5 is 1, $R^{21b}$ is hydrogen, $R^{22b}$ is methyl, and $R^{25}$ is OH.

In another embodiment is a compound of Formula (VIB) wherein X is a group of formula

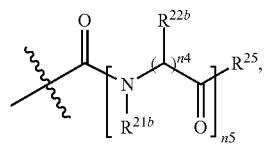

n4 is 1, n5 is 1, $R^{21b}$ is hydrogen, $R^{22b}$ is methyl, and $R^{25}$ is $NH_2$.

In another embodiment is a compound of Formula (VIB) wherein X is a group of formula

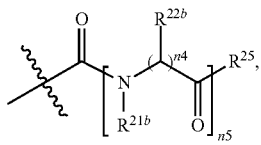

n4 is 1, n5 is 1, $R^{21b}$ is hydrogen, $R^{22b}$ is methyl, and $R^{25}$ is

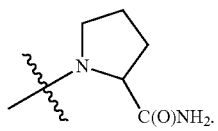

In another embodiment is a compound of Formula (VIB) wherein X is a group of formula

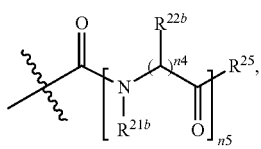

n4 is 1, n5 is 1, $R^{21b}$ is hydrogen, $R^{22b}$ is methyl, and $R^{25}$ is

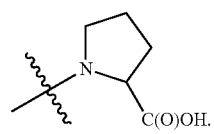

In another embodiment is a compound of Formula (VIB) wherein X is a group of formula

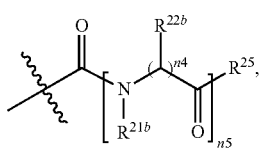

n4 is 1, n5 is 1, $R^{21b}$ is hydrogen, $R^{22b}$ is methyl, and $R^{25}$ is —NHSO$_2$Me.

In another embodiment is a compound of Formula (VIB) wherein X is a group of formula

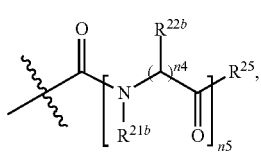

n4 is 1, n5 is 1, $R^{21b}$ is hydrogen, $R^{22b}$ is methyl, and $R^{25}$ is H.

In another embodiment is a compound of Formula (VIB) wherein X is a group of formula

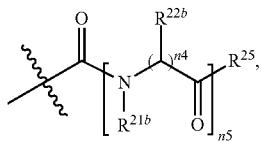

n4 is 1, n5 is 1, $R^{21b}$ is hydrogen, $R^{22b}$ is hydrogen, and $R^{25}$ is OH.

In another embodiment is a compound of Formula (VIB) wherein X is a group of formula

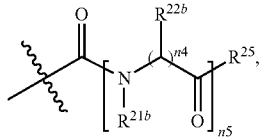

n4 is 1, n5 is 1, $R^{21b}$ is hydrogen, $R^{22b}$ is hydrogen, and $R^{25}$ is NH$_2$.

In another embodiment is a compound of Formula (VIB) wherein X is a group of formula

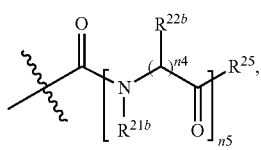

n4 is 1, n5 is 1, $R^{21b}$ is hydrogen, $R^{22b}$ is hydrogen, and $R^{25}$ is

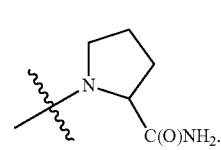

In another embodiment is a compound of Formula (VIB) wherein X is a group of formula

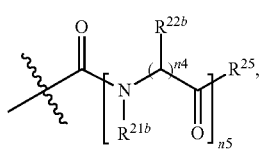

n4 is 1, n5 is 1, $R^{21b}$ is hydrogen, $R^{22b}$ is hydrogen, and $R^{25}$ is

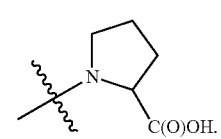

In another embodiment is a compound of Formula (VIB) wherein X is a group of formula

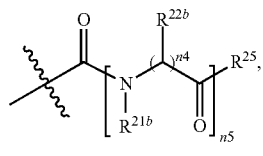

n4 is 1, n5 is 1, $R^{21b}$ is hydrogen, $R^{22b}$ is hydrogen, and $R^{25}$ is —NHSO$_2$Me.

In another embodiment is a compound of Formula (VIB) wherein X is a group of formula

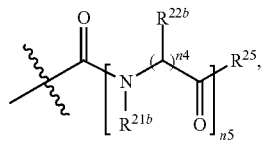

n4 is 1, n5 is 1, $R^{21b}$ is hydrogen, $R^{22b}$ is hydrogen, and $R^{25}$ is H.

In another embodiment is a compound of Formula (VIB) wherein X is a group of formula

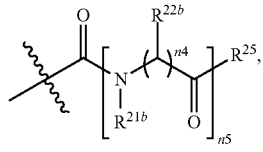

n4 is 2, n5 is 1, $R^{21b}$ is hydrogen, each $R^{22b}$ is independently hydrogen or hydroxy, and $R^{25}$ is NH$_2$.

In another embodiment is a compound of Formula (VIB) wherein X is a group of formula

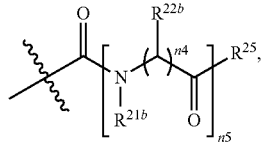

n4 is 2, n5 is 1, $R^{21b}$ is hydrogen, each $R^{22b}$ is independently hydrogen or hydroxy, and $R^{25}$ is NHMe.

In another embodiment is a compound of Formula (VIB) wherein X is a group of formula

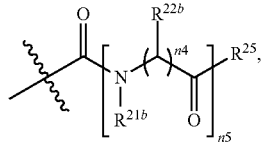

n4 is 2, n5 is 1, $R^{21b}$ is hydrogen, each $R^{22b}$ is independently hydrogen or hydroxy, and $R^{25}$ is OH.

In another embodiment is a compound of Formula (VIB) wherein X is a group of formula

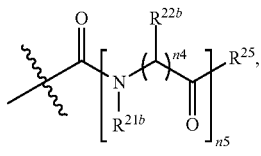

n4 is 2, n5 is 1, $R^{21b}$ is hydrogen, each $R^{22b}$ is independently hydrogen or hydroxy, and $R^{25}$ is OMe.

In another embodiment is a compound of Formula (VIB) wherein X is a group of formula

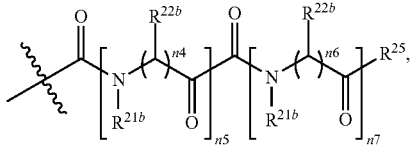

n4 is 1, n5 is 1, n7 is 0, $R^{21b}$ is hydrogen, $R^{22b}$ is methyl, and $R^{25}$ is —NH$_2$.

In another embodiment is a compound of Formula (VIB) wherein X is a group of formula

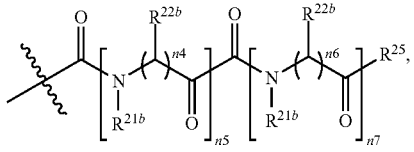

n4 is 1, s 1, n5 is 1, n7 is 0, $R^{21b}$ is hydrogen, R is methyl, and $R^{25}$ is —NHMe.

In another embodiment is a compound of Formula (VIB) wherein X is a group of formula

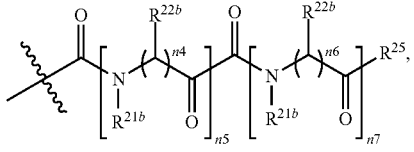

n4 is 1, n5 is 1, n7 is 0, $R^{21b}$ is hydrogen, $R^{22b}$ is methyl, and $R^{25}$ is —NMe$_2$.

In another embodiment is a compound of Formula (VIB) wherein X is a group of formula

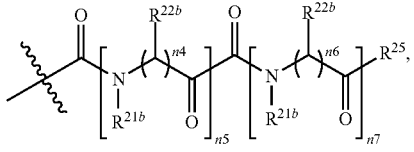

n4 is 1, n5 is 1, n7 is 0, $R^{21b}$ is hydrogen, $R^{22b}$ is hydrogen, and $R^{25}$ is —NH$_2$.

In another embodiment is a compound of Formula (VIB) wherein X is a group of formula

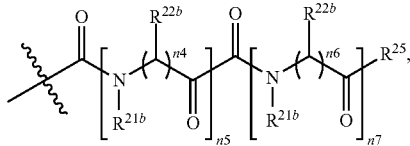

n4 is 1, n5 is 1, n7 is 0, $R^{21b}$ is hydrogen, $R^{22b}$ is hydrogen, and $R^{25}$ is OH.

In another embodiment is a compound of Formula (VIB) wherein X is $C(O)R^{20}$ and $R^{20}$ is optionally substituted alkyl. In another embodiment is a compound of Formula (VIB) wherein X is $C(O)R^{20}$ and $R^{20}$ is optionally substituted alkoxy. In some embodiments is a compound of Formula (VIB) wherein $R^{20}$ is alkoxy substituted with $NH_2$.

In another embodiment is a compound of Formula (VIB) wherein X is $C(O)R^{20}$ and $R^{20}$ is $NR^{20a}R^{20b}$, $R^{20a}$ is optionally substituted alkyl, and $R^{20b}$ is H. In further embodiments is a compound of Formula (VIB) wherein X is $C(O)R^{20}$ and $R^{20}$ is $NR^{20a}R^{20b}$, $R^{20a}$ is alkyl substituted with a hydroxyl group, and $R^{20b}$ is H. In further embodiments is a compound of Formula (VIB) wherein X is $C(O)R^{20}$ and $R^{20}$ is $NR^{20a}R^{20b}$, $R^{20a}$ is alkyl substituted with two hydroxyl groups, and $R^{20b}$ is H. In a further embodiment is a compound of Formula (VIB) wherein X is $C(O)R^{20}$ and $R^{20}$ is $NR^{20a}R^{20b}$, $R^{20a}$ is alkyl substituted with three hydroxyl groups, and $R^{20b}$ is H. In a further embodiment is a compound of Formula (VIB) wherein X is $C(O)R^{20}$ and $R^{20}$ is $NR^{20a}R^{20b}$, $R^{20a}$ is alkyl substituted with a hydroxyl group and a heteroaryl group, and $R^{20b}$ is H. In another embodiment is a compound of Formula (VIB) wherein X is $C(O)R^{20}$ and $R^{20}$ is $NR^{20a}R^{20b}$, $R^{20a}$ is alkyl substituted with methoxy, and $R^{20b}$ is H. In another embodiment is a compound of Formula (VIB) wherein X is $C(O)R^{20}$ and $R^{20}$ is optionally substituted alkoxy. In some embodiments is a compound of Formula (VIB) wherein $R^{20}$ is alkoxy substituted with $NH_2$.

In another embodiment is a compound of Formula (VIB) wherein X is selected from

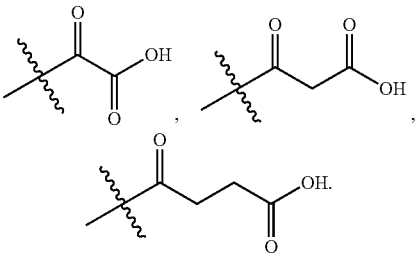

In another embodiment is a compound of Formula (VIB) wherein X is $CO_2H$, $CH_2CO_2H$, $C(=O)NHCH_2C(=O)H$, $CH_2C(=O)H$, or $C(=O)NHCH_2B(OR^B)_2$ wherein $R^B$ is H or $(C_1-C_6)$alkyl. In some embodiments is a compound of Formula (VIB) wherein X is $CO_2H$. In some embodiments is a compound of Formula (VIB) wherein X is $CH_2C(=O)H$. In some embodiments is a compound of Formula (VIB) wherein X is $C(=O)NHCH_2B(OR^B)_2$ and $R^B$ is H or $(C_1-C_6)$alkyl.

In another embodiment is a compound of Formula (VIB) wherein $R^1$ comprises a group of formula (IID), (IIE), or (IIF)

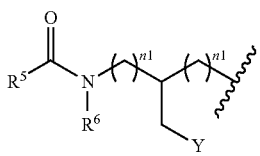

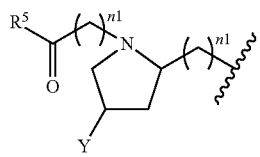

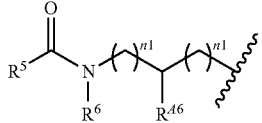

wherein n1 is at each occurrence 0; Y is $(CH_2)_{0-2}H$, or $(CH_2)_{0-2}OH$; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (VIB) bearing $R^1$. In one embodiment, Y is H. In another embodiment, Y is OH. In another embodiment, Y is $CH_2OH$. In yet another embodiment, Y is $CH_2OC(=O)CH_3$.

In some embodiments is a compound of Formula (VIB) wherein $R^5$ is a linear or branched alkyl chain of about 1-22 carbon atoms, wherein $R^5$ is bonded to the carbonyl carbon to which it is attached directly or by an $NR^4$, to provide an amide or urea linkage, respectively; optionally comprising within the chain or at a chain terminus optionally substituted aryl, optionally substituted heteroaryl, or optionally substituted

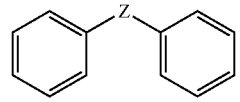

wherein Z is a bond, O, S, NH, $CH_2$ or C≡C. In some embodiments is a compound of Formula (VIB) wherein $R^5$ is a linear or branched alkyl chain of about 1-22 carbon atoms, wherein $R^5$ is bonded to the carbonyl carbon to which it is attached directly to provide an amide linkage.

In any of the aforementioned embodiments of Formula (VIB) is a compound wherein $R^4$ and $R^6$ are each independently at every occurrence hydrogen or $(C_1-C_6)$alkyl. In any of the aforementioned embodiments of Formula (VIB) is a compound wherein $R^4$ and $R^6$ are each independently at every occurrence hydrogen or methyl. In any of the aforementioned embodiments of Formula (VIB) is a compound wherein $R^{44}$ is hydrogen and $R^{45}$ is methyl. In any of the aforementioned embodiments of Formula (VIB) is a compound wherein $R^{44}$ is methyl and $R^{45}$ is methyl.

In yet a further embodiment is a compound of any of Formulas I-VI, wherein $R^1$ is a group of Formula (IIAS), (IIBS), (IICS), or (IIDS)

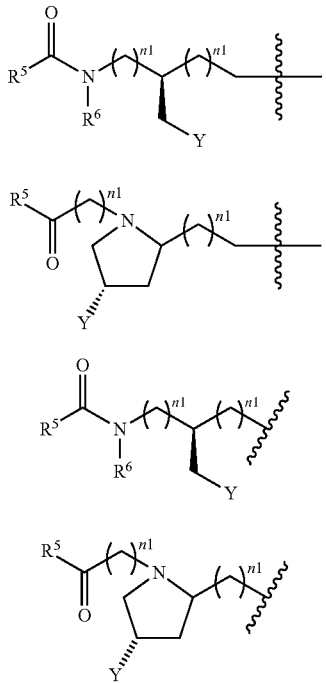

wherein n1, n2, p, $R^5$, $R^6$, and Y, are as defined herein and a wavy line indicates a point of attachment of $R^1$ to an atom bonded to $R^1$ in Formulas (I-VI); or a pharmaceutically acceptable salt, solvate, or prodrug thereof.

In one embodiment is a compound of any of Formulas I-VI, wherein $R^5$ is linear or branched alkyl.

In another embodiment is a compound of any of Formulas I-VI, wherein $R^5$ is linear or branched alkyl substituted within the alkyl chain or alkyl chain terminus with one or more optionally substituted aryl, optionally substituted heteroaryl, or optionally substituted

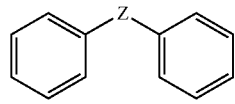

wherein Z is a bond, O, S, NH, $CH_2$ or $C\equiv C$.

In another embodiment is a compound of any of Formulas I-VI, wherein $R^5$ is aryl.

In another embodiment is a compound of any of Formulas I-VI, wherein $R^5$ is heteroaryl.

In a further embodiment is a compound of any of Formulas I-VI wherein $R^5$ is any of the following groups:

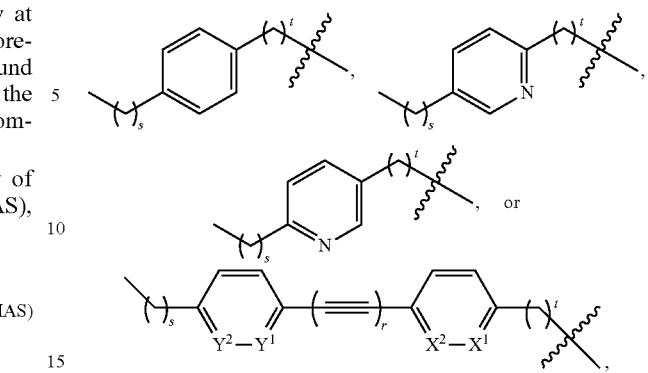

wherein r is 0-1, s is 0-14, t is 0-14, provided that $s+t \leq 22$, and $X^1$, $X^2$, $Y^1$ and $Y^2$ are each independently C or N, provided that no more than one of $X^1$ and $X^2$, and no more than one of $Y^1$ and $Y^2$, is N, wherein a wavy line indicates a point of attachment of $R^5$ to an atom bonded to $R^5$ in formula (IIA), (IIB), (IIC), (IID), (IIE), or (IIF).

In yet another embodiment is a compound of any of Formulas I-VI wherein $R^5$ is any of the following: methyl, ethyl, $(C_3-C_{22})$-n-alkyl, $(C_3-C_{22})$-isoalkyl, $(C_4-C_{22})$-anteisoalkyl, naphthyl, $(C_2-C_{10})$ naphthyl, naphthylmethyl, $(C_2-C_{10})$ naphthylmethyl, biphenyl, $(C_2-C_{10})$alkylbiphenyl, biphenylmethyl, $(C_2-C_{10})$alkylbiphenylmethyl, $(C_4-C_{12})$ phenyl, $(C_4-C_{12})$benzyl, $(C_2-C_{10})$-1,2-diphenylethynyl, or (Z)- or (E)-$(C_2-C_{10})$-1,2-diphenylethenyl.

In a further embodiment is a compound of any of Formulas I, II, IV, or V, wherein $E^1$ and $E^2$ is each independently phenyl, pyridyl, pyrazinyl, pyrimidyl, or pyridazinyl.

In a further embodiment is a compound of any of Formulas I-VI, wherein at least one $R^2$ and $R^3$ is hydrogen.

In a further embodiment is a compound of any of Formulas I-VI, wherein $R^2$ and $R^3$ are each independently nitro, halo, cyano, hydroxy, glycosyloxy, amino, $(C_1-C_4)$alkoxy, or $(C_1-C_4)$alkyl.

In a further embodiment is a compound of any of Formulas I-VI, wherein n2 is 1 and n3 is 1.

In a further embodiment is a compound of any of Formulas I-VI wherein at least one $R^2$ and $R^3$ is hydroxy.

In a further embodiment is a compound of any of Formulas I-VI wherein any of $R^{41}$, $R^{42}$ and $R^{44}$ are hydrogen, any of $R^{43}$ and $R^{45}$ are methyl, or any combination thereof.

In a further embodiment is a compound of any of Formulas I-VI wherein $R^{43}$ is hydrogen, methyl, ethyl, n-propyl, isopropyl, n-butyl, isobutyl, 3-hydroxypropyl, 4-hydroxybutyl, or 2,2,2-trifluoroethyl.

In a further embodiment is a compound of any of Formulas I-VI wherein all of $R^4$ and $R^6$ are independently hydrogen or methyl.

In another embodiment is a compound of any of Formulas I-VI, wherein at least one $R^2$ and $R^3$ is nitro, halo, cyano, hydroxy, glycosyloxy, amino, $(C_1-C_4)$alkoxy, or $(C_1-C_4)$alkyl, and n2 or n3 respectively, or both, is 2.

In another embodiment are provided compounds of Formulas I, IV, and V wherein $L^1$ is a bond, O, S, $NR^4$.

In another embodiment are provided compounds of Formulas I, IV, and V wherein $L^1$ is a bond, O, S, $NR^4$ and $E^1$ and $E^2$ is each independently aryl or heteroaryl.

In another embodiment are provided compounds of Formulas I, IV, and V wherein $L^1$ is a bond, O, S, $NR^4$ and $E^1$ and $E^2$ is each independently phenyl, pyridyl, pyrazinyl, pyrimidyl, or pyridazinyl.

In another embodiment are provided compounds of Formulas I-VI wherein $L^2$ is a bond and X is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1\text{-}C_6)$alkyl.

In another embodiment are provided compounds of Formulas I-VI wherein $L^2$ is a bond and X is a group of formula

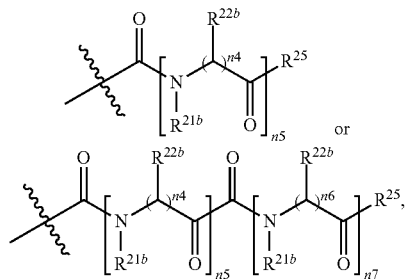

wherein n4, n5, and n6 are each independently 1, 2 or 3; n7 is 0, 1 or 2; $R^{21b}$ and $R^{22b}$ are independently at each occurrence hydrogen, hydroxy, $(C_1\text{-}C_6)$alkyl, $(C_3\text{-}C_7)$cycloalkyl, 5- to 7-membered heteroaryl, 5- to 7-membered heterocyclyl, or $(C_6\text{-}C_{10})$ aryl, wherein any alkyl, cycloalkyl, heterocyclyl, aryl or heteroaryl is optionally substituted with 1 to 3 J; $R^{25}$ is H, OH, $OR^C$,

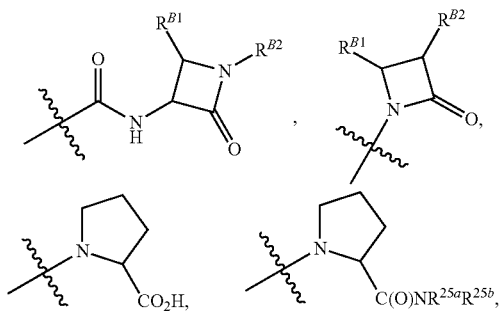

or $NR^{25a}R^{25b}$ where $R^{25a}$ and $R^{25b}$ are each independently H, $SO_2(C_1\text{-}C_6)$alkyl, or optionally substituted alkyl; $R^{B1}$ and $R^{B2}$ are each independently H, $(C_1\text{-}C_6)$ alkyl, $(C_3\text{-}C_6)$ cycloalkyl, $OR^C$, $C(=O)N(R^C)_2$, $OC(=O)N(R^C)_2$, $C(=O)OR^C$, $OC(=O)OR^C$, nitro, trifluoromethyl, trifluoromethoxy, $(C_1\text{-}C_6)$alkoxy, $(C_1\text{-}C_6)$thioalkoxy, $N(R^C)_2$, 5-7 membered heterocyclyl or 5-7 membered heteroaryl, or $(C_6\text{-}C_{10})$ aryl; $R^C$ is independently at each occurrence H or $(C_1\text{-}C_6)$ alkyl, and a wavy line indicates a point of attachment of X to a carbon of formula (I-VI) bearing X.

In another embodiment are provided compounds of Formulas I-VI wherein $L^2$ is a bond and X is $C(O)R^{20}$, $S(O)_2R^{20}$, or $C(O)NR^{21a}C(R^{22a})(R^{23a})B(OR^{24})_2$ wherein $R^{21a}$, $R^{22a}R^{23a}$ are independently at each occurrence hydrogen, $(C_1\text{-}C_6)$alkyl, $(C_3\text{-}C_7)$cycloalkyl, 5- to 7-membered heteroaryl, 5- to 7-membered heterocyclyl, or $(C_6\text{-}C_{10})$ aryl, where at least one of $R^{21a}$, $R^{22a}$, $R^{23a}$ is not hydrogen, wherein any alkyl, cycloalkyl, heterocyclyl, aryl or heteroaryl is optionally substituted with 1 to 3 J; $R^{24}$ is H or $(C_1\text{-}C_6)$alkyl; and $R^{20}$ is optionally substituted alkyl, optionally substituted alkoxy, or $NR^{20a}R^{20b}$, where $R^{20a}$ is H, optionally substituted alkyl, heteroalkyl, or $SO_2(C_1\text{-}C_6)$ alkyl; and $R^{20b}$ is H or optionally substituted alkyl.

In another aspect are hydrates or metabolites comprising any of the aforementioned compounds.

In another aspect are pharmaceutical compositions comprising any of the aforementioned compounds together with a pharmaceutically acceptable excipient.

In another aspect described herein is the use of a compound described herein in the manufacture of a medicament for treatment of a bacterial infection in a patient.

In another aspect are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with arylomycin A2. In a further embodiment, the causative bacteria species of the bacteria infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Rhodococcus opacus, Staphylococcus capitis, Staphylococcus caprae, Staphylococcus carnosus, Staphylococcus cohnii, Staphylococcus epidermidis, Staphylococcus haemolyticus, Staphylococcus hominis, Staphylococcus hominis* subsp. *hominis, Staphylococcus hominis* subsp. novobiosepticus, *Staphylococcus lugdunensis, Streptococcus agalactiae, Streptococcus dysgalactiae, Streptococcus mitis, Streptococcus oralis, Streptococcus pyogenes, Streptococcus pnemoniae*, and/or *Yersinia pestis*. In another embodiment the bacterial infection is an infection involving a gram negative bacteria. In a further embodiment, the bacterial infection is an infection involving a gram positive bacteria.

In another aspect are methods of treating a mammal in need of such treatment comprising administering to the mammal arylomycin A and/or arylomycin B and/or any of the aforementioned compounds, wherein the infection involves a bacterial species that expresses a signal peptidase without a proline residue within 10 amino acids N-terminal to the signal peptidase catalytic serine. In a further embodiment, the bacterial species encodes or expresses an SPase enzyme without a proline residue 5 to 7 amino acids N-terminal to the SPase catalytic serine. In another embodiment, the bacteria infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Staphylococcus carnosus, Staphylococcus cohnii, Staphylococcus haemolyticus, Staphylococcus hominis, Staphylococcus hominis* subsp. *hominis, Staphylococcus hominis* subsp. novobiosepticus, *Staphylococcus lugdunensis, Streptococcus agalactiae, Streptococcus dysgalactiae, Streptococcus mitis, Streptococcus oralis, Streptococcus pyogenes*, and/or *Streptococcus pnemoniae*. In another embodiment the bacterial infection is an infection involving a gram negative bacteria. In another embodiment, administering comprises a topical administration.

In another aspect are methods of treating a mammal in need of such treatment comprising administering to the mammal any one or any combination of the aforementioned compounds, wherein the infection involves a bacterial species that expresses a signal peptidase without a proline residue within 10 amino acids N-terminal to the signal peptidase catalytic serine. In a further embodiment, the bacterial species encodes or expresses an SPase enzyme without a proline residue 5 to 7 amino acids N-terminal to the SPase catalytic serine. In another embodiment, the bacteria infection is an infection involving *Staphylococcus capitis, Staphylococcus caprae* and/or *Yersinia pestis*.

In a further embodiment are methods of treating a mammal in need of such treatment comprising administering to the mammal a second therapeutic agent to any of the aforementioned methods of treatment. In another embodiment, the second therapeutic agent is a non-arylomycin antibiotic. In another embodiment, the non-arylomycin antibiotic is an aminoglycoside antibiotic, fluoroquinolone antibiotic, penicillin antibiotic, cephalosporin antibiotic, macrolide antibiotic, glycopeptide antibiotic, rifampicin, chloramphenicol, fluoramphenicol, colistin, mupirocin, bacitracin, daptomycin, or linezolid.

In one embodiment, is a compound described herein which displays antibiotic activity useful in the treatment of bacterial infections, such as by way of example only, various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

Methicillin-Resistant *Staphylococcus aureus*

*Staphylococcus aureus* (*S. aureus*), a spherical bacterium, is the most common cause of staph infections. *S. aureus* has been known to cause a range of illnesses from minor skin infections, such as pimples, impetigo, boils, cellulitis folliculitis, furuncles, carbuncles, scalded skin syndrome, abscesses, to life-threatening diseases such as pneumonia, meningitis, osteomyelitis endocarditis, toxic shock syndrome, and septicemia. Further, *S. aureus* is one of the most common causes of nosocomial infections, often causing postsurgical wound infections.

Methicillin was introduced in the late 1950s to treat infections caused by penicillin-resistant *S. aureus*. It has been reported previously that *S. aureus* isolates had acquired resistance to methicillin (methicillin-resistant *S. aureus*, MRSA). The methicillin resistance gene (mecA) encodes a methicillin-resistant penicillin-binding protein that is not present in susceptible strains. mecA is carried on a mobile genetic element, the staphylococcal cassette chromosome mec (SCCmec), of which four forms have been described that differ in size and genetic composition. The methicillin-resistant penicillin-binding protein allows for resistance to β-lactam antibiotics and obviates their clinical use during MRSA infections.

In one aspect is a method for treating a subject having a resistant bacterium comprising administering to the subject a compound of Formula (I)-(VI) or a pharmaceutically acceptable salt, ester, solvate, alkylated quaternary ammonium salt, stereoisomer, tautomer or prodrug thereof. In one embodiment, the bacterium is a Gram-positive bacteria. In another embodiment, the Gram-positive bacterium is *S. aureus*. In further embodiment, the *S. aureus* is resistant or refractory to a beta-lactam antibiotic. In yet a further embodiment, the beta-lactam antibiotic belongs to the class of penicillins. In a further embodiment, the beta-lactam antibiotic is methicillin. In yet another embodiment, the subject has a methicillin-resistant *S. aureus* bacteria. In one embodiment the beta-lactam antibiotic is flucloxacillin. In another embodiment is a method for treating a subject having a dicloxacillin-resistant bacteria comprising administering to the subject a compound of Formula (I)-(VI) or a pharmaceutically acceptable salt, ester, solvate, alkylated quaternary ammonium salt, stereoisomer, tautomer or prodrug thereof wherein the subject is refractory to dicloxacillin. Also disclosed herein is a method for treating a subject having a methicillin-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject has been determined to have a methicillin-resistant bacteria. In one embodiment the subject is screened for methicillin-resistant bacteria. In another embodiment, the subject screening is performed through a nasal culture. In a further embodiment the methicillin-resistant bacteria is detected by swabbing the nostril(s) of the subject and isolating the bacteria. In another embodiment, Real-time PCR and/or Quantitative PCR is employed to determine whether the subject has a methicillin-resistant bacteria.

In one embodiment is a method for treating a subject having a first-generation cephalosporin-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject is refractory to a first-generation cephalosporin. In one embodiment, the bacteria is resistant to a first-generation cephalosporin. In a further embodiment, the bacteria is resistant to cefacetrile. In another embodiment, the bacteria is resistant to cefadroxil. In yet another embodiment, the bacteria is resistant to cefalexin. In one embodiment, the bacteria is resistant to cefaloglycin. In another embodiment, the bacteria is resistant to cefalonium. In another embodiment, the bacteria is resistant to cefaloridine. In yet another embodiment, the bacteria is resistant to cefalotin. In a further embodiment, the bacteria is resistant to cefapirin. In yet a further embodiment, the bacteria is resistant to cefatrizine. In one embodiment, the bacteria is resistant to cefazaflur. In another embodiment, the bacteria is resistant to cefazedone. In yet another embodiment, the bacteria is resistant to cefazolin. In a further embodiment, the bacteria is resistant to cefradine. In yet a further embodiment, the bacteria is resistant to cefroxadine. In one embodiment, the bacteria is resistant to ceftezole.

In one embodiment is a method for treating a subject having a second-generation cephalosporin-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject is refractory to a second-generation cephalosporin. In another embodiment, the bacteria is resistant to a second-generation cephalosporin. In a further embodiment, the bacteria is resistant to cefaclor. In another embodiment, the bacteria is resistant to cefonicid. In yet another embodiment, the bacteria is resistant to cefprozil. In one embodiment, the bacteria is resistant to cefuroxime. In another embodiment, the bacteria is resistant to cefuzonam. In another embodiment, the bacteria is resistant to cefmetazole. In yet another embodiment, the bacteria is resistant to cefotetan. In a further embodiment, the bacteria is resistant to cefoxitin.

In one embodiment is a method for treating a subject having a third-generation cephalosporin-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject is refractory to a third-generation cephalosporin. In another embodiment, the bacteria is resistant to a third-generation cephalosporin. In a further embodiment, the bacteria is resistant to cefcapene. In another embodiment, the bacteria is resistant to cefdaloxime. In yet another embodiment, the bacteria is resistant to cefdinir. In one embodiment, the bacteria is resistant to cefditoren. In another embodiment, the bacteria is resistant to cefixime. In another embodiment, the bacteria is resistant to cefmenoxime. In yet another embodiment, the bacteria is resistant to cefodizime. In a further embodiment, the bacteria is resistant to cefotaxime. In yet a further embodiment, the bacteria is resistant to cefpimizole. In one embodiment, the bacteria is resistant to cefpodoxime. In another embodiment, the bacteria is resistant to cefteram. In yet another embodiment, the bacteria is resistant to ceftibuten. In a further embodiment, the bacteria is resistant to ceftiofur. In yet a further embodiment, the bacteria is resistant to ceftiolene. In one embodiment, the bacteria is resistant to ceftizoxime. In another embodiment, the bacteria is resistant to ceftriaxone. In yet another embodiment, the bacteria is resistant to cefoperazone. In yet a further embodiment, the bacteria is resistant to ceftazidime.

In one embodiment is a method for treating a subject having a fourth-generation cephalosporin-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject is refractory to a fourth-generation cephalosporin. In another embodiment, the bacteria is resistant to a fourth-generation cephalosporin. In a further embodiment, the bacteria is resistant to cefclidine. In another embodiment, the bacteria is resistant to cefepime. In yet another embodiment, the bacteria is resistant to cefluprenam. In one embodiment, the bacteria is resistant to cefoselis. In another embodiment, the bacteria is resistant to cefozopran. In another embodiment, the bacteria is resistant to cefpirome. In yet another embodiment, the bacteria is refractory to cefquinome.

In one embodiment is a method for treating a subject having a carbapenem-resistant bacteria comprising administering a compound of Formula (I)-(VI) or a pharmaceutically acceptable salt, ester, solvate, alkylated quaternary ammonium salt, stereoisomer, tautomer or prodrug thereof wherein the subject is refractory to a carbapenem. In another embodiment, the bacteria is resistant to a carbapenem. In a further embodiment, the bacteria is resistant to imipenem. In another embodiment, the bacteria is resistant to meropenem. In yet another embodiment, the bacteria is resistant to ertapenem. In one embodiment, the bacteria is resistant to faropenem. In another embodiment, the bacteria is resistant to doripenem. In another embodiment, the bacteria is resistant to panipenem. In yet another embodiment, the bacteria is resistant to biapenem, Vancomycin-Intermediate and Vancomycin-Resistant *Staphylococcus aureus*

Vancomycin-intermediate *Staphylococcus aureus* and vancomycin-resistant *staphylococcus aureus* are specific types of antimicrobial-resistant Staph bacteria that are refractory to vancomycin treatment. *S. aureus* isolates for which vancomycin MICs are 4-8 µg/mL are classified as vancomycin-intermediate and isolates for which vancomycin MICs are ≥16 µg/mL are classified as vancomycin-resistant (Clinical and Laboratory Standards Institute/NC-CLS. Performance Standards for Antimicrobial Susceptibility Testing. Sixteenth informational supplement. M100-S16. Wayne, Pa.: CLSI, 2006).

As used herein, the term "minimum inhibitory concentration" (MIC) refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic is determined from the tube with the lowest concentration that shows no turbidity (no growth).

In one aspect is a method of treating a subject having a bacterial infection comprising administering to the subject a compound of Formula (I)-(VI) or a pharmaceutically acceptable salt, ester, solvate, alkylated quaternary ammonium salt, stereoisomer, tautomer or prodrug thereof wherein the bacterial infection comprises a vancomycin-intermediate *Staphylococcus aureus* bacterium. In one embodiment, the vancomycin-intermediate *Staphylococcus aureus* bacterium has a MIC of between about 4 to about 8 µg/mL. In another embodiment, the vancomycin-intermediate *Staphylococcus aureus* bacterium has a MIC of about 4 µg/mL. In yet another embodiment, the vancomycin-intermediate *Staphylococcus aureus* bacterium has a MIC of about 5 µg/mL. In a further embodiment, the vancomycin-intermediate *Staphylococcus aureus* bacterium has a MIC of about 6 µg/mL. In yet a further embodiment, the vancomycin-intermediate *Staphylococcus aureus* bacterium has a MIC of about 7 µg/mL. In one embodiment, the vancomycin-intermediate *Staphylococcus aureus* bacterium has a MIC of about 8 µg/mL.

In another aspect is a method of treating a subject having a bacterial infection comprising administering to the subject a compound of Formula (I)-(VI) or a pharmaceutically acceptable salt, ester, solvate, alkylated quaternary ammonium salt, stereoisomer, tautomer or prodrug thereof wherein the bacterial infection comprises a vancomycin-resistant *Staphylococcus aureus* bacterium. In one embodiment, the vancomycin-resistant *Staphylococcus aureus* bacterium has a MIC of between about 16 µg/mL. In another embodiment, the vancomycin-resistant *Staphylococcus aureus* bacterium has a MIC of about ≥16 µg/mL. In yet another embodiment, the vancomycin-resistant *Staphylococcus aureus* bacterium has a MIC of about 20 µg/mL. In a further embodiment, the vancomycin-resistant *Staphylococcus aureus* bacterium has a MIC of about 25 µg/mL.

In one embodiment, conditions treated by the compounds described herein include, but are not limited to, endocarditis, osteomyelitis, neningitis, skin and skin structure infections, genitourinary tract infections, abscesses, and necrotizing infections. In another embodiment, the compounds disclosed herein are used to treat conditions, such as, but not limited to, diabetic foot infections, decubitus ulcers, burn infections, animal or human bite wound infections, synergistic-necrotizing gangrene, necrotizing fascilitis, intra-abdominal infection associated with breeching of the intestinal barrier, pelvic infection associated with breeching of the intestinal barrier, aspiration pneumonia, and post-operative wound infections. In another embodiment, the conditions listed herein are caused by, contain, or result in the presence of VISA and/or VRSA.

Vancomycin-Resistant Enterococci

Enterococci are bacteria that are normally present in the human intestines and in the female genital tract and are often found in the environment. These bacteria sometimes cause infections. In some cases, enterococci have become resistant to vancomycin (also known as vancomycin-resistant enterococci or VRE.) Common forms of resistance to vancomycin occur in enterococcal strains that involve the acquisition of a set of genes endoding proteins that direct peptidoglycan precursors to incorporate D-Ala-D-Lac instead of D-Ala-D-Ala. The six different types of vancomycin resistance shown by *enterococcus* are: Van-A, Van-B, Van-C, Van-D, Van-E and Van-F. In some cases, Van-A VRE is resistant to both vancomycin and teicoplanin, while in other cases, Van-B VRE is resistant to vancomycin but sensitive to teicoplanin; in further cases Van-C is partly resistant to vancomycin, and sensitive to teicoplanin.

In one aspect, is a method of treating a subject having a vancomycin-resistant enterococci comprising administering to the subject a compound of Formula (I)-(VI) or a pharmaceutically acceptable salt, ester, solvate, alkylated quaternary ammonium salt, stereoisomer, tautomer or prodrug thereof wherein the enterococci has developed resistance to vancomycin. In one embodiment, the subject has been previously treated with vancomycin for a sustained period of time. In another embodiment, the subject has been hospitalized. In yet another embodiment, the subject has a weakened immune system such as patients in Intensive Care Units or in cancer or transplant wards. In a further embodiment, the subject has undergone surgical procedures such as, for example, abdominal or chest surgery. In yet a further embodiment, the subject has been colonized vith VRE. In one embodiment, the subject has a medical device such that an infection has developed. In another embodiment, the medical device is a urinary catheter or central intravenous (IV) catheter.

In another embodiment, is a method of treating a subject having a vancomycin-resistant enterococci comprising administering to the subject a compound of Formula (I)-(VI) or a pharmaceutically acceptable salt, ester, solvate, alkylated quaternary ammonium salt, stereoisomer, tautomer or prodrug thereof wherein the *enterococcus* has Van-A resistance.

In another embodiment, is a method of treating a subject having a vancomycin-resistant enterococci comprising administering to the subject a compound of Formula (I)-(VI) or a pharmaceutically acceptable salt, ester, solvate, alkylated quaternary ammonium salt, stereoisomer, tautomer or prodrug thereof wherein the *enterococcus* has Van-B resistance.

In another embodiment, is a method of treating a subject having a vancomycin-resistant enterococci comprising administering to the subject a compound of Formula (I)-(VI) or a pharmaceutically acceptable salt, ester, solvate, alky- lated quaternary ammonium salt, stereoisomer, tautomer or prodrug thereof wherein the *enterococcus* has Van-C resistance.

General Synthetic Schemes

Compounds disclosed herein are made by the methods depicted in the reaction schemes shown below. Compounds disclosed herein are in some embodiments prepared either by semi-synthesis starting with an arylomycin compound isolated from a fermentation procedure, or by total chemical synthesis. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds described herein where $L^1$ is a bond can be prepared by synthesizing tripeptides by solution phase peptide couplings and then cyclization via Suzuki-Miyaura macrocyclization (the final step shown in the above retrosynthetic analysis) according to Scheme 1.

Scheme 1

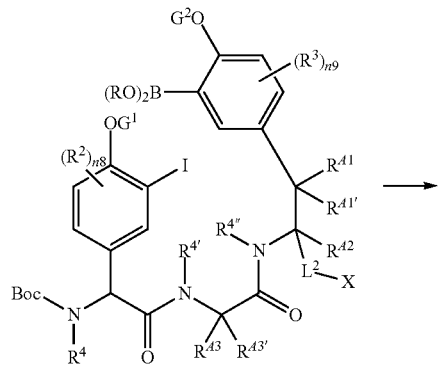

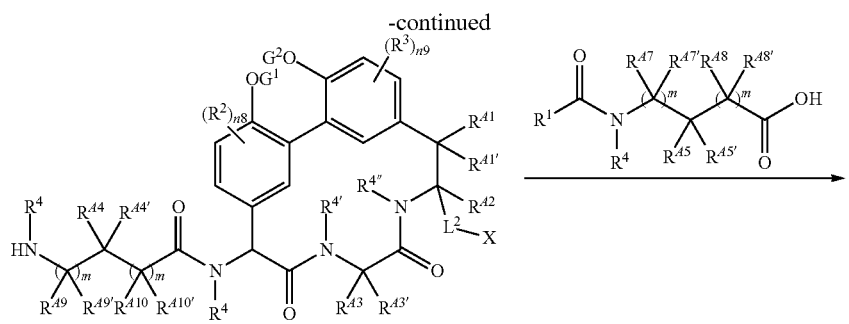
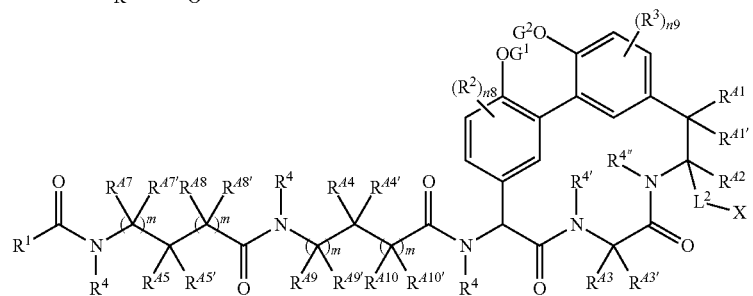
In a similar fashion, compounds described herein where $L^1$ is not a bond can be synthesized according to Scheme 2. The cyclization step is carried out by a nucleophilic substitution reaction by methods known in the literature.
Scheme 2
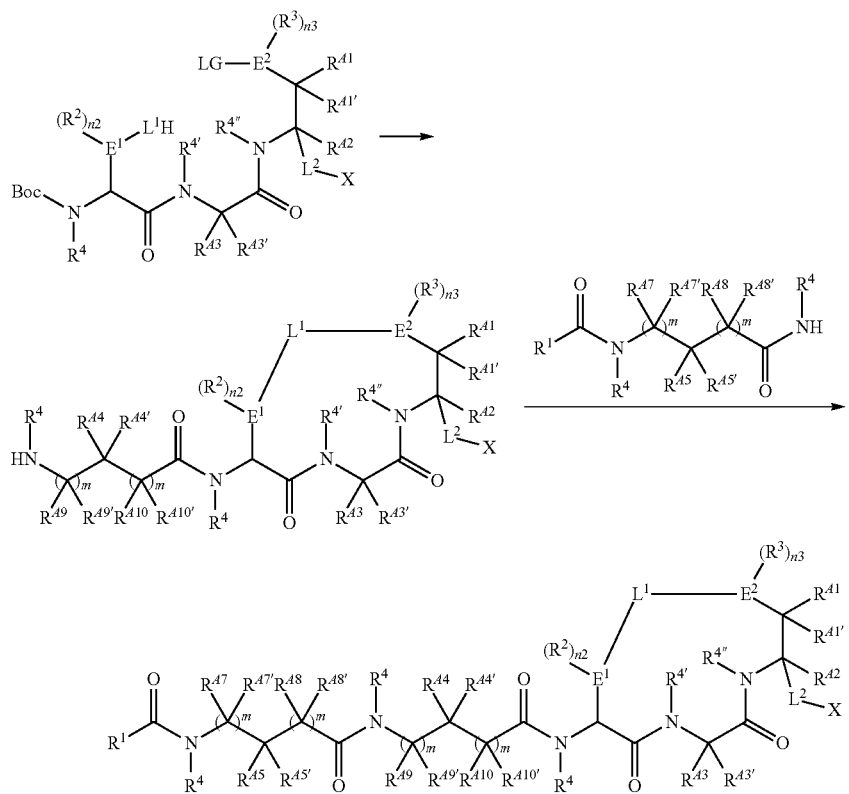

Compounds described herein where X is $CO_2H$ can be further elaborated as shown in Scheme 3. Coupling of a requisite amine to the carboxy group under standard peptide coupling conditions yields the amide product. Other sidechains can be coupled to the carboxy under similar known methods to provide additional compounds of Formulae I-V. Alternatively, the sequence of steps can be modified to elaborate the carboxy group prior to cyclization step.

Scheme 3

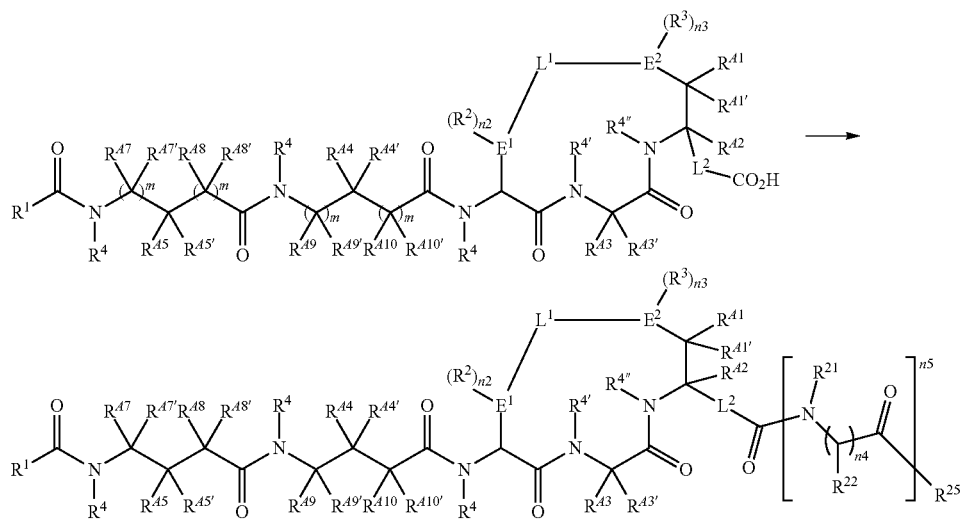

Alternatively, natural product arylomycins can provide a core for further synthetic elaboration in some cases, depending upon the desired substituent pattern.

Starting with a cyclic core, for example by a total synthesis approach as shown above and exemplified in the Examples section, below, the exocyclic peptide/peptidomimetic domain, and the lipophilic tail domain, can be elaborated using approaches and methods described herein and those within the knowledge of the person of ordinary skill. See, for example, T. Roberts, et al. (2007), *J. Am. Chem. Soc.* 129, 15830-15838; Dufour, J.; Neuville, L.; Zhu, J. P. *Synlett* 2008, 2355-2359.

The various lipopeptide tails can be assembled via solution phase peptide couplings and then coupling to the macrocyclic core. The molecule can be considered to include three major domains: the cyclic core, an exocyclic peptide or peptidomimetic moiety, and a lipophilic tail moiety. In the natural product arylomycins, such as arylomycin A2, the lipophilic tail is an n-alkanoyl, isoalkanoyl, or anteisoalkanoyl acyl group; in compounds described herein, groups are introduced into the lipophilic tail that are adapted to provide a more favorable binding interaction of the inventive arylomycin analog with an SPase including a proline residue at the −5 and −7 position relative to the catalytic SPase serine residue, as shown in the X-ray crystal structure of arylomycin bound to a fragment of a resistant form of SPase. As discussed above, the presence of a proline residue at one of these positions has been found by the inventors herein to provide resistance of the SPase to inhibition by natural product arylomycins such as arylomycin A2. The inventive compounds can overcome this resistance by designing the lipophilic tail to bind more effectively to SPase forms having the proline residue(s).

The $R^5$ group is a linear or branched alkyl chain that can be bonded to the exocyclic peptide moiety via acyl, carbamate, or urea linkages, which can be formed as described below, for the three classes of linkages. Furthermore, the $R^5$ group can be optionally substituted within the alkyl chain or at the terminus of the alkyl chain with optionally substituted aryl, optionally substituted heteroaryl, or optionally substituted

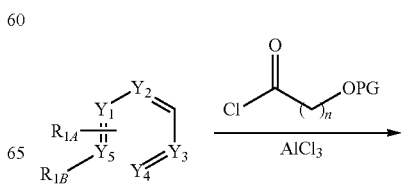

wherein Z is a bond, O, S, NH, $CH_2$ or C≡C. Synthetic approaches appropriate for each class of $R^5$ group are provided below where $Y_1$-$Y_5$ are C or N, $R_{1A}$ are optional substituents and $R_{1B}$ is the terminus of the alkyl chain.

For compounds where the $R^5$ group is substituted with aryl and the $R^5$ linkage to the peptide is an acyl group and where the aryl ring is connected directly to the acyl group these compounds can be synthesized by peptide coupling of commercially available benzoic or heterocyclic acids that had been substituted by electrophilic aromatic substitution, nucleophilic aromatic substitution or palladium catalyzed processes (and appropriately protected using standard protecting groups[S1]) to the N-terminus of the peptide chain. Heterocycles where the commercially available acids are not available can be synthesized via any one of a number of methods for synthesizing pyridines, pyrazines, pyrimidines or pyradizines[S2].

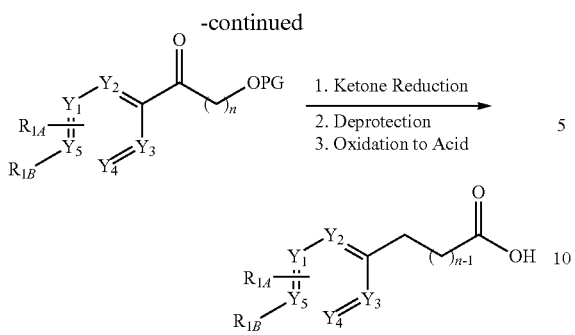

For compounds where the $R^5$ group is substituted with aryl and the $R^5$ linkage to the peptide is an acyl group and where the aryl ring is not connected directly to the acyl group, these compounds can be synthesized via the above scheme. Appropriately functionalized or unfunctionalized aryl rings (appropriately protected using standard protecting groups[S1]) can be subjected to Friedel-Crafts acylation conditions with an alkyl chain bearing an acid chloride and a protected hydroxyl group. The ketone can then be reduced, the protected hydroxyl group deprotected, the hydroxyl oxidized to an acid, and the resulting acid coupled to the N-terminus of the peptide.

For compounds where the $R^5$ group is substituted with aryl and the $R^5$ linkage to the peptide is a carbamate and the aryl ring is attached directly to the carbamate, functionalized phenols (appropriately protected using standard protecting groups[S1]) can be treated with phosgene to create the aryl carbamoyl chloride which can then be used to acylate the N-terminus of the peptide.

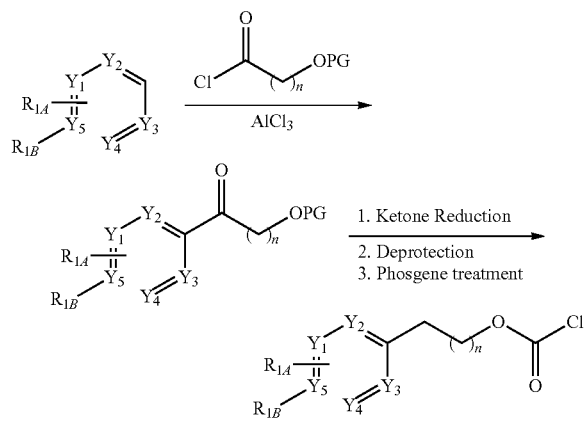

For compounds where the $R^5$ group is substituted with aryl and the $R^5$ linkage to the peptide is a carbamate and the aryl ring is not attached directly to the carbamate, the compounds can be synthesized via the route shown in the above scheme. Appropriately functionalized benzenes (appropriately protected using standard protecting groups[S1]) can be subjected to Friedel-Crafts acylation conditions with an alkyl chain bearing an acid chloride and a protected hydroxyl group. The ketone of the resulting compound can be reduced and the protecting group removed. The compound can then be treated with phosgene to form the carbamoyl chloride[S3] and this compound can be used to acylate the N-terminus of the peptide. Heterocycles where Friedel-Crafts acylations are not possible can be halogenated (and appropriately protected using standard protecting groups[S1]) and the appropriate length hydrocarbon chain terminated on one end with a protected alcohol and the other end with a halogen or boronic acid/ester can be attached via palladium mediated coupling.

For compounds where the $R^5$ group is substituted with aryl and the $R^5$ linkage to the peptide is a urea and the aryl ring is attached directly to the carbamate, functionalized aryl amines can be treated with phosgene to create the aryl ureayl chloride which can then be used to acylate the N-terminus of the peptide.

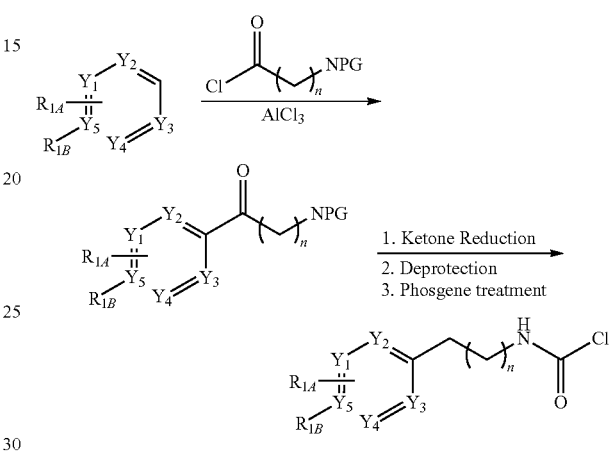

For compounds where the $R^5$ group is substituted with aryl and the $R^5$ linkage to the peptide is a urea and the aryl ring is not attached directly to the carbamate, the compounds can be synthesized via the route shown in the above scheme. Appropriately functionalized can be subjected to Friedel-Crafts acylation conditions with an alkyl chain bearing an acid chloride and a protected amine. The ketone of the resulting compound can be reduced and the protecting group be removed. The compound can then be treated with phosgene to form the ureayl chloride[S4] and this compound can be used to acylate the N-terminus of the peptide. Heterocycles where Friedel-Crafts acylations are not possible can be halogenated (and appropriately protected using standard protecting groups[S1]) and an appropriate length hydrocarbon chain terminated on one end with a protected amine and the other end with a halogen or boronic acid/ester attached via palladium mediated coupling.

For compounds where the $R^5$ group is substituted with optionally substituted

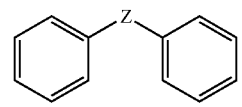

where Z is O, S, NH, or $CH_2$, in addition to the procedures outlined above for attachment to the peptide, compounds of this functionality are synthesized by employment of the Buchwald-Hartwig coupling conditions when Z=O or N. Where a para-halogen substituted protected benzoic acid, homologated benzoic acid or precursor is coupled with a phenol functionalized by electrophilic or nucleophilic aromatic substitution or palladium catalyzed processes (and appropriately protected using standard protecting groups). When Z=S these compounds can be formed using transition metal catalyzed couplings of a para-halogen substituted protected benzoic acid, homologated benzoic acid or precursor combined with an appropriately functionalized thiophenol.

For compounds where the $R^5$ group is substituted with optionally substituted

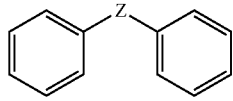

wherein Z is C≡C, in addition to the procedures outlined above for attachment to the peptide, compounds of this functionality can be synthesized by employment of Sonagashira reaction conditions on a para-halogen substituted protected benzoic acid, homologated benzoic acid or precursor combined with the appropriately functionalized by electrophilic or nucleophilic aromatic substitution or palladium catalyzed processes (and appropriately protected using standard protecting groups) aryl acetylene as shown in the below scheme.

The various embodiments of compounds disclosed herein with the variants of the $R^5$ group can be synthesized using the above approaches, in conjunction with ordinary knowledge concerning the use of any protecting or blocking groups that may be necessary. See, for example, Protective Groups in Organic Synthesis, Greene, T. W.; Wuts, P. G. M., John Wiley & Sons, New York, N.Y., (3rd Edition, 1999).

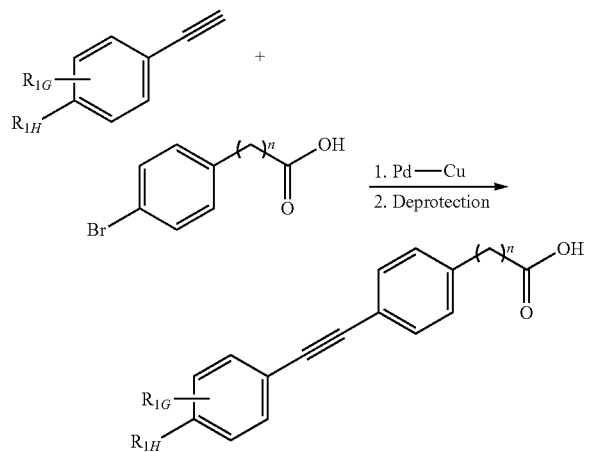

The peptidic tail can be assembled analogously to procedures described herein using standard solution or solid phase peptide couplings. Constituent amino acids containing substituents at the $R^{43}$, $R^{44}$, and $R^{45}$ positions, and the groups of formulas (IIA), (IIB), and (IIC), can either be purchased commercially or synthesized via amino acid synthesis procedures described in the literature[S7-S9]

Peptidic tails where any $R^4$ or $R^6$ are not hydrogen can be assembled using literature protocols for peptide-peptoid conjugates[S10]. The monomers can be synthesized using amine alkylation protocols[S11] for example an amino acid with a protected carboxylate is protected at the amine with a nosyl group, the nosylated amine is selectively alkylated with base and an electrophile and the nosyl group is deprotected by thiolate anion.

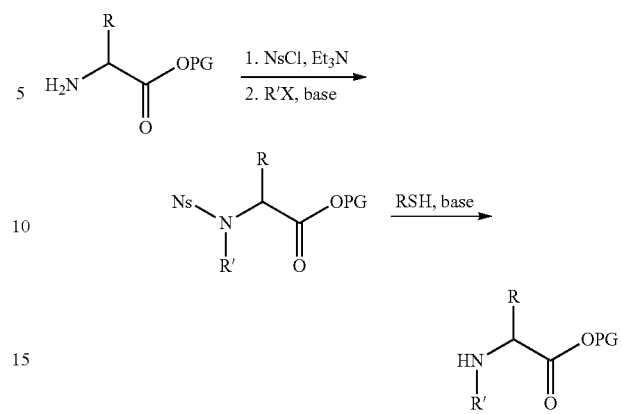

Where m, n1, or n2 are either 0 or 1, amino acids building blocks where m, n1, and n2 are equal to 1 are commercially available or can be synthesized via methods found in the literature[S12], for example from succinates where one acid is protected with a carboxyl protecting group and the other attached to a chiral auxiliary which then allows asymmetric monoalkylation. The protected carboxyl can then be deprotected and transformed into an amine via a Curtius rearrangement followed by cleavage of the chiral auxillary with peroxide.

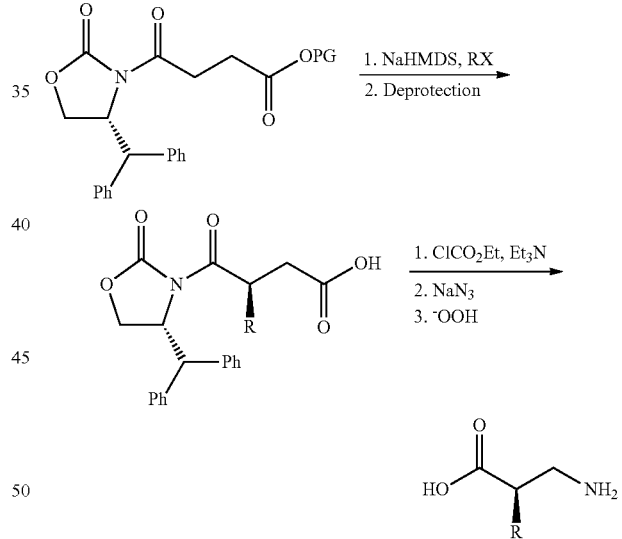

Where m, n1, and n2 are 0, 1 or 2, amino acids building blocks where m, n1, and n2 are equal to 1 or 2 can be synthesized analogously wherein the differentially protected aspartic or glutamic acid is functionalized at the free carboxylate attached to the alpha carbon by any number of strategies including but not limited to peptide coupling, reduction whereby the acid can be converted to a functionalized ketone via a Weinreb amide or reduction whereby the acid is converted to an alcohol that is subsequently converted to a tosylate and either displaced by a nucleophile or coupled to another aryl or alkyl group via a palladium mediated process:

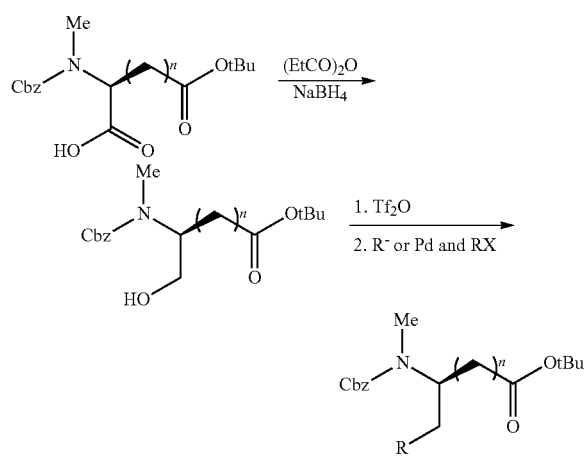

These amino acids can be synthesized via protocols found in the literature[S12-S13] for example Arndt Eistert homologation(s) as shown in the below scheme.

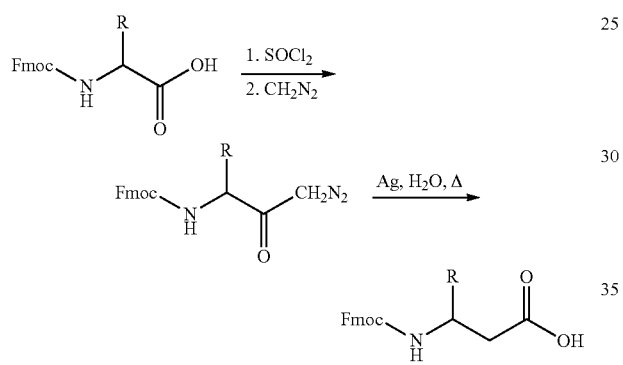

Amino acids building blocks for the synthesis of compounds where $R^2$ and $R^3$ are each independently not hydrogen can either be purchased commercially or can be synthesized via amino acid synthesis procedures known in the art and appropriately protected using standard protecting groups.

Where $OG^1$ and $OG^2$ hydroxyl, O-alkyl, or O-glycosyl, compounds can be synthesized by protocols developed for synthesis of the arylomycin natural product.

Where $R^{41}$ is not hydrogen can be synthesized by the methods described for the synthesis of the arylomycin macrocycle. The tyrosine derivatives required as building blocks for that synthesis can be synthesized as described by Michaux et. al. (2009) Chem. Soc. Rev. 38, 2093 and the references described therein. A Horner Wadsworth Emmons reaction can be used, followed by halogenations of the alkene Suzuki coupling of the desired substituent and asymmetric catalytic hydrogenation to the desired tyrosine derivative.

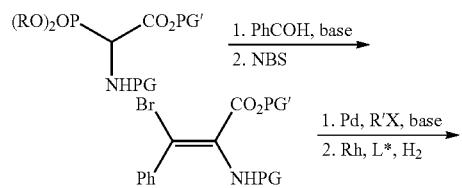

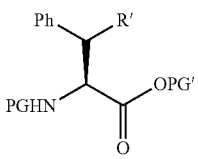

Where $R^{42}$ is not hydrogen, compounds can be synthesized using protocols for the synthesis of the natural product and protocols for peptide coupling of disubstituted amino acids. The amino acid building blocks can be synthesized by known protocols. For example the amino and carboxyl groups of an appropriately protected tyrosine can be condensed with benzaldehyde to form an oxazolidinone which can then be asymmetrically alkylated with strong base and an electrophile and hydrolyzed to yield the substituted tyrosine derivative.

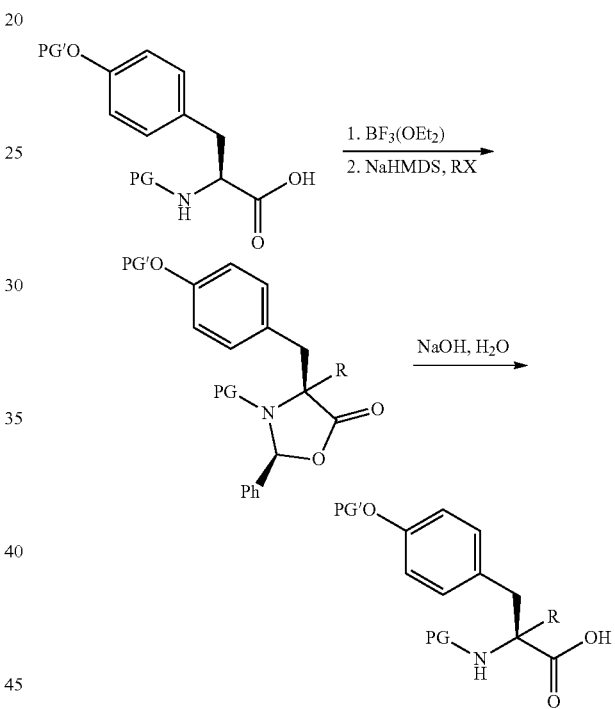

Compounds where a carbonyl group is directly attached to the scaffold at B can be synthesized from the fully deprotected arylomycin. Peptide coupling to an amino acid where the carboxylate is replaced by a protected or unprotected electrophilic moiety can install the aldehydes, boronic acids/esters, and phosphonates. Azetidinones that are attached to the arylomycin through an amine at the 3-position of the azetidinone ring can be synthesized via peptide coupling of the amine of the azetidinone to the carboxylate of arylomycin. Azetidinones that are attached to the arylomycin through the cyclic nitrogen can be synthesized by peptide coupling of the cyclic NH to the arylomycin carboxylate. The azetidinone building blocks can be synthesized via known protocols.

Administration and Pharmaceutical Composition

Pharmaceutical compositions described herein comprise a therapeutically effective amount of a compound described herein (i.e., a compound of any of Formula I, Formula II, Formula III, Formula IV, Formula V, or Formula VI) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula I, Formula II, Formula III, Formula IV, Formula V, or Formula VI) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents.

They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of a aerosol particles having with a mass medium average diameter predominantly between 1 to 5μ. Further, the formulation preferably has balanced osmolarity ionic strength and chloride concentration, and the smallest aerosolizable volume able to deliver effective dose of the compounds described herein compound described herein (i.e., a compound of any of Formula I, Formula II, Formula III, Formula IV, Formula V, or Formula VI) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula I, Formula II, Formula III, Formula IV, Formula V, or Formula VI) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound of any of Formula I, Formula II, Formula III, Formula IV, Formula V, or Formula VI) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Example 1: Synthesis of Compound 28 and Compound 29 g, 5.29 mmol) was added at ambient temperature under $N_2$ atmosphere. Then the resulting solution was stirred at ambient temperature for 12 hrs, and then the mixture was concentrated and purified by column chromatography to give the product 28B (1.5 g, yield: 60%).

Step 2

To a solution of 28B (100 mg, 0.21 mmol) in anhydrous DCM (5 mL) was bubbled through $O_3$ for 15 minutes at −78° C., then $MeNH_2$/DCM solution (2 mL) was added into the mixture, then the reaction mixture was stirred for 30 min-

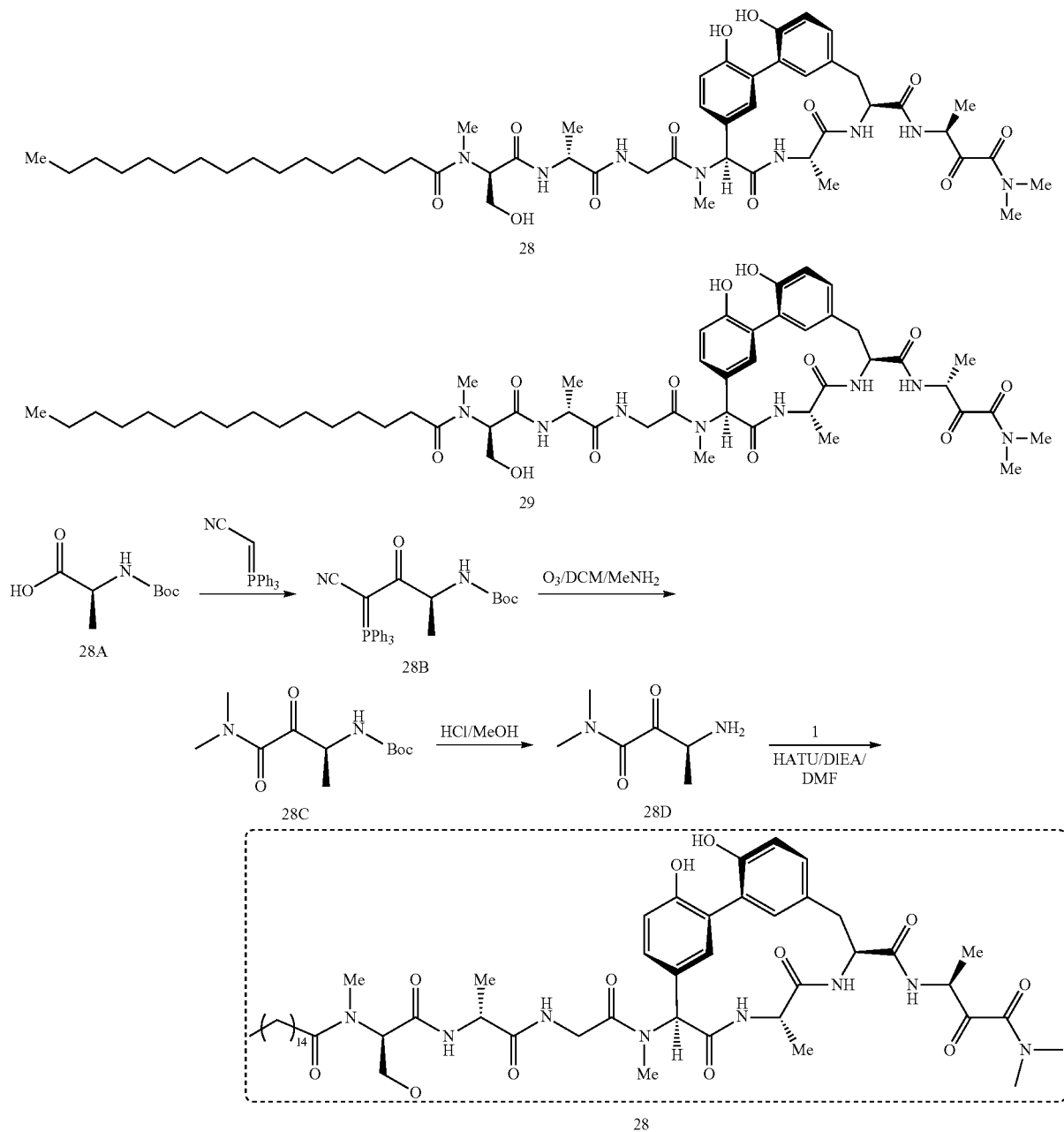

Step 1

To a solution of 28A (1 g, 5.29 mmol) in DCM (10 mL) was added EDCI (1.32 g, 6.87 mmol) and DMAP (65 mg, 0.53 mmol) under $N_2$ protection, and the mixture was stirred for 20 minutes. (Cyanomethylene)triphenylphophorane (1.6 utes, then the mixture was concentrated and purified by prep-TLC to give the product 28C (15 mg, yield: 29%).

Step 3

28C (15 mg, 0.06 mmol) was treated with HCl/MeOH (3 mL), and the mixture was stirred for 3 hours at room temperature, then the reaction mixture was concentrated to give the product 28D (8 mg, yield: 90%).
Step 4
To a solution of arylomycin $C_{16}$ (1) (10 mg, 0.011 mmol) in anhydrous DMF (2 mL) was added HATU (6 mg, 0.016 mmol) and DIEA (2.6 mg, 0.02 mmol), then the mixture was stirred at room temperature for 15 minutes, then 28D (8 mg, 0.056 mmol) was added and the reaction mixture was stirred at room temperature for 10 hours, then the reaction mixture was concentrated to give the crude product 28, which purified by prep-HPLC to give the product 28, 4.5 mg and diastereomer 29, 1.7 mg (total yield: 52%). Compound 28 MS (ESI) m/z 1007.3 (M+H)$^+$. Compound 29 MS (ESI) m/z 1007.5 (M+H)$^+$.

Example 2: Synthesis of Compound 33

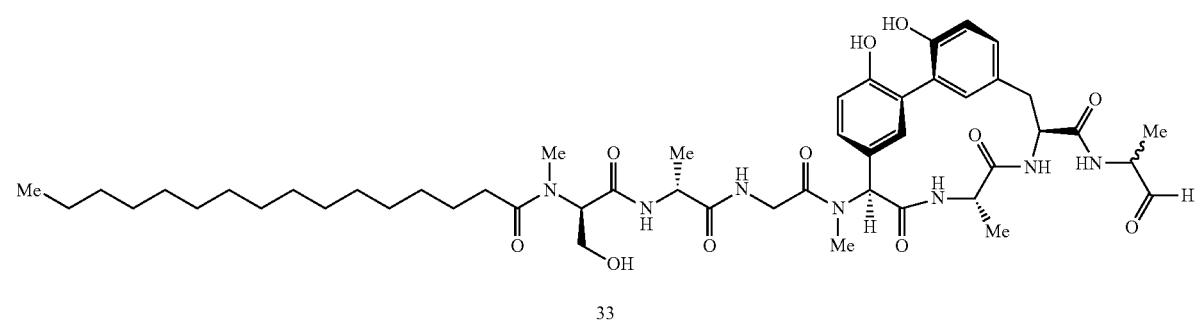

33

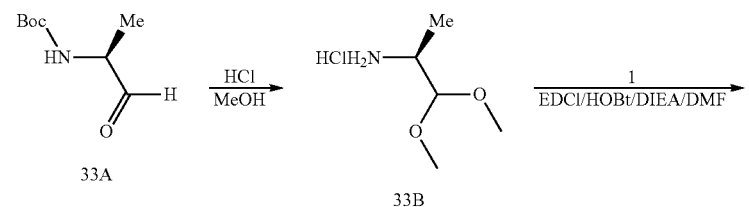

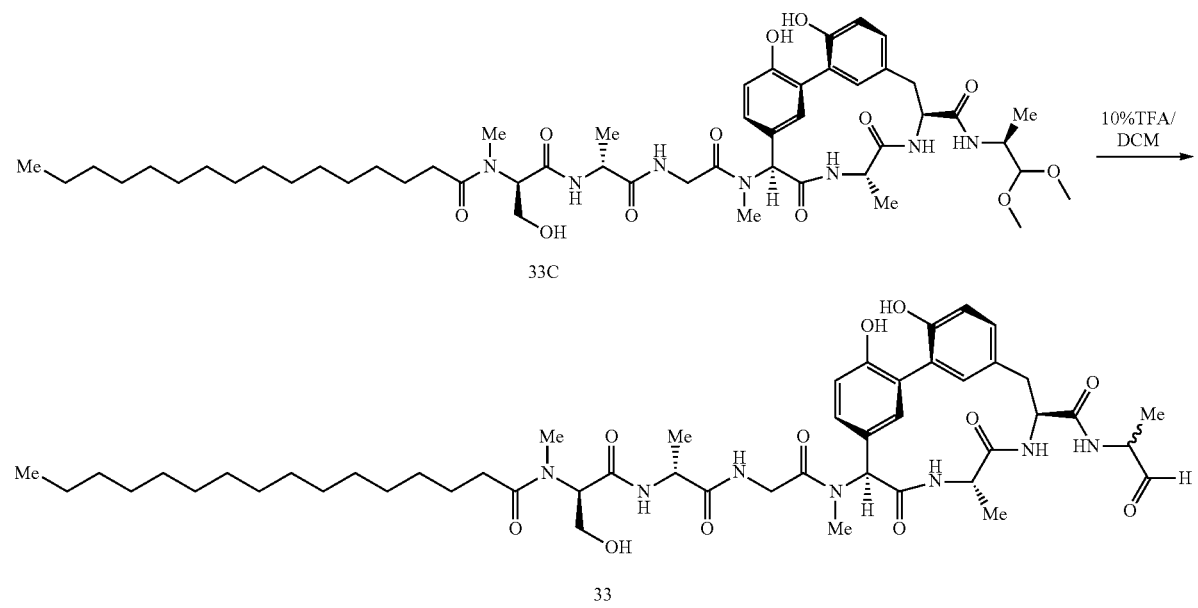

Step 1

33A (100 mg, 0.58 mmol) was treated with HCl/MeOH (5 mL), and the reaction mixture was stirred at 20° C. for 4 hrs, then the mixture was concentrated at 20° C. to give the product 33B (40 mg, yield: 58.2%).

concentrated and purified by prep-HPLC to give the product 33 (2.2 mg, yield: 13.8% via 2 steps). Compound 33 MS (ESI) m/z 936.2.

Example 3: Synthesis of Compound 25

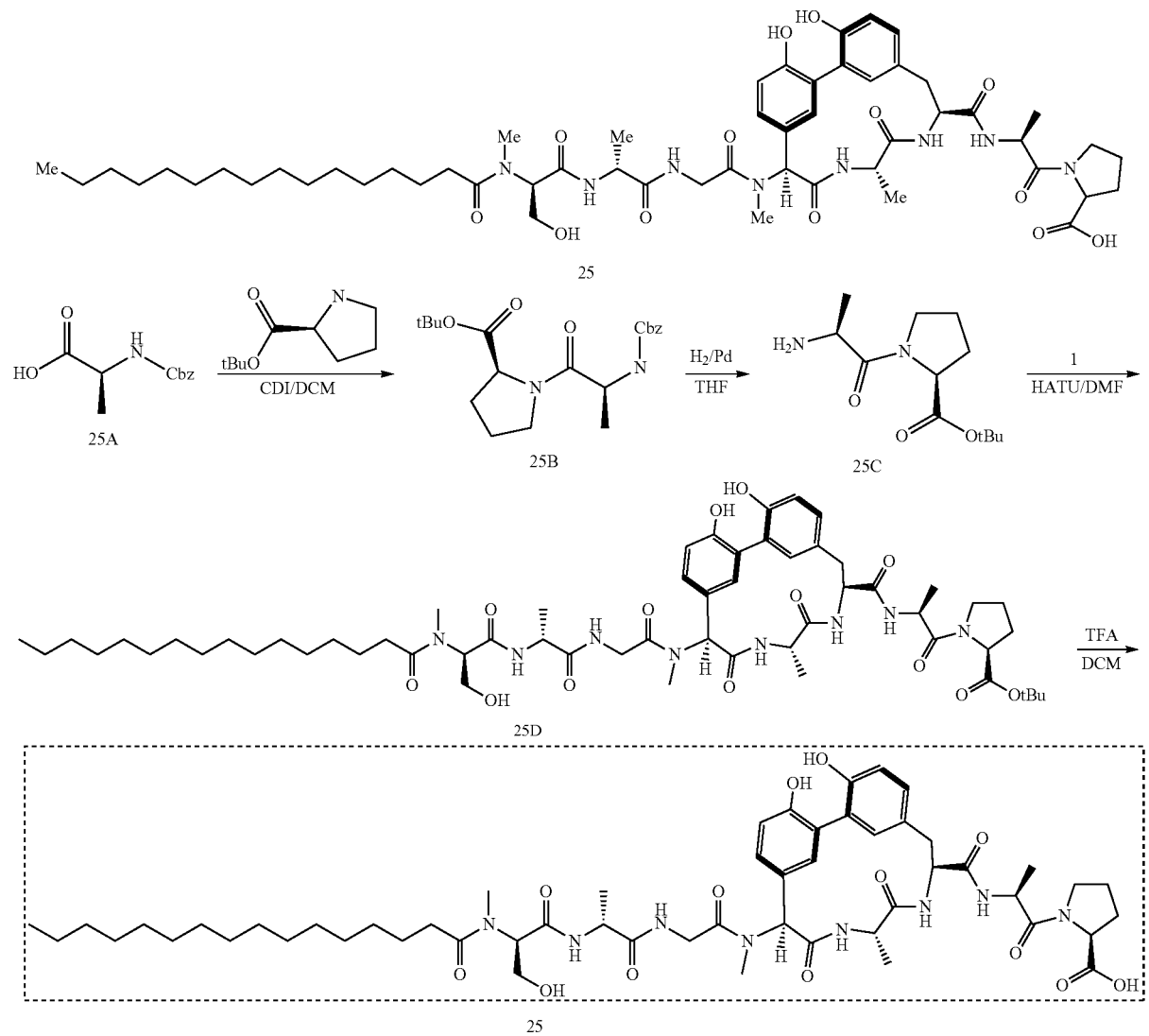

Step 2

To a solution of 1 (15 mg, 0.017 mmol) in anhydrous DMF (2 mL) was added EDCI (4.8 mg, 0.025 mmol), HOBt (3.4 mg, 0.025 mmol) and DIEA (4.6 mg, 0.035 mmol), then the mixture was stirred at room temperature for 15 minutes, then 33B (20 mg, 0.168 mmol) was added and the reaction mixture was stirred at room temperature for 10 hours, then the reaction mixture was concentrated to give the crude product 33C (crude 35 mg), which was used in the next step without further purification.

Step 3

To a solution of 33C (35 mg crude) in anhydrous DCM (5 mL) was added TFA (0.5 mL) at 0° C., then the mixture was stirred at room temperature for 5 hours, then the mixture was Step 1

To a solution of 25A (1 g, 4.48 mmol) in anhydrous DCM (15 mL) was added CDI (0.78 g, 4.8 mmol), then the mixture was stirred at room temperature for 15 minutes, then pyrrolidine-2-carboxylic acid tert-butyl ester (0.77 g, 4.48 mmol) was added, then the mixture was stirred at room temperature for 10 hours, then the mixture was concentrated and extracted with DCM/H2O, the organic layer was combined and dried with $Na_2SO_4$, then the organic layer was concentrated to give the product 25B (1.2 g, yield: 71%).

Step 2

To a solution of 25B (300 mg, 0.798 mmol) in anhydrous THF (5 mL) was hydrogenated with Pd/C (80 mg) at 40 psi for 10 hours, then the catalyst was filtered and the filtrate was concentrated to give the product 25C (120 mg, yield: 62%).

Step 3

To a solution of 1 (35 mg, 0.040 mmol) in anhydrous DMF (3 mL) was added HATU (22.8 mg, 0.06 mmol) and DIEA (10.4 mg, 0.08 mmol), then the mixture was stirred at room temperature for 15 minutes, then 25C (40 mg, 0.165 mmol) was added and the reaction mixture was stirred at room temperature for 10 hrs, then the reaction mixture was concentrated to give the crude product 25D (110 mg crude) which was used in the next step without further purification.

Step 4

To a solution of 25D (110 mg crude) in anhydrous DCM (5 mL) was added TFA (1 mL) at 0° C., then the mixture was stirred at room temperature for 5 hrs, then the mixture was concentrated and purified by prep-HPLC to give the product 25 (6.9 mg, yield: 16.6% via 2 steps).

Example 4: Synthesis of Compound 31 and Compound 32

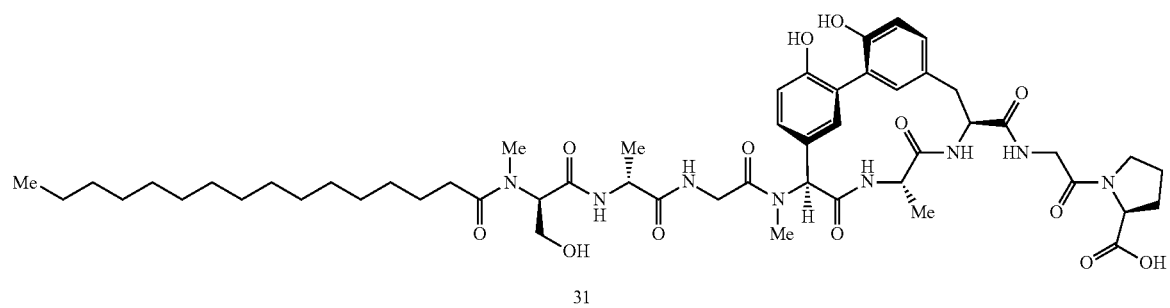
31

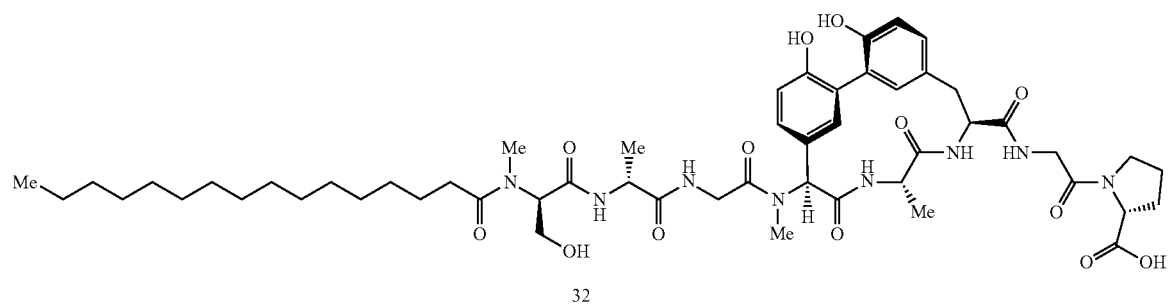
32

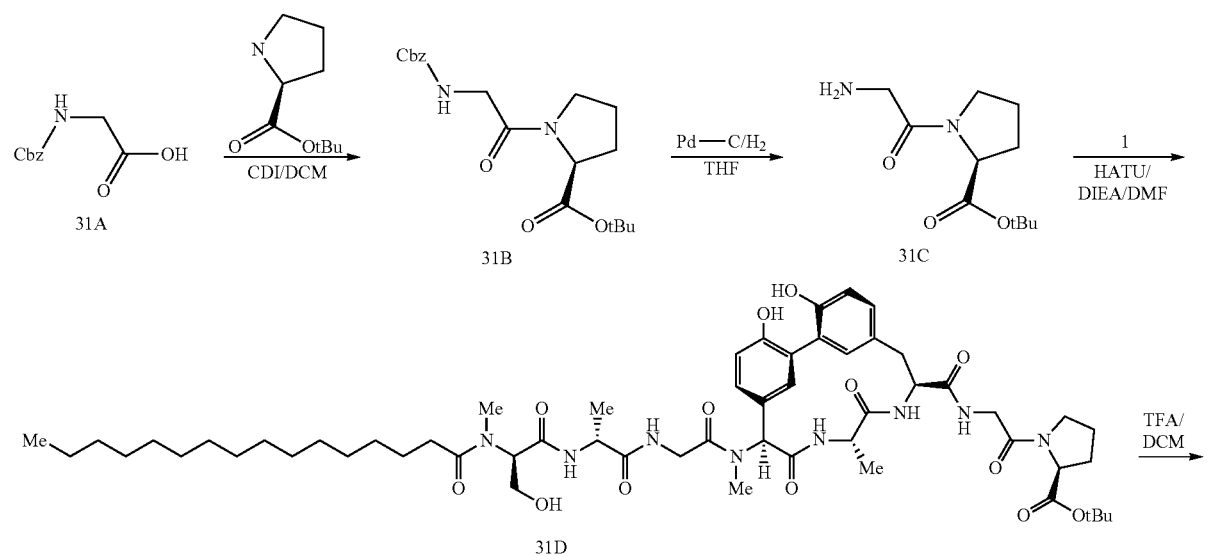

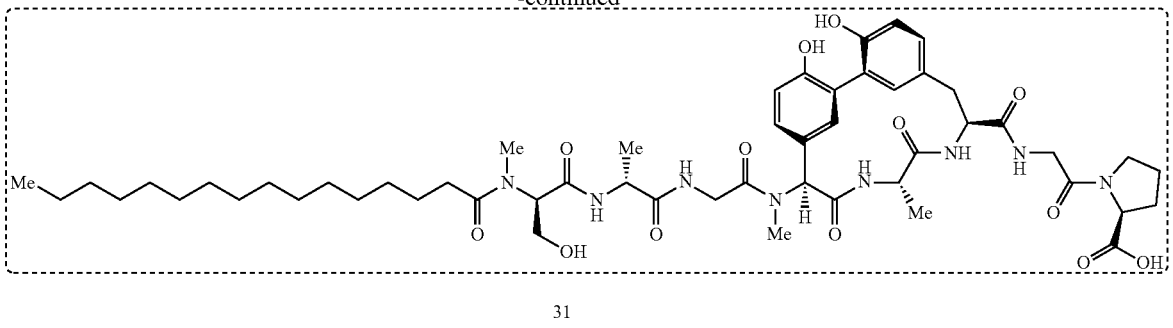

31

Step 1

To a solution of 31A (200 mg, 0.96 mmol) in anhydrous DCM (5 mL) was added CDI (162 mg, 1 mmol), then the mixture was stirred at room temperature for 15 minutes, then pyrrolidine-2-carboxylic acid tert-butyl ester (164 mg, 0.96 mmol) was added, then the mixture was stirred at room temperature for 10 hours, then the mixture was concentrated and extracted with DCM/H2O, the organic layer was combined and dried with Na2SO4, then the organic layer was concentrated to give the product 31B (200 mg, yield: 58%).\

Step 2

To a solution of 31B (200 mg, 0.552 mmol) in anhydrous THF (5 mL) was hydrogenated with Pd/C (80 mg) at 40 psi for 10 hours, then the catalyst was filtered and the filtrate was concentrated to give the product 31C (100 mg crude), which was used in the next step without further purification.

Step 3

To a solution of 1 (30 mg, 0.034 mmol) in anhydrous DMF (3 mL) was added HATU (19 mg, 0.05 mmol) and DIEA (9.1 mg, 0.07 mmol), then the mixture was stirred at room temperature for 15 minutes, then 31C (30 mg, 0.132 mmol) was added and the reaction mixture was stirred at room temperature for 10 hours, then the reaction mixture was concentrated to give the crude product 31D (70 mg crude) which was used in the next step without further purification.

Step 4

To a solution of 31D (70 mg crude) in anhydrous DCM (5 mL) was added TFA (1 mL) at 0° C., then the mixture was stirred at room temperature for 5 hrs, then the mixture was concentrated and purified by prep-HPLC to give the product 31 2.4 mg, as well as diastereomer 32, 1 mg (total yield: 9.6% via 2 steps). Compound 31 MS (ESI) m/z 1035.5 (M+H)⁺. Compound 32 MS (ESI) m/z 1035.4.

Example 5: Synthesis of Compound 9

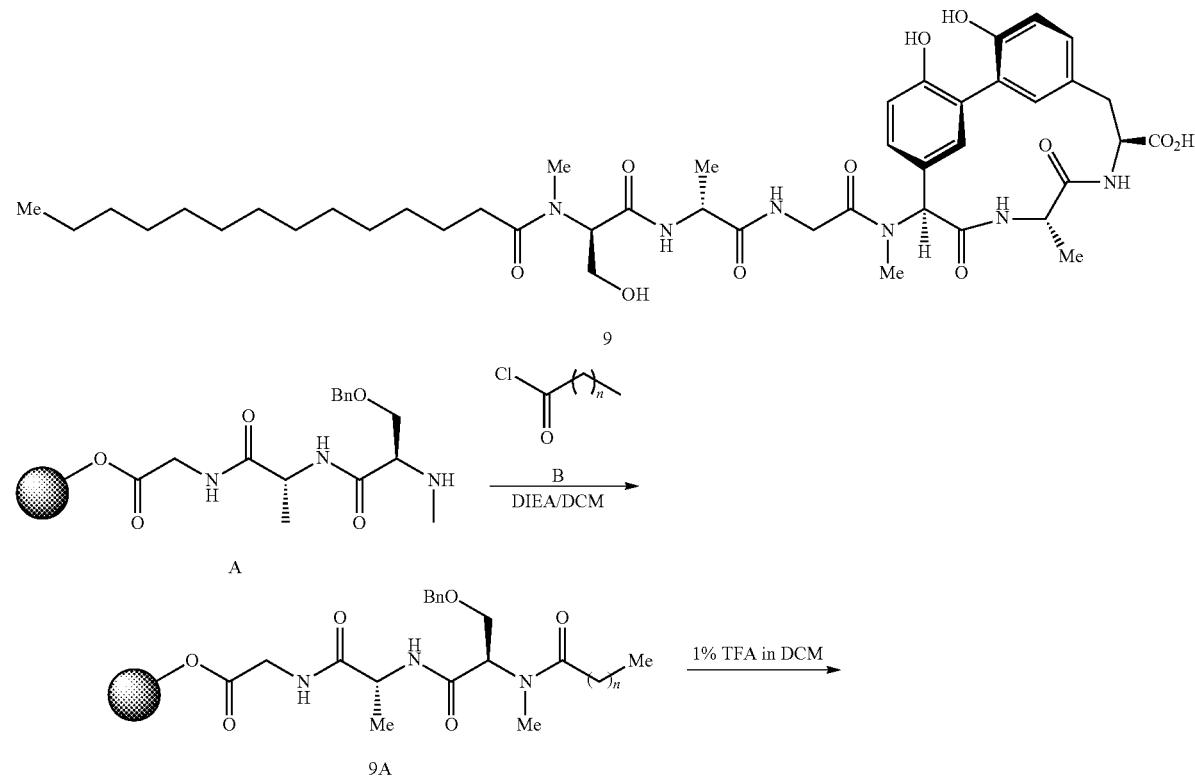

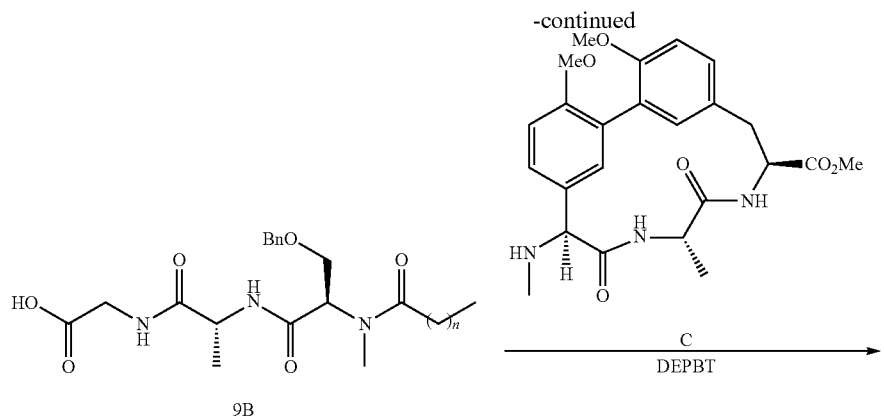

9B

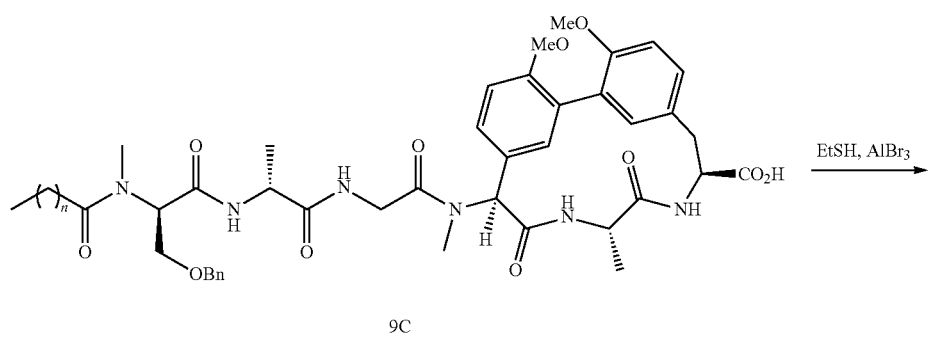

9C

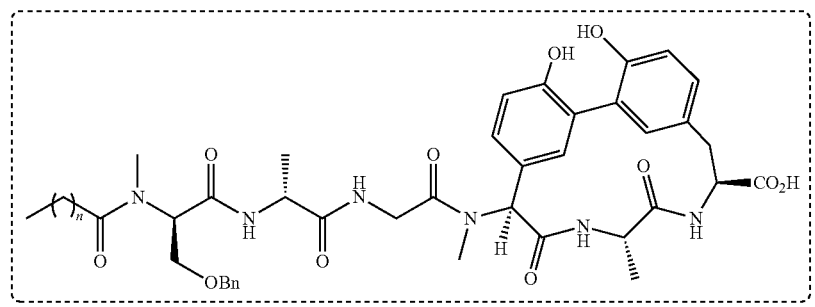

9 n = 12

Step 1

To a suspension of A (0.7 g) in DCM (10 mL) was added DIEA (1 mL). Then a solution of B (n=12) (0.2 mL) in DCM (10 mL) was added at 0° C. Then the resulting mixture was shaked at room temperature for 1 hr. The mixture was filtered and the cake was washed with DCM (20 mL*3), DMF (20 mL*3), DCM (20 mL*3) to give 9A.

Step 2

A suspension of 9A was treated with 1% TFA/DCM (10 mL). The mixture was shaked at room temperature for 20 mins. Then the mixture was filtered and the filtrate was concentrated to give 9B, as a yellow oil.

Step 3

A mixture of 9B (200 mg, 0.39 mmol), C (109 mg, 0.24 mmol), NaHCO₃ (20 mg, 0.24 mmol) and DEPBT (109 mg, 0.39 mmol) in dry THF (20 mL) was heated to reflux overnight. After ELSD showed the reaction was complete, the mixture was concentrated. The residue was treated with H₂O (10 mL), then extracted with EA (20 mL*3). The combined organic layers were washed with brine, dried over Na₂SO₄. The solvent was removed and the crude product was purified by prep-HPLC to give 9C (45 mg, yield 15%).

Step 4

To a mixture of 9C (40 mg, 0.042 mmol) in EtSH (2 mL) was added 1.0M AlBr3 in CH₂Br₂ (1.6 mL) under Ar. Then the mixture was heated to 50° C. for 4 hrs. After HPLC showed the reaction was complete, the mixture was treated with MeOH (2 mL) and the solvent was removed. The crude product was purified by prep-HPLC to give 9 (2 mg, yield: 6%).

Example 6: Synthesis of Compound 19

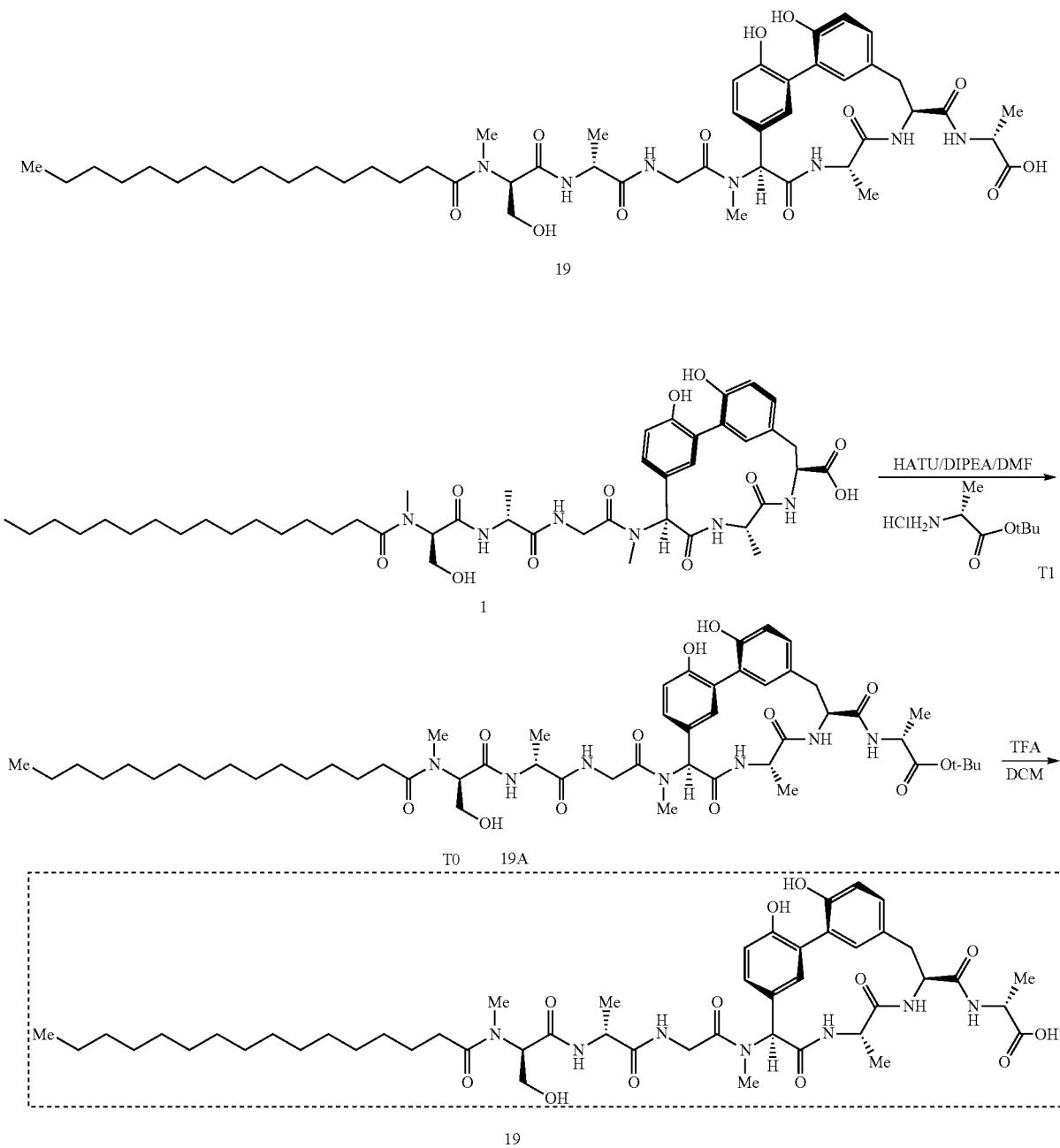

Step 1

A mixture of 1 (40 mg, 0.046 mmol), HATU (21 mg, 0.056 mmol) and DIEA (18 mg, 0.14 mmol) in DMF (2 mL) was stirred at room temperature for 30 mins. Then (R)-alanine t-butyl ester hydrochloride (17 mg, 0.092 mmol) was added. The resulting mixture was stirred at room temperature overnight. After HPLC showed the reaction was complete, the solvent was removed to give 19A (70 mg, crude) and the crude product was used directly without further purification.

Step 2

A mixture of 1 (0 mg, 0.046 mmol), HATU (21 mg, 0.056 mmol) and DIEA (18 temperature for 5 hrs. After HPLC showed the reaction was complete, the solvent was removed and the crude product was purified by prep-HPLC to give 19 (1.9 mg, yield: 3%).

Example 7: Synthesis of Compound 20

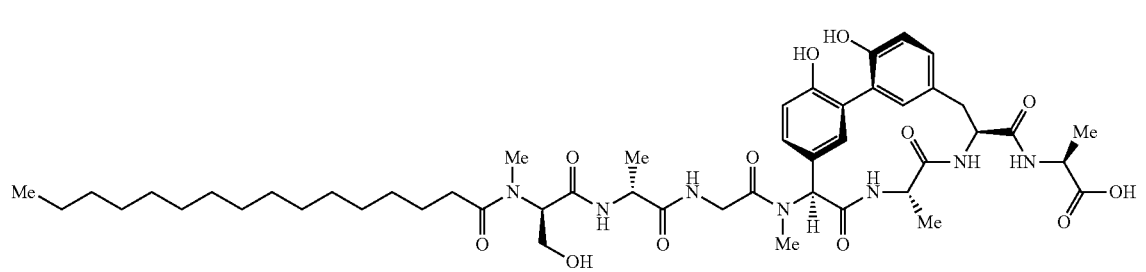

Compound 20 (5.4 mg) was synthesized using the procedure of Example 6, but substituting (S)-alanine t-butyl ester hydrochloride for (R)-alanine t-butyl ester hydrochloride in Step 1. Compound 20 MS (ESI) m/z 952.5.

Example 8: Synthesis of Compound 24

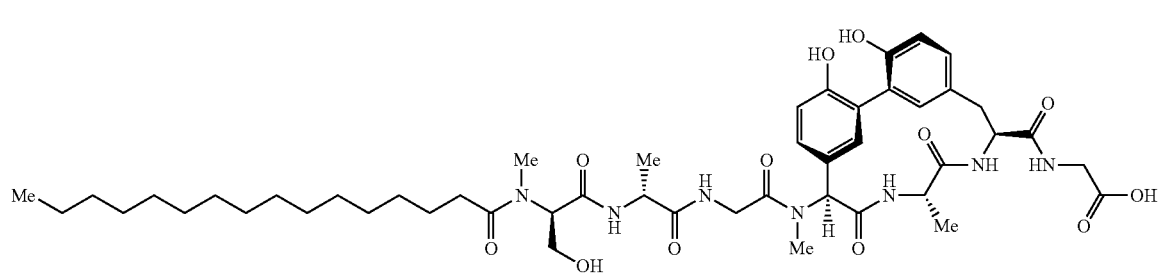

Compound 24 (3.8 mg) was synthesized using the procedure of Example 6, but substituting glycine t-butyl ester hydrochloride for (R)-alanine t-butyl ester hydrochloride in Step 1.

Example 9: Synthesis of Compound 26

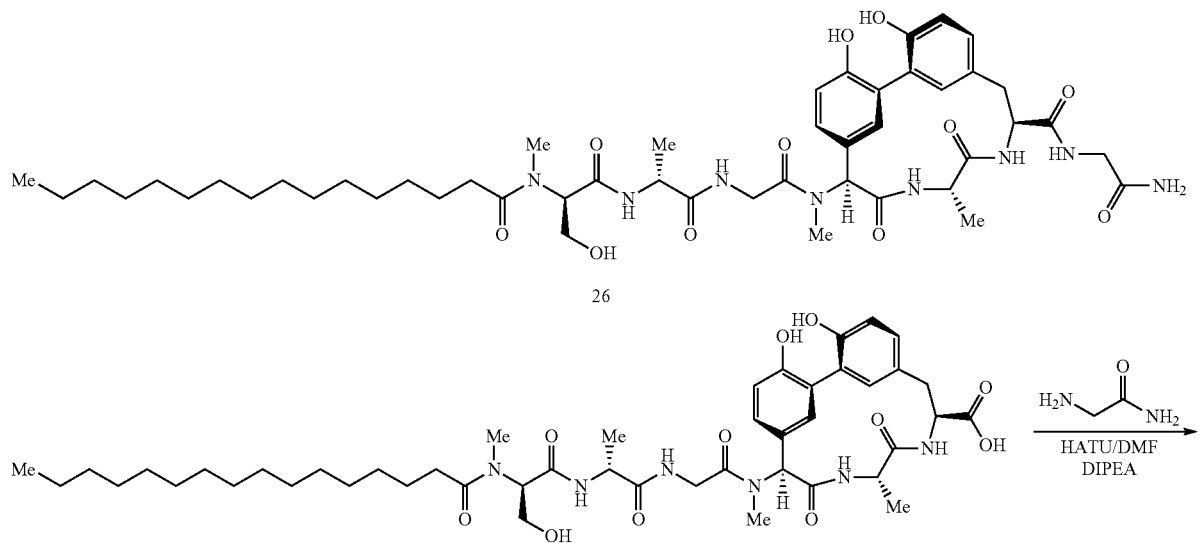

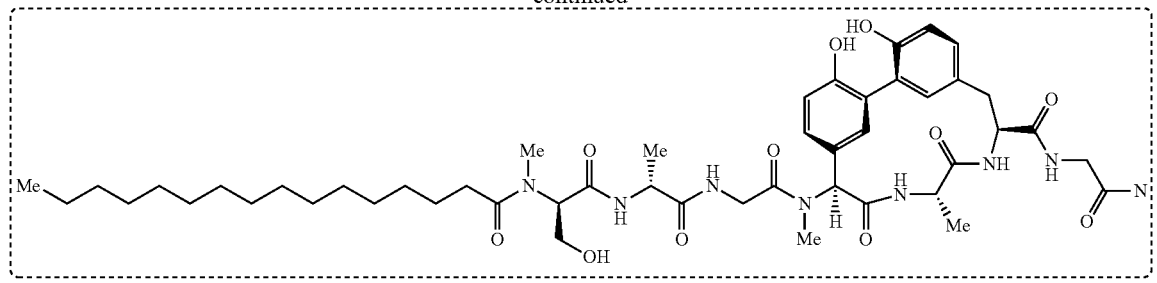

26

A mixture of 1 (20 mg, 0.023 mmol), HATU (10 mg, 0.027 mmol) and DIEA (8 mg, 0.068 mmol) in DMF (2 mL) was stirred at room temperature for 30 mins. Then 2-amino-acetamide (7 mg, 0.068 mmol) was added. The resulting mixture was stirred at room temperature overnight. After HPLC showed the reaction was complete, the solvent was removed and the crude product was purified by prep-HPLC to give 26 (2.1 mg, yield: 9.9%), as an off-white solid. Compound 26 MS (ESI) m/z 937.5.

Example 10: Synthesis of Compound 11

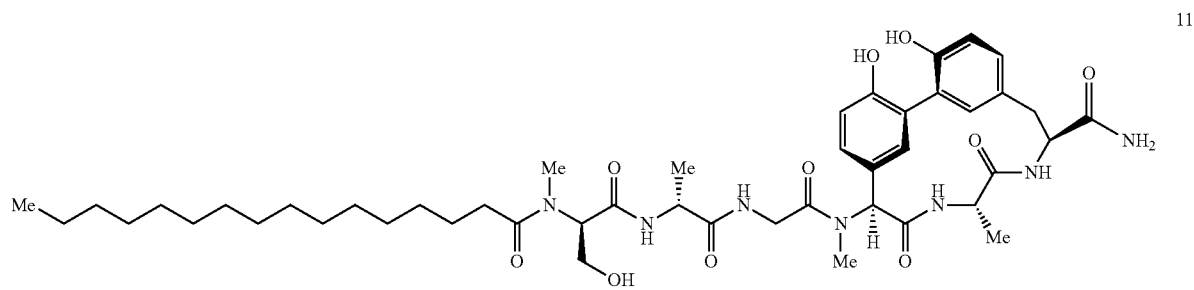

11

Compound 11 (16 mg) was synthesized using the procedure of Example 9, but substituting ammonia for 2-aminoacetamide.

Example 11: Synthesis of Compound 12

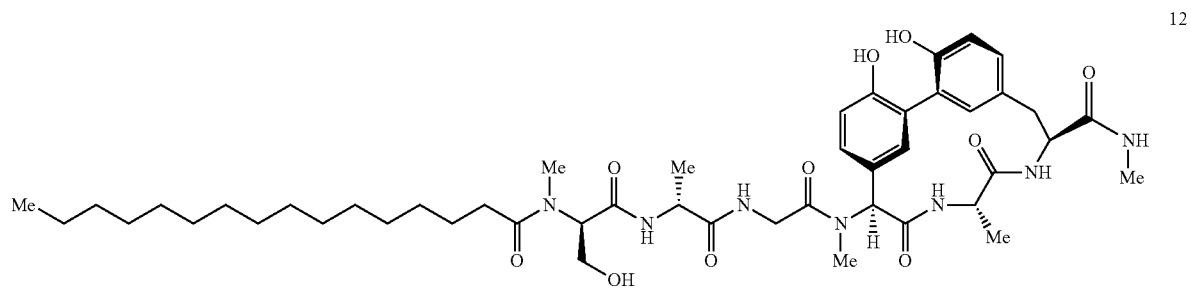

12

Compound 12 (4.2 mg) was synthesized using the procedure of Example 9, but substituting methylamine for 2-aminoacetamide. Compound 12 MS (ESI) m/z 894.4.
Example 12: Synthesis of Compound 13
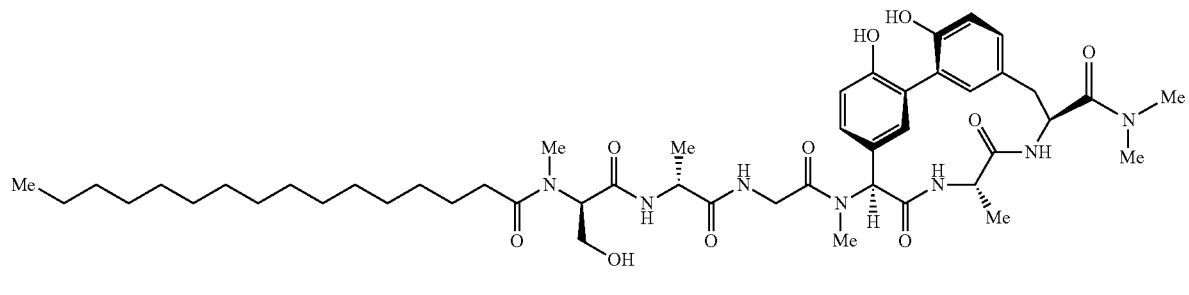
Compound 13 (5 mg) was synthesized using the procedure of Example 9, but substituting dimethylamine for 2-aminoacetamide. Compound 13 MS (ESI) m/z 908.5.
Example 13: Synthesis of Compound 22
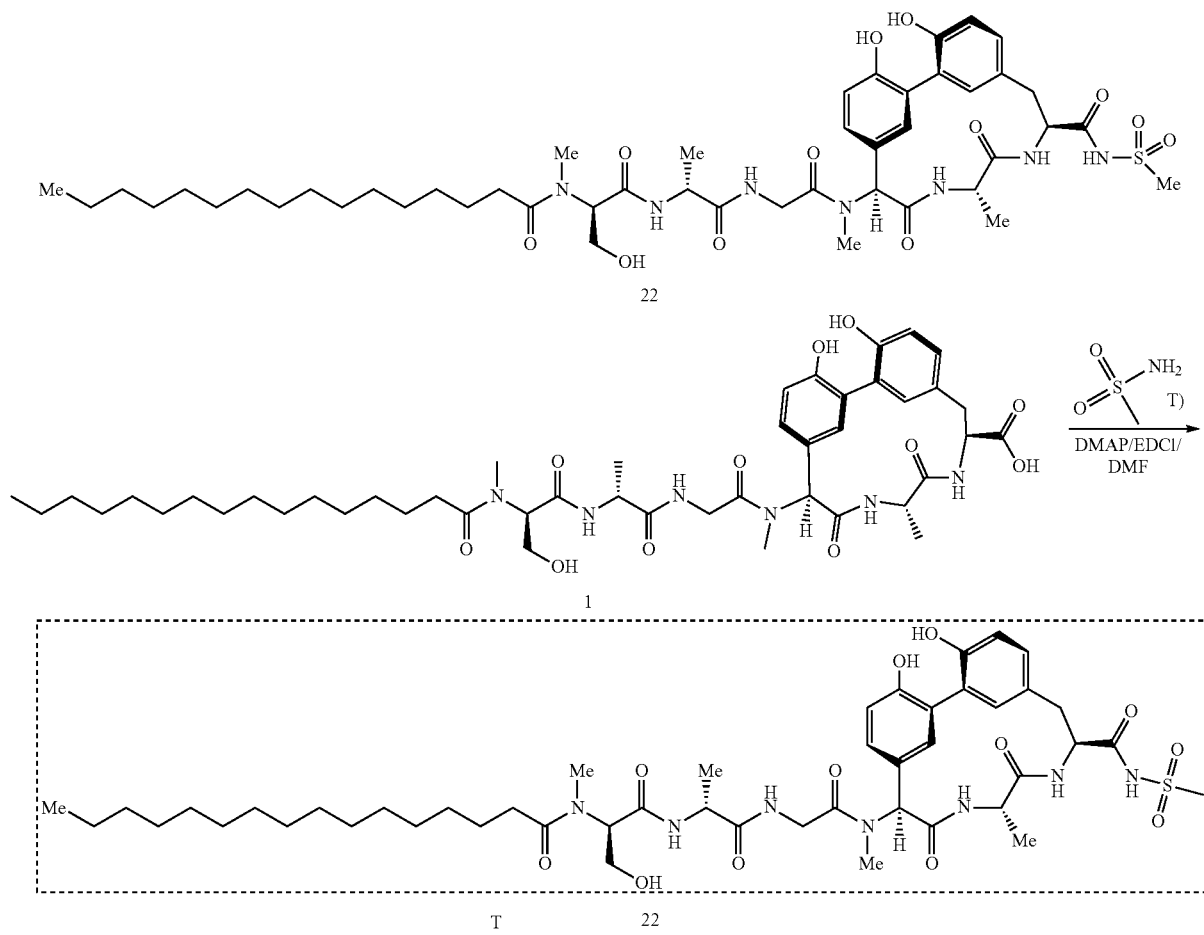

A mixture of 1 (30 mg, 0.034 mmol), methanesulfonamide (10 mg, 0.082 mmol), DMAP (17 mg, 0.14 mmol) and EDCI (8 mg, 0.041 mmol) in DMF (2 mL) was stirred at room temperature overnight. After HPLC showed the reaction was complete, the solvent was removed and the crude product was purified by prep-HPLC to give 22 (2.8 mg, yield: 8.6%), as a grey oil.

Example 14: Synthesis of Compound 23

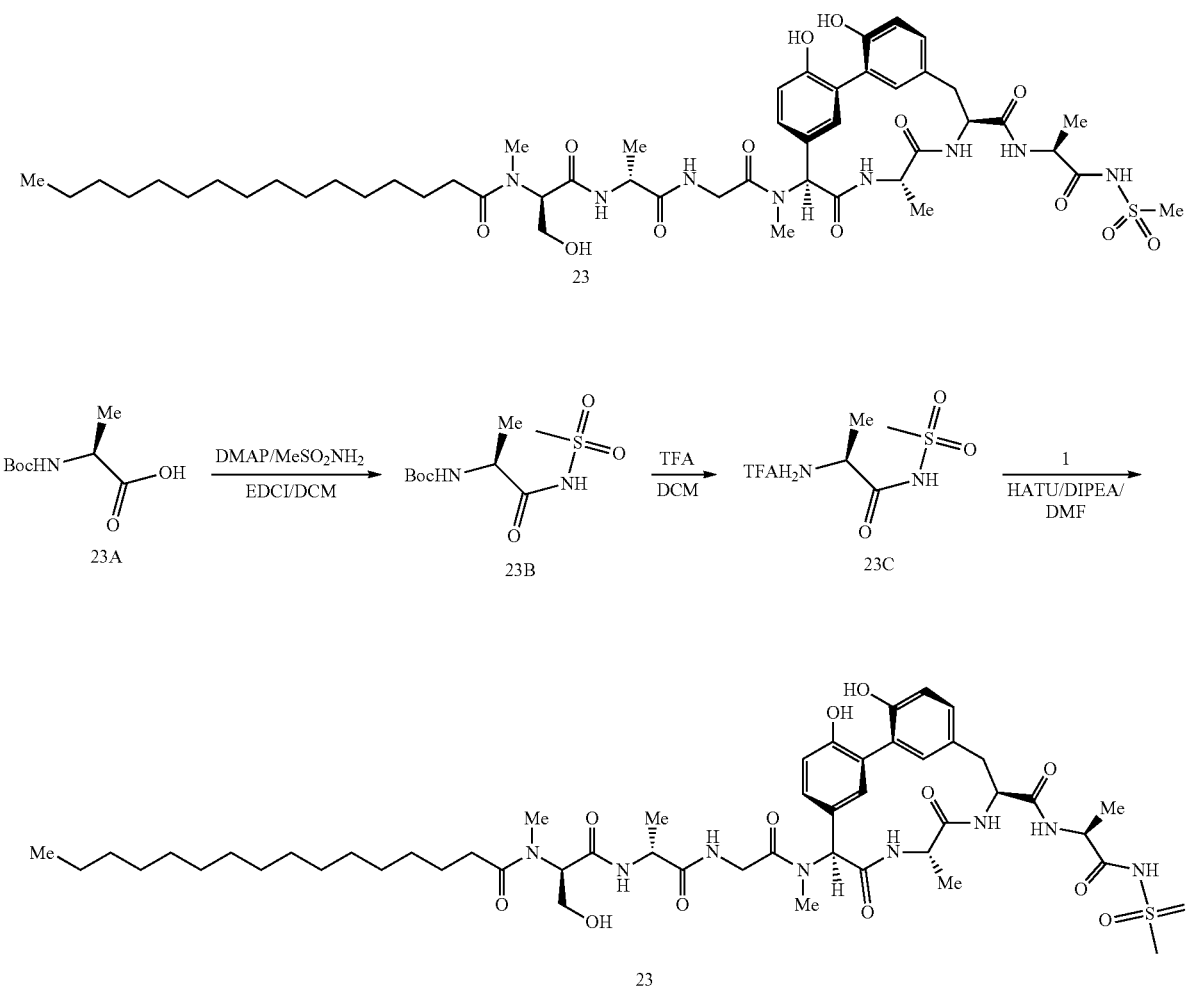

Step 1

A mixture of 23A (1 g, 5.3 mmol), methanesulfonamide (0.7 g, 6.4 mmol), DMAP (2.6 g, 21.2 mmol) and EDCI (1.2 g, 6.4 mmol) in DCM (50 mL) was stirred at room temperature overnight. After ELSD showed the reaction was complete, the mixture was treated with H₂O (10 mL). Then the resulting mixture was treated with DCM (30 mL*3). The combined organic layers were washed with brine, dried over Na₂SO₄. The solvent was removed to give 23B (1.2 g, yield: 85.3%).

Step 2

A solution of 23B (1.2 g, 7.2 mmol) was stirred in 20% TFA/DCM (20 mL) at room temperature for 3 hrs. After ELSD showed the reaction was complete, the solvent was removed to give 23C (0.6 g, yield: 50%), which was used directly without any purification.

Step 3

A mixture of 1 (50 mg, 0.057 mmol), HATU (26 mg, 0.068 mmol) and DIEA (22 mg, 0.17 mmol) in DMF (2 mL) was stirred at room temperature for 30 mins. Then 23C (42 mg, 0.17 mmol) was added. The resulting mixture was stirred at room temperature overnight. After HPLC showed the reaction was complete, the solvent was removed and the crude product was purified by prep-HPLC to give 23 (4.1 mg, yield: 7.0%), as an off-white solid.

Example 15: Synthesis of Compound 27

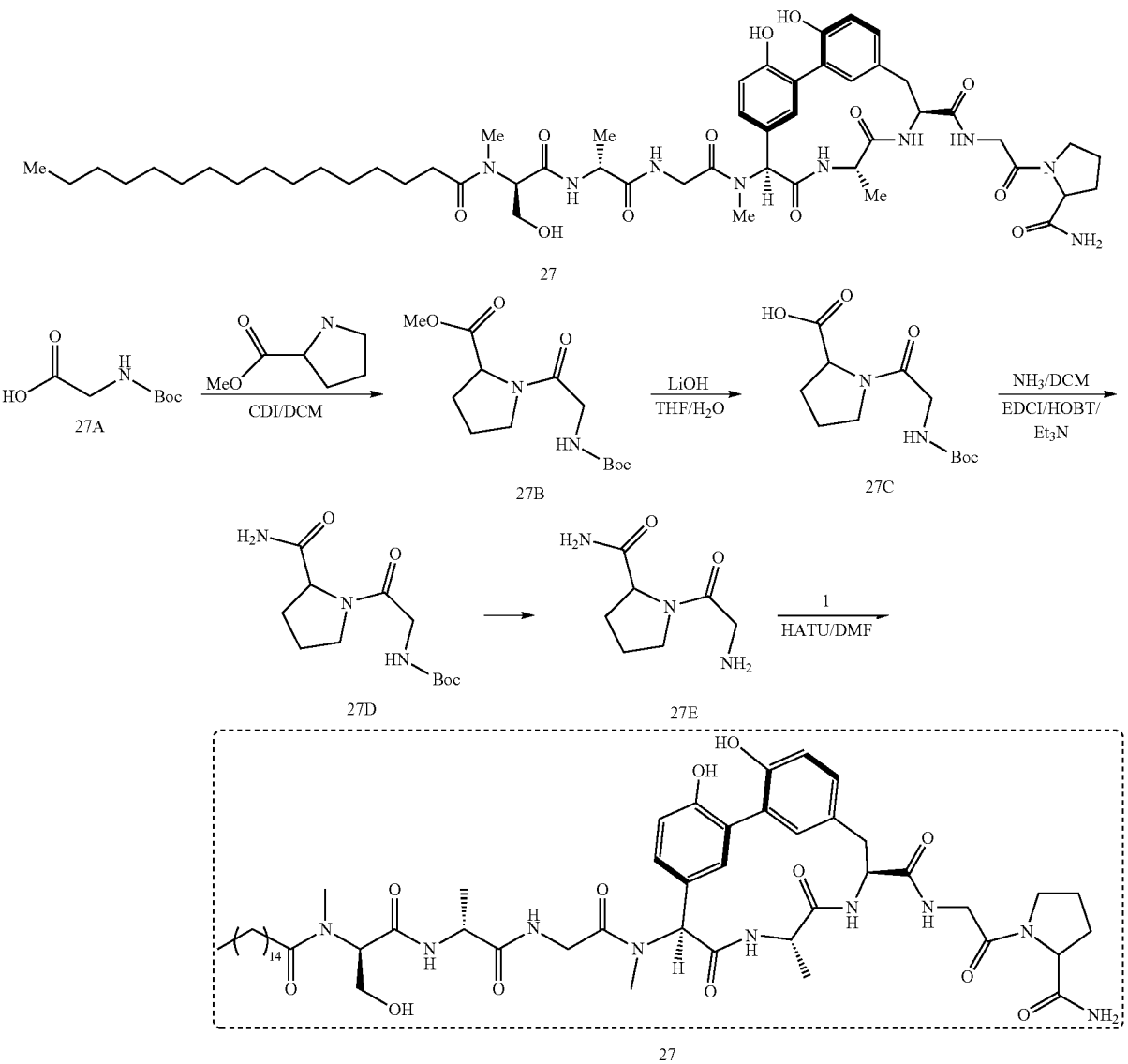

Step 1

A mixture of 27A (2.4 g, 13.9 mmol) and CDI (2.3 g, 13.9 mmol) in dry DCM (50 mL) was stirred at RT for 1 hr, then proline methyl ester (2.3 g, 13.9 mmol) was added. The mixture was stirred at RT overnight. After ELSD showed the reaction was complete, the mixture was treated with water, then extracted with DCM (30 mL*3). The combined organic layers were washed with brine, dried over sodium sulfate. The solvent was removed to give 27B (3.8 g, yield: 97%), as an off-white solid.

Step 2

To a solution of 27B (3.8 g, 13.3 mmol) in THF (30 mL) was added a solution of LiOH.H2O (1.1 g, 26.2 mmol) in water (30 mL). The reaction mixture was stirred at RT for 1 hr. After TLC showed the reaction was complete, the solvent was evaporated. The residue was adjusted pH=3-4 with citric acid. The resulting mixture was extracted with EA (30 mL*3). The combined organic layers were washed with brine, dried over $Na_2SO_4$. The solvent was removed to give 27C (2 g, yield: 55.3%), as an off-white solid.

Step 3

To a solution of 27C (600 mg, 2.2 mmol) in DCM (30 mL) was added HOBt (445 mg, 3.3 mmol) and EDCI (546 mg, 2.86 mmol). The mixture was stirred at room temperature for 30 mins, and then $NH_3$/DCM (6 mL) was added. The resulting mixture was stirred overnight. The crude product was purified by HPLC to give 27D (550 mg, yield: 92%).

Step 4

To a solution of 27D (550 mg, 2.0 mmol) in DCM (10 mL) was added TFA (2 ml), then the reaction mixture was stirred at RT for 2 hrs. After HPLC showed the reaction was complete, the solvent was removed. The residue was treated with water (10 mL) and the mixture was extracted with DCM (20 mL*3). The combine organic layers were washed with saturated $NaHCO_3$, brine. The solvent was removed to give 27E (300 mg, yield: 86.4%).

Step 5

To solution of 1 (20 mg, 0.023 mmol) in DMF (2 mL) was added HATU (10 mg, 0.023 mmol) and DIEA (8 mg, 0.046 mmol). After stirring at RT for 20 mins, 27E (40 mg, 0.23 mmol) was added. The mixture was stirred overnight. After ELSD showed the reaction was complete, the solvent was removed. The crude product was purified by prep-HPLC to give 27 (3 mg, yield: 12.8%), as a brown solid.

Example 16: Synthesis of Compound 14 (Scheme XI)

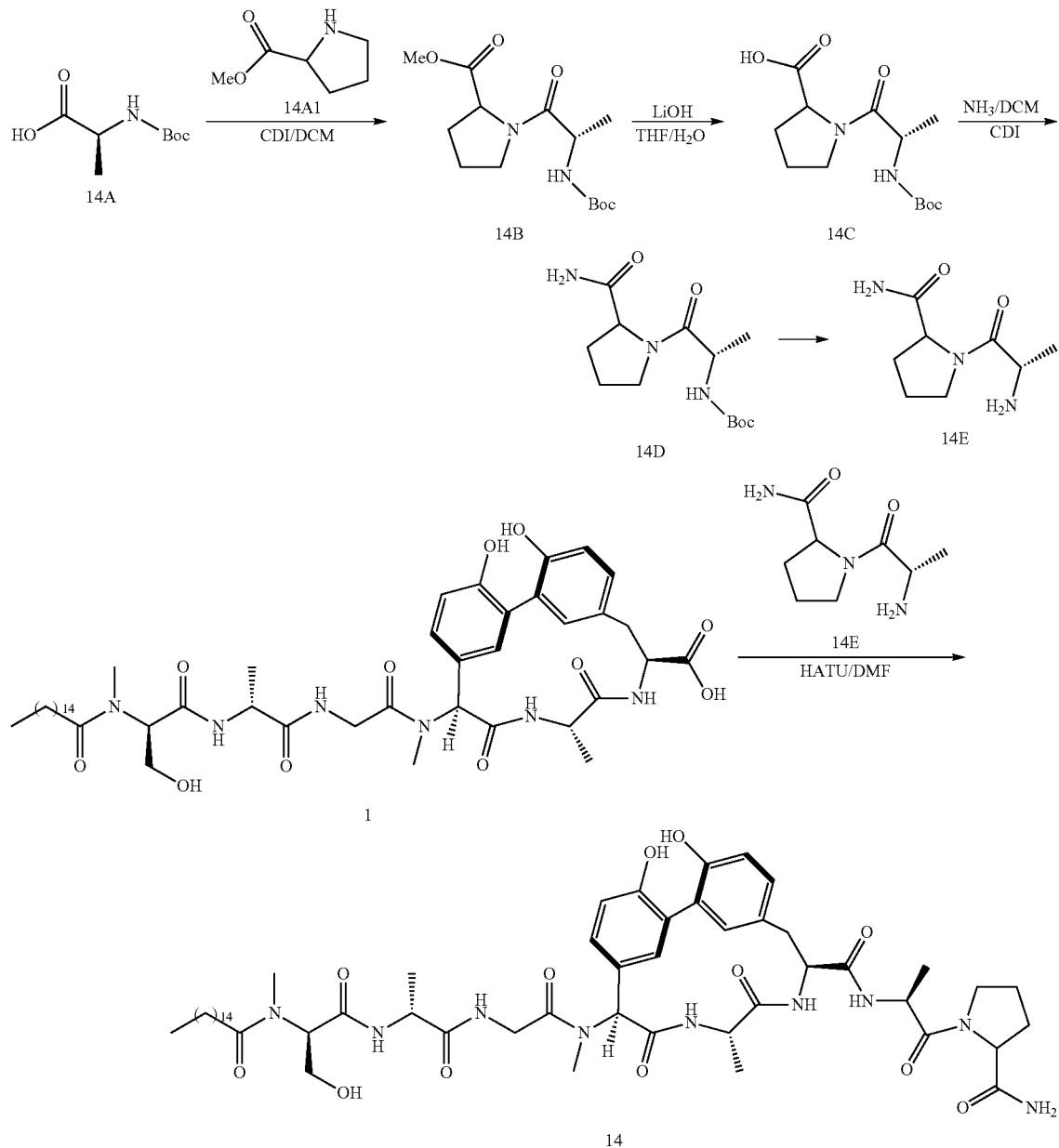

A mixture of 14A (2 g, 11 mmol) and CDI (1.8 g, 10.8 mmol) in dry DCM (50 mL) was stirred at 20° C. for 1 hr, then 14A1 (1.4 g, 10.8 mmol) was added. The mixture was stirred at 20° C. overnight. After ELSD showed the reaction was complete, the reaction was quenched with water, and then extracted with DCM (30 mL*3). The combined organic layers were washed with brine, dried over sodium sulfate and concentrated to give 14B (3.1 g, yield: 94%), as an off-white solid without further purification.

To a solution of 14B (1.2 g, 4.2 mmol) in THF (30 mL) was added a solution of LiOH.H$_2$O (0.35 g, 8.4 mmol) in water (30 mL). The reaction mixture was stirred at 20° C. for 1 hr. After TLC showed the reaction was complete, the solvent was evaporated. The residue was adjusted to pH=3-4 with citric acid and extracted with EtOAc (30 mL*3). The combined organic layers were washed with brine, dried over Na$_2$SO$_4$ and concentrated to give 14C (1 g, yield: 88%), as an off-white solid without further purification.

To a solution of 14C (0.5 g, 1.8 mmol) in DCM (15 mL) was added CDI (0.3 g, 1.8 mmol). The mixture was stirred at 20° C. for 30 mins, and then NH$_3$/DCM (4 mL) was added. The resulting mixture was stirred at 20° C. overnight until no starting material was detected by LC-MS. The reaction was quenched with water (30 mL), and the resulting mixture was extracted with DCM (30 mL*3). The combined organic layers were washed with brine, dried over Na$_2$SO$_4$ and concentrated to give 14D (0.35 g, yield: 72%), as an off-white solid without further purification.

To a solution of 14D (160 mg, 0.59 mmol) in DCM (5 mL) was added TFA (1 mL), and then the reaction mixture was stirred at 20° C. for 2 hrs. After LC-MS showed the reaction was complete, the solvent was removed. The residue was treated with water (10 mL) and the mixture was extracted with DCM (20 mL*3). The combine organic layers were washed with saturated NaHCO$_3$ (20 mL), brine (20 mL), dried over Na$_2$SO$_4$ and concentrated to give 14E without further purification (100 mg, yield: 99%).

General Method 1:

HATU coupling of an amine to Compound 1. A mixture of Compound 1 (1 eq), HATU (1.2 eq), diisopropylethylamine (DIEA) (2 eq) in DMF (0.02-0.2 mmol) was stirred at 20° C. for 0.5 h. An amine (2 eq) was added and the mixture was stirred at 20° C. overnight. After ELSD or LC-MS showed the reaction went to completion, the crude material was purified directly by prep HPLC to afford the desired amide.

Compound 14 was prepared according to General method 1 from 14E to afford Compound 14 (6 mg, 30% yield). MS (ESI) m/z 1048.5 (M+H)$^+$.

Example 17: Synthesis of Compound 15 (Scheme XII)

Compound 15 was prepared according to General Method 1 (Example 16) from Compound 1 and (S)-2-aminopropanamide. MS (ESI) m/z 951.5 (M+H)$^+$.

Example 18: Solid Phase Peptide Coupling on 2-chlorotrityl Resin

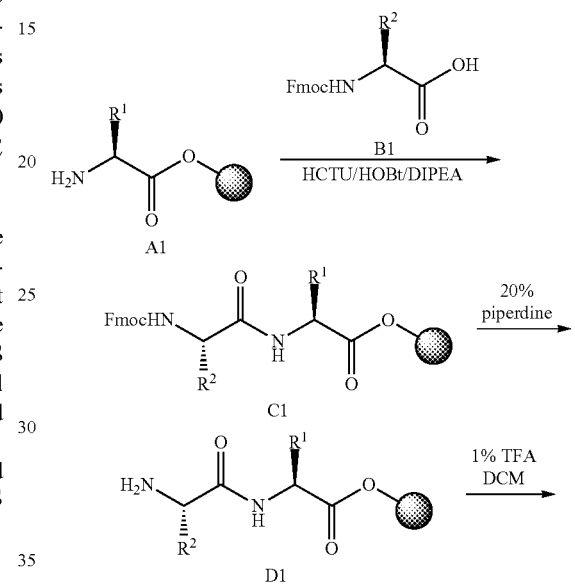

Scheme XIII

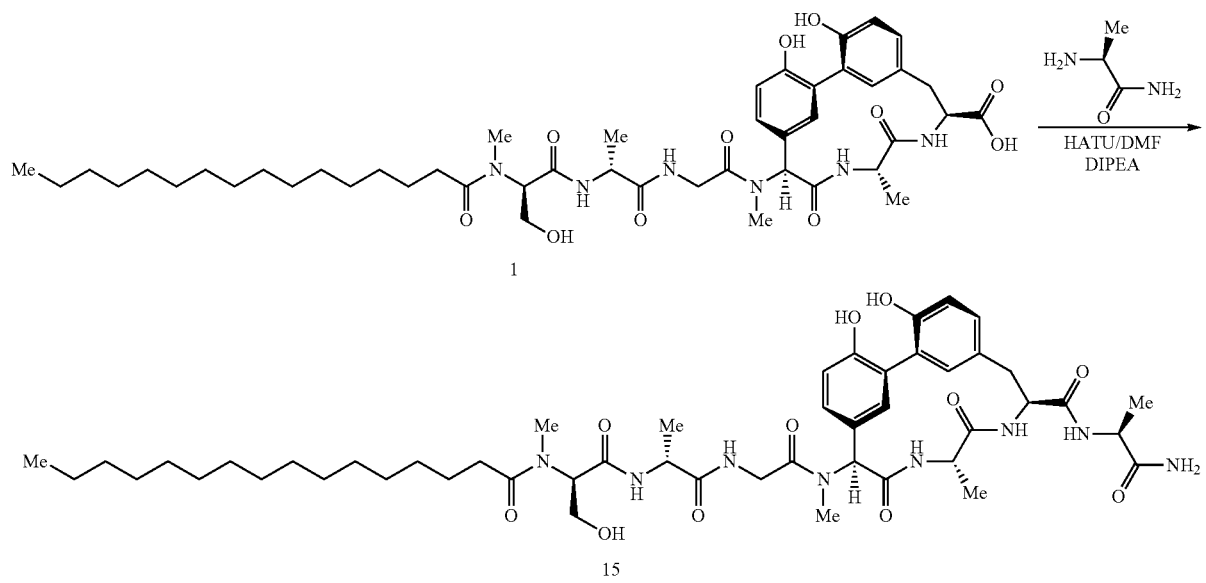

Scheme XII

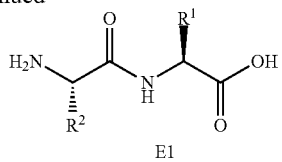

E1

General Method 2:

The coupling of a carboxylic acid to an aminoacid bound to chlorotrityl resin is depicted in Scheme XIII. To a mixture of a carboxylic acid B1 (0.94 g, 2 mmol, 2 eq) in dry DMF (15 mL/mmol) was added HCTU (826 mg, 2 mmol, 2 eq) and HOBt (270 mg, 2 mmol, 2 eq) at 0° C., whereupon DIEA (258 mg, 2 mmol, 2 eq) was added. The mixture was stirred at 12° C. for 30 min. Then the solution of active ester was added to the suspension of corresponding trityl-bound amino acid A1 (1 mmol, 1 eq) in DMF (5 mL/mmol). The mixture was bubbled with $N_2$ at 12° C. for 2 hrs. The mixture was filtered and the cake was washed with DMF (30 mL*3), DCM (30 mL*3). In cases where a protected alpha-amino acid is used, the Fmoc-group is used as the protecting group.

An analytical portion of resin C1 was treated and mixed in 1% TFA/DCM to cleave the peptide from the resin, and the desired product was detected by MS with confirmation that no starting material remains. In cases where the peptide coupling is slow or does not go to completion, HCTU can be replaced with EDCI.

General Method 3:

Fmoc deprotection of the chlorotrityl bound peptide. In cases where the terminal peptide has an Fmoc protecting group, it can be cleaved using the following procedure. The resultant Fmoc-peptide C1 (1 mmol) in piperidine/dry DMF (20%, 30 mL/mmol) was shaken at 12° C. for 10 mins. After filtering, a new batch of piperidine/dry DMF (20%, 30 mL/mmol) was added and shaken at 12° C. for another 10 min. The mixture was filtered and the filter cake was washed with DMF (30 mL*3), DCM (30 mL*3) to afford D1. This cycle can be repeated to lengthen the peptide sequence as needed.

General Method 4:

Cleavage of a 2-chlorotrityl-bound polypeptide to afford the polypeptide carboxylic acid. A 2-chlorotrityl-bound polypeptide is treated with 1% TFA in DCM for 30 min. The DCM solution was neutralized to pH 7-8 using aqueous $NaHCO_3$, then acidified to pH 3-4 with aqueous citric acid. The aqueous layer was extracted three times with DCM. The combined organic layers were dried over $Na_2SO_4$, filtered and concentrated under reduced pressure to afford the peptide E1.

Example 19: Synthesis of Compound 30 (Scheme XIV)

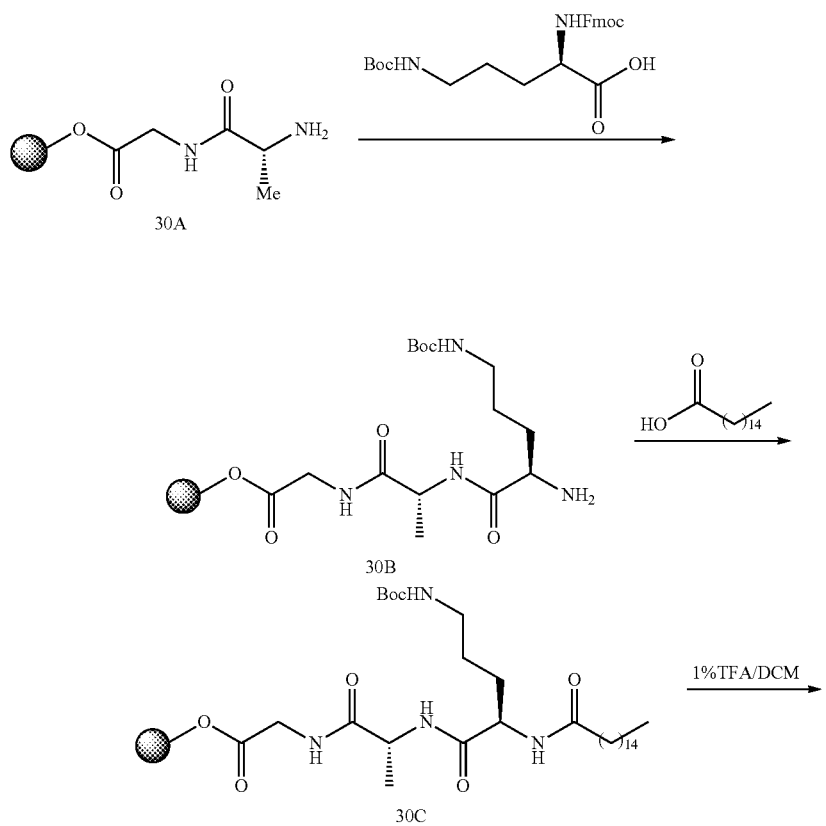

-continued

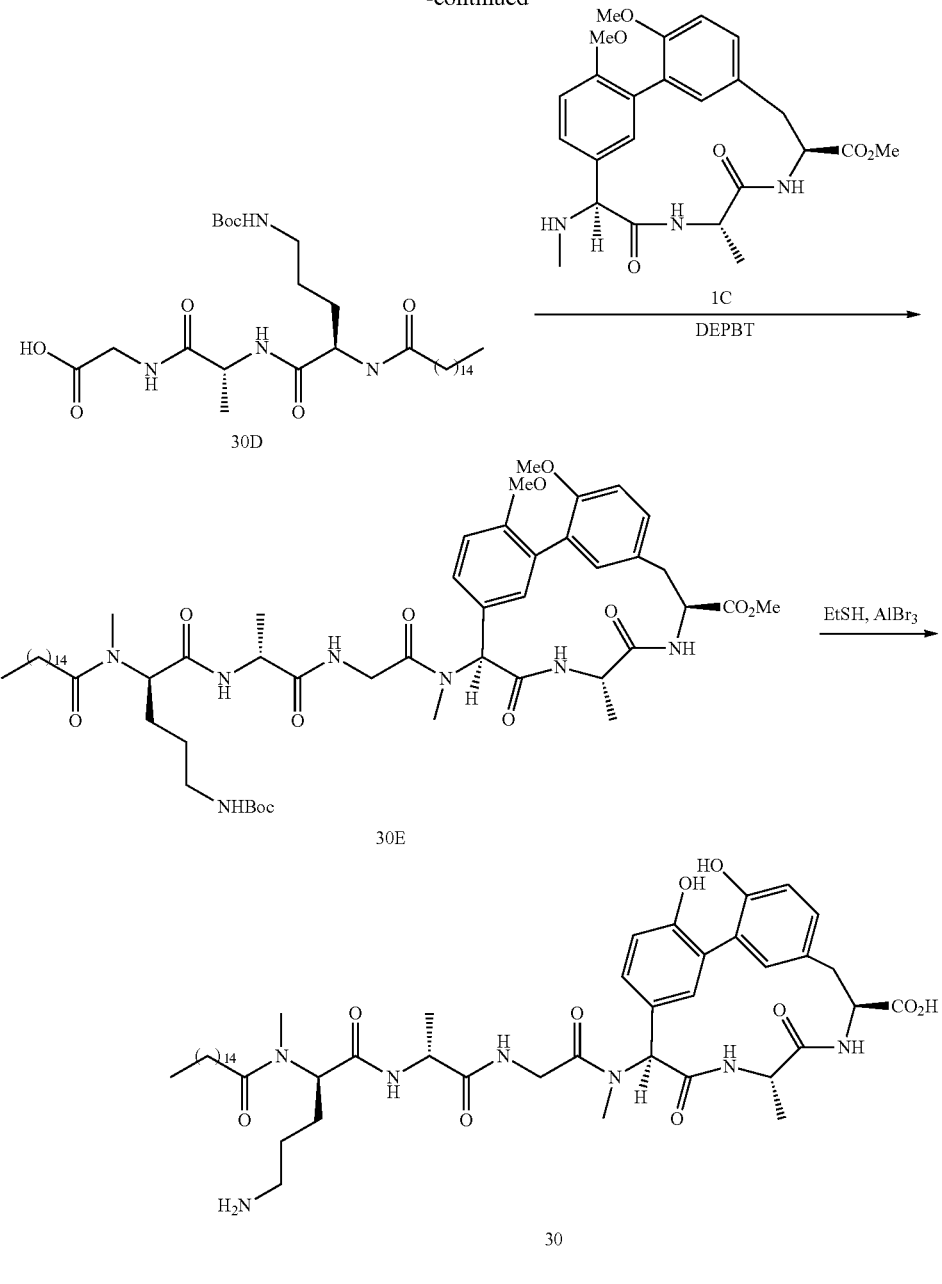

The synthesis of Compound 30 is shown in Scheme XIV. Compound 30C was prepared from Compound 30A using General Methods 2 and 3 (Example 18). Compound 30D was prepared from Compound 30C using General Method 4.

General Method 5:

Coupling of an N-methyl peptide to a carboxylic acid using DEPBT. A mixture of a carboxylic acid (1.2 eq), N-methyl peptide 1C (1.0 eq) NaHCO$_3$ (5 eq), and DEPBT (3 eq) in dry THF (0.01 to 0.1 M) was heated to reflux overnight. After HPLC analysis showed the reaction to be complete, the mixture was concentrated under reduced pressure. The residue was treated with water and extracted with EtOAc (3×). The combined organic layers were washed with brine, dried over Na$_2$SO$_4$, filtered, and concentrated. Purification by preparative HPLC (AcCN/H$_2$O with 0.05% TFA) followed by lyophilization afforded the desired compound.

Compound 30E was prepared from Compound 30D (100 mg, 0.19 mmol) using General Method 5 to afford 130 mg (70%) of Compound 30E.

General Method 6:

Deprotection of bis-arylmethyl ethers with AlBr$_3$ and EtSH. To a mixture of the bis-arylmethyl ether (1 eq) in EtSH (50 mL/mmol) was added 1.0 M AlBr$_3$ (25 eq) under Ar. The mixture was heated to 50° C. for 4 hr. After HPLC analysis showed the reaction was complete, the reaction was quenched with MeOH (16 mL/mmol), and then the solvent was evaporated to give a crude product, which was purified by preparative HPLC to afford the desired bis-phenol.

Compound 30 was prepared according to General Method 6 from Compound 30E. MS (ESI) m/z 916.5 (M+H)$^+$.

Example 20: Synthesis of Compound 34 (Scheme XV)
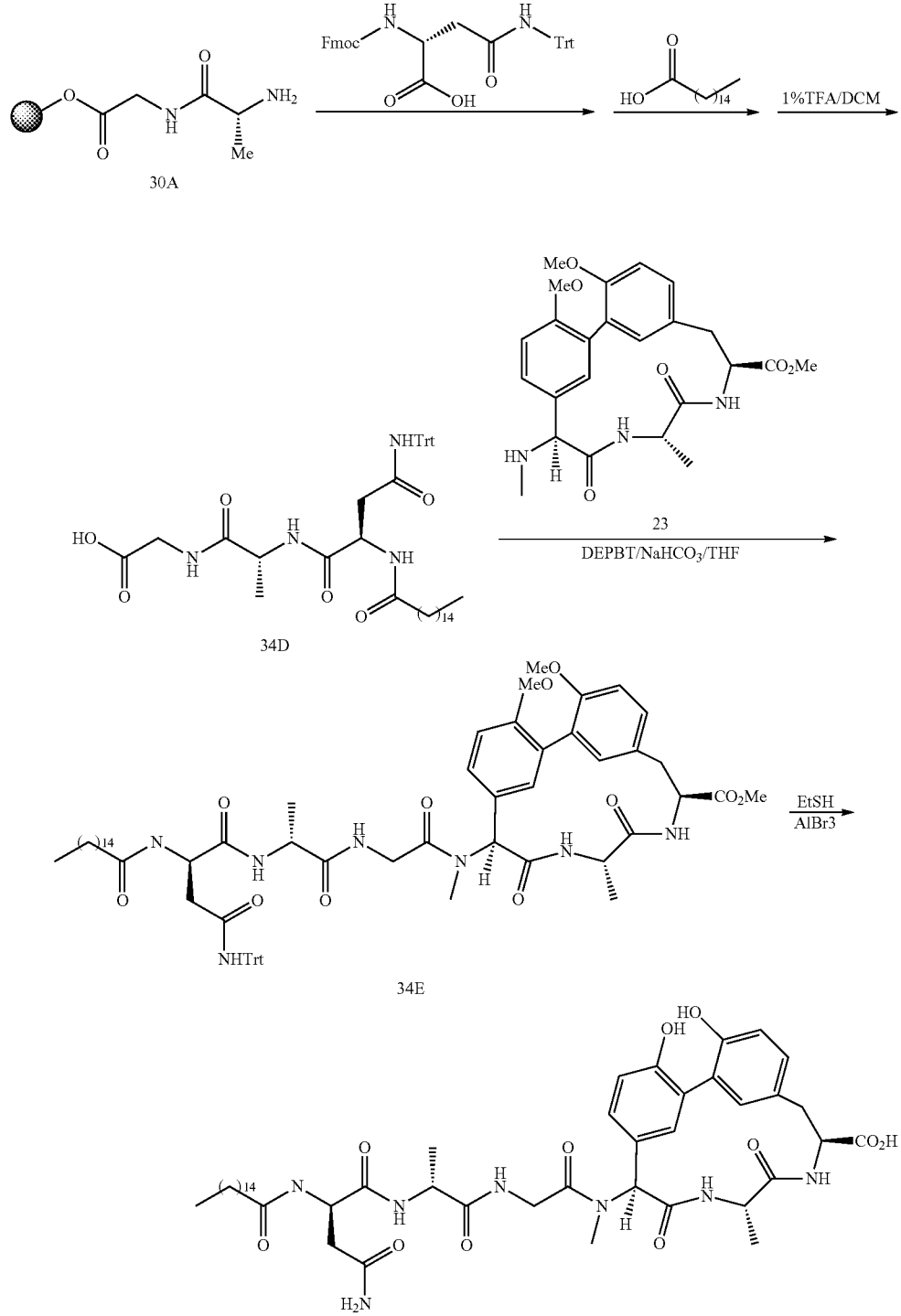

The synthesis of Compound 34 is depicted in Scheme XV. This compound was prepared according to General Methods 2-6 (Examples 18-19) from Compound 30A to afford Compound 34.
Example 21: Synthesis of Compound 39 (Scheme XVI)
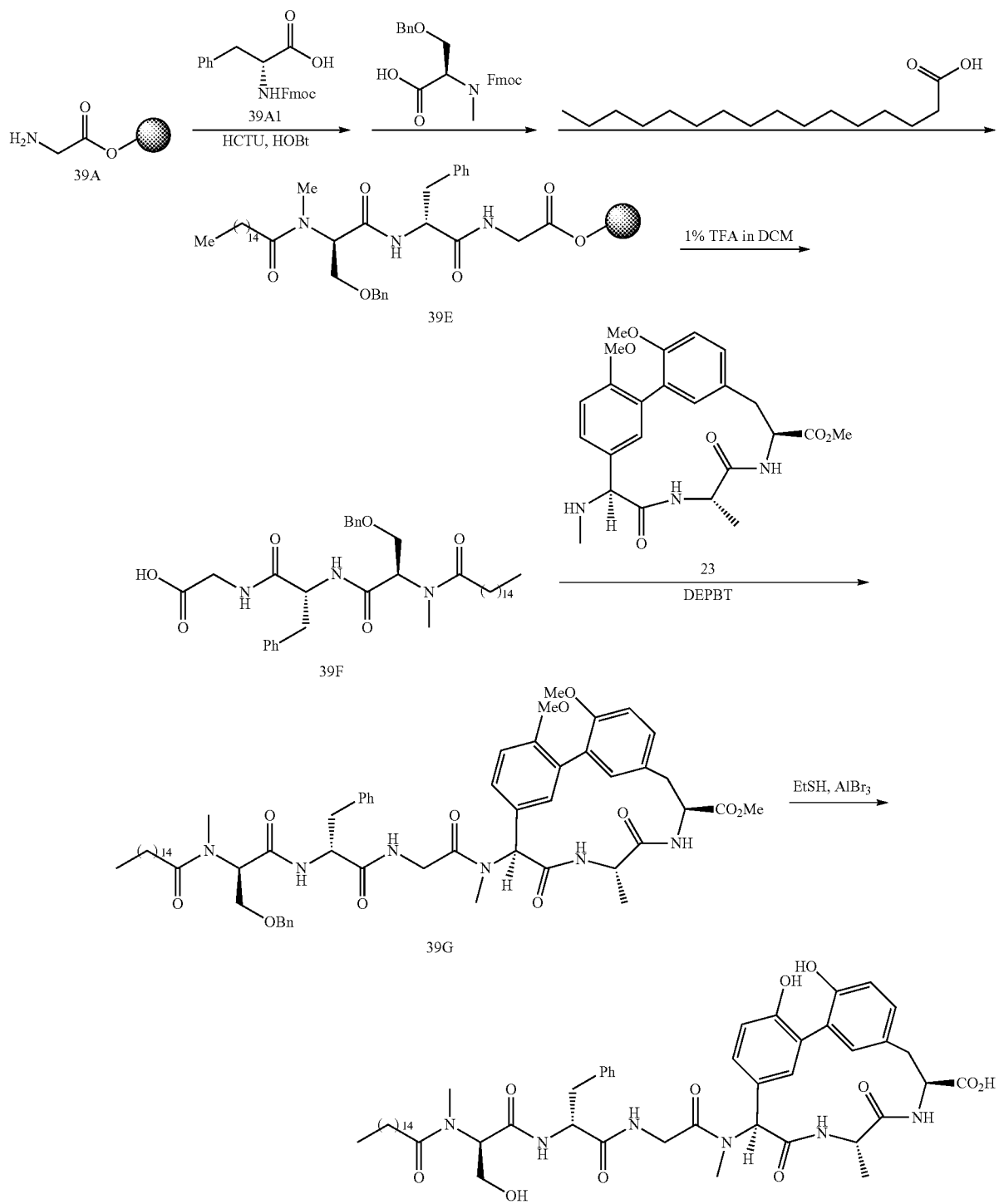

The synthesis of Compound 39 is depicted in Scheme XVI. This compound was prepared according to General Methods 2-6 (Examples 18 and 19) from 39A to afford Compound 39. MS (ESI) m/z 957.5 (M+H)$^+$.
Example 22: Synthesis of Compound 41 (Scheme XVII)
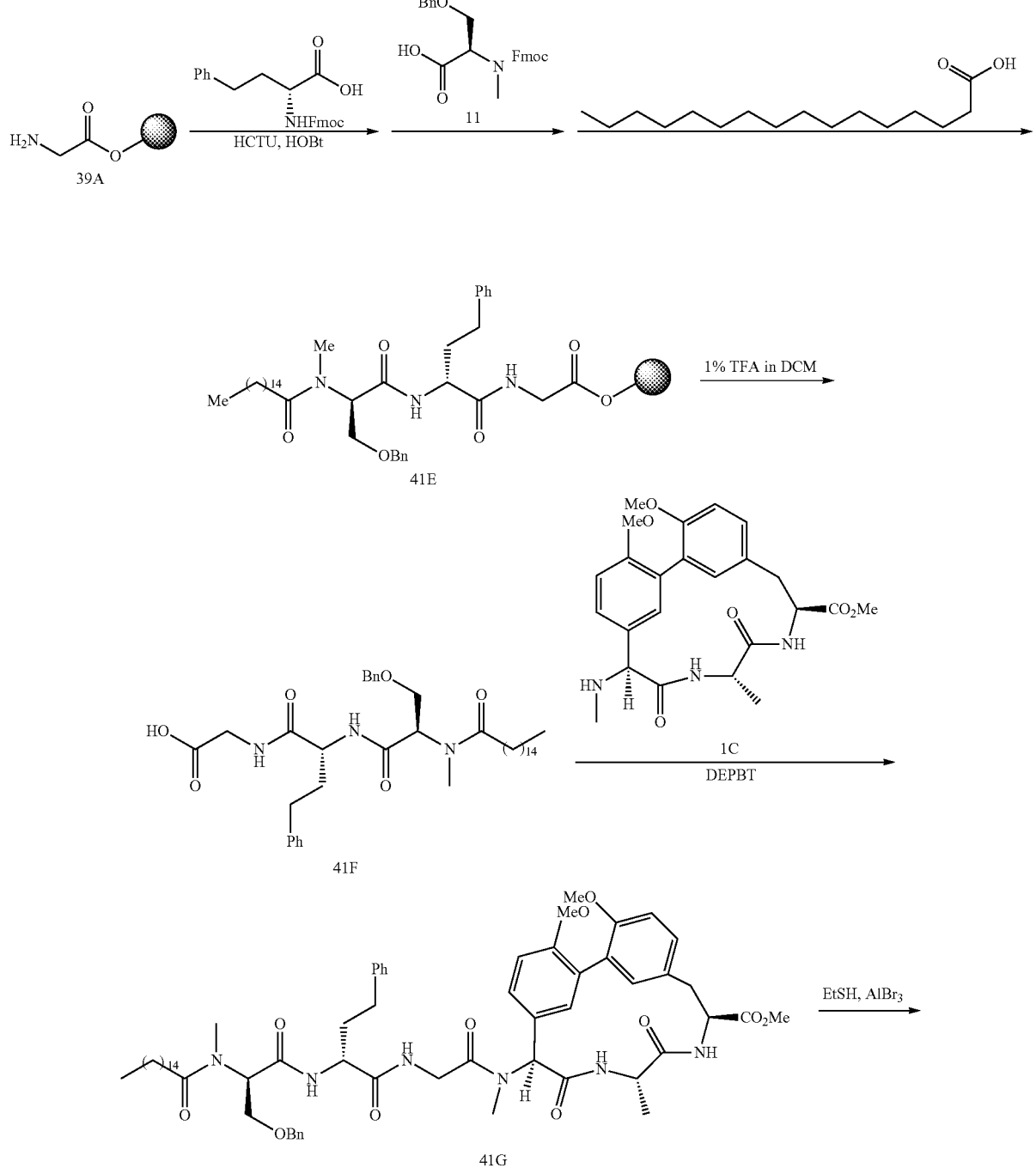

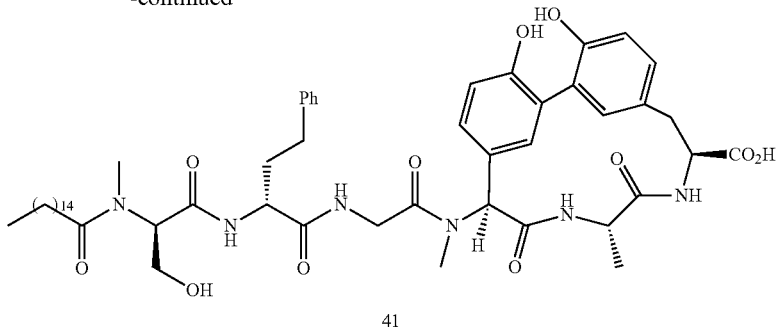
41
The synthesis of Compound 41 is depicted in Scheme XVII. This compound was prepared according to General Methods 2-6 (Examples 18 and 19) to afford Compound 41. MS (ESI) m/z 971.4 (M+H)$^+$.
Example 23: Synthesis of Compound 52 (Scheme XIX)
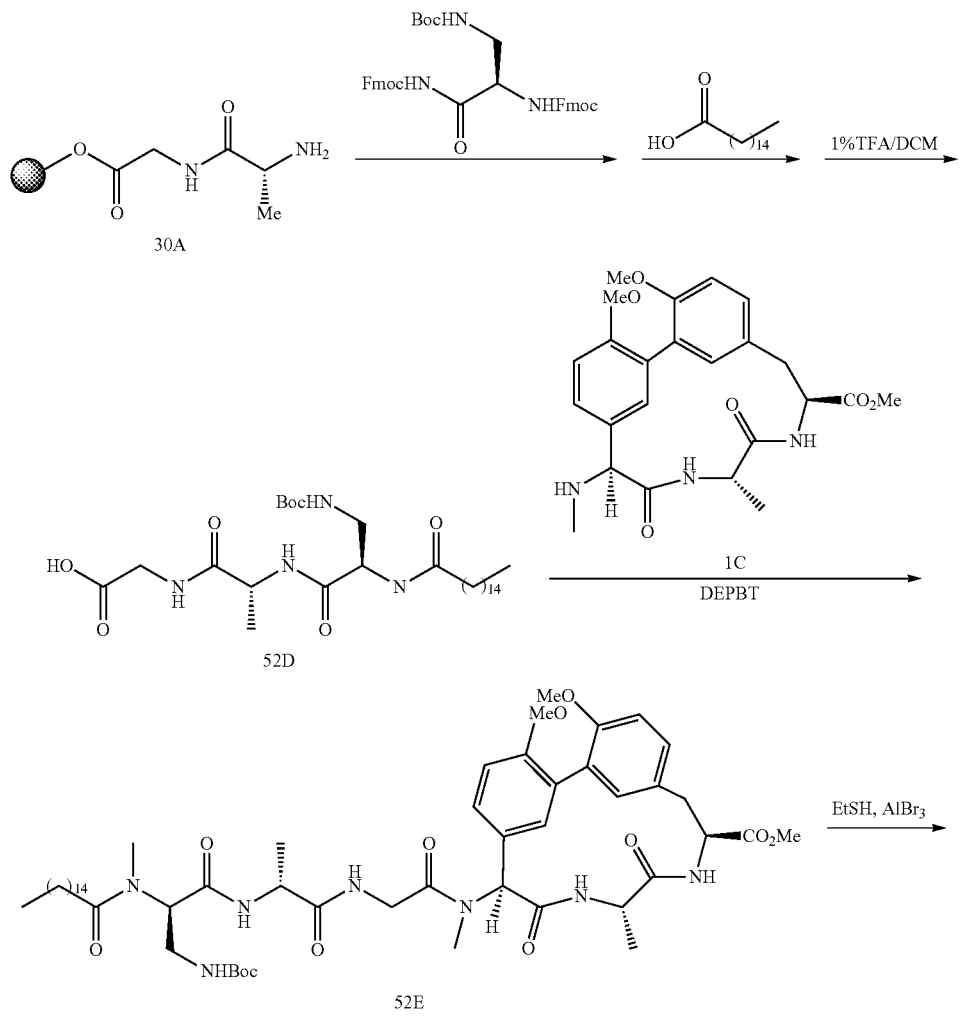

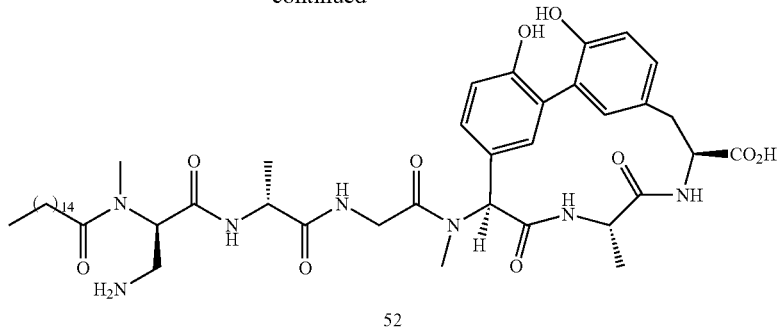
The synthesis of Compound 52 is depicted in Scheme XIX. This compound was prepared according to General Methods 2-6 (Examples 18 and 19) from Compound 30A to afford Compound 52.
Example 24: Synthesis of Compound 53 (Scheme XX)
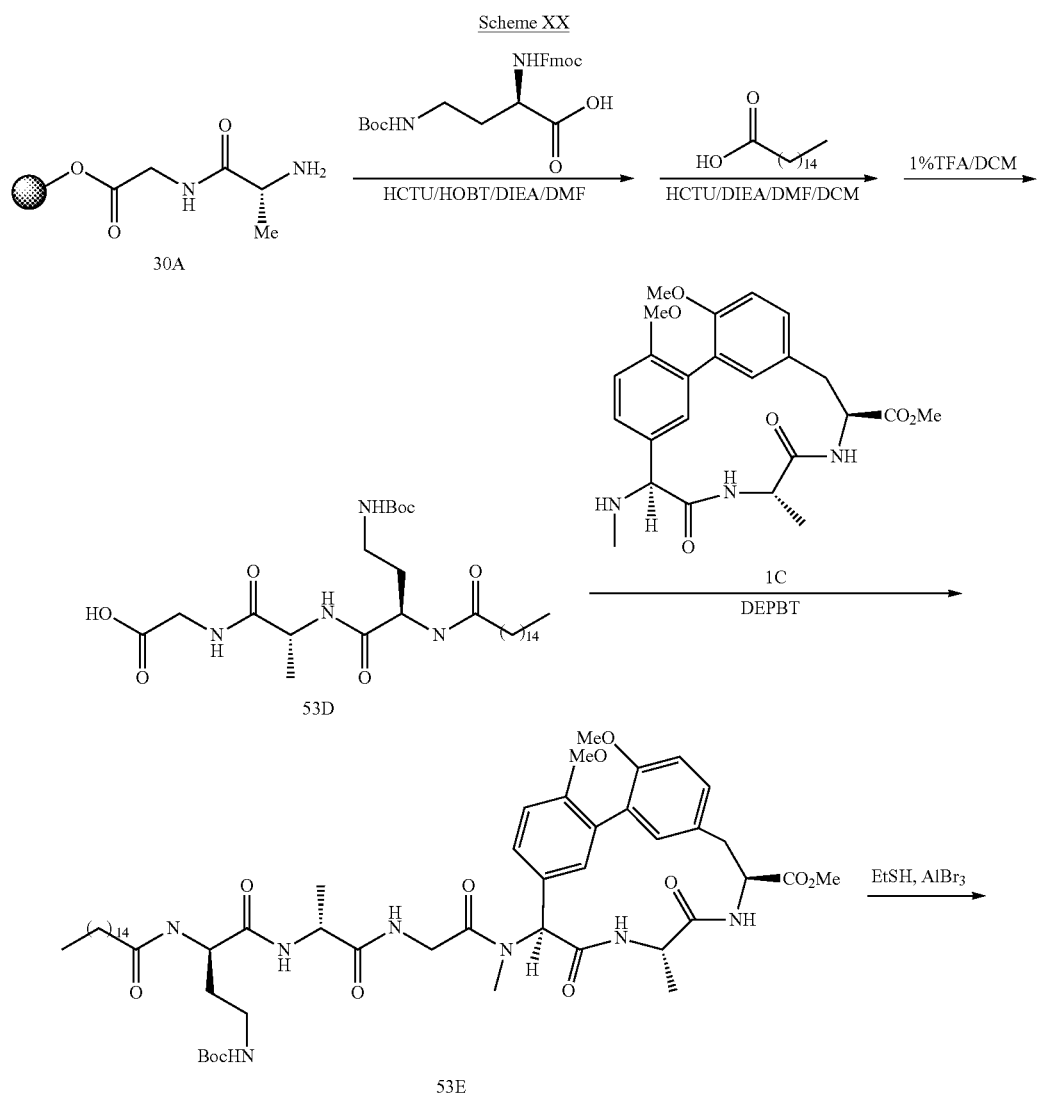

-continued
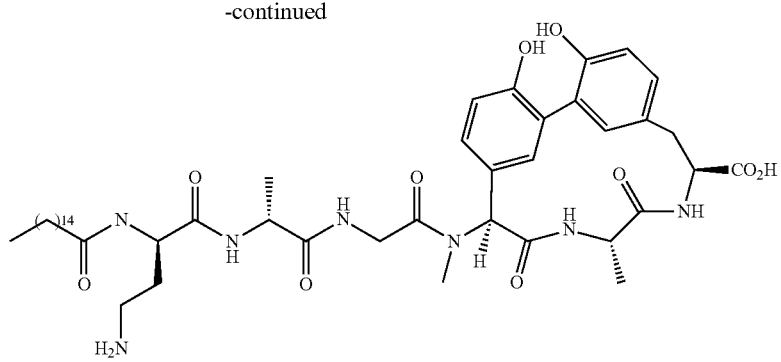
53
The synthesis of Compound 53 is depicted in Scheme XX. This compound was prepared according to General Methods 2-6 (Examples 18 and 19) from Compound 30A to afford Compound 53.
Example 25: Synthesis of Compound 54 and Compound 55 (Scheme XXI)
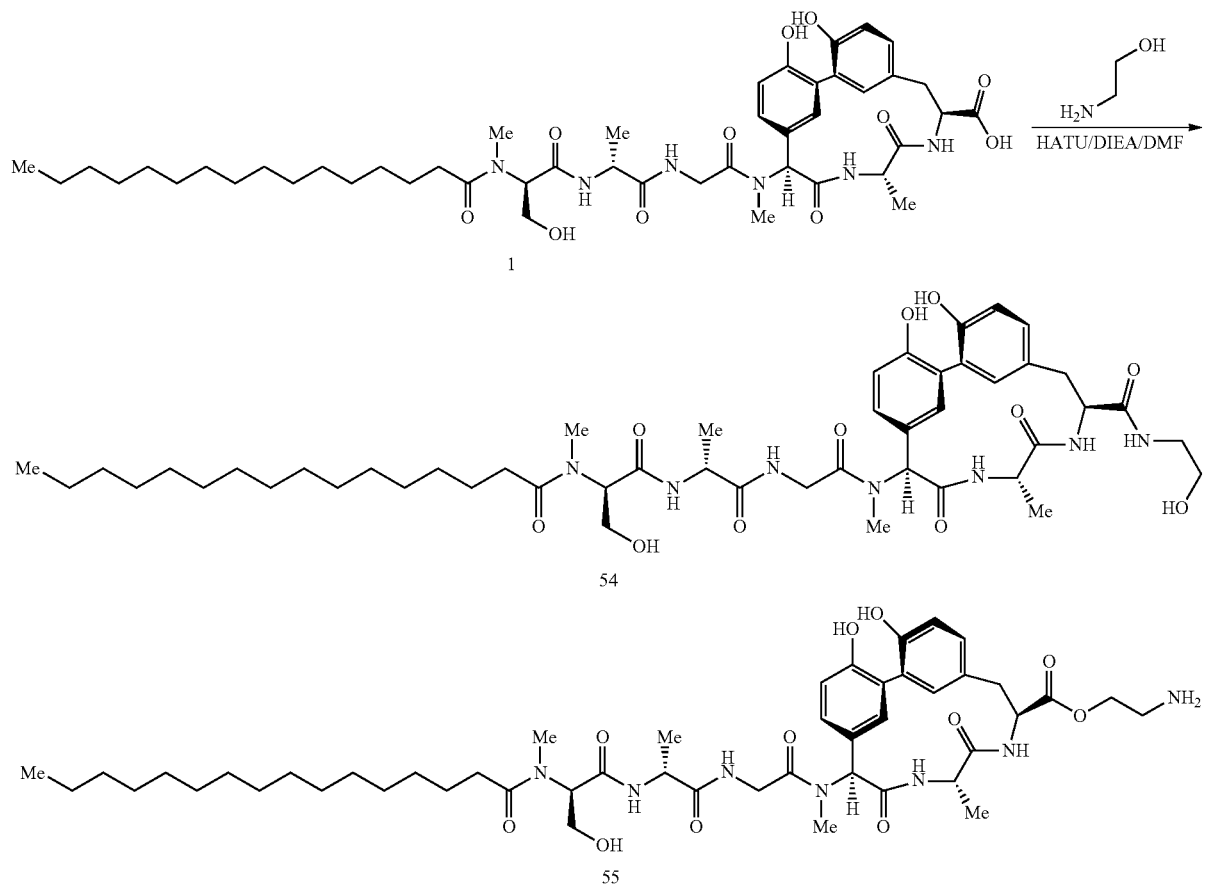

The synthesis of Compound 54 and 55 is depicted in Scheme XXI. A mixture of 1 (16 mg, 0.018 mmol), HATU (8 mg, 0.021 mmol) and DIEA (2.7 mg, 0.021 mmol) in DMF (1 mL) was stirred at 15° C. for 30 mins. Then ethanolamine (4.4 mg, 0.072 mmol) was added. The resulting mixture was stirred at 15° C. overnight. After ELSD showed the reaction was complete, the crude product was purified by pre-HPLC to give 54 (4 mg, yield 23.8%) and 55 (1 mg, 6%). Compound 54 MS (ESI) m/z 924.5 (M+H)$^+$. $t_R$ 3.23 min (C18). Compound 55 MS (ESI) m/z 924.5 (M+H)$^+$. $t_R$ 2.85 min (C18).

Example 26: Synthesis of Compound 56 and Compound 57 (Scheme XXII)

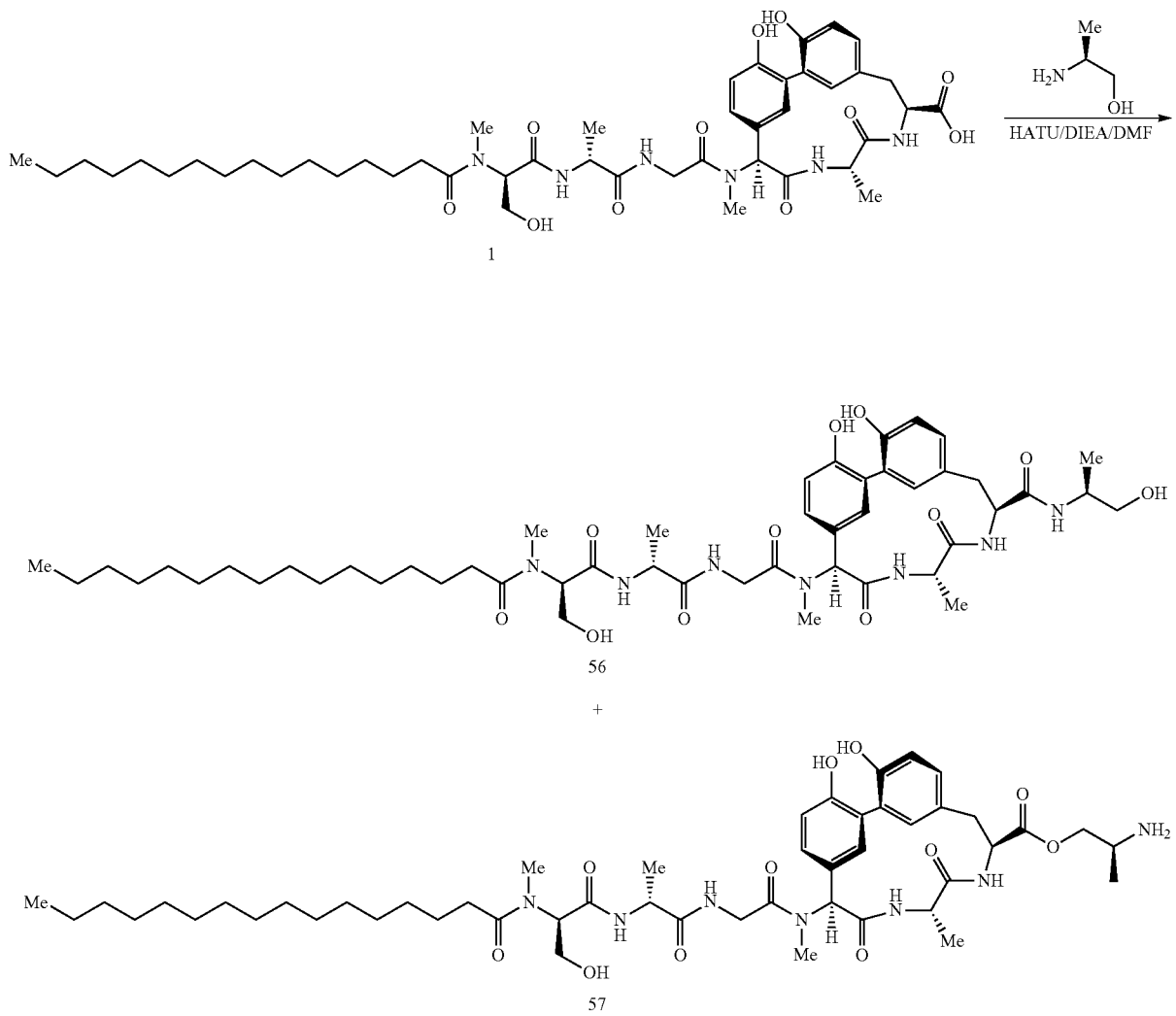

The synthesis of Compound 56 and 57 is depicted in Scheme XXII. A mixture of 1 (16 mg, 0.018 mmol), HATU (8 mg, 0.021 mmol) and DIEA (2.7 mg, 0.021 mmol) in DMF (1 mL) was stirred at 15° C. for 30 mins. Then (S)-2-amino-1-propanol (5.4 mg, 0.072 mmol) was added. The resulting mixture was stirred at 15° C. overnight. After ELSD showed the reaction was complete, the crude product was purified by preparative HPLC to give 56 (4 mg, yield 23.5%) and 1 mg (6%) of 57. Compound 56 MS (ESI) m/z 938.5 (M+H)$^+$. $t_R$ 3.27 min (C18). Compound 57 MS (ESI) m/z 938.5 (M+H)$^+$. $t_R$ 2.88 min (C18).

Example 27: Synthesis of Compound 59 (Scheme XXIII)

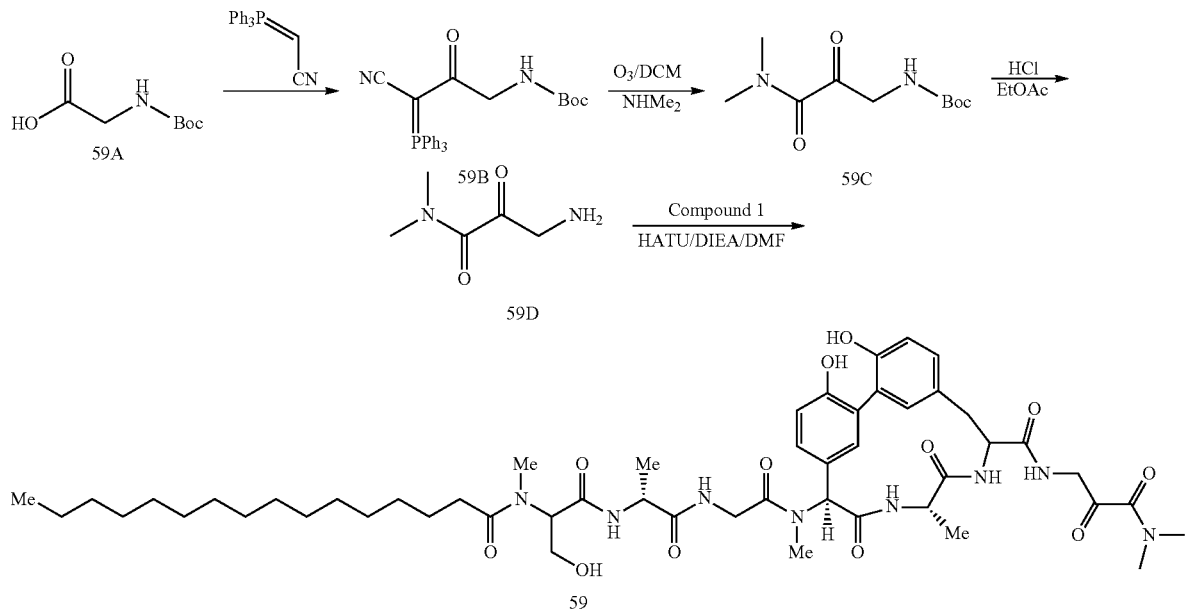

The synthesis of Compound 59 is depicted in Scheme XXIII. A mixture of 59A (1 g, 5.3 mmol), (triphenylphosphanylidene)acetonitrile (1.6 g, 5.3 mmol), EDCI (1.3 g, 6.9 mmol) and DMAP (65 mg, 0.5 mmol) in DCM (20 mL) was stirred at 15° C. overnight. After TLC showed the reaction was completed, the mixture was treated with H$_2$O (20 mL). The mixture was extracted with DCM (20 mL*3). The combined organic layers were washed with brine, dried over Na$_2$SO$_4$ and concentrated to give the crude product, which was purified by column chromatography on silica gel to give 59B (1 g, yield: 41.7%).

A stream of O$_3$ was bubbled through a solution of 59B (200 mg, 0.44 mmol) in dry DCM (10 mL) at −78° C. for 15 mins. Then a stream of O$_2$ was bubbled through the solution for 5 mins, whereupon Me$_2$NH/DCM (1 mL) was added. The resulting mixture was stirred at −78° C. under N$_2$ for 1 hr. After no more desired product was detected by ELSD, the solvent was removed and the crude product was purified by preparative HPLC to give 59C (30 mg, yield: 30%).

A mixture of 59C (30 mg, 0.13 mmol) in HCl/EA (2 mL) was stirred at 15° C. for 30 min. After TLC showed the reaction was complete, the solvent was removed to give 59D without further purification (13 mg, yield: 76.5%).

Compound 59 was prepared according to General Method 1 (Example 16) from Compound 1 and 59D.

Example 28: Synthesis of Compound 60 (Scheme XXIV)

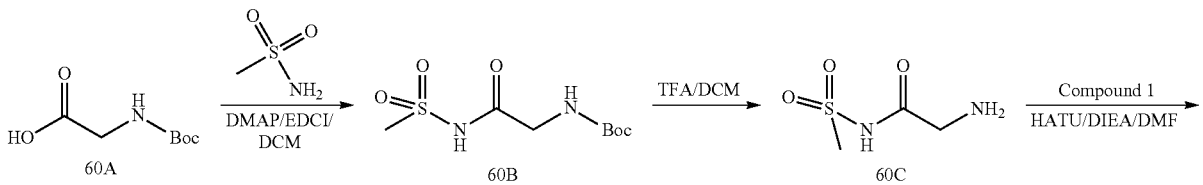

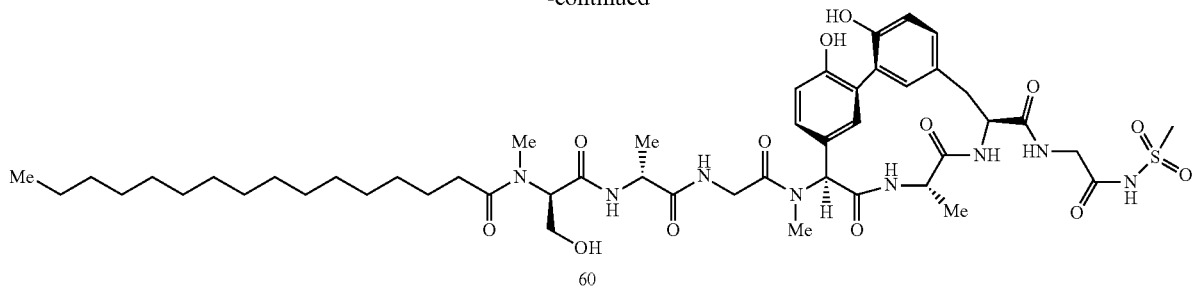

60

The synthesis of Compound 60 is depicted in Scheme XXIV. To a solution of 60A (1.5 g, 8.8 mmol) in DCM (70 mL) was added DMAP (4.3 g, 35 mmol), methanesulfonamide (1 g, 10.5 mmol) and EDCI (2 g, 10.5 mmol). The mixture was stirred at 15° C. for 16 hours, and then evaporated to give a residue, which was dissolved in DCM (100 mL) and washed with 1M hydrochloric acid (20 mL). The organic layers were concentrated to give 60B without further purification (1.5 g, yield: 63%).

To a solution of 60B (100 mg, 0.4 mmol) in DCM (5 mL) was added TFA (1 mL). Then the reaction mixture was stirred at 15° C. until TLC showed there was no starting material. The mixture was concentrated to give a crude product, which was purified by prep-HPLC to give 60C (30 mg, yield: 50%).

To a solution of Compound 1 (20 mg, 0.023 mmol) in DMF (1 mL) was added HATU (8.6 mg, 0.023 mmol), DIEA (3 mg, 0.023 mmol) and 60C (30 mg, 0.19 mmol). Then the reaction mixture was stirred at 15° C. overnight until ELSD showed the reaction was complete. The crude mixture was purified by prep-HPLC directly to afford Compound 60 (1.3 mg, yield: 5.7%). MS (ESI) m/z 1015.4 (M+H)$^+$.

Example 29: Synthesis of Compound 61 (Scheme XXV)

Scheme XXV

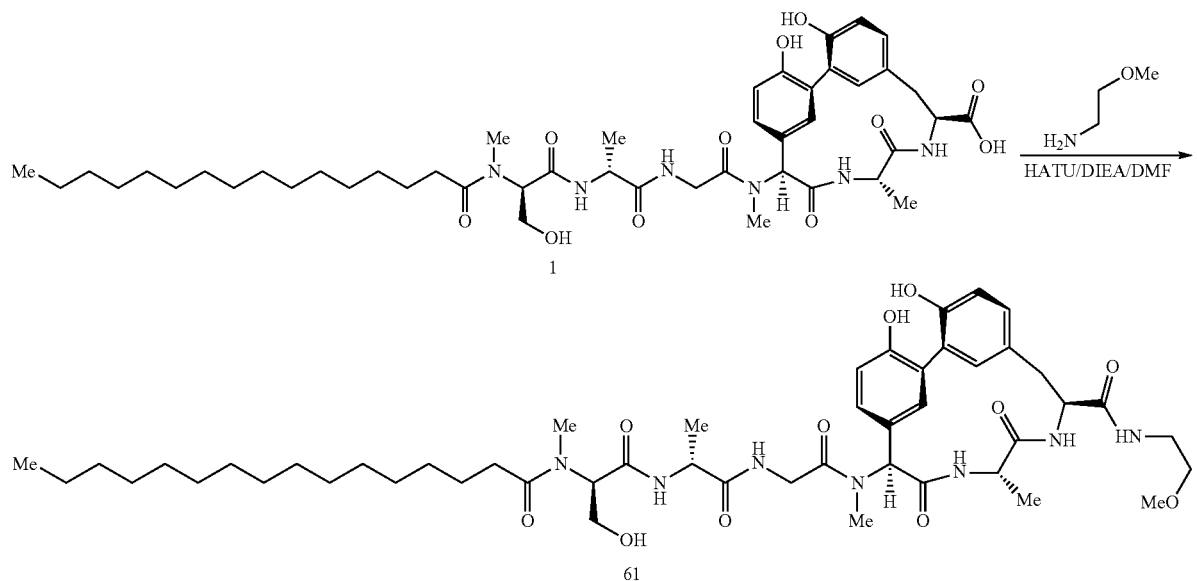

Compound 61 was prepared according to General Method 1 (Example 16) from Compound 1 and 2-methoxyethylamine. MS (ESI) m/z 938.5 (M+H)+.
Example 30: Synthesis of Compound 62 (Scheme XXVI)
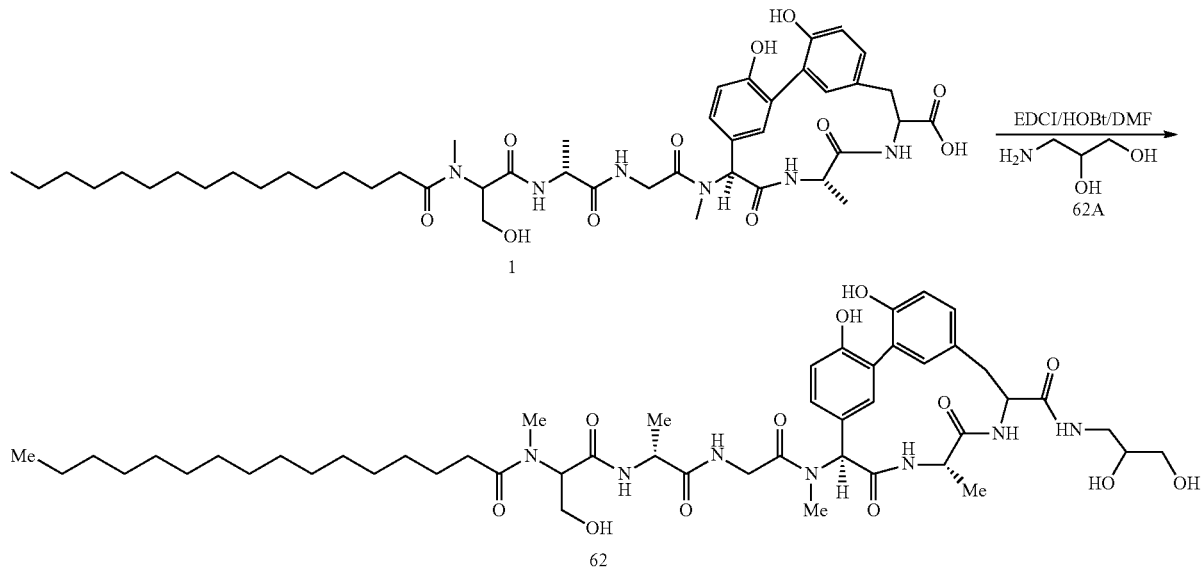
Compound 62 was prepared according to General Method 1 (Example 16) from Compound 1 and 62A. MS (ESI) m/z 954.3 (M+H)+.
Example 31: Synthesis of Compound 63 (Scheme XXVII)
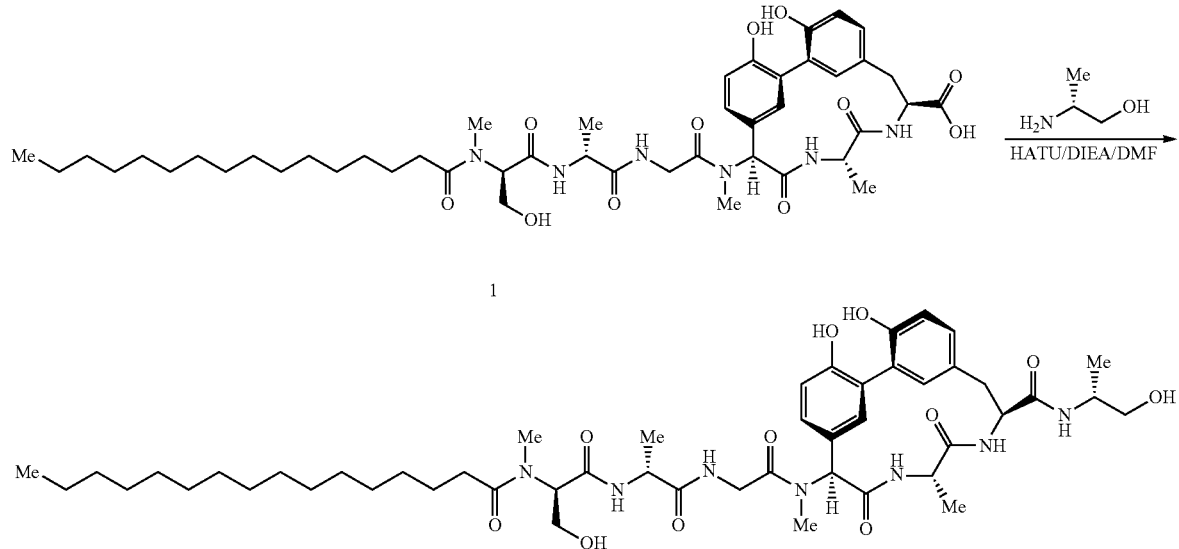

Compound 63 was prepared according to General Method 1 (Example 16) from Compound 1 and (R)-2-amino-1-propanol. MS (ESI) m/z 960.5 (M+H)$^+$.
Example 32: Synthesis of Compound 64 (Scheme XXVIII)
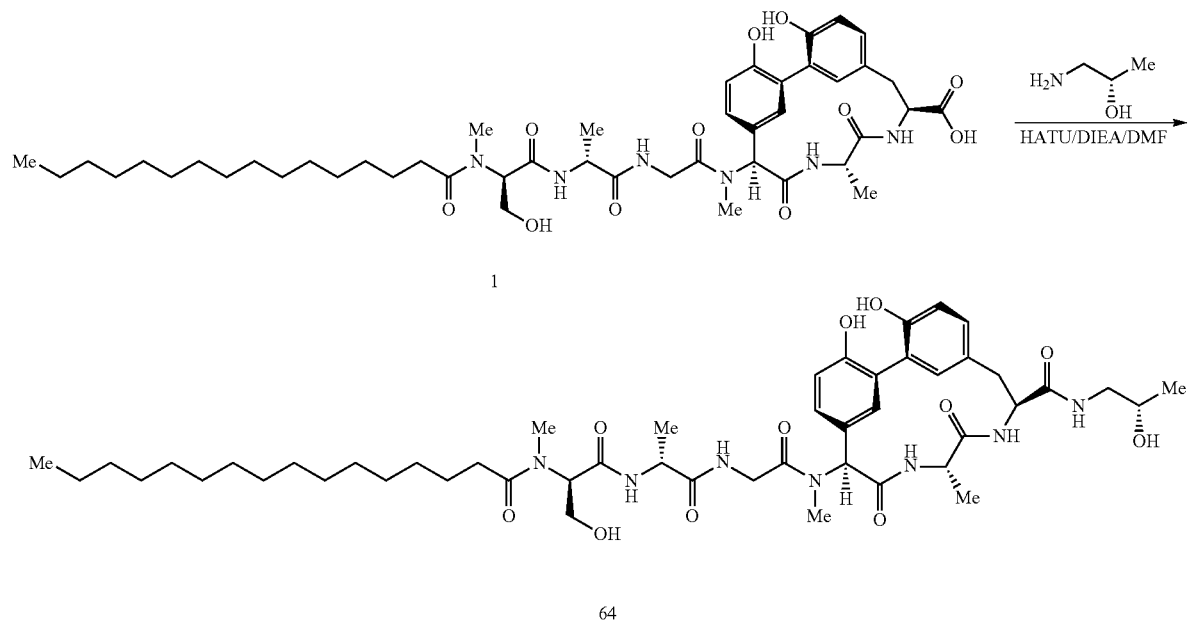
Compound 64 was prepared according to General Method 1 (Example 16) from Compound 1 and (S)-1-amino-2-propanol. MS (ESI) m/z 938.5 (M+H)$^+$.
Example 33: Synthesis of Compound 65 (Scheme XXIX)
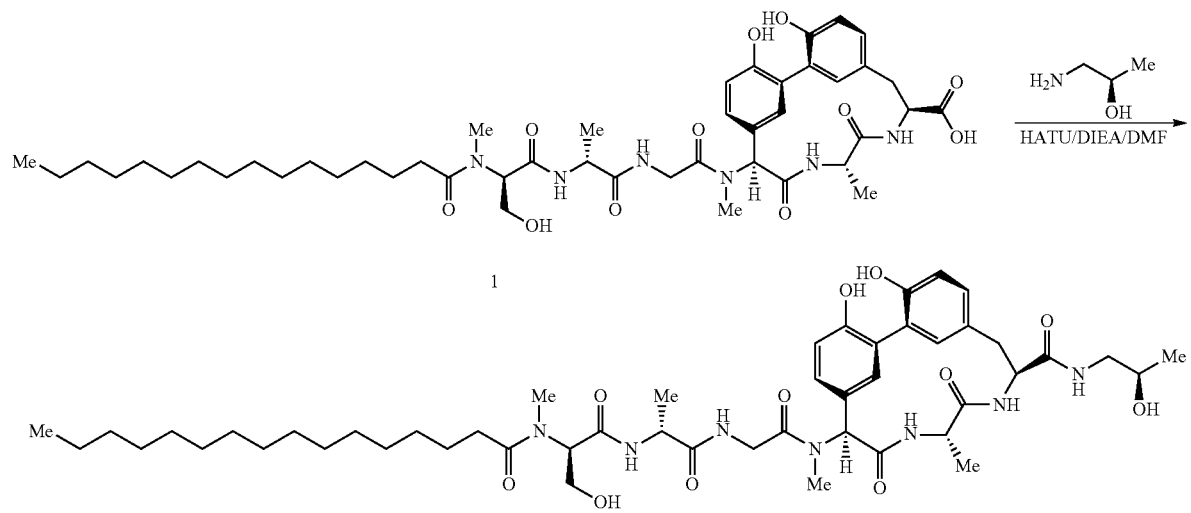

Compound 65 was prepared according to General Method 1 (Example 16) from Compound 1 and (R)-1-amino-2-propanol. MS (ESI) m/z 938.5 (M+H)$^+$.
Example 34: Synthesis of Compound 66 (Scheme XXX)
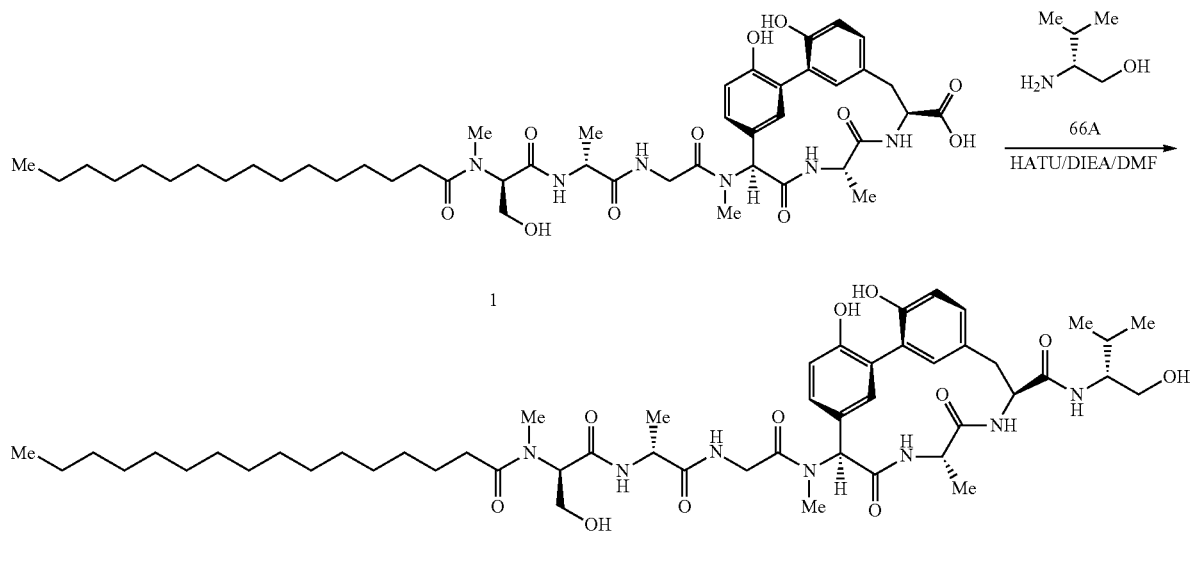
Compound 66 was prepared according to General Method 1 (Example 16) from Compound 1 and (R)-1-amino-2-propanol. MS (ESI) m/z 966.5 (M+H)$^+$.
Example 35: Synthesis of Compound 67 (Scheme XXXI)
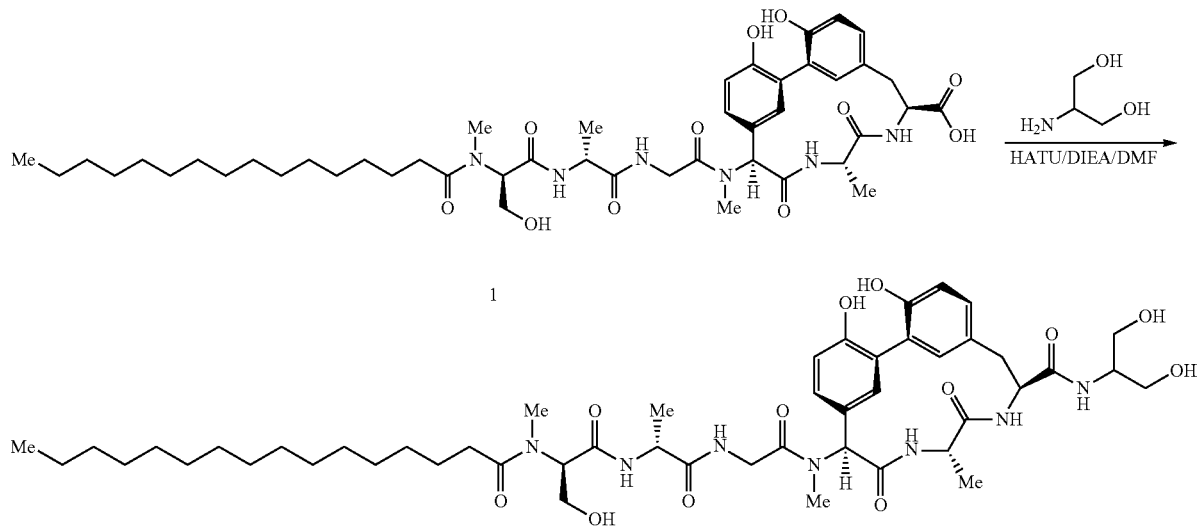

Compound 67 was prepared according to General Method 1 (Example 16) from Compound 1 and 2-amino-1,3-propanediol. MS (ESI) m/z xxx (M+H)+.
Example 36: Synthesis of Compound 68 (Scheme XXXII)
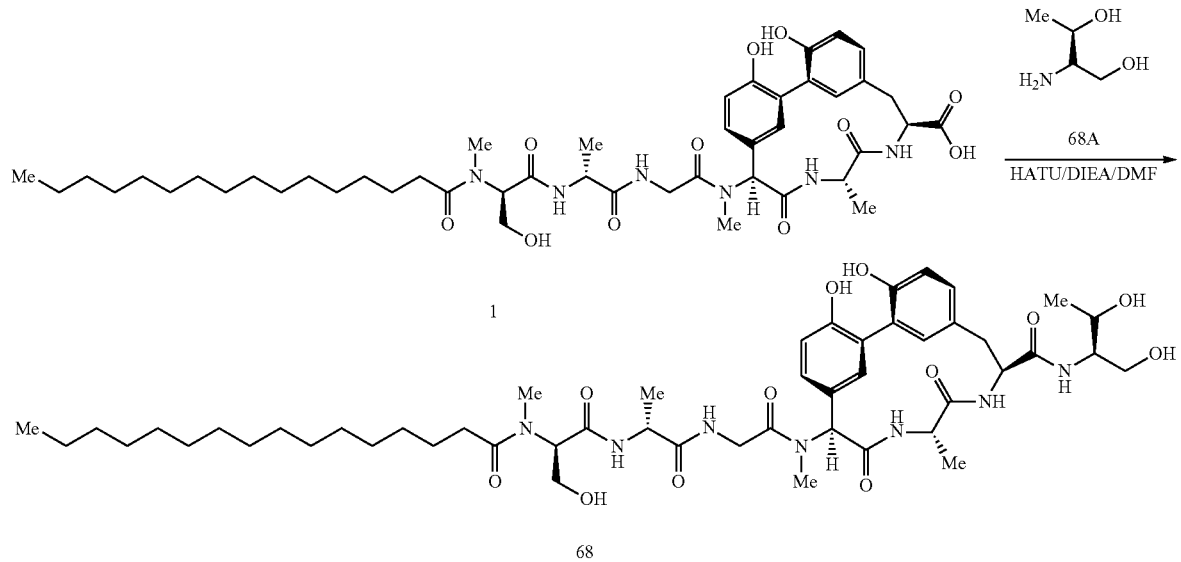
Compound 68 was prepared according to General Method 1 (Example 16) from Compound 1 and 68A. MS (ESI) m/z 968.5 (M+H)+.
Example 37: Synthesis of Compound 69 (Scheme XXXIII)
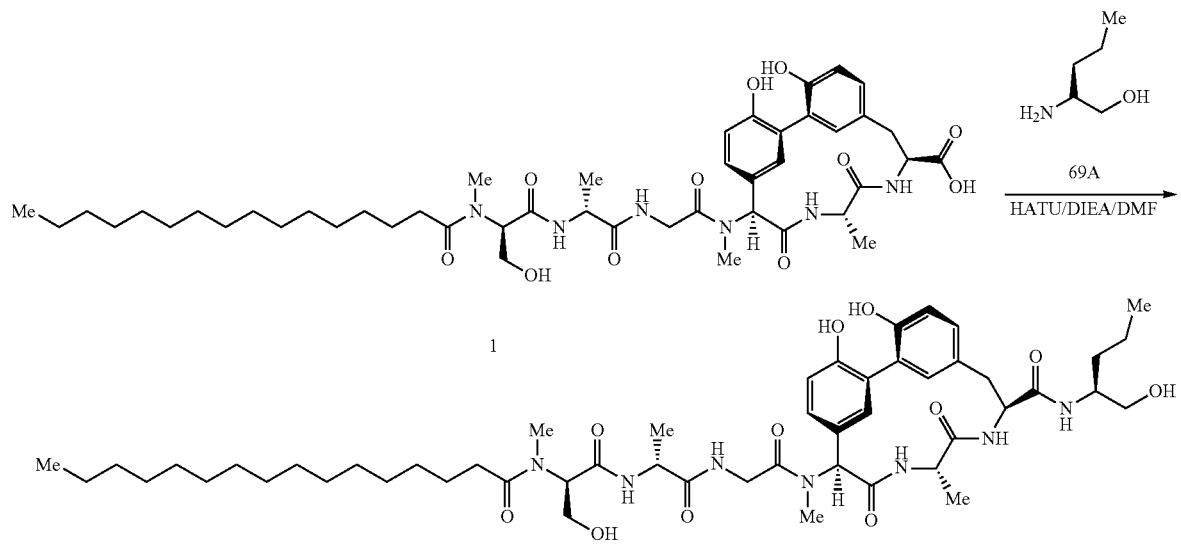

Compound 69 was prepared according to General Method 1 (Example 16) from Compound 1 and 69A. MS (ESI) m/z 966.3 (M+H)$^+$.
Example 38: Synthesis of Compound 70 (Scheme XXXIV)
Scheme XXXIV
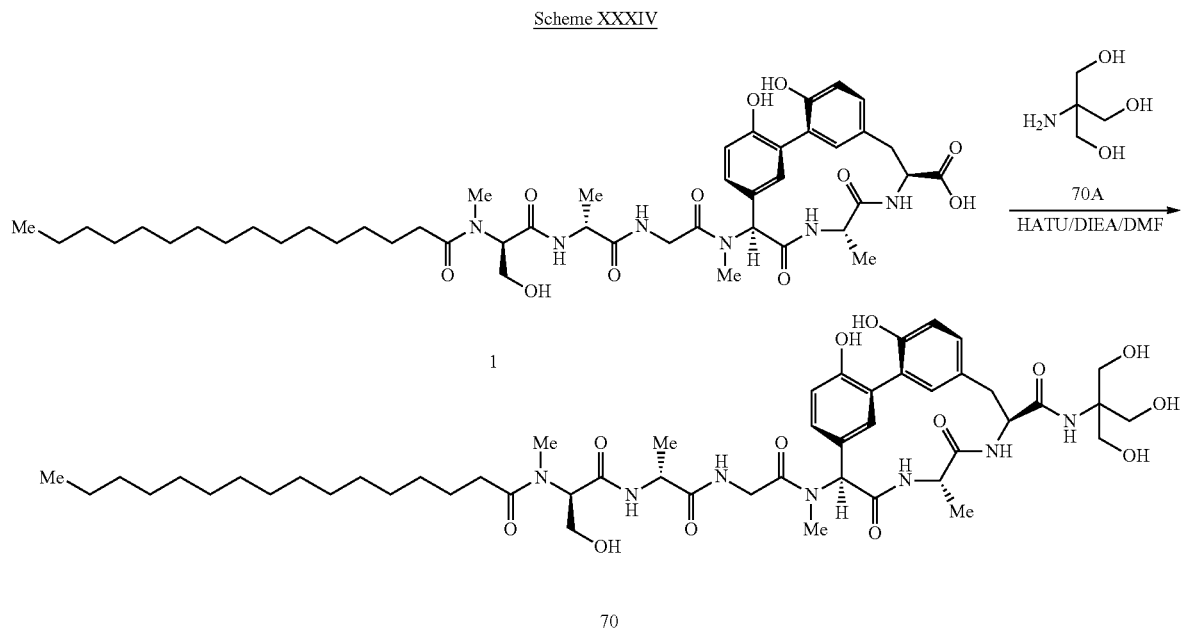
Compound 70 was prepared according to General Method 1 (Example 16) from Compound 1 and 70A. MS (ESI) m/z 984.4 (M+H)$^+$.
Example 39: Synthesis of Compound 71 (Scheme XXXV)
Scheme XXXV
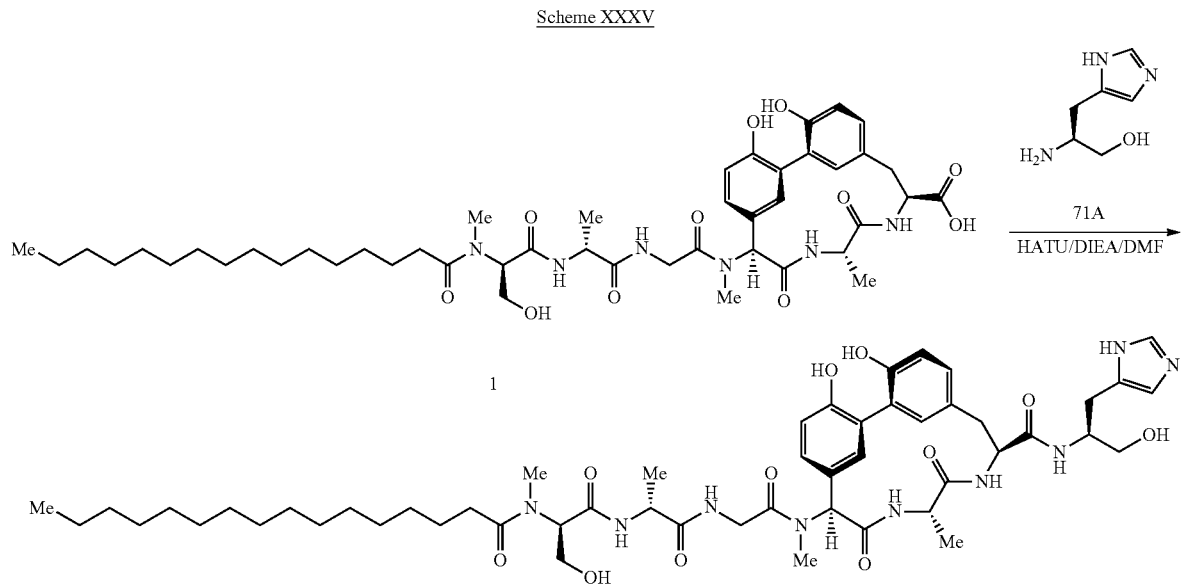

Compound 71 was prepared according to General Method 1 (Example 16) from Compound 1 and 71A. MS (ESI) m/z 1004.3 (M+H)+.
Example 40: Synthesis of Compound 72 (Scheme XXXVI)
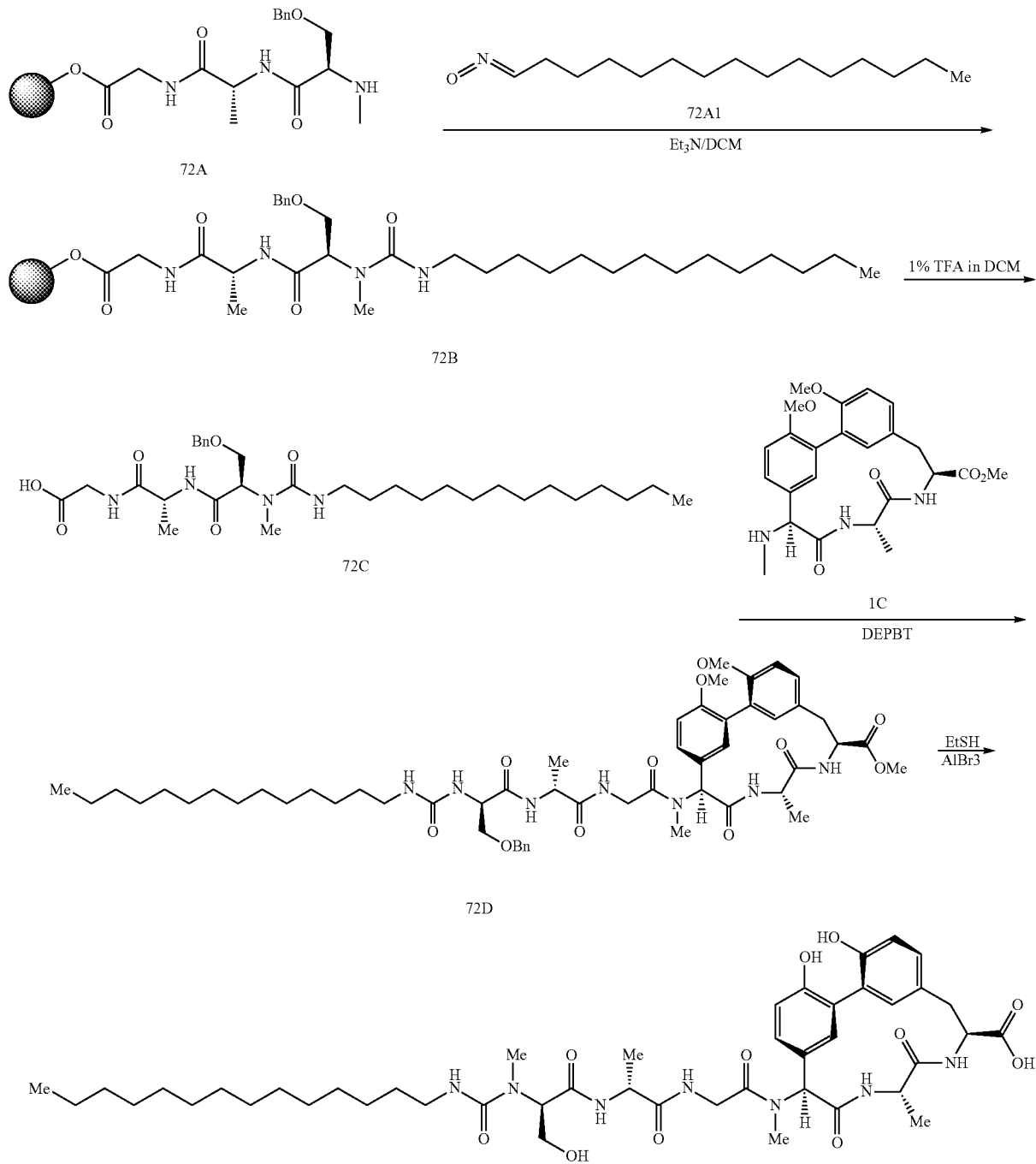

To a suspension of 72A (400 mg) and Et₃N (80 mg, 0.8 mmol) in dry DCM (10 mL) was added 72A1 (96 mg, 0.4 mmol) at 0° C. Then the mixture was shaken for 30 mins. After ELSD showed the reaction was complete, the mixture was filtered. The filter cake was washed with DCM (10 mL*3), DMF (10 mL*3) and DCM (10 mL*3). Then the mixture was filtered and the filtrate was concentrated to give 72B without further purification.

Compound 72B was treated according to General Methods 4, 5 and 6 (Examples 18 and 19) to afford Compound 72. MS (ESI) m/z 882.4 (M+H)⁺.

Example 41: Synthesis of Compound 74 (Scheme XXXVII)

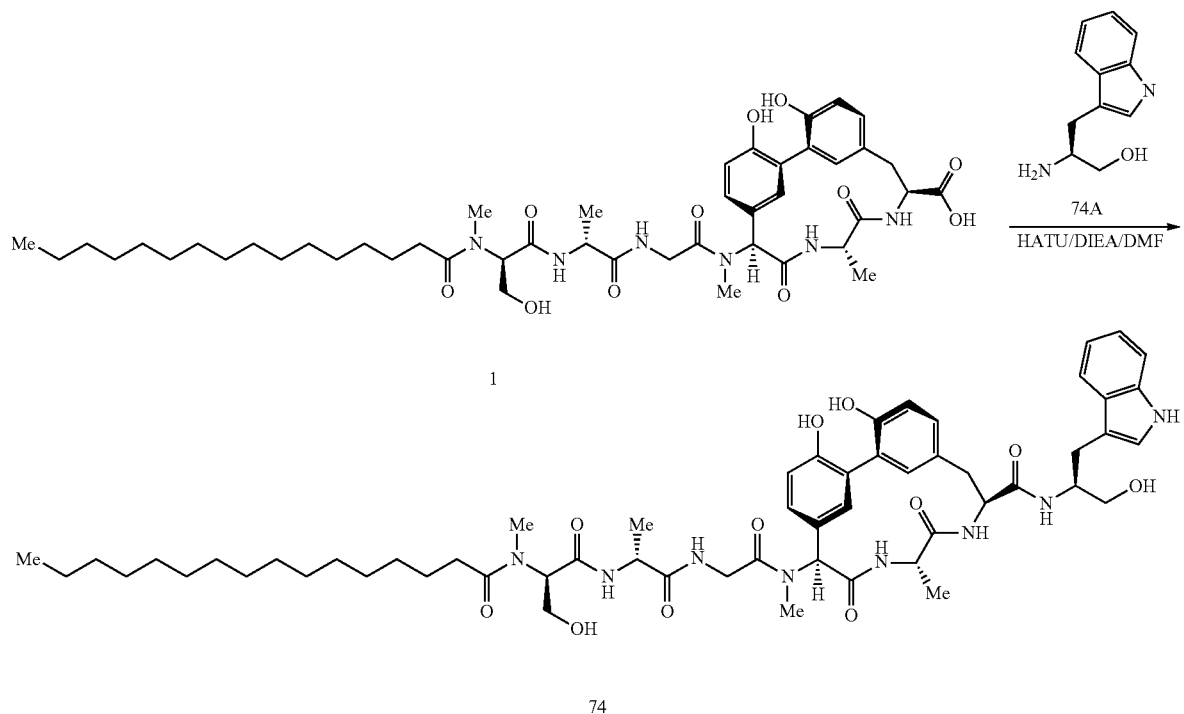

Compound 74 was prepared according to General Method 1 (Example 16) from Compound 1 and 74A.

Example 42: Synthesis of Compound 77 (Scheme XXXVIII)

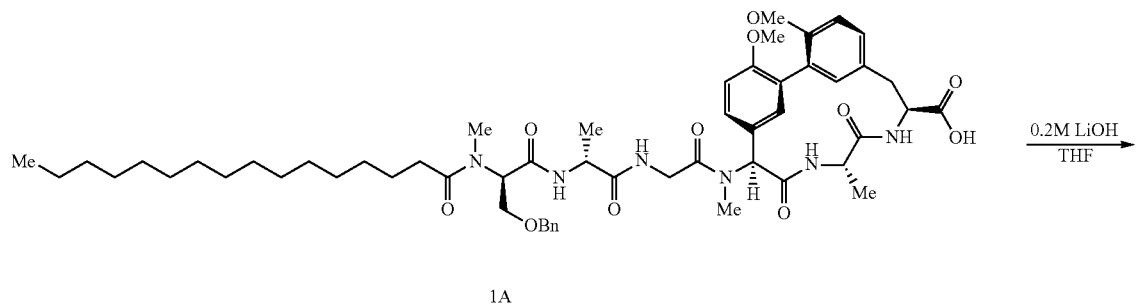

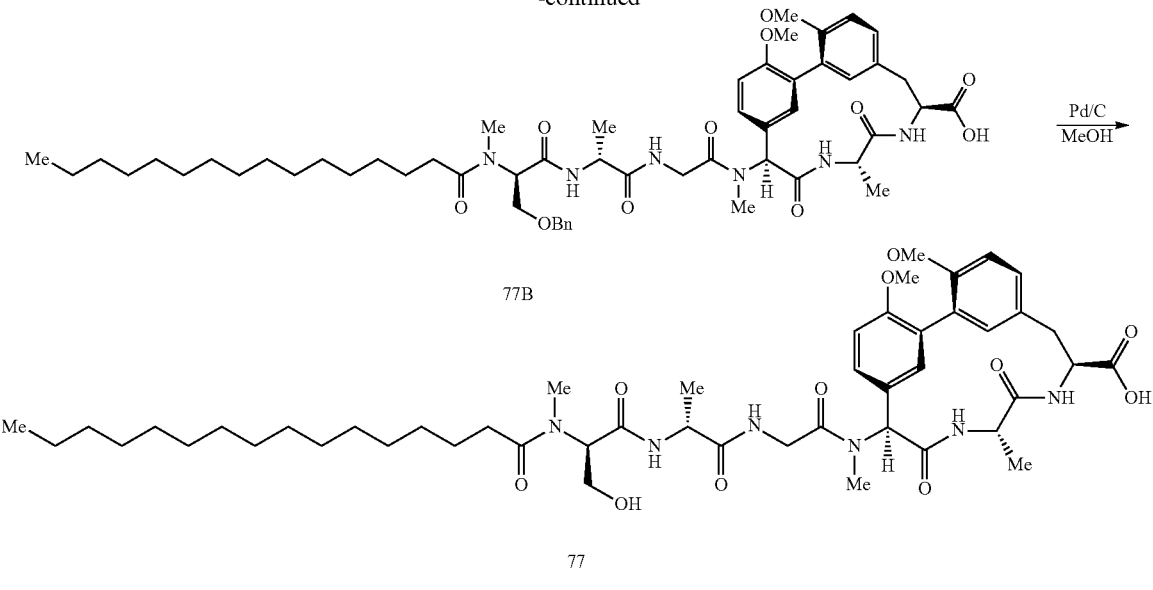

77B

77

The synthesis of Compound 77 is depicted in Scheme XXXVIII. A mixture of 1A (50 mg, 0.049 mmol), 0.2 M LiOH (0.2 mL) in THF (2 mL) was stirred at 0° C. for 20 mins. After HPLC showed the reaction was complete, saturated NH₄Cl (1 mL) was added to the mixture. The solvent was removed and the crude product was purified by prep-HPLC to give 77B (22 mg, yield: 45%), as an off-white solid.

A stream of H₂ was bubbled through a mixture of 77B (22 mg, 0.022 mmol) and Pd/C (10 mg) in MeOH (5 mL) at 15° C. for 1 hr. After ELSD showed the reaction was complete, the solvent was removed and the crude product was purified by prep-HPLC to give Compound 77 (4 mg, yield: 22.2%), as an off-white solid. MS (ESI) m/z 909.4 (M+H)⁺.

Example 43: Synthesis of Compound 78 (Scheme XXXIX)

Scheme XXXIX

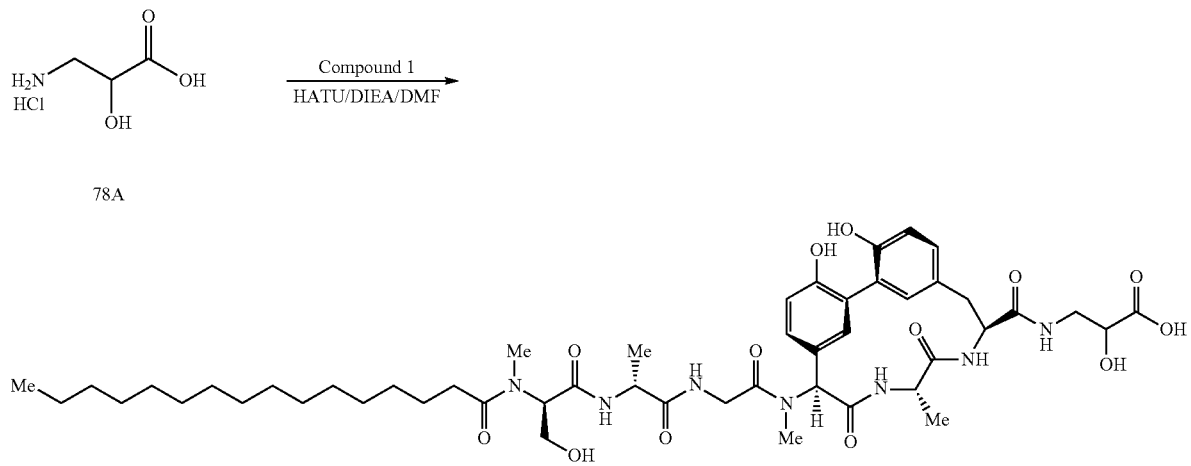

78

Compound 78 was prepared according to General Method 1 (Example 16) from Compound 1 and 78A. MS (ESI) m/z 968.5 (M+H)+.
Example 43a: Synthesis of Compound 75 (Scheme XXXIXa)
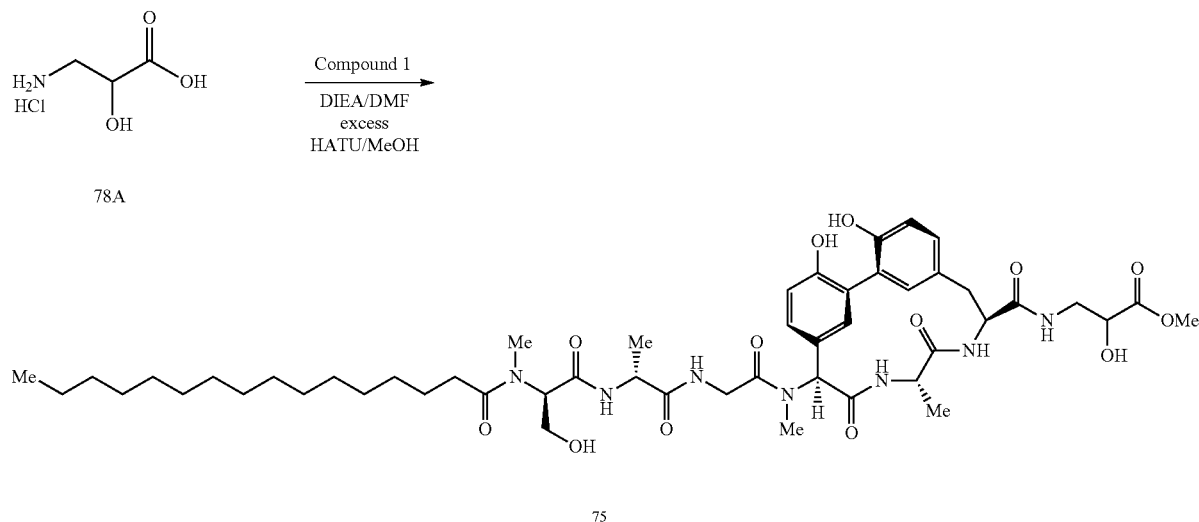
Compound 75 was prepared according to General Method 1 (Example 16) from Compound 1 and 78A except excess HATU was employed and the reaction was quenched with MeOH. MS (ESI) m/z 982.5 (M+H)+.
Example 44: Synthesis of Compound 80 (Scheme XL)
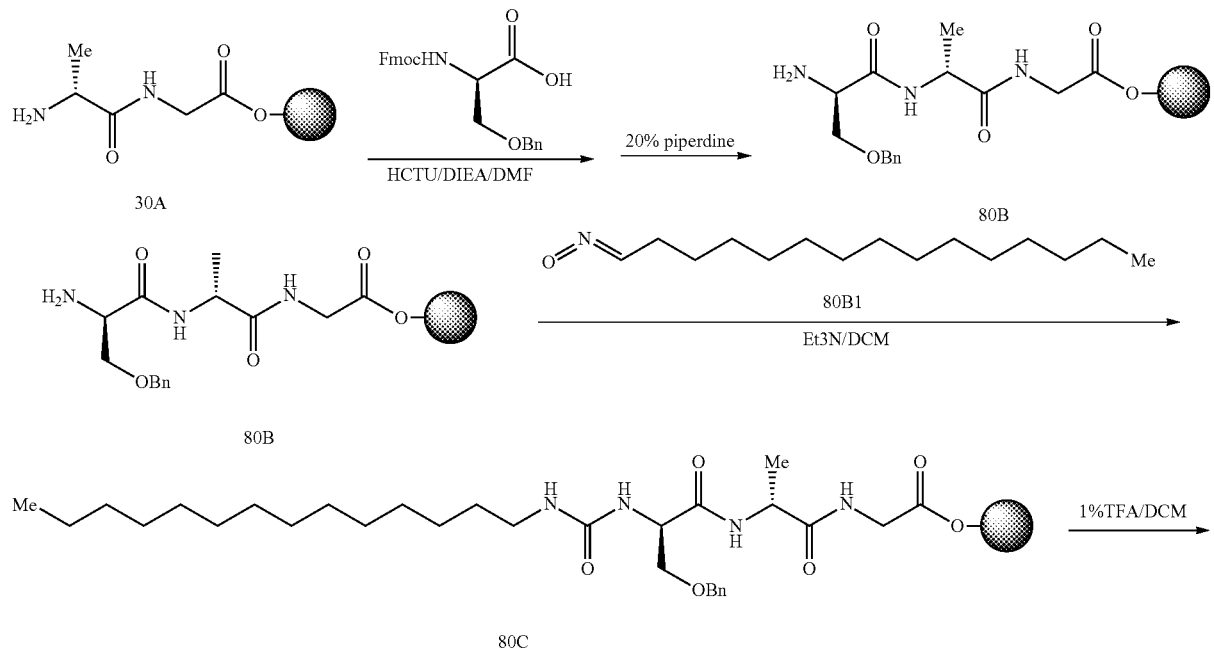

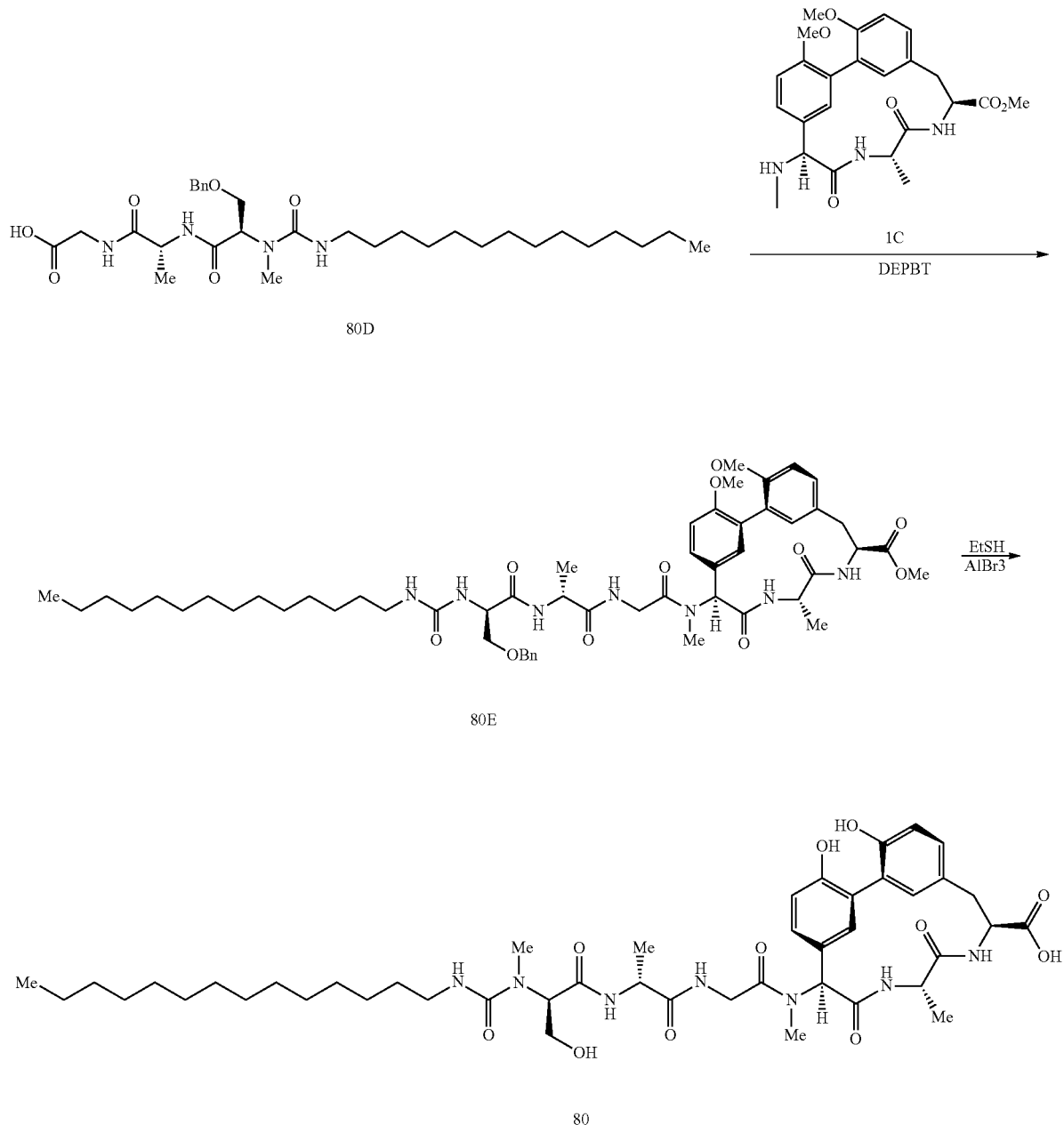

To a mixture of Fmoc-D-Ser (BZL)-OH (0.63 g, 1.5 mmol) in dry DMF (20 mL) was added HCTU (0.63 g, 1.5 mmol), HOBt (0.2 g, 1.5 mmol), DIEA (0.2 g, 1.5 mmol). Then the mixture was stirred at 15° C. for 30 mins. The mixture was added to a suspension of 30A (1.0 mmol) in DMF (10 mL). The mixture was shaken at 15° C. for 2 hrs. The mixture was filtered and the filter cake was washed with DMF (20 mL*3), DCM (20 mL*3), MeOH (20 mL*3). After ELSD showed the reaction was complete, the crude reaction was treated with 20% piperidine in DMF (20 mL*2). The resulting mixture was shaken for 30 mins. Then the mixture was filtered and the cake was washed with DMF (20 mL*3), DCM (20 mL*3) to give 80B.

To a suspension of 80B (1 mmol), Et$_3$N (150 mg, 1.5 mmol) in dry DCM (10 mL) was added 80B1 (270 mg, 1.2 mmol) at 0° C. Then the resulting mixture was shaken at 15° C. for 30 mins. After ELSD showed the reaction was complete, the mixture was filtered. The filter cake was washed with DMF (10 mL*3) and DCM (10 mL*3). After ELSD showed the reaction was complete, the filter cake 80C was treated with 1% TFA in DCM (10 mL). The resulting mixture was shaken for 30 mins, and then filtered. The filtrate was concentrated to give 80D (0.5 g, yield: 89.3% via 4 steps).

80D was treated according to General Methods 5 and 6 (Example 19) to afford Compound 80. MS (ESI) m/z 868.4 (M+H)$^+$.

Example 45: Synthesis of Compound 82 (Scheme XLI)
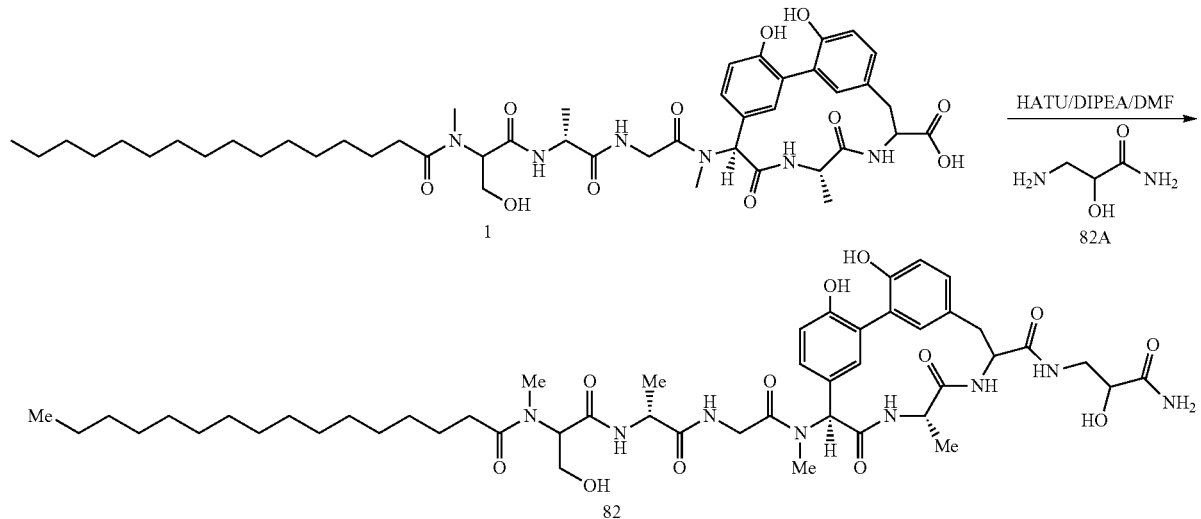
Compound 82 was prepared according to General Method 1 (Example 16) from Compound 1 and 82A. MS (ESI) m/z 967.3 (M+H)$^+$.
Example 46: Synthesis of Compound 83 (Scheme XLII and Scheme XLIII)
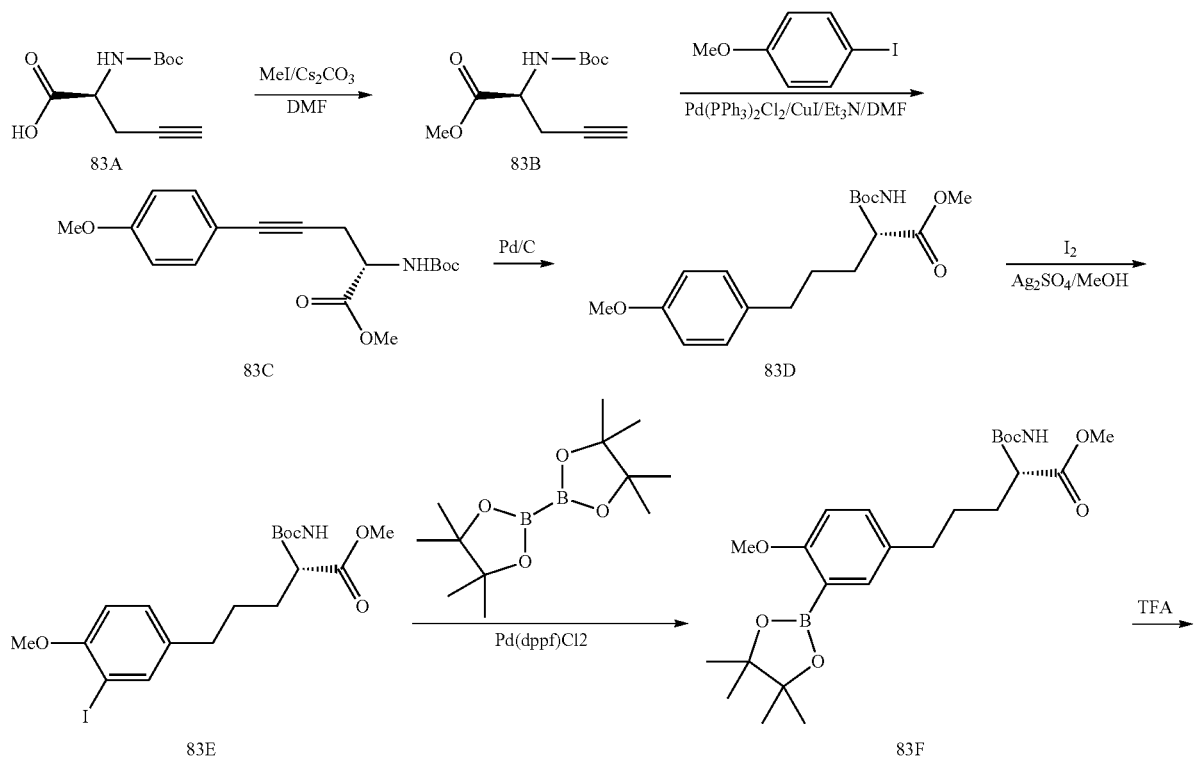

-continued

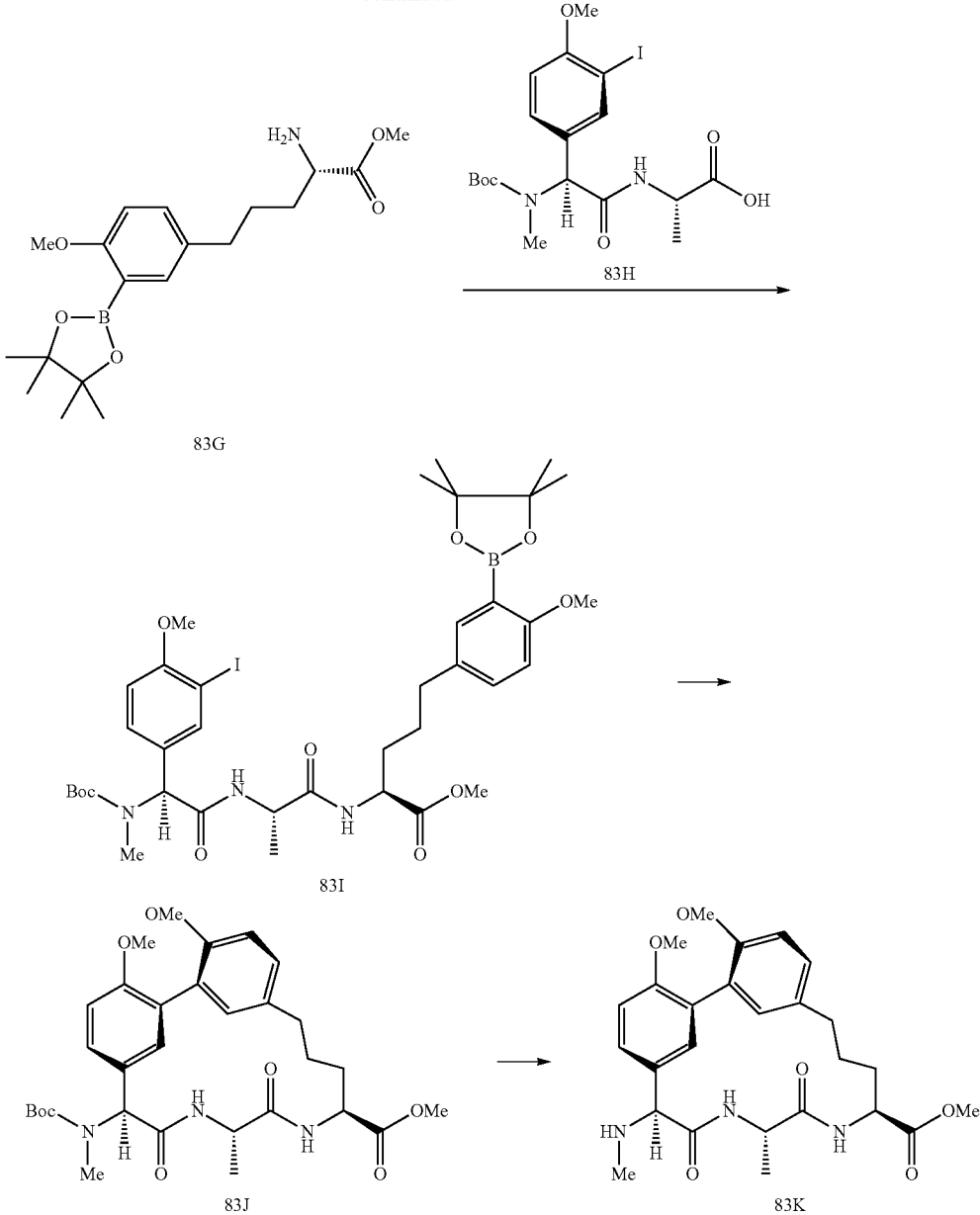

A solution of 83A (4 g, 18.8 mmol) and $Cs_2CO_3$ (6.1 g, 18.8 mmol) in DMF (20 mL) was stirred for 45 mins at 15° C., then MeI (5.3 g, 37.6 mmol) was added. The reaction was stirred overnight at 15° C. After TLC showed the reaction was complete, the mixture was filtered and the filtrate was treated with water. The aqueous layer was extracted with ethyl acetate (20 mL*3). The combined organic layers was washed with brine, dried over sodium sulfate and concentrated to give 83B (3.6 g, yield: 84.5%).

A mixture of 1-iodo-4-methoxybenzene (4.45 g, 19 mmol), CuI (0.3 g, 1.59 mmol) and $PdCl_2(PPh_3)_2$ (0.56 g, 0.79 mmol), $Et_3N$ (11.7 mL, 87.2 mmol) was stirred in degassed DMF (30 mL) at 15° C. for 30 mins. A solution of 83B (3.6 g, 15.9 mmol) in degassed DMF (5 mL) was added over 30 mins and the resulting mixture was stirred at 15° C. until the starting material was complete disappeared (detected by TLC analysis). DCM (30 mL) was added and the mixture was treated with 5% $NaHCO_3$ (20 mL). The organic layer was washed with water (2*20 mL), separated and dried with $Na_2SO_4$. After removing solvent under reduced pressure, the crude product was purified by column chromatography on silica gel to give 83C (3 g, yield: 57%).

A stream of $H_2$ was bubbled through a suspension of 83C (3 g, 9 mmol), Pd/C (0.8 g) in methanol (30 mL) at 15° C. for 3 hrs. After LC-MS showed the reaction was complete, the catalyst was filtered, and the filtrate was concentrated under reduced pressure to give 83D (2.1 g, yield: 69%).

To a solution of 83D (2.1 g, 6.2 mmol) in methanol (40 mL) was added sequentially $Ag_2SO_4$ (2.0 g, 6.5 mmol) and $I_2$ (1.66 g, 6.5 mmol). After LCMS showed the reaction was completed, a solution of 10% (w/w) sodium thiosulfate was added till the reaction turned pale yellow. Most of the methanol was evaporated and the residue was treated with water. The aqueous layer was extracted with ethyl acetate (20 mL*3). The combined organic layers were washed with brine, dried over sodium sulfate and concentrated to give a crude product, which was purified by abbreviated silica gel column chromatography to give 83E (2.2 g, yield: 76%).

A solution of 83E (2.2 g, 6.1 mmol) was dissolved under argon in anhydrous DMSO (50 mL) and to the solution was added X1 (3.1 g, 12.2 mmol) and KOAc (1.8 g, 18.3 mmol). The mixture was purged with argon for 20 mins, then was added Pd (dppf)Cl$_2$ (0.2 g, 0.3 mmol). The mixture was degased with argon and stirred at 80° C. under argon for 45 mins, then cooled to room temperature and poured into water (150 mL). The aqueous layer was extracted with ethyl acetate (20 mL*3) and the combined organic layers were dried over Na$_2$SO$_4$. The solvent was removed and the crude product was purified by column chromatography on silica gel to give 83F (0.55 g, yield: 25%).

83F (0.55 g, 1.56 mmol) was dissolved in dichloromethane (10 mL) and treated with TFA (2 mL). The reaction was allowed to stir at 15° C. until TLC showed the disappearance of product. The mixture was concentrated, and the resulting residue was treated with EtOAc and washed with saturated sodium bicarbonate. The organic layer was then dried over sodium sulfate, filtered and concentrated to give 83G (0.38 g, yield: 90%).

To a solution of 83G (0.38 g, 1.05 mmol) and 1D (0.52 g, 1.05 mmol) in acetonitrile/DMF (2.2:1, 20 mL) was added HOBt (0.35 g, 2.6 mmol) and EDC (0.44 g, 2.3 mmol). The reaction was stirred at 15° C. overnight then diluted with citric acid (until pH=3) was added and the aqueous layer was extracted with ethyl acetate (20 mL*3). The combined organic layers were washed with saturated NaHCO$_3$ solution (10 mL), brine (10 mL), water (10 mL), dried over sodium sulfate and then concentrated to give a crude product 83H, which was used to the next step without further purification (0.8 g, crude).

83H (0.8 g, 0.95 mmol,) and NaHCO$_3$ (0.8 g, 9.5 mmol) were sealed under an atmosphere of argon in a flask with a condenser. Then PdCl$_2$(dppf) (0.14 g, 0.19 mmol) in DMF (20 mL) in a separate flask was purged with argon for sever times. The reaction mixture was bubbled with argon for 15 minutes via needle. Then the palladium in DMF was transferred to the reaction mixture via syringe. The resulting mixture was degassed with Ar then stirred at 100° C. overnight. After that, the mixture was cooled to 15° C. and water was added. The aqueous phase was extracted with EtOAc (20 mL), and the organic layers were washed with water and brine, dried over sodium sulfate and concentrated to give a crude product, which was purified by column chromatography to give 83I (300 mg, yield: 61% via 2 steps), as a brown solid.

83I (300 mg, 0.51 mmol) was dissolved in DCM (5 mL) and treated with TFA (1 mL) at 15° C. The volatiles were evaporated under a stream of nitrogen until no starting material was detected by TLC. The crude residue was then dissolved in EtOAc (20 mL), and the organic layer was washed with saturated NaHCO$_3$ (10 mL), dried over sodium sulfate and concentrated to give 83J (260 mg, crude). The crude product was used directly without further purification.

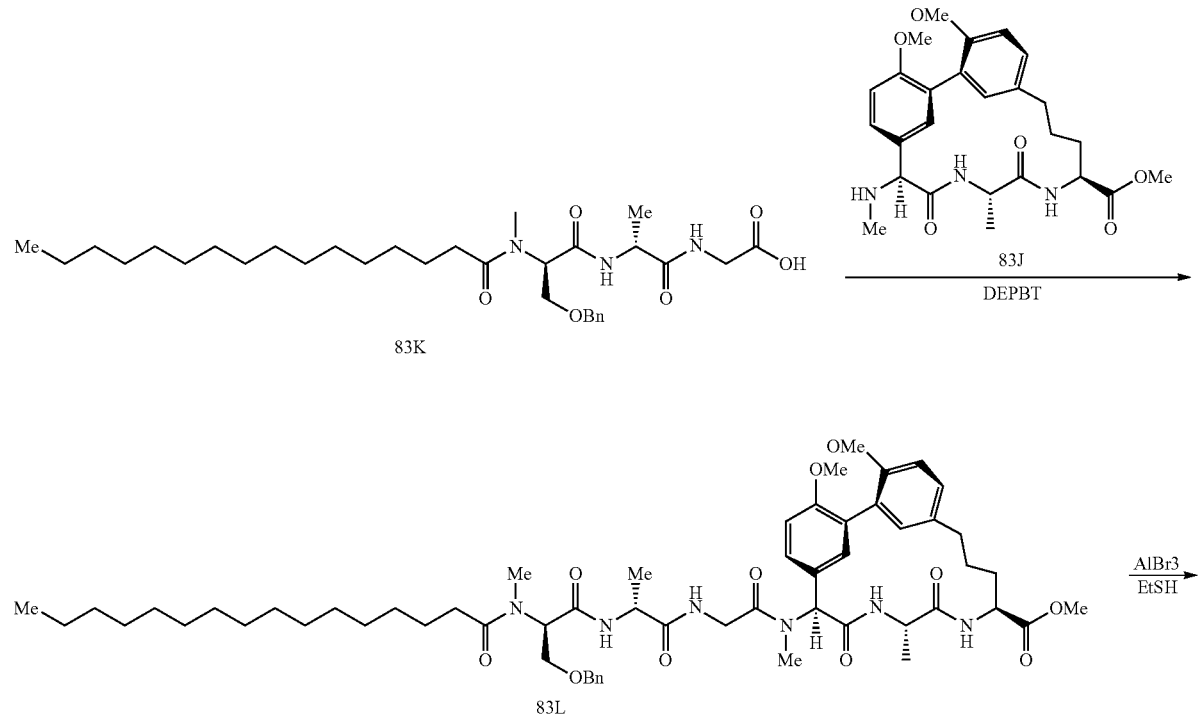

Scheme XLIII

-continued

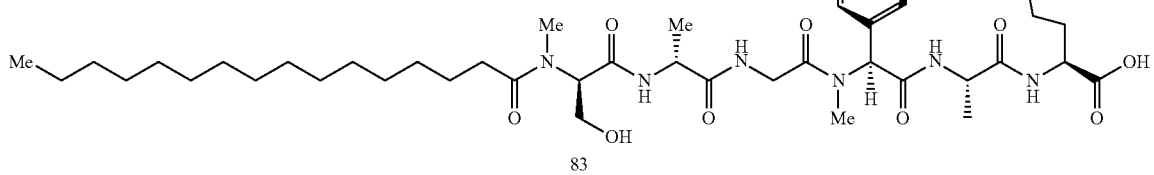

83

To a solution of 83J (260 mg, 0.54 mmol) and 83K (309 mg, 0.54 mmol) in THF (15 mL) at 0° C. was added DEPBT (320 mg, 1.08 mmol) and NaHCO$_3$ (86 mg, 1.08 mmol). The reaction was then allowed to stirred at 70° C. overnight. After ELSD showed the reaction was completed, the solvent was removed under vacuum. The crude product was purified by column chromatography on silica gel to give 83L (500 mg, crude).

83L (500 mg, 0.48 mmol) was dissolved in ethanethiol (12 mL) under Ar, and then treated with 1.0 M AlBr$_3$ in CH$_2$Br$_2$ (10.7 mL, 10.7 mmol). The reaction vial was sealed and warmed to 50° C. for 4 h. The mixture was cooled to 15° C. and MeOH (0.5 mL) was added, then the volatiles were evaporated under a stream of nitrogen to give a crude product. The crude product was purified by prep-HPLC to give Compound 83 (60 mg, yield: 16%, via two steps). MS (ESI) m/z 909.5 (M+H)$^+$.

Example 47: Synthesis of Compound 84 (Scheme XLIV)

Scheme XLIV
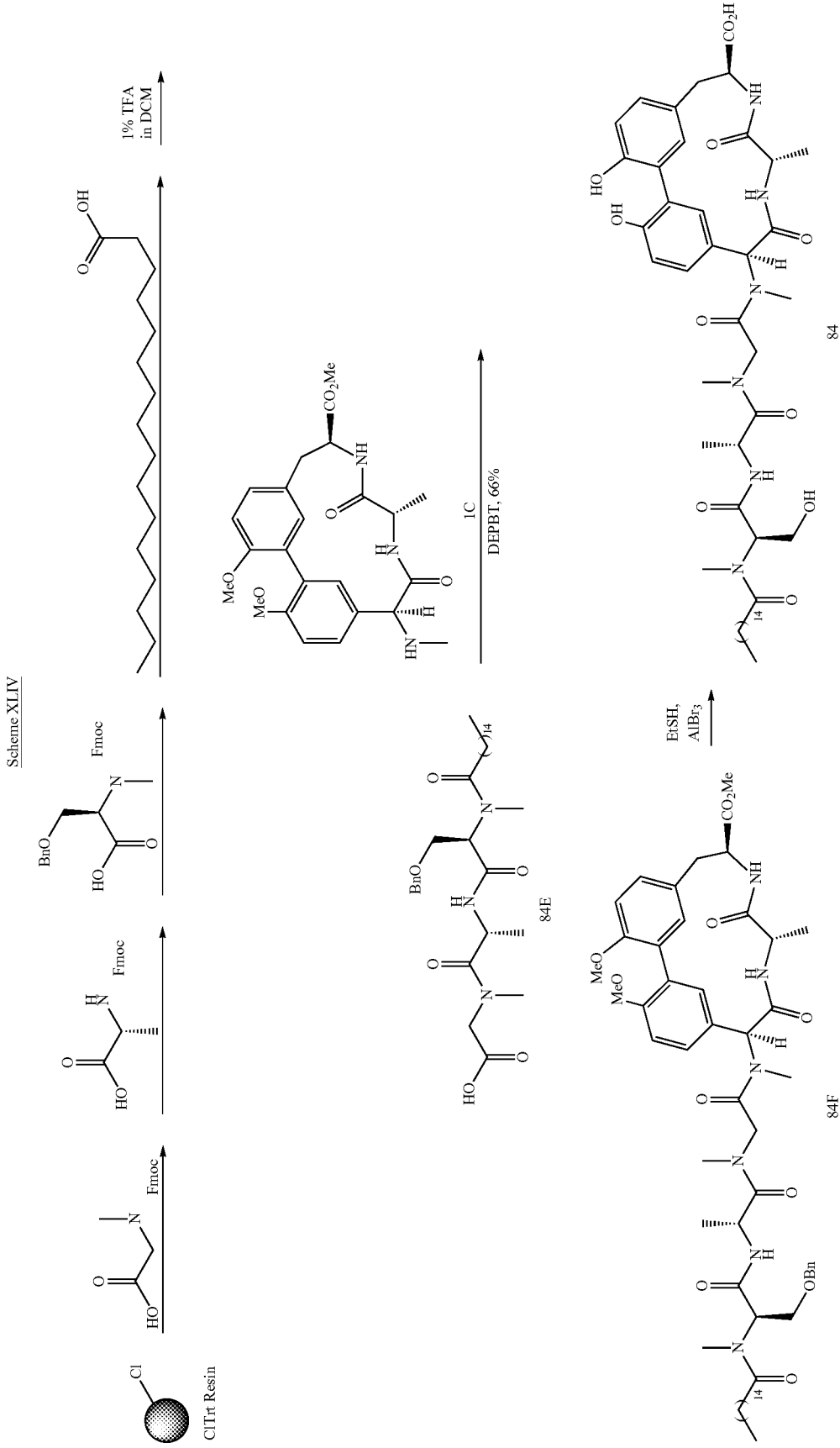

Compound 84 was prepared according to General Methods 2-6 (Examples 18 and 19) as depicted in Scheme XLIV to afford Compound 84. MS (ESI) m/z 895.3 (M+H)$^+$.

Example 48: Synthesis of Compound 85 (Scheme XLV)

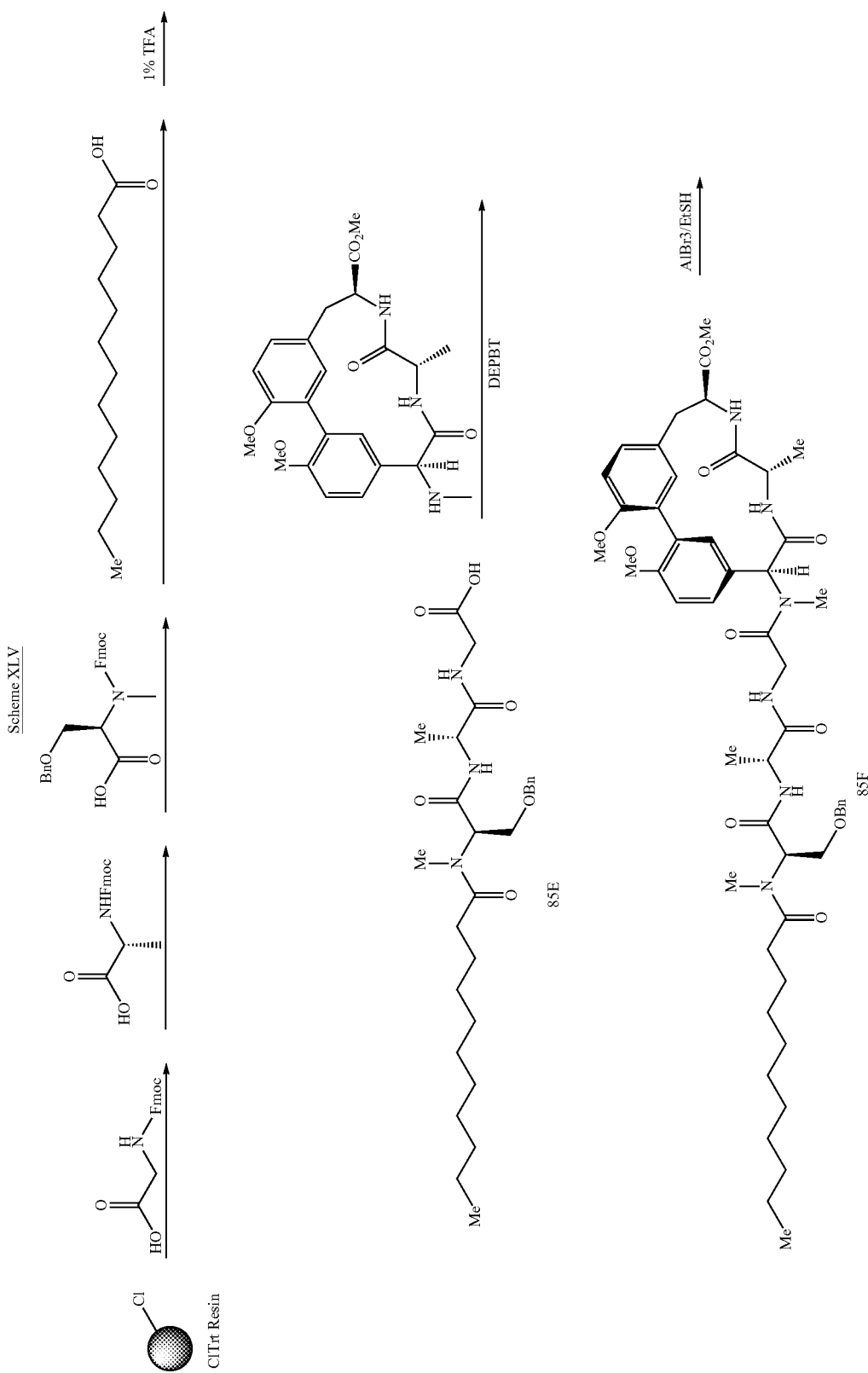

-continued
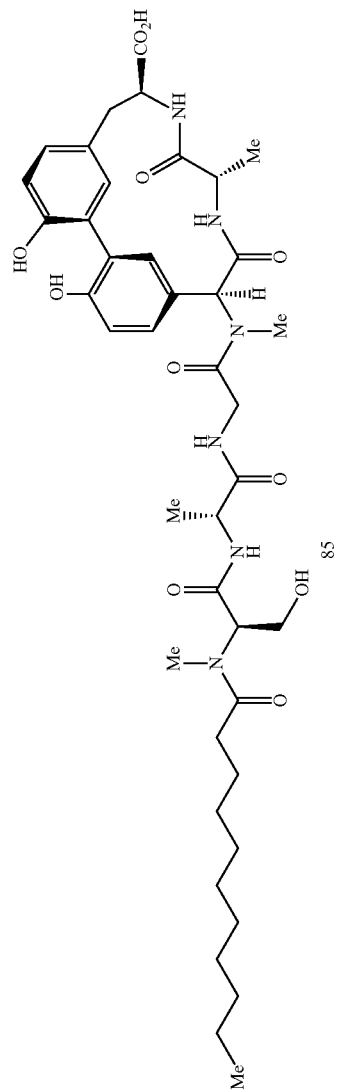
85

Compound 85 was prepared according to General Methods 2-6 (Examples 18 and 19) as depicted in Scheme XLV to afford Compound 85. MS (ESI) m/z 811.3 (M+H)+.
Example 49: Synthesis of Compound 86 (Scheme XLVI)
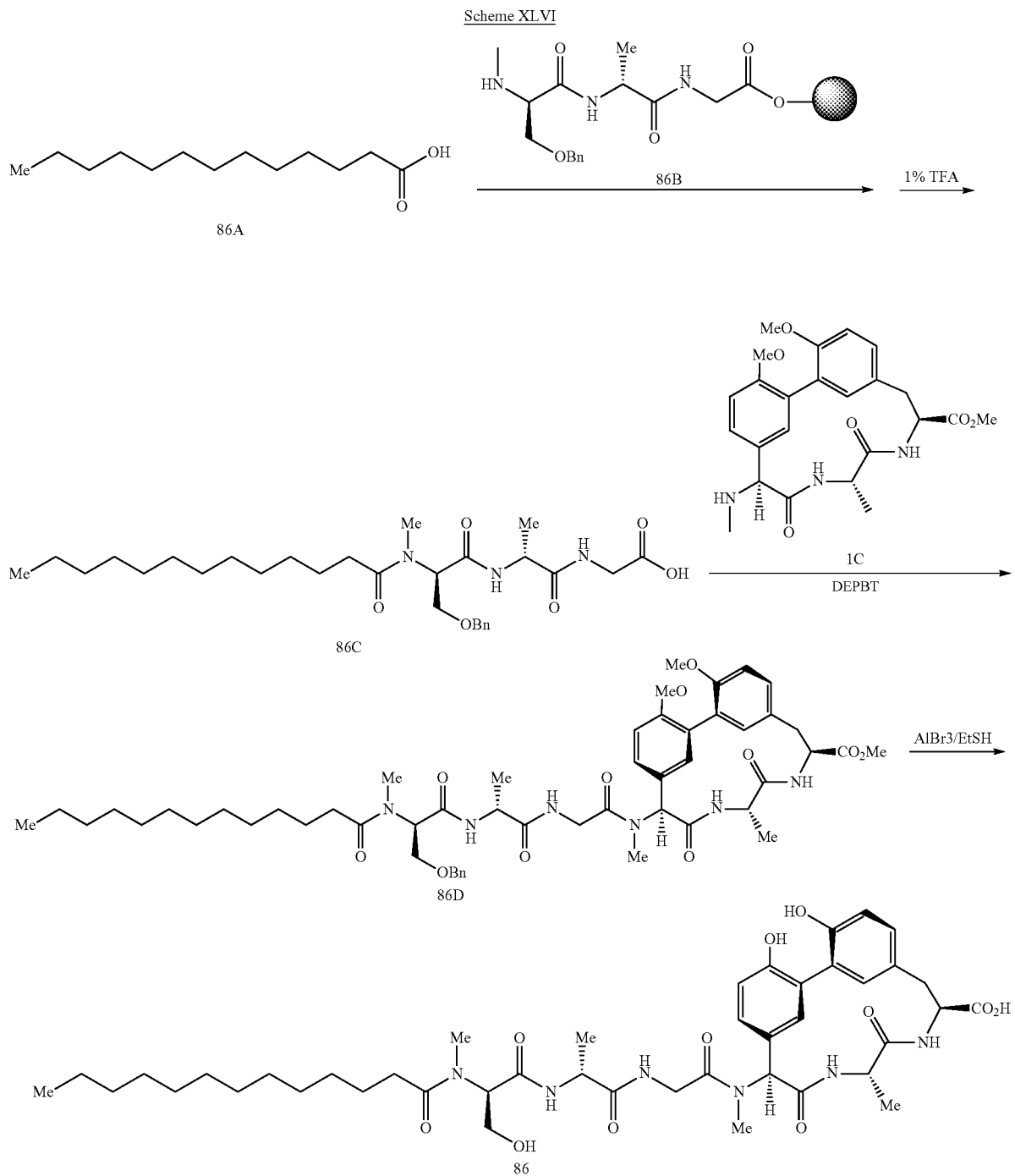

Compound 86 was prepared using General Methods 2-6 (Examples 18 and 19) as depicted in Scheme XLVI to afford Compound 86. MS (ESI) m/z 839.3 (M+H)$^+$.

Example 50: Synthesis of Compound 87 (Scheme XLVII)

Scheme XLVII
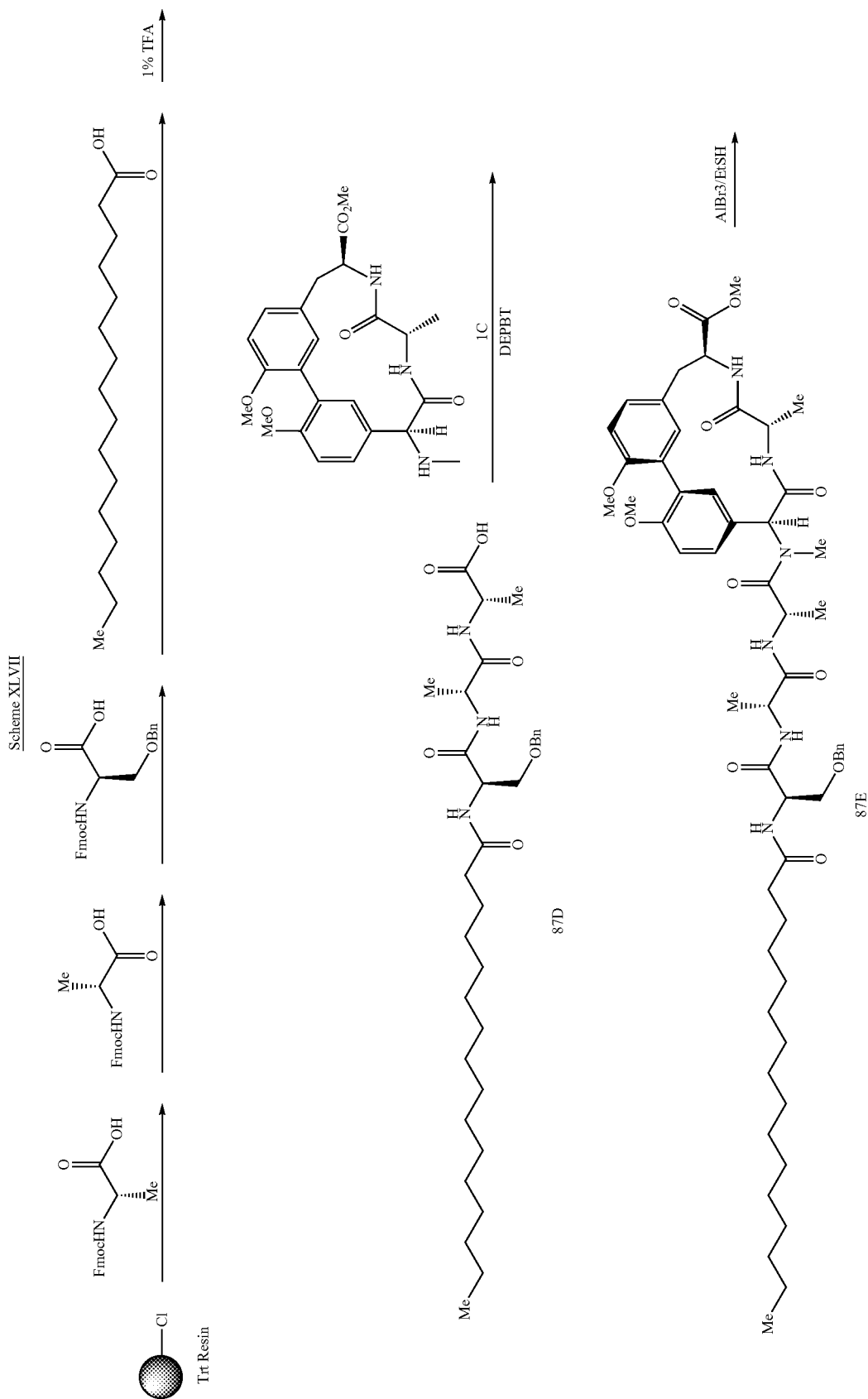

-continued
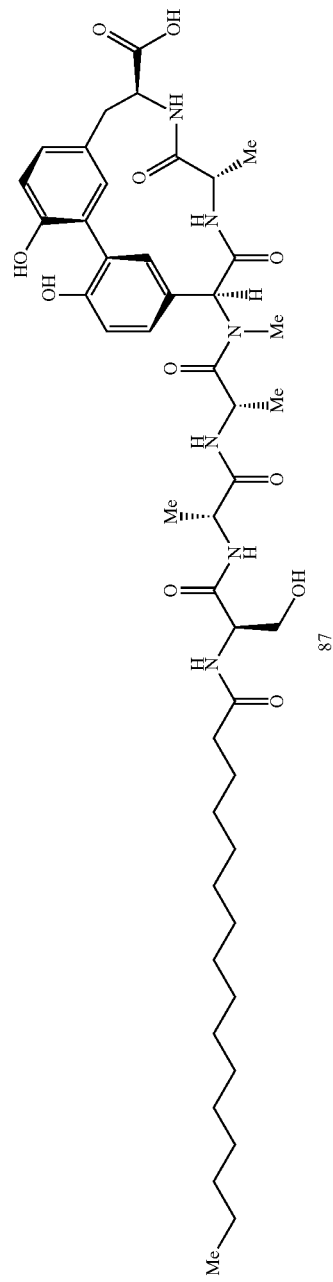
87

Compound 87 was prepared using General Methods 2-6 (Examples 18 and 19) as depicted in Scheme XLVII to afford Compound 87. MS (ESI) m/z 881.5 (M+H)$^+$.

Example 51: Synthesis of Compound 90 (Scheme XLVIII)

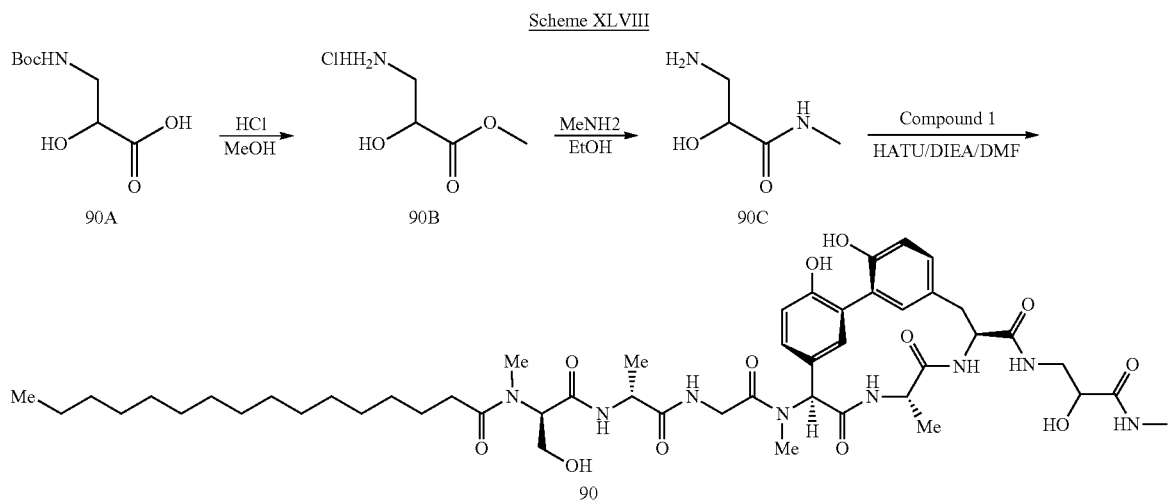

A solution of 90A (750 mg, 3.6 mmol) in HCl saturated MeOH (10 mL) was stirred at 15° C. for 12 h. The solvent was removed under reduced pressure to give 90B (550 mg, yield: 97%) without purification.

To a solution of 90B (100 mg, 0.46 mmol) in EtOH (0.5 mL) was added 5 mL of 30% MeNH$_2$ in EtOH. The reaction mixture was heated at 100° C. for 1 h. The solvent was concentrated at reduced pressure to give crude 90C (70 mg, yield: 71%) without purification.

Compound 90 was prepared from Compound 1 and 90C according to General Method 1 (Example 16) to afford Compound 90. MS (ESI) m/z 981.2 (M+H)$^+$.

Example 52: Synthesis of Compound 91 (Scheme XLIX)

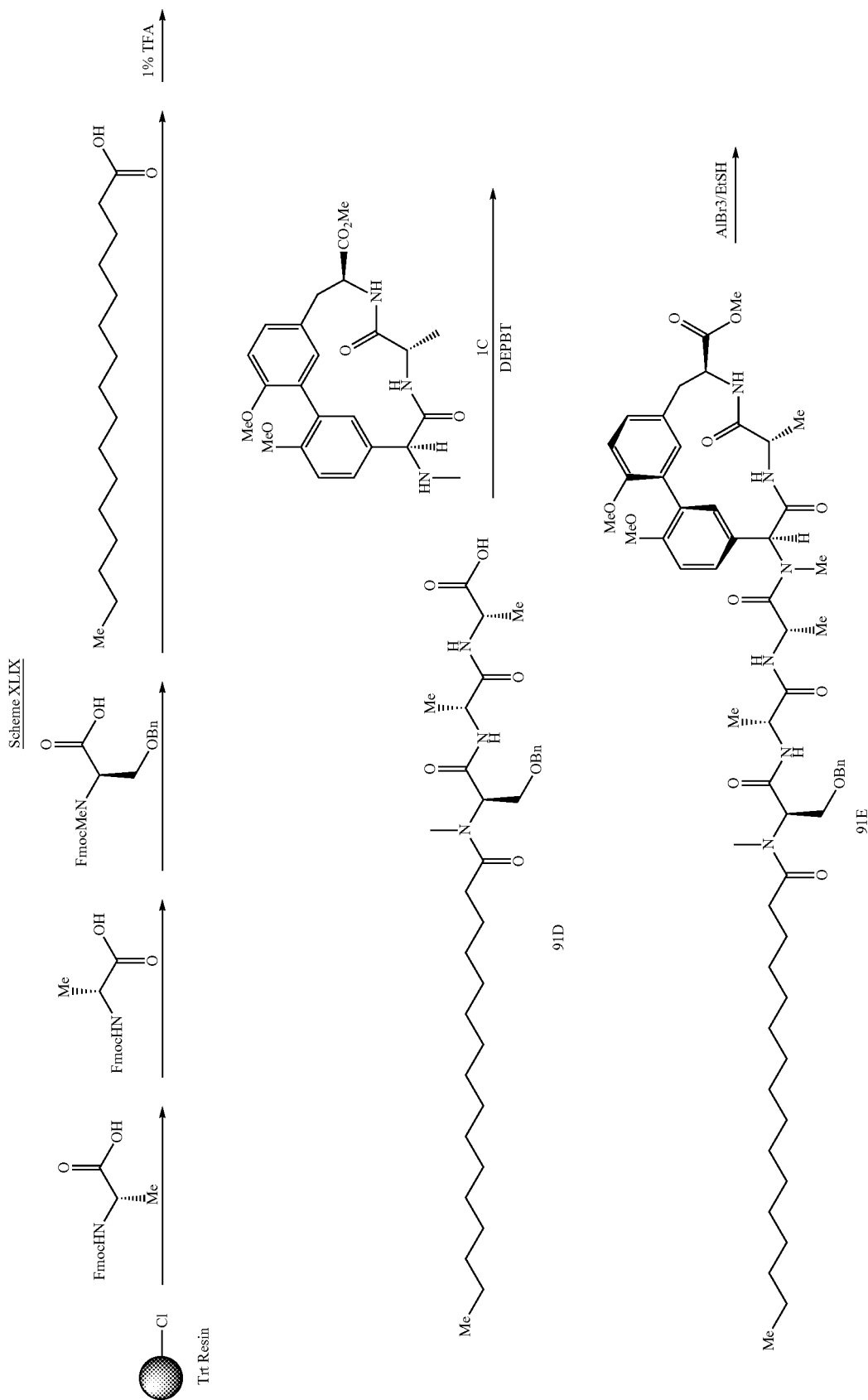

-continued
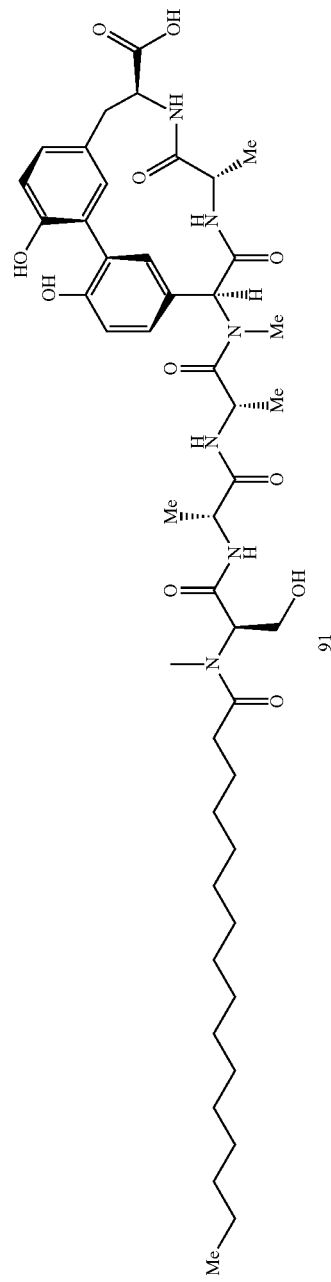
91

Compound 91 was prepared using General Methods 2-6 (Examples 18 and 19) as depicted in Scheme XIX to afford Compound 91. MS (ESI) m/z 895.3 (M+H)+.

Example 53: Synthesis of Compound 94 (Scheme L)

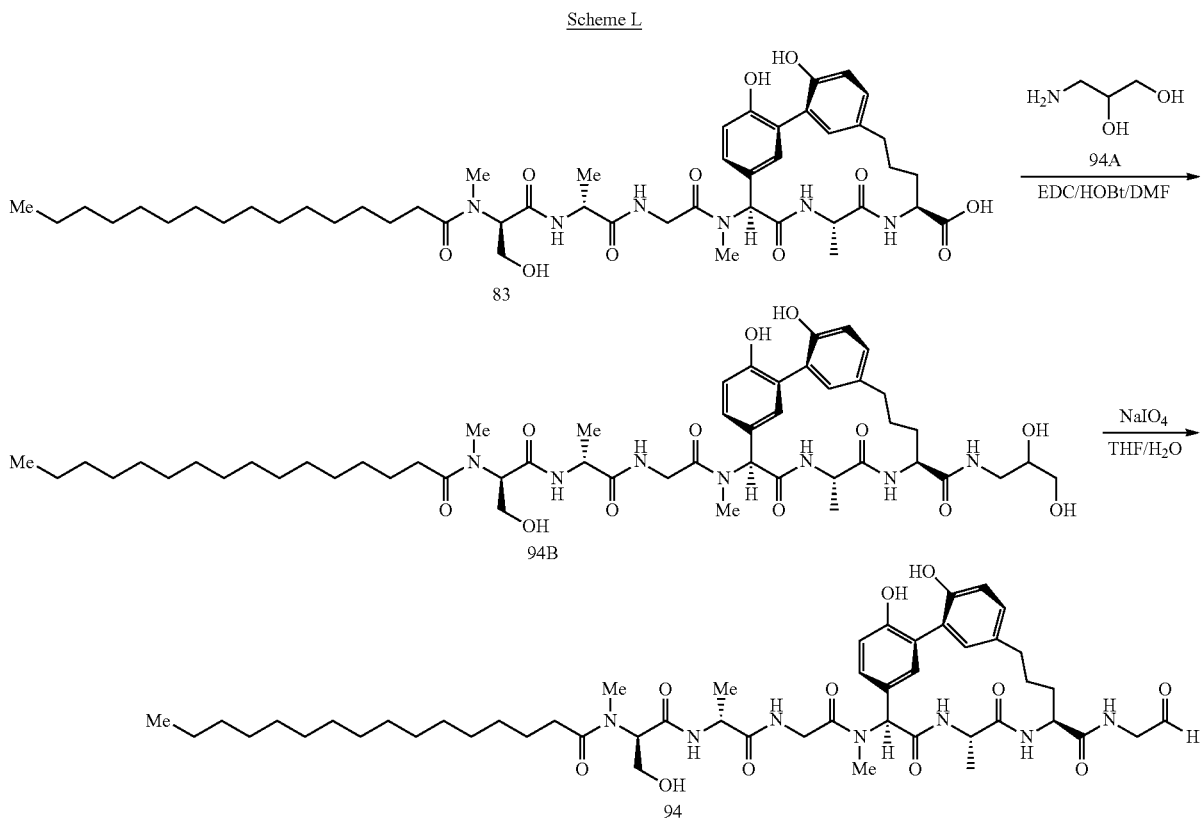

A mixture of Compound 83 (20 mg, 0.022 mmol), EDCI (9 mg, 0.044 mmol), HOBt (6 mg, 0.044 mmol) in DMF (1 mL) was stirred at 15° C. for 20 mins under Ar. Then 94A (18 mg, 0.22 mmol) was added. The resulting mixture was stirred at 15° C. overnight. After ELSD showed the reaction was complete, the crude product was purified by prep-HPLC to give 94B (4.2 mg, yield: 37%).

A mixture of 94B (4.2 mg, 4.2 mmol), NaIO$_4$ in THF/H$_2$O (0.5 mL, 12.6 mmol) was stirred at 15° C. for 16 hrs. After ELSD showed the reaction was complete, the crude product was purified by prep-HPLC to give 94 (1.4 mg, yield: 34%). MS (ESI) m/z 950.2 (M+H)+.

Example 54: Synthesis of Compound 95 (Scheme LI)

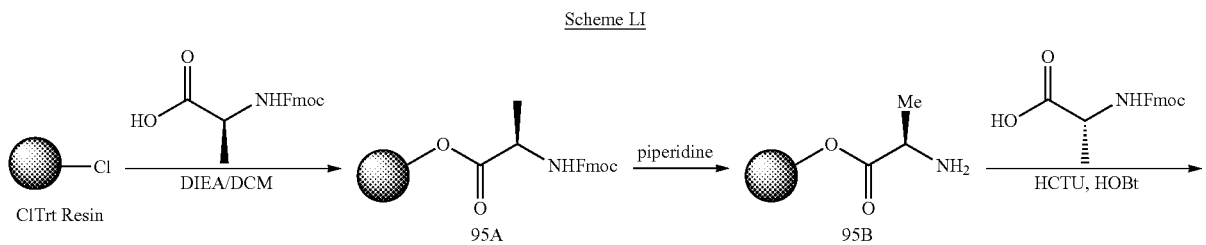

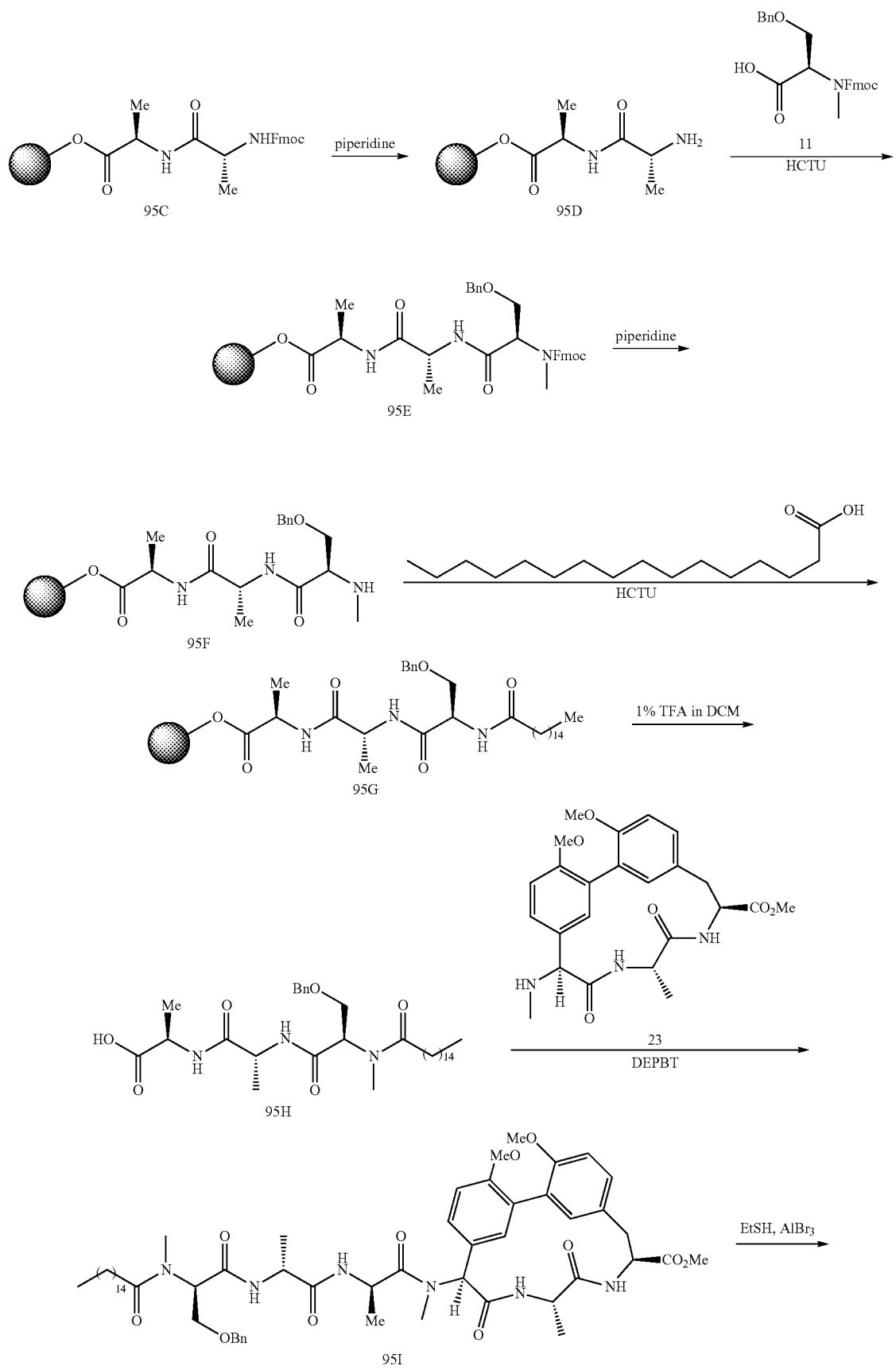

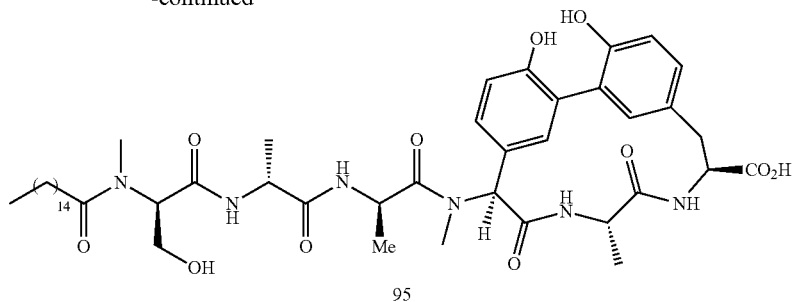
Compound 95 was prepared using General Methods 2-6 (Examples 18 and 19) as depicted in Scheme LI to afford Compound 95. MS (ESI) m/z 895.4 (M+H)$^+$.
Example 55: Synthesis of Compound 96 (Scheme LII and LIII)
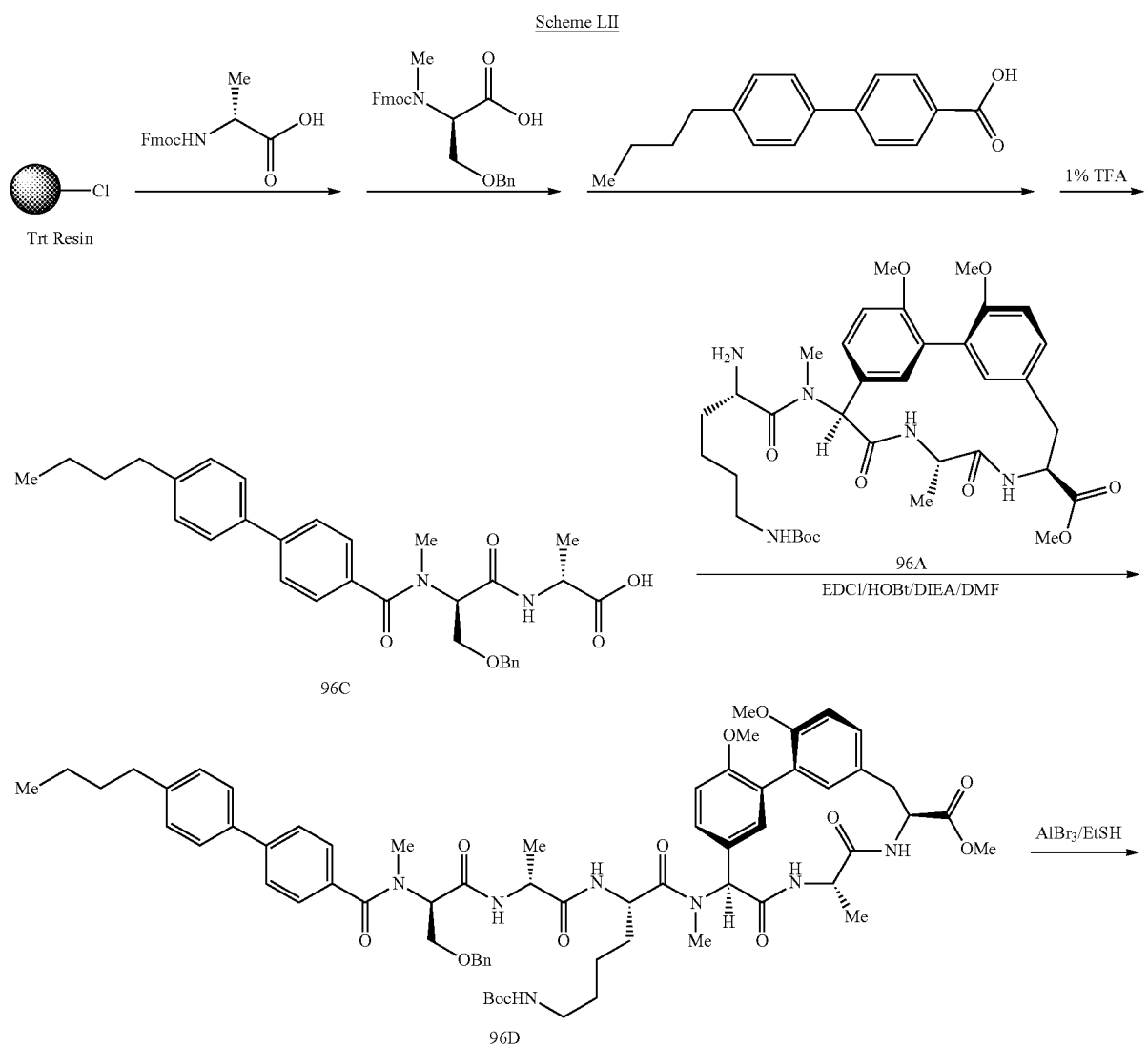

-continued

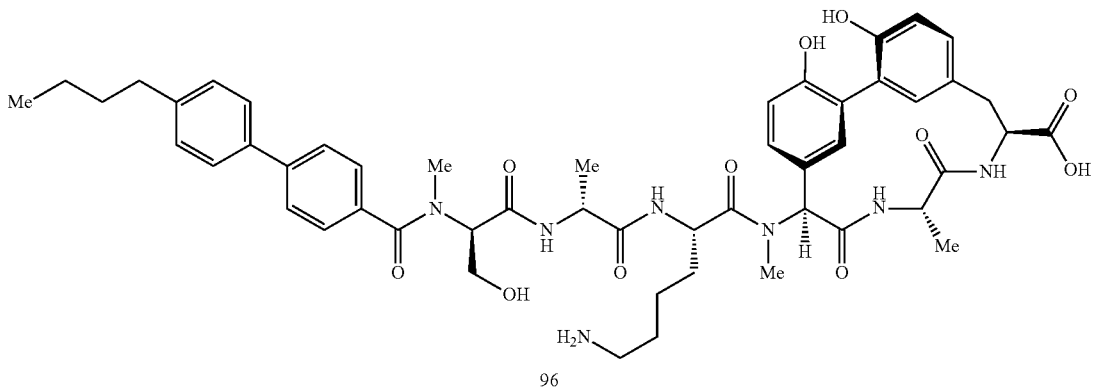

96

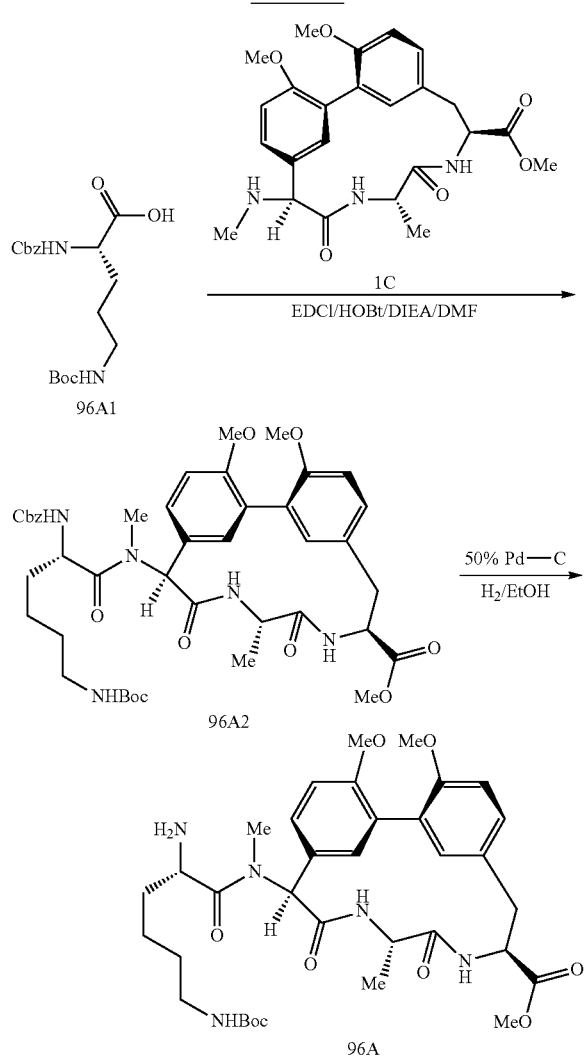

To a solution of 1C (275 mg, 0.73 mmol) in DMF (2 mL) were added HOBT (267.3 mg, 1.98 mmol), DIPEA (255.4 mg, 1.98 mmol), 96A1 (300 mg, 0.66 mmol) and EDCI (378.2 mg, 1.98 mmol). The resulting solution was stirred at 20° C. overnight and diluted with water. The precipitate was filtered and the resulting filter cake was washed with water and dried by aspiration to give a crude product, which was recrystallized from PE to give 96A2 (0.5 g, yield: 84.3%), as a white solid.

To a suspension of 96A2 (500 mg, 0.61 mmol) and 50% Pd/C (0.7 g) in EtOH (15 mL) was stirred at 20° C. overnight until LC-MS showed the reaction was completed. Then the catalyst was filtered and the solvent was evaporated to afford the desired material 96A (350 mg, yield: 90.3%), which was used without further purification.

To a solution of 96C (prepared according to General Methods 2, 3, and 4 (Example 18) as depicted in Scheme LII) (166 mg, 0.32 mmol) in DMF (2 mL) were added EDCI (166 mg, 0.87 mmol), HOBt (117 mg, 0.87 mmol) and DIPEA (112 mg, 0.87 mmol). The solution was stirred at 20° C. for 30 mins, then 96A (200 mg, 0.29 mmol) was added. The resulting solution was stirred at 20° C. overnight until LC-MS showed the reaction was completed. The mixture was diluted with water, the precipitate was filtered and the filter cake was washed with water and dried by aspiration to give 96D without further purification (190 mg, yield: 54.9%).

Compound 96 was prepared according to General Method 6 (Example 19) from Compound 96D. MS (ESI) m/z 950.4 (M+H)$^+$.

Example 56: Synthesis of Compound 97 (Scheme LIV)
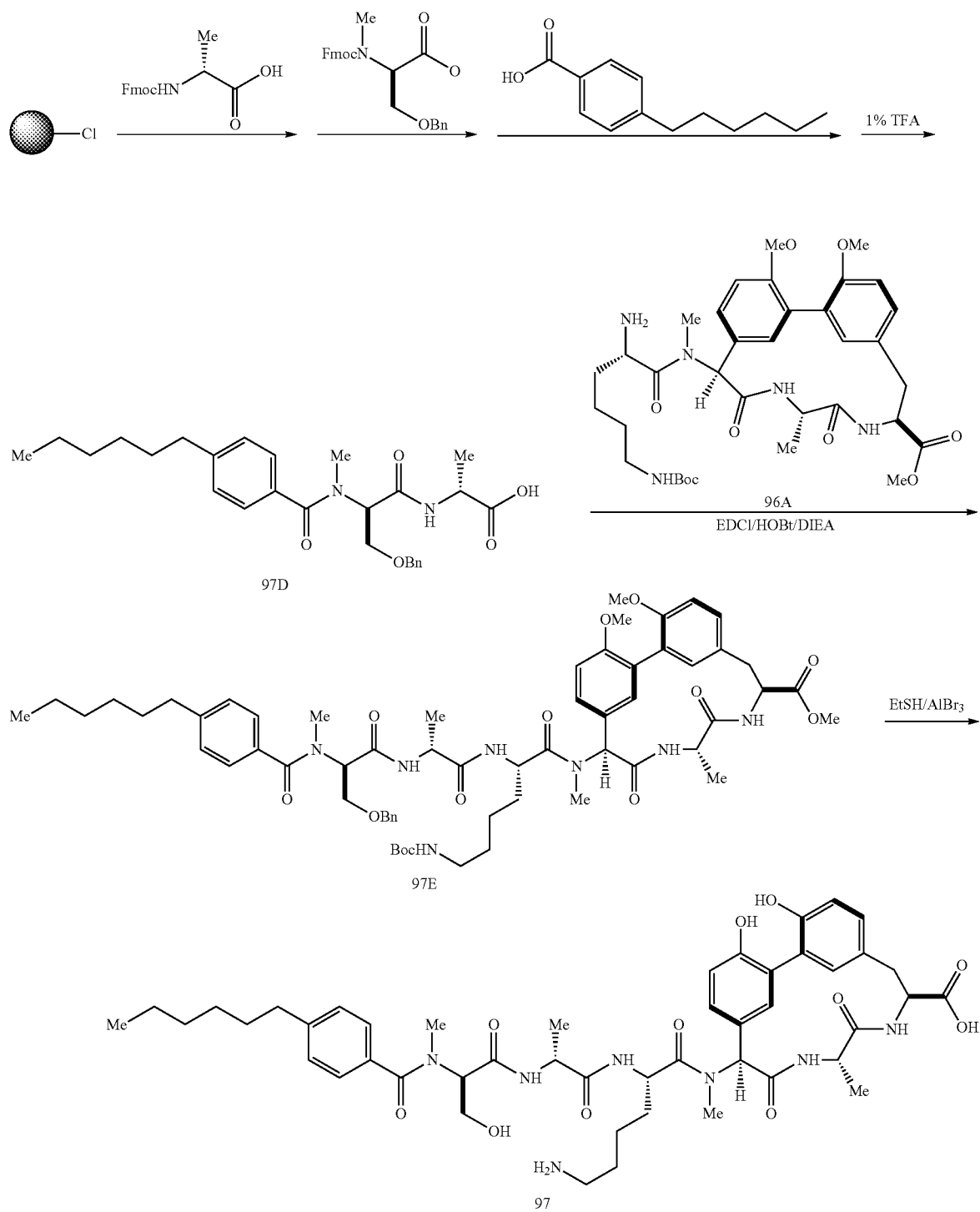

Compound 97 was prepared using General Methods 2-6 (Examples 18 and 19) as depicted in Scheme LIV to afford Compound 97. MS (ESI) m/z 902.5 (M+H)⁺.
Example 57: Synthesis of Compound 98 (Scheme LV)
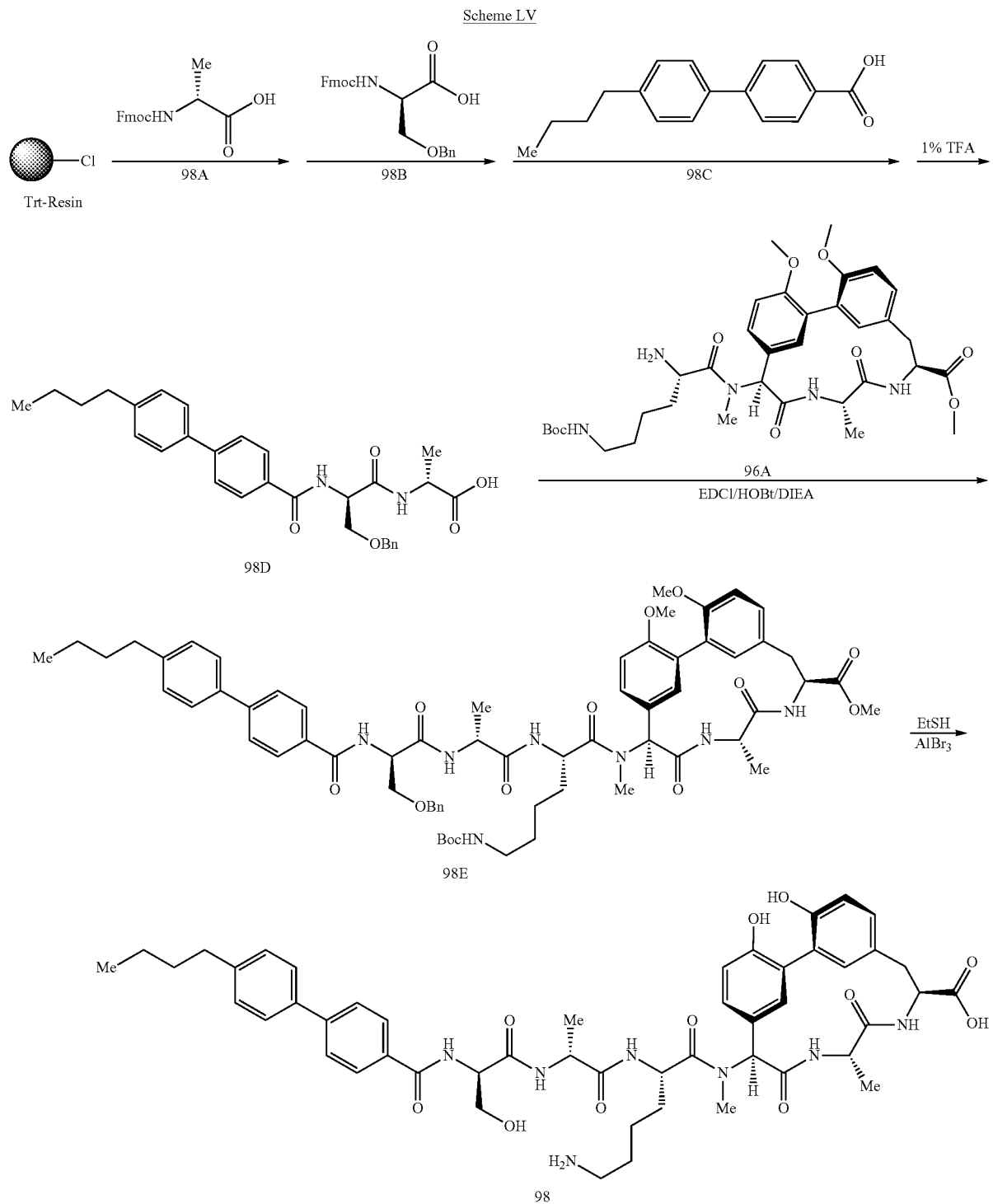

Compound 98 was prepared using General Methods 2-6 (Examples 18 and 19) as depicted in Scheme LIV to afford Compound 98. MS (ESI) m/z 936.4 (M+H)$^+$.

Biological Data

Protein Expression

Full length His-tagged *E. coli* SPase proteins were expressed in *E. coli* BL21(DE3) containing the plasmid pET23-lepB, P. A. Smith et al. *Chem Biol* 2010, 1223-1231. Briefly, saturated overnight cultures grown in 20 ml of Luria-Bertani medium supplemented with ampicillin were subcultures into 1.5 L of Luria-Bertani, and shaken at 37° C. until an optical density at 600 nm of 0.4-0.5 was achieved. Protein expression was induced with Isopropyl β-D-1-thio-galactopyranoside (ITPG) at a final concentration of 0.5 μM, and purified using nickel affinity chromatography. Full length His-tagged *S. aureus* SPase protein was expressed similarly from *E. coli* BL21(DE3) containing the plasmid pCDF1-SaSpsB or pCDF1-SaSpsB(P29S) and purified similarly to the *E. coli* protein with the following exceptions. SPase protein was solubilized using 300 mM NaCl, 20 mM Tris pH 8.06, 5 mM Imidazole, 10% glycerol, 1% Triton X-100, prior to purification in Ni-NTA Superflow resin and resin bound protein was washed in a similar buffer containing 1% Elugent in place of Triton X-100 prior to protein eluted in wash buffer supplemented with 300 mM imidazole. Protein purify was judged to exceed 95% by visual inspection of SDS-PAGE followed by Comassie staining. All protein concentrations were determined by BCA assay.

Example 58: In Vitro Antimicrobial Activity

In vitro antimicrobial activity of each compound was determined by measuring minimal inhibitor concentrations (MICs) using the broth micro-dilution technique as approved by the Clinical and Laboratory Standards Institute (CLSI). The microbiological panel examined contains a number of bacterial species including *E. coli* MG1655, *P. aeruginosa, S. aureus*, and *S. epidermidis*. In addition, the panel includes previously described pseudo-isogenic strains of these four species (P. A. Smith et al. *Chem Biol* 2010, 1223-1231), in which a specific proline residue in SPase (called LepB in Gram-negative organisms an SpsB in Gram-positive organisms) has been mutated to a different amino acid. The resulting strains have increased susceptibility to the arylomycin class of antibiotics. Analysis of the strains lacking this proline residue will increases the dynamic range of the assay, and comparison of the sensitivities of the isogenic pairs provides ongoing confirmation that the activity gained through derivatization is specific to the inhibition of SPase. Briefly, bacterial streaks were grown on Mueller Hinton Agar II (Difco™) with or without 5% lysed horse blood for a period of 24 hours at either 35° C. or 28° C. Bacterial colonies were suspended in cation adjusted Mueller Hinton broth and diluted to a final concentration of 1*10$^7$ colony forming units/ml. Two-fold serial dilutions of each compound were arrayed into 96-well plates (100 μl final volume per well) and 5 ul of the bacterial suspension will be added. Plates were incubated in humidified incubators at 35° C. or 28° C. for 22 hours after which MICs were determined as the lowest concentration of compound that completely prevented visible growth. MICs were periodically checked plating serial dilutions of MIC wells and quantitatively determining viable colonies.

TABLE 1

In Vitro Antibiotic Activity of example compounds

| | MIC (μg/ml) Compound: | | | | | | | | | |
|---|---|---|---|---|---|---|---|---|---|---|
| Strain | 1 | 11 | 12 | 13 | 14 | 15 | 19 | 20 | 22 | 23 | 24 |
| *E. coli* MIG1655 LepB(P84L) | 1 | 4 | 8 | 16 | 16 | 8 | 8 | 32 | 16 | 8 | 4 |
| *E. coli* MIG1655 | >64 | nd | nd | nd | nd | nd | nd | nd | nd | nd | nd |
| *P. aeruginosa* PA01 LepB(P84L) | 8 | >64 | >64 | >64 | >64 | >64 | >64 | >64 | >64 | >64 | 32 |
| *P. aeruginosa* PA01 | >64 | nd | nd | nd | nd | nd | nd | nd | nd | nd | nd |
| *S. aureus* NCTC-8325 SpsB(P295) | 4 | 32 | nd | nd | 8 | 8 | >64 | >64 | >64 | 8 | 32 |
| *S. aureus* ATCC 29213 | >64 | nd | nd | nd | | >64 | >64 | >64 | >64 | >64 | >64 |
| *S. epidermidis* RP62A | 0.3 | 2 | 2 | 64 | 2 | 2 | 8 | 4 | 2 | 2 | 2 |
| *S. epidermidis* RP62A SpsIB(S29P) | 8 | >64 | 64 | >64 | >64 | >64 | >64 | 32 | >64 | 16 | >64 |
| *S. epidermidis* RP62A SpsIB(S31P) | >64 | >64 | >64 | >64 | >64 | >64 | >64 | >64 | >64 | >64 | >64 |
| *S. epidermidis* ATCC 12228 | 2 | nd | nd | nd | nd | >64 | 32 | 32 | >64 | 8 | 32 |
| *S. pneumoniae* R800 | 8 | nd | nd | nd | nd | 16 | 32 | 32 | 16 | 8 | 8 |
| *S. pneumoniae* D39 | 4 | 64 | >64 | >64 | 8 | 8 | 16 | 16 | 16 | 8 | 4 |
| *S. agalactiae* COH-1 | >64 | nd | nd | nd | nd | >64 | >64 | >64 | >64 | >64 | >64 |
| *S. agalactiae* ATCC 13813 | 16 | nd | nd | nd | nd | >64 | 32 | 32 | 32 | 32 | 64 |
| *S. pyogenes* M15448 | 16 | nd | nd | nd | nd | 16 | 32 | 64 | 16 | 16 | 16 |
| *S. pyogenes* ATCC 19615 | 16 | nd | nd | nd | nd | 16 | 16 | 32 | 16 | 16 | 8 |
| *C. glutamicum* DSM 44475 | 8 | nd | nd | nd | nd | >64 | 16 | 64 | 8 | 8 | 64 |
| *R. equi* DSM 6939 | 16 | nd | nd | nd | nd | nd | nd | nd | nd | >64 | >64 |

| | MIC (μg/ml) Compound: | | | | | | | | |
|---|---|---|---|---|---|---|---|---|---|
| Strain | 25 | 26 | 27 | 28 | 29 | 30 | 31 | 32 | 33 | 34 |
| *E. coli* MIG1655 LepB(P84L) | 8 | 8 | 8 | 8 | 16 | 16 | 16 | 16 | 64 | >64 |
| *E. coli* MIG1655 | nd | nd | nd | nd | nd | nd | nd | nd | >64 | >64 |
| *P. aeruginosa* PA01 LepB(P84L) | >64 | >64 | >64 | >64 | >64 | >64 | >64 | >64 | >64 | >64 |
| *P. aeruginosa* PA01 | nd | nd | nd | nd | nd | nd | nd | nd | >64 | >64 |
| *S. aureus* NCTC-8325 SpsB(P295) | >64 | >64 | >64 | 32 | >64 | 8 | >64 | >64 | 64 | >64 |
| *S. aureus* ATCC 29213 | 64 | >64 | >64 | >64 | >64 | 32 | >64 | >64 | >64 | >64 |
| *S. epidermidis* RP62A | 4 | 4 | 8 | 4 | 8 | 4 | 8 | 4 | 64 | >64 |

TABLE 1-continued

In Vitro Antibiotic Activity of example compounds

| | | | | | | | | | | |
|---|---|---|---|---|---|---|---|---|---|---|
| S. epidermidis RP62A SpsIB(S29P) | 64 | >64 | >64 | >64 | >64 | 16 | >64 | >64 | 64 | >64 |
| S. epidermidis RP62A SpsIB(S31P) | >64 | >64 | >64 | >64 | >64 | >64 | >64 | >64 | 64 | >64 |
| S. epidermidis ATCC 12228 | 16 | 32 | 32 | 16 | 32 | 4 | 32 | 16 | >64 | >64 |
| S. pneumoniae R800 | 8 | 16 | 32 | 16 | 32 | 16 | 8 | 16 | 32 | >64 |
| S. pneumoniae D39 | 8 | 8 | 16 | 8 | 16 | 16 | 4 | 4 | 32 | >64 |
| S. agalactiae COH-1 | >64 | >64 | 32 | 32 | 64 | >64 | >64 | >64 | 64 | >64 |
| S. agalactiae ATCC 13813 | 8 | 16 | 32 | 16 | 32 | 32 | 8 | 8 | >64 | >64 |
| S. pyogenes M15448 | 16 | >64 | 32 | 32 | 64 | 16 | 16 | 32 | 16 | >64 |
| S. pyogenes ATCC 19615 | 16 | 8 | 32 | 16 | 16 | 16 | 8 | 16 | 16 | >64 |
| C. glutamicum DSM 44475 | 64 | 32 | 32 | 32 | 32 | 8 | >64 | 16 | 64 | >64 |
| R. equi DSM 6939 | >64 | 64 | >64 | >64 | >64 | >64 | >64 | 64 | 64 | >64 |

*nd = not determined

TABLE 2

| Compound | E. coli ATCC 25922 | E. col ATCC 25922 LepB(P84L) | S. aurues NCTC-8325 | S. aureus NCTC-8325 SpsB(P295) | S. epidermidis RP62A | S. pneumoniae D39 |
|---|---|---|---|---|---|---|
| 39 | a | c | d | a | b | b |
| 41 | a | a | d | a | c | a |
| 52 | a | a | d | b | b | b |
| 53 | a | a | d | a | b | b |
| 54 | a | c | d | b | c | c |
| 55 | a | b | d | a | c | c |
| 56 | a | a | d | a | c | b |
| 57 | a | b | d | a | c | b |
| 59 | a | b | a | a | c | b |
| 60 | a | c | a | a | c | c |
| 61 | a | b | a | a | a | c |
| 62 | a | b | a | a | a | b |
| 63 | a | a | a | a | b | b |
| 64 | a | b | a | a | c | c |
| 65 | a | b | a | a | c | b |
| 66 | a | b | a | a | b | b |
| 67 | a | b | a | a | b | b |
| 68 | a | b | a | a | b | b |
| 69 | a | c | a | a | b | b |
| 70 | a | c | a | a | c | b |
| 71 | a | a | a | a | a | b |
| 72 | a | c | a | b | c | b |
| 74 | a | a | a | a | a | b |
| 75 | a | c | a | a | c | c |
| 77 | a | c | a | b | a | b |
| 78 | a | a | a | a | a | b |
| 80 | a | c | a | a | c | a |
| 82 | a | a | a | a | a | b |
| 83 | a | c | a | b | c | c |
| 84 | a | a | a | a | b | c |
| 85 | a | b | a | a | c | a |
| 86 | a | c | a | c | b | b |
| 87 | a | a | a | a | c | a |
| 90 | a | a | a | a | c | c |
| 91 | a | a | a | a | c | c |
| 94 | a | a | a | a | c | b |
| 95 | d | a | a | b | b | b |
| 96 | a | b | a | a | b | a |
| 97 | a | b | a | d | b | a |
| 98 | a | c | a | d | b | a | a: MIC >64 µg/ml
b: MIC 16-64 µg/ml
c: MIC ≤8 µg/ml
d: MIC not determined

Example 59: $K_d$ Determination

Steady state binding constants ($K_d$s) of compounds were determined by measuring an increase in fluorescence (λex=280 nm, λem=405 nm) that occurs upon binding to E. coli or S. aureus SPase protein. Two-fold serial dilutions of compounds were prepared in 100% DMSO, and compounds were diluted into binding buffer consisting of 100 mM NaCl, 20 mM Tris-HCl pH 7.4, 1 mM EDTA, 1% n-octyl-3-glucopyranoside (Anatrace), and 10% glycerol, with the final DMSO concentration equal to 1%. 70 µl of the resulting solutions containing various concentrations of compound in binding buffer were aliquoted into triplicate wells of a black polystyrene 384-well plate. 5 µl of blank solution or E. coli or *S. aureus* protein at concentrations of 750 or 3750 nM respectively, were added to each set of wells for a given inhibitor concentration. Plates were incubated for 14 hours and fluorescence read on an EnVision Multilable plate reader (Perkin Elmer™). Differences in fluorescence values between wells with and without protein were determined and background corrected for protein auto fluorescence. The corrected fluorescence difference data was fit to the quadratic equilibrium binding curve using the non-linear regression analysis software Solver (Frontline Systems®) run in Excel 2010, (Microsoft®), using experimentally determined quantum efficiency constants to convert fluorescence into nanomoles of protein/compound complex.

TABLE 3

In Vitro Equilibrium $K_d$ Values of Compounds against *E. coli* and *S. aureus* SPase

| Compound | $K_d$ (µM) | |
|---|---|---|
| | *E. coli* SPase | *S. aureus* SPase |
| 1 | 0.075 | 0.75 |
| 11 | 0.10 | 2.1 |
| 12 | 0.24 | 0.60 |
| 13 | 2 | >100 |
| 14 | 2.8 | 0.6 |
| 15 | 5.8 | 2.0 |
| 19 | 2.8 | 18 |
| 20 | 12 | 7.8 |
| 22 | 1.0 | 19 |
| 23 | 3.0 | 8.9 |
| 24 | 1.1 | 2.9 |

TABLE 4

| Compound 12 | % Comp calc | % Comp obs | Compound 1 | % Comp calc | % Comp obs |
|---|---|---|---|---|---|
| *E. coli* SPase | | | | | |
| 0.E+00 | 0 | 1 | 0.E+00 | 0 | −1 |
| 4.E+00 | 2 | 2 | 4.E+00 | | |
| 8.E+00 | 3 | 5 | 8.E+00 | 9 | 10 |
| 2.E+01 | 6 | 10 | 2.E+01 | 17 | 16 |
| 3.E+01 | 11 | 16 | 3.E+01 | 31 | 32 |
| 6.E+01 | 20 | 24 | 6.E+01 | 51 | 53 |
| 1.E+02 | 34 | 33 | 1.E+02 | 71 | 69 |
| 3.E+02 | 51 | 48 | 3.E+02 | 85 | 81 |
| 5.E+02 | 68 | 64 | 5.E+02 | 92 | 92 |
| 1.E+03 | 81 | 89 | 1.E+03 | 96 | 98 |
| 2.E+03 | 90 | 84 | 2.E+03 | 98 | 102 |
| 4.E+03 | 95 | 90 | 4.E+03 | 99 | 95 |
| *S. aurues* SPase | | | | | |
| 0 | 0 | −1 | | | |
| 3.E+01 | 3 | 3 | 15.625 | 1.9 | 1.7 |
| 6.E+01 | 7 | 6 | 31.25 | 3.8 | 4.9 |
| 1.E+02 | 13 | 11 | 62.5 | 7.4 | 6.4 |
| 3.E+02 | 24 | 26 | 125 | 14.0 | 13.7 |
| 5.E+02 | 41 | 44 | 250 | 25.4 | 25.6 |
| 1.E+03 | 61 | 62 | 500 | 42.0 | 38.6 |
| 2.E+03 | 78 | 72 | 1000 | 61.1 | 59.1 |
| 4.E+03 | 88 | 87 | 2000 | 77.1 | 86.1 |
| 8.E+03 | 94 | 102 | 4000 | 87.6 | 87.3 |
| 2.E+04 | 97 | 96 | 8000 | 93.6 | 87.8 |
| 3.E+04 | 99 | 94 | | | |

Example 60: Enzymatic Substrate Cleavage Assay for $IC_{50}$ Determination

Figure 1D:
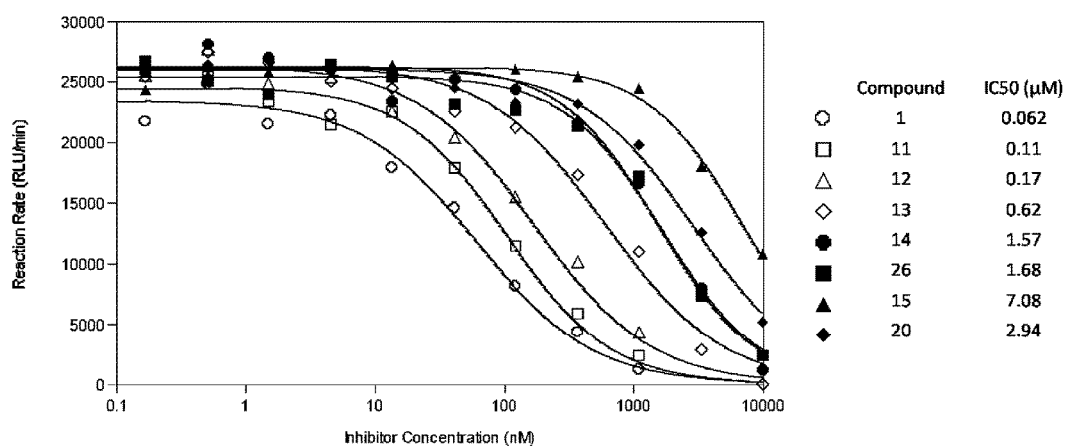
FIG. 1D shows data for *E. coli* LepB cleavage assay with representative example compounds.

In addition to the equilibrium binding assays, compound activity is also characterized by measuring inhibition of *E. coli* and *S. aureus* substrate cleavage reactions using fluorogenic peptides developed at RQx Pharmaceuticals. Briefly, two fluorogenic peptide substrates (decanoyl-LSSPAY$^{NO2}$A⇓ADK$^{abz}$PD (SEQ ID NO: 1) and decanyol-LTPTAY$^{NO2}$A⇓ASKK$^{abz}$DD (SEQ ID NO: 2)) have been synthesized, where abz is the fluorescence donor 2-aminobenzamide, $Y_{NO2}$ is the fluorescence acceptor 3-nitrotyrosine, and the cleavage site is indicated with an arrow. These substrates are processed with a second order rate constant ($K_{cat}/K_M$) of $10^5$ $M^{-1}s^{-1}$ for *E. coli* and *S. aureus* SPase enzymes, and cleavage results in a greater than 10-fold increase in fluorescence signal (excitation at 314 nm, emission at 416 nm) as measured using a SpectraMax M2 fluorescence microplate reader. Two-folder serial dilutions of compound are prepared in cleavage reaction buffer consisting of: 50 mM Tris-HCl pH 8.0, 100 mM NaCl, 10% glycerol, 1 mM EDTA, detergent (1% NP-40 or 0.1% Elugent™ for *E. coli* LepB or *S. aureus* SpsB respectively) and either 2.5 nM of *E. coli* SPase enzyme or 10 nM of *S. aureus* SPase enzyme. 40 µl aliquots of the compound dilution series in the protein/buffer solution is transferred to black 384-well polypropylene plates, and 10 µl of fluorogenic peptide at a concentration of 100 µM is added to initiate the reaction. The increase in fluorescence, corresponding to substrate cleavage, is monitored continuously at room temperature for 30 minutes and initial reaction rates are calculated based in the linear increase in fluorescence from the initial 30 minutes of the reaction. Reaction rates are plotted as a function of compound concentration, and $IC_{50}$ values are determined nonlinear regression analysis (SoftMax® Pro v5.4) of the sigmoidal dose-response curve. Example data for *E. coli* LepB cleavage assay with representative example compounds is shown in FIG. 1D. Additional IC50 potency data for example compounds against *E. coli* LepB and *S. aureus* SpsB proteins are tabulated below (Table 5).

TABLE 5

| Compound | *E. coli* SPase | *S. aureus* SPase |
|---|---|---|
| 39 | c | c |
| 41 | c | c |
| 52 | b | c |
| 53 | b | c |
| 54 | c | b |
| 55 | b | b |
| 56 | b | a |
| 57 | b | b |
| 59 | c | b |
| 60 | c | b |
| 61 | b | a |
| 62 | b | a |
| 63 | a | a |
| 64 | b | a |
| 65 | c | b |
| 66 | b | a |
| 67 | a | a |
| 68 | b | a |
| 69 | b | a |
| 70 | c | a |
| 71 | a | a |
| 72 | c | c |
| 74 | b | a |
| 75 | c | a |
| 77 | a | b |
| 78 | c | a |
| 80 | c | c |
| 82 | b | a |
| 83 | b | c |
| 84 | c | c |
| 85 | c | b |
| 86 | c | c |

TABLE 5-continued

| Compound | E. coli SPase | S. aureus SPase |
| --- | --- | --- |
| 87 | c | c |
| 90 | b | b |
| 91 | c | c |
| 94 | c | c |
| 95 | b | b |
| 96 | d | d |
| 97 | d | d |
| 98 | d | d | a: IC50 > 10 μM
b: IC50 1-10 μM
c: IC50 < 1 μM
d: IC50 not determined

Example 61: Clinical Trial of the Safety and Efficacy of Compounds of Formula (I)-(VI) in Patients with C. Difficile-Associated Diarrhea Purpose:

This study aims to determine the safety and efficacy of compounds presented herein for the treatment of symptoms of C. difficile-associated diarrhea and lowering the risk of repeat episodes of diarrhea. The compounds are evaluated in comparison to current standard antibiotic treatment, so all patients will receive active medication. All study-related care is provided including doctor visits, physical exams, laboratory tests and study medication. Total length of participation is approximately 10 weeks.

Patients:

Eligible subjects will be men and women 18 years and older.

Criteria:
Inclusion Criteria:
Be at least 18 years old;
Have active mild to moderate C. difficile-Associated Diarrhea (CDAD);
Be able to tolerate oral medication;
Not be pregnant or breast-feeding; and
Sign and date an informed consent form.

Study Design:

This a randomized, double-blind, active control study of the efficacy, safety, and tolerability of a compound of Formula (I)-(VI) in patients with C. difficile-associated diarrhea.

Example 62: Clinical Trial Comparing a Compound of Formula (I)-(VI) with Vancomycin for the Treatment of MRSA Osteomyleitis purpose: this study aims to determine the efficacy of compounds presented herein as compared to vancomycin for the treatment of methicillin-resistant Staphylococcus aureus (MRSA) osteomyelitis.

patients: eligible subjects will be men and women 18 years and older.

Criteria:
Inclusion Criteria:
Culture-proven MRSA, obtained in operating room or sterile biopsy procedure from bone site. The infection and sampling site is either within the bone or a deep soft-tissue site that is contiguous with bone; OR radiographic abnormality consistent with osteomyelitis in conjunction with a positive blood culture for MRSA;
Surgical debridement of infection site, as needed;
Subject is capable of providing written informed consent; and
Subject capable of receiving outpatient parenteral therapy for 12 weeks.

Exclusion Criteria:
Hypersensitivity to a compound of Formula (I)-(VI) or vancomycin;
S. aureus resistant to a compound of Formula (I)-(VI) or vancomycin;
Osteomyelitis that develops directly from a chronic, open wound;
Polymicrobial culture (the only exception is if coagulase-negative staphylococcus is present in the culture and the clinical assessment is that it is a contaminant);
Subject has a positive pregnancy test at study enrollment;
Baseline renal or hepatic insufficiency that would preclude administration of study drugs;
Active injection drug use without safe conditions to administer intravenous antibiotics for 3 months; and
Anticipated use of antibiotics for greater than 14 days for an infection other than osteomyelitis.

Study Design:

This a randomized, open-label, active control, efficacy trial comparing vancomycin with a compound of Formula (I)-(VI) for the treatment of MRSA Osteomyelitis.

Example 63: Clinical Trial Evaluating a Compound of Formula (I)-(VI) in Selected Serious Infections Caused by Vancomycin-Resistant Enterococcus (VRE)

Purpose:

This study aims to determine the safety and efficacy of a compound of Formula (I)-(VI) in the treatment of selected serious infections caused by VRE.

Patients:

Eligible subjects will be men and women 18 years and older.

Criteria:
Inclusion Criteria:
Isolation of one of the following multi-antibiotic resistant bacteria: vancomycin-resistant Enterococcus faecium, vancomycin-resistant Enterococcus faecalis alone or as part of a polymicrobial infection; and
Have a confirmed diagnosis of a serious infection (eg, bacteremia [unless due to an excluded infection], complicated intra-abdominal infection, complicated skin and skin structure infection, or pneumonia) requiring administration of intravenous (IV) antibiotic therapy.

Exclusion Criteria:
Subjects with any concomitant condition or taking any concomitant medication that, in the opinion of the investigator, could preclude an evaluation of a response or make it unlikely that the contemplated course of therapy or follow-up assessment will be completed or that will substantially increase the risk associated with the subject's participation in this study.
Anticipated length of antibiotic therapy less than 7 days Study Design:

This a randomized, double-blind, safety and efficacy study of a compound of Formula (I)-(VI) in the treatment of selected serious infections caused by VRE.

Pharmaceutical Compositions
I. Parenteral Composition

To prepare a parenteral pharmaceutical composition suitable for administration by injection, 100 mg of a compound of Formulas (I)-(VI) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
|---|---|
| Compound of Formulas (I)-(VI) | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Oral Composition

To prepare a pharmaceutical composition for oral delivery, 100 mg of a compound of Formulas (I)-(VI) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
|---|---|
| compound of Formulas (I)-(VI) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
|---|---|
| compound of Formulas (I)-(VI) | 200 |
| lactose, spray-dried | 148 |
| magnesium stearate | 2 |

In yet another embodiment, the following ingredients are mixed to form a solution/suspension for oral administration:

| Ingredient | Amount |
|---|---|
| Compound of Formulas (I)-(VI) | 1 g |
| Anhydrous Sodium Carbonate | 0.1 g |
| Ethanol (200 proof), USP | 10 mL |
| Purified Water, USP | 90 mL |
| Aspartame | 0.003 g |

Topical Gel Composition

To prepare a pharmaceutical topical gel composition, 100 mg of a compound of Formulas (I)-(VI) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A compound of Formula (I):

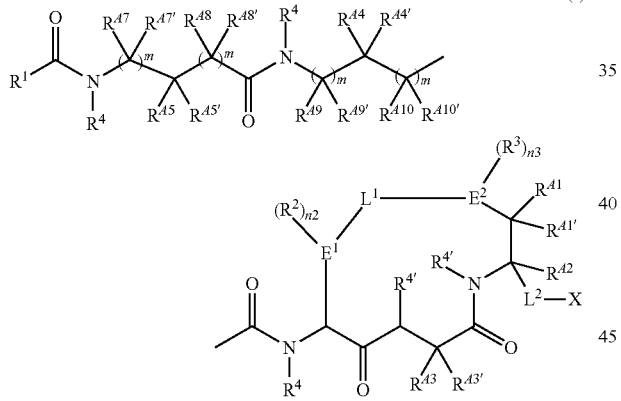

Formula (I)

wherein:

$E^1$ and $E^2$ are each independently $(C_1$-$C_6)$alkyl, $(C_2$-$C_7)$alkenyl, $(C_2$-$C_7)$alkynyl, $(C_3$-$C_7)$cycloalkyl, heterocyclyl, heteroaryl, or aryl;

$L^1$ is a bond, —O—, —S—, —NR$^4$—, —C(O)—, —CH$_2$O—, —OCH$_2$—, —CH$_2$S—, —SCH$_2$—, —CH$_2$NR$^4$—, —NR$^4$CH$_2$—, —NR$^4$C(O)—, —C(O) NR$^4$—, —NR$^4$S(O)$_2$—, —S(O)$_2$NR$^4$—, —NR$^4$C(O) NR$^4$—, —NR$^4$C(O)O—, —OC(O)NR$^4$—, or $(C_1$-$C_4)$ alkylene optionally substituted with OH, CN, NO$_2$, halogen, or $(C_1$-$C_6)$alkyl;

$L^2$ is a bond, or optionally substituted $(C_1$-$C_6)$alkylene;

X is C(O)R$^{20}$ or S(O)$_2$R$^{20}$; R$^{20}$ is optionally substituted alkyl, optionally substituted alkoxy, or NR$^{20a}$R$^{20b}$, where R$^{20a}$ is H or SO$_2$(C$_1$-C$_6$)alkyl; and R$^{20b}$ is H; or X is a group of formula

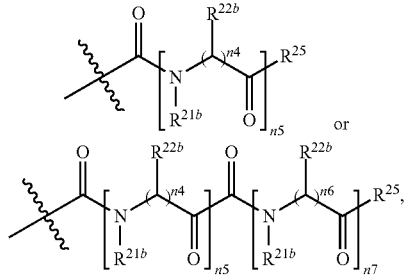

wherein n4, n5, and n6 are each independently 1, 2 or 3; n7 is 0, 1 or 2;

R$^{21b}$ and R$^{22b}$ are independently at each occurrence hydrogen, hydroxy, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl is optionally substituted with 1 to 3 J; R$^{25}$ is OH, OR$^C$,

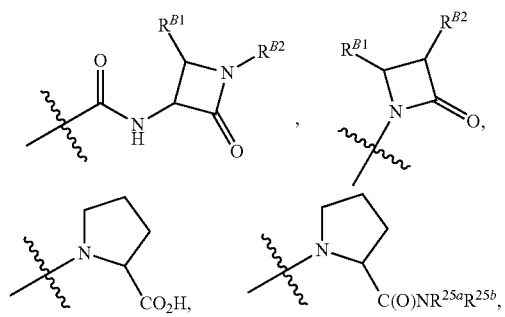

or NR$^{25a}$R$^{25b}$ where R$^{25a}$ and R$^{25b}$ are each independently H, SO$_2$(C$_1$-C$_6$)alkyl, or optionally substituted alkyl; R$^{B1}$ and R$^{B2}$ are each independently H, (C$_1$-C$_6$) alkyl, (C$_3$-C$_6$) cycloalkyl, OR$^C$, C(=O)N(R$^C$)$_2$, OC(=O)N(R$^C$)$_2$, C(=O) OR$^C$, OC(=O)OR$^C$, nitro, trifluoromethyl, trifluoromethoxy, (C$_1$-C$_6$)alkoxy, (C$_1$-C$_6$)thioalkoxy, N(R$^C$)$_2$, 5-7 membered heterocyclyl, 5-7 membered heteroaryl, or ($C_6$-$C_{10}$) aryl; $R^C$ is independently at each occurrence H or ($C_1$-$C_6$) alkyl, and a wavy line indicates a point of attachment of X to a carbon of formula (I) bearing X; or X is

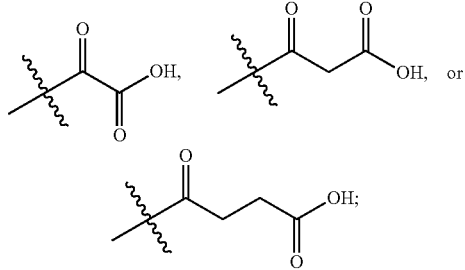

$R^1$ comprises a group of formula (IID), (IIE), or (IIF):

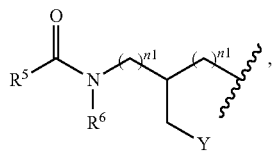
(IID)

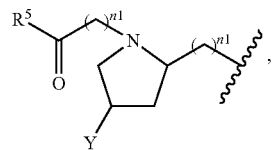
(IIE)

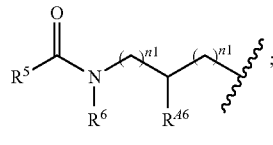
(IIF)

wherein each n1 is independently at each occurrence 0, 1, or 2; Y is $(CH_2)_{0-2}H$, $(CH_2)_{0-2}OH$, or $(CH_2)_{0-2}OC(=O)(C_1$-$C_6)$alkyl; $R^{46}$ is hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, ($C_1$-$C_6$)alkoxy, ($C_1$-$C_6$)alkyl, ($C_3$-$C_7$)cycloalkyl, ($C_1$-$C_6$)-mono- or di-alkylamino, ($C_1$-$C_6$)alkoxycarbonyl, ($C_1$-$C_6$)alkylhydroxycarbonyl, ($C_1$-$C_6$)alkylaminocarbonyl, ($C_1$-$C_6$)alkylsulfonylamino, and ($C_6$-$C_{10}$)-arylsulfonylamino; and a wavy line indicates a point of attachment of $R^1$ to an atom of formula (I) bearing $R^1$;

$R^5$ is aryl, heteroaryl, or a linear or branched alkyl chain of about 1-22 carbon atoms, wherein $R^5$ is bonded to the carbonyl carbon to which it is attached directly or by an O or $NR^4$, to provide an amide, carbamate, or urea linkage, respectively; optionally comprising within the chain or at a chain terminus optionally substituted aryl, optionally substituted heteroaryl, or optionally substituted

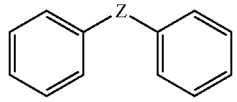

wherein Z is a bond, O, S, NH, $CH_2$ or C≡C;

$R^2$ and $R^3$ are each independently nitro, halo, cyano, hydroxy, glycosyloxy, amino, ($C_1$-$C_4$)alkoxy, ($C_1$-$C_4$) acyloxy, ($C_1$-$C_4$)alkyl, or a group cleavable under physiological conditions to provide a compound of formula (I) wherein $R^2$ or $R^3$ respectively is hydroxy, wherein any carbon atom is optionally substituted with J; or wherein two $R^2$ groups taken together, and/or two $R^3$ groups taken together, optionally comprise fused cycloalkyl, aryl, heterocyclyl, or heteroaryl ring or rings, any of which is optionally substituted with 1 to 3 J;

n2 and n3 are independently 0, 1, 2, 3 or 4;

each m is independently 0, 1, or 2;

$R^4$, $R^{4'}$, $R^{4''}$ and $R^6$ are each independently at every occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

$R^{41}$, $R^{41'}$, $R^{42}$, $R^{43}$, $R^{43'}$, $R^{44}$, $R^{44'}$, $R^{45}$, $R^{45'}$, $R^{47}$, $R^{47'}$, $R^{48}$, $R^{48'}$, $R^{49}$, $R^{49'}$, $R^{410}$, and $R^{410'}$ are independently at each occurrence hydrogen, ($C_1$-$C_6$)alkyl, ($C_3$-$C_7$) cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl is optionally substituted with 1 to 3 J;

J is halogen, R', OR', CN, $CF_3$, $OCF_3$, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH-C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R)SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;

wherein p is 4, each R' is independently at each occurrence hydrogen, ($C_1$-$C_6$)-alkyl, ($C_2$-$C_7$)-alkenyl, ($C_2$-$C_7$)-alkynyl, ($C_3$-$C_{10}$)-cycloalkyl, ($C_3$-$C_{10}$)-cycloalkenyl, aryl, or heteroaryl wherein any alkyl, alkenyl, alkynyl, cycloalkyl, cycloalkenyl, aryl or heteroaryl is optionally substituted with F, Cl, Br, I, —CN, —$NO_2$, —OH, —$CF_3$, —$OCF_3$, —$OCH_3$, —$NH_2$, —$N((C_1$-$C_4)$alkyl$)_2$-, —NH($C_1$-$C_4$)alkyl, $C_3$-$C_8$cycloalkyl, or $C_1$-$C_6$heteroalkyl;

or, when two R' are bound to a nitrogen atom or to two adjacent nitrogen atoms, the two R' groups together with the nitrogen atom or atoms to which they are bound form a 3- to 8-membered monocyclic heterocyclic ring, or an 8- to 20-membered, bicyclic or tricyclic, heterocyclic ring system, wherein any ring or ring system further contains 1-3 additional heteroatoms selected from the group consisting of N, NR', O, S, S(O) and S(O)$_2$, wherein each ring is substituted with 0-3 substituents selected independently from F, Cl, Br, I, —CN, —NO$_2$, —OH, —CF$_3$, —OCF$_3$, —OCH$_3$, —NH$_2$, —N((C$_1$-C$_4$)alkyl)$_2$-, —NH(C$_1$-C$_4$)alkyl, C$_1$-C$_6$alkyl, C$_3$-C$_8$cycloalkyl, or C$_1$-C$_6$heteroalkyl; wherein, in any bicyclic or tricyclic ring system, each ring is linearly fused, bridged, or spirocyclic, wherein each ring is either aromatic or nonaromatic, wherein each ring is optionally fused to an aryl, heteroaryl, (C$_3$-C$_{10}$)cycloalkyl, or mono- or bicyclic 3-10 membered heterocyclyl; or a pharmaceutically acceptable salt, solvate, or prodrug thereof.

2. The compound of claim 1 wherein the compound is of Formula (TB):

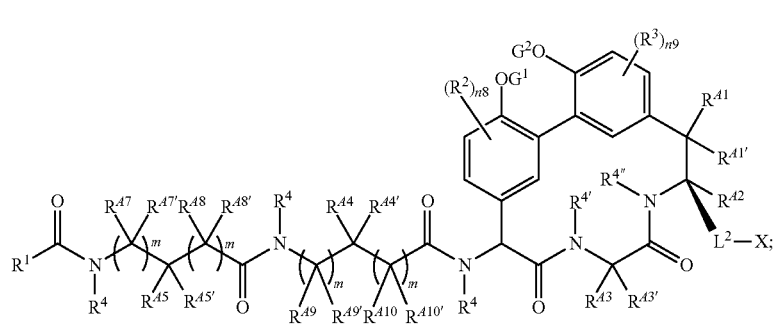

Formula (IB)

wherein n8 and n9 are each independently 0, 1, 2, or 3; G$^1$ and G$^2$ are each independently a hydrogen or a glycosyl residue, or a group cleavable under physiological conditions to provide a compound of formula (IB) wherein G$^1$ or G$^2$ respectively is hydrogen; or a pharmaceutically acceptable salt, solvate or prodrug thereof.

3. The compound of claim 1 wherein R$^1$ is a group of formula (IICS) or (IIDS):

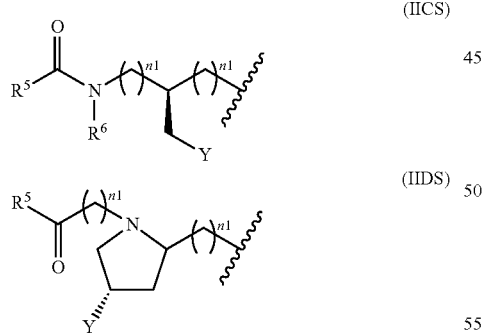

wherein a wavy line indicates a point of attachment of R$^1$ to an atom bonded to R$^1$ in formula (I);
or a salt thereof.

4. The compound of claim 1 wherein R$^5$ is (C$_1$-C$_{22}$) linear or branched alkyl.

5. The compound of claim 1 wherein R$^5$ is (C$_1$-C$_{22}$) linear or branched alkyl, substituted within the alkyl chain or alkyl chain terminus with one or more optionally substituted aryl, optionally substituted heteroaryl, or optionally substituted

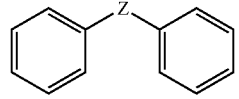

wherein Z is a bond, O, S, NH, CH$_2$ or C≡C.

6. The compound of claim 1 wherein R$^5$ is aryl.

7. The compound of claim 1 wherein R$^5$ is heteroaryl.

8. The compound of claim 1 wherein R$^5$ is any of the following groups

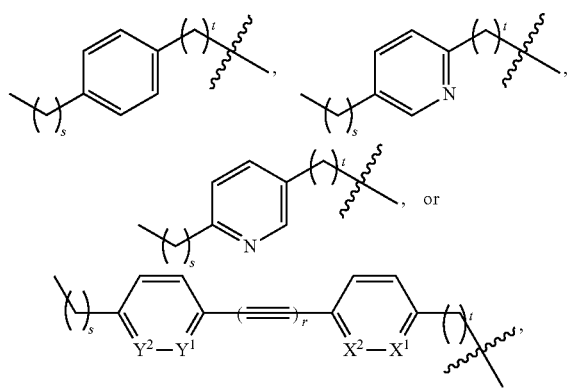

wherein r is 0-1; s is 0-14, t is 0-14, provided that s+t≤22; and X$^1$, X$^2$, Y$^1$ and Y$^2$ are each independently CH or N, provided that no more than one of X$^1$ and X$^2$, and no more than one of Y$^1$ and Y$^2$, is N, wherein a wavy line indicates a point of attachment of R$^5$ to an atom bonded to R$^5$ in formula (IID), (IIE), or (IIF).

9. The compound of claim 1 wherein R$^5$ is methyl, ethyl, (C$_3$-C$_{22}$)-n-alkyl, (C$_3$-C$_{22}$)-isoalkyl, (C$_4$-C$_{22}$)-anteisoalkyl, naphthyl, (C$_2$-C$_{10}$)alkylnaphthyl, naphthylmethyl, (C$_2$-C$_{10}$) alkylnaphthylmethyl, biphenyl, (C$_2$-C$_{10}$)alkylbiphenyl, biphenylmethyl, (C$_2$-C$_{10}$)alkylbiphenylmethyl, (C$_4$-C$_{12}$) alkylphenyl, (C$_4$-C$_{12}$)alkylbenzyl, (C$_2$-C$_{10}$)alkyl-1,2-diphenylethynyl, or (Z)- or (E)-(C$_2$-C$_{10}$)alkyl-1,2-diphenylethenyl.

10. The compound of claim 1 wherein E$^1$ and E$^2$ is each independently phenyl, pyridyl, pyrazinyl, pyrimidyl, or pyridazinyl.

11. The compound of claim 1 wherein R$^2$ and R$^3$ are each independently nitro, halo, cyano, hydroxy, glycosyloxy, amino, (C$_1$-C$_4$)alkoxy, or (C$_1$-C$_4$)alkyl.

12. The compound of claim 1 wherein n2 is 1 and n3 is 1.

13. The compound of claim 1 wherein $R^2$ and $R^3$ are hydroxy.

14. The compound of claim 1 wherein any of $R^{A1}$, $R^{A2}$ and $R^{A4}$ are hydrogen, any of $R^{A3}$ and $R^{A5}$ are methyl, or any combination thereof.

15. The compound of claim 1 wherein $R^{A3}$ is hydrogen, methyl, ethyl, n-propyl, isopropyl, n-butyl, isobutyl, 3-hydroxypropyl, 4-hydroxybutyl, or 2,2,2-trifluoroethyl.

16. The compound of claim 1 wherein all of $R^4$ and $R^6$ are independently hydrogen or methyl.

17. A compound selected from

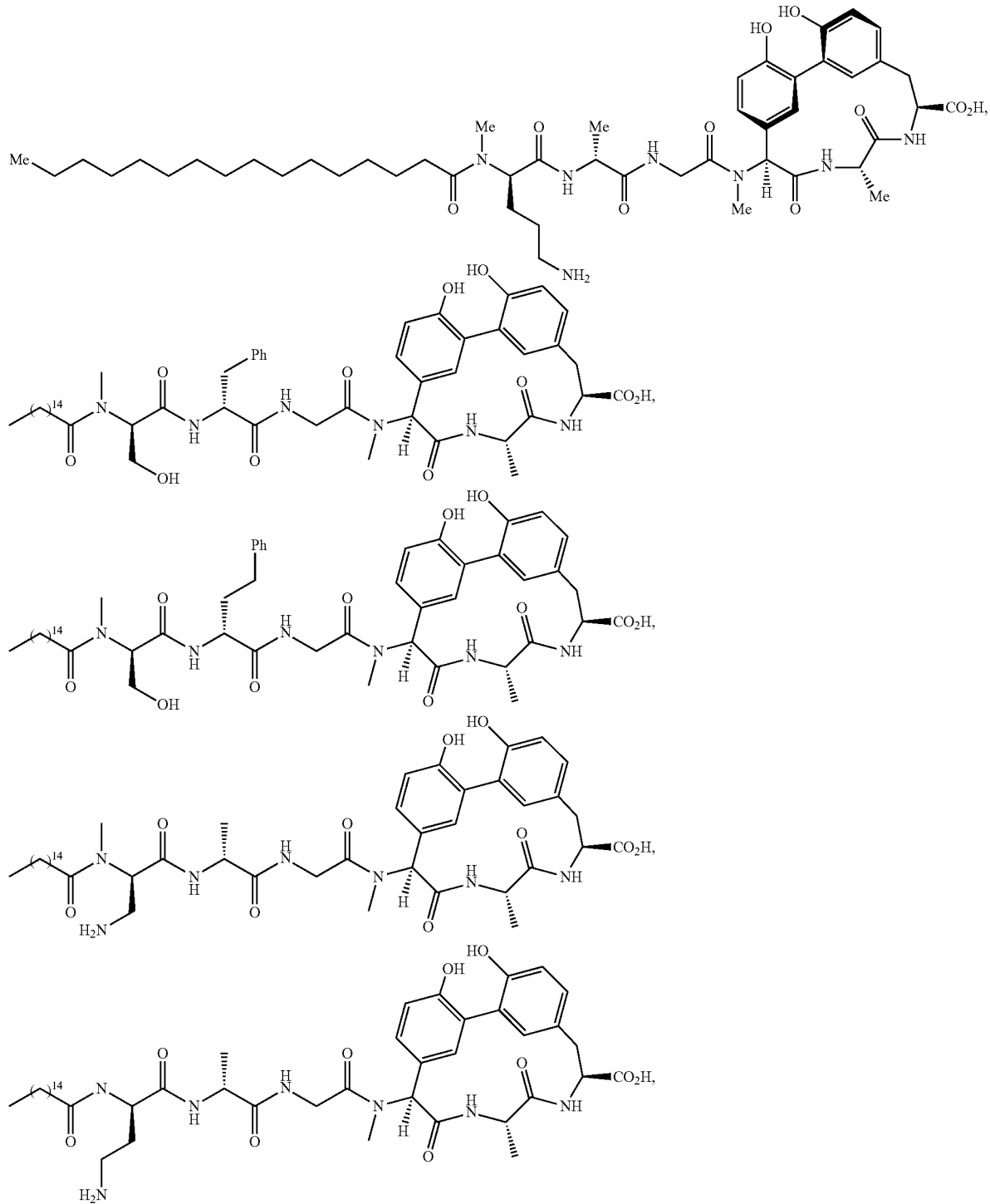

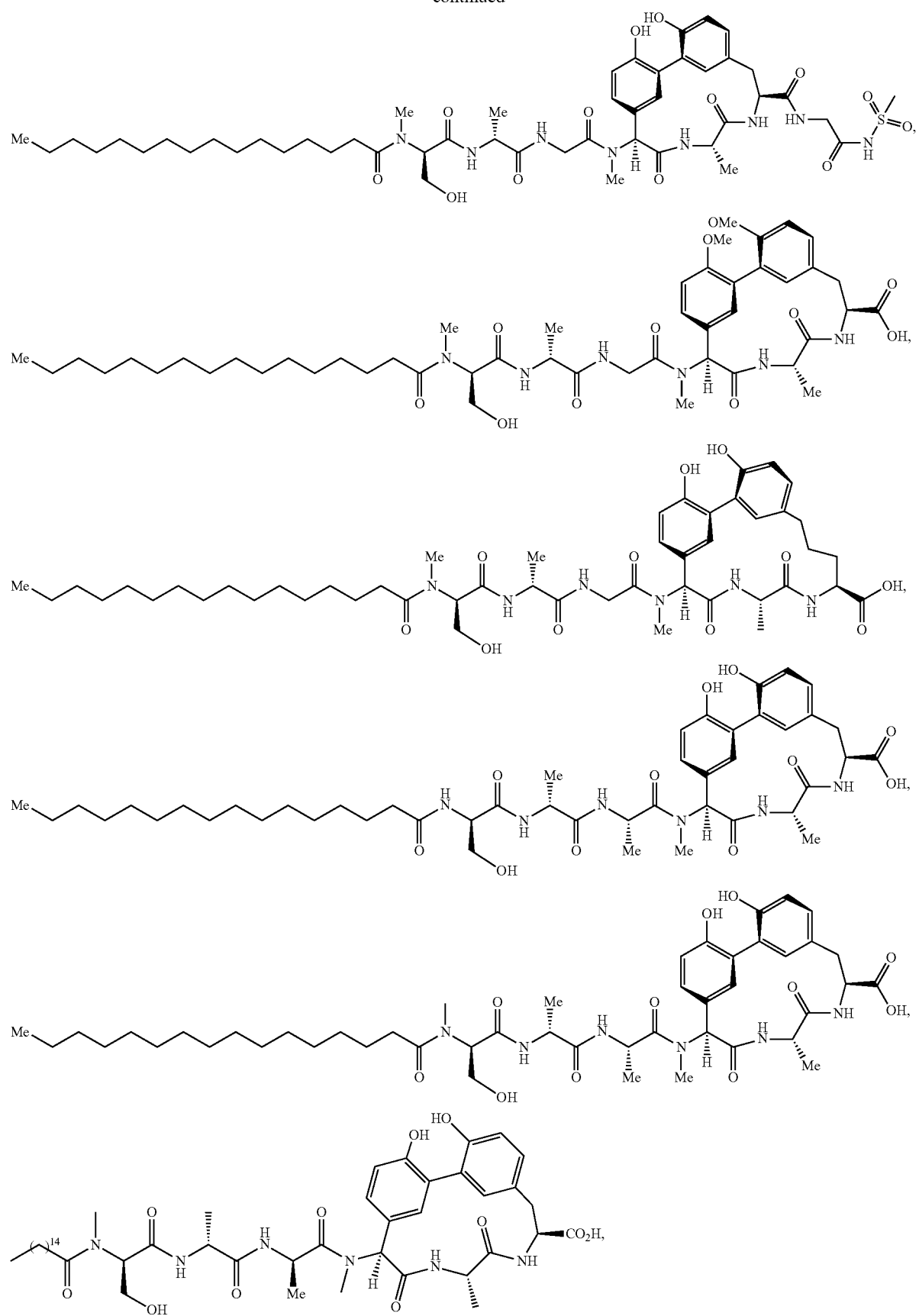

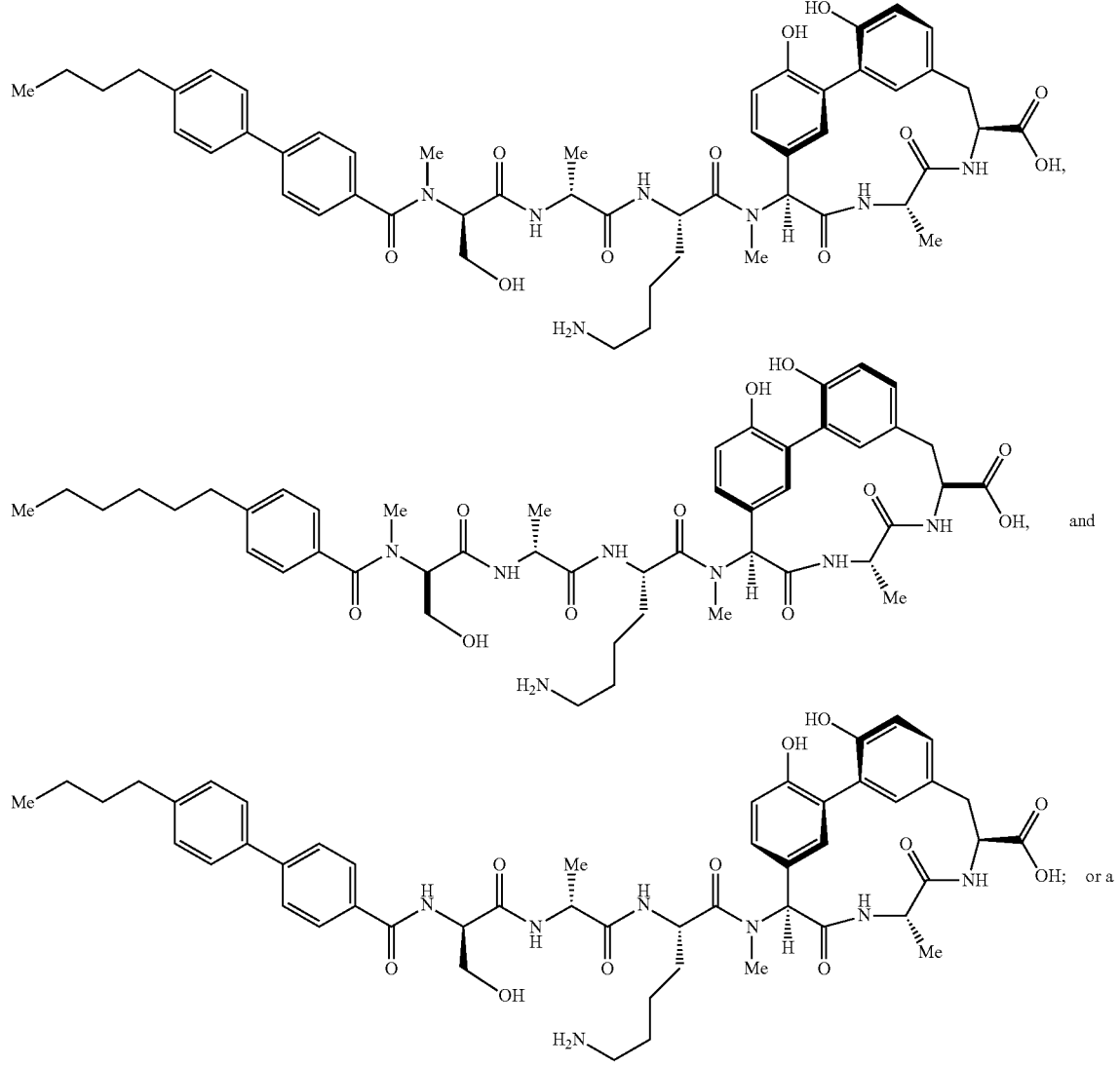

pharmaceutically acceptable salt, solvate or prodrug thereof.

18. A pharmaceutical composition comprising the compound of claim 1 and a pharmaceutically acceptable excipient.

19. A method of treatment of a bacterial infection in a patient comprising administering to the patient a therapeutically effective amount of a compound of claim 1, or a pharmaceutically acceptable salt or solvate thereof.

* * * * *